(12) United States Patent
Clube

(10) Patent No.: US 11,141,481 B2
(45) Date of Patent: *Oct. 12, 2021

(54) SELECTIVELY ALTERING MICROBIOTA FOR IMMUNE MODULATION

(71) Applicant: SNIPR Technologies Limited, London (GB)

(72) Inventor: Jasper Clube, London (GB)

(73) Assignee: SNIPR Technologies Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/005,121

(22) Filed: Aug. 27, 2020

(65) Prior Publication Data

US 2020/0390886 A1 Dec. 17, 2020

Related U.S. Application Data

(63) Continuation of application No. 16/453,598, filed on Jun. 26, 2019, which is a continuation of application No. 16/192,752, filed on Nov. 15, 2018, now Pat. No. 10,363,308, which is a continuation of application No. 15/820,296, filed on Nov. 21, 2017, now Pat. No. 10,195,273, which is a continuation of application No. PCT/EP2017/063593, filed on Jun. 4, 2017.

(30) Foreign Application Priority Data

Jun. 5, 2016 (GB) .................................. 1609811

(51) Int. Cl.

| A61K 39/395 | (2006.01) |
| A61K 39/00 | (2006.01) |
| A61P 37/00 | (2006.01) |
| A61P 35/00 | (2006.01) |
| A61K 31/7105 | (2006.01) |
| A61K 35/15 | (2015.01) |
| A61K 35/17 | (2015.01) |

(52) U.S. Cl.

CPC ...... *A61K 39/3955* (2013.01); *A61K 31/7105* (2013.01); *A61K 35/15* (2013.01); *A61K 35/17* (2013.01); *A61P 35/00* (2018.01); *A61P 37/00* (2018.01); *A61K 39/0011* (2013.01); *A61K 2039/505* (2013.01)

(58) Field of Classification Search

CPC .................................................. A61K 39/3955
See application file for complete search history.

(56) References Cited

U.S. PATENT DOCUMENTS

| 4,626,504 A | 12/1986 | Puhler |
| 5,633,154 A | 5/1997 | Schaefer |
| 8,241,498 B2 | 8/2012 | Summer |
| 8,252,576 B2 | 8/2012 | Campbell |
| 8,906,682 B2 | 12/2014 | June |
| 8,911,993 B2 | 12/2014 | June |
| 8,916,381 B1 | 12/2014 | June |
| 8,975,071 B1 | 3/2015 | June |
| 9,101,584 B2 | 8/2015 | June |
| 9,102,760 B2 | 8/2015 | June |
| 9,102,761 B2 | 8/2015 | June |
| 9,113,616 B2 | 8/2015 | Stevens |
| 9,328,156 B2 | 5/2016 | June |
| 9,464,140 B2 | 10/2016 | June |
| 9,481,728 B2 | 11/2016 | June |
| 9,499,629 B2 | 11/2016 | June |
| 9,518,123 B2 | 12/2016 | June |
| 9,540,445 B2 | 1/2017 | June |
| 9,701,964 B2 | 7/2017 | Clube |
| 9,758,583 B2 | 9/2017 | Wang |
| 9,822,372 B2 | 11/2017 | Zhang |
| 9,879,269 B2 | 1/2018 | Barrangou |
| 10,066,233 B2 | 9/2018 | Barrangou |
| 10,136,639 B2 | 11/2018 | Wuest |
| 10,136,649 B2 | 11/2018 | Barrangou |
| 10,195,273 B2 | 2/2019 | Clube |
| 10,300,138 B2 * | 5/2019 | Clube ................ A61K 39/0011 |
| 10,300,139 B2 * | 5/2019 | Clube ..................... A61P 37/00 |
| 10,363,308 B2 * | 7/2019 | Clube .................... A61K 35/15 |

(Continued)

FOREIGN PATENT DOCUMENTS

| CA | 3010891 A1 | 7/2017 |
| EP | 2325332 A1 | 5/2011 |

(Continued)

OTHER PUBLICATIONS

Aklujkar et al. (2010) "Interference With Histidyl-tRNA Synthetase by a CRISPR Spacer Sequence as a Factor in the Evolution of Pelobacter Carbinolicus," BMC Evolutionary Biology 10:203, 15 pages.

American Lung Association (2019). "Preventing COPD," retrieved from https://www.lung.org/lung-health-and-diseases/lung-disease-lookup/copd/symptoms-causes-risk-factors/preventing-copd.html, last visited Aug. 5, 2019, 1 page.

(Continued)

*Primary Examiner* — Gary B Nickol
*Assistant Examiner* — Lakia J Jackson-Tongue
(74) *Attorney, Agent, or Firm* — Morrison & Foerster LLP

(57) ABSTRACT

The invention relates to methods of modulating immune cells in a patient by altering microbiota of the patient. The invention also relates to methods of modulating treatments or therapies in a subject organism by altering microbiota of the subject. The invention also relates to cell populations, systems, arrays, cells, RNA, kits and other means for effecting this. In an example, advantageously selective targeting of a particular species in a human gut microbiota using guided nucleic acid modification is carried out to effect the alteration.

24 Claims, 19 Drawing Sheets

Specification includes a Sequence Listing.

(56) References Cited

U.S. PATENT DOCUMENTS

| | | |
|---|---|---|
| 10,463,049 B2 | 11/2019 | Clube |
| 10,506,812 B2 | 12/2019 | Clube |
| 10,524,477 B2 | 1/2020 | Clube |
| 10,596,255 B2 | 3/2020 | Clube |
| 10,603,379 B2* | 3/2020 | Clube ............ A61K 35/17 |
| 10,760,065 B2 | 9/2020 | Lu et al. |
| 10,765,740 B2 | 9/2020 | Clube et al. |
| 10,920,222 B2 | 2/2021 | Sommer et al. |
| 2003/0049841 A1 | 3/2003 | Short |
| 2004/0096974 A1 | 5/2004 | Herron |
| 2005/0118719 A1 | 6/2005 | Schmidt |
| 2009/0155768 A1 | 6/2009 | Scholl |
| 2010/0076057 A1 | 3/2010 | Sontheimer |
| 2010/0093617 A1 | 4/2010 | Barrangou |
| 2011/0002889 A1 | 1/2011 | Barrangou |
| 2011/0143997 A1 | 6/2011 | Henry et al. |
| 2012/0269859 A1 | 10/2012 | Minato |
| 2013/0011828 A1 | 1/2013 | Barrangou |
| 2013/0109053 A1 | 5/2013 | Macdonald |
| 2013/0121968 A1 | 5/2013 | Quay |
| 2013/0287748 A1 | 10/2013 | June |
| 2013/0288368 A1 | 10/2013 | June |
| 2013/0309258 A1 | 11/2013 | June |
| 2014/0068797 A1 | 3/2014 | Doudna |
| 2014/0105912 A1 | 4/2014 | Noelle |
| 2014/0106449 A1 | 4/2014 | June |
| 2014/0107092 A1 | 4/2014 | Meyerson |
| 2014/0179726 A1 | 6/2014 | Bajaj |
| 2014/0199767 A1 | 7/2014 | Barrangou |
| 2014/0234972 A1 | 8/2014 | Zhang |
| 2014/0341920 A1 | 11/2014 | Noelle |
| 2014/0370017 A1 | 12/2014 | June |
| 2015/0031134 A1 | 1/2015 | Zhang |
| 2015/0050699 A1 | 2/2015 | Siksnys |
| 2015/0050729 A1 | 2/2015 | June |
| 2015/0064138 A1 | 3/2015 | Lu |
| 2015/0093822 A1 | 4/2015 | June |
| 2015/0099299 A1 | 4/2015 | June |
| 2015/0118202 A1 | 4/2015 | June |
| 2015/0125463 A1 | 5/2015 | Cogswell |
| 2015/0132263 A1 | 5/2015 | Liu et al. |
| 2015/0132419 A1 | 5/2015 | Arvik |
| 2015/0139943 A1 | 5/2015 | Campana |
| 2015/0140001 A1 | 5/2015 | Lee |
| 2015/0184139 A1 | 7/2015 | Zhang |
| 2015/0232881 A1 | 8/2015 | Glucksmann |
| 2015/0290244 A1 | 10/2015 | June |
| 2015/0353905 A1 | 12/2015 | Weiss |
| 2016/0009805 A1 | 1/2016 | Kowanetz |
| 2016/0009813 A1 | 1/2016 | Themeli |
| 2016/0024510 A1 | 1/2016 | Bikard |
| 2016/0040215 A1 | 2/2016 | Henn et al. |
| 2016/0081314 A1 | 3/2016 | Thurston |
| 2016/0115488 A1 | 4/2016 | Zhang |
| 2016/0115489 A1 | 4/2016 | Zhang |
| 2016/0130355 A1 | 5/2016 | June |
| 2016/0159905 A1 | 6/2016 | Abdiche |
| 2016/0159907 A1 | 6/2016 | June |
| 2016/0160186 A1 | 6/2016 | Parsley |
| 2016/0194404 A1 | 7/2016 | June |
| 2016/0208012 A1 | 7/2016 | June |
| 2016/0281053 A1 | 9/2016 | Sorek |
| 2016/0324938 A1 | 11/2016 | Bikard |
| 2016/0333348 A1 | 11/2016 | Clube |
| 2016/0345578 A1 | 12/2016 | Barrangou |
| 2016/0347836 A1 | 12/2016 | Grosso |
| 2016/0354416 A1 | 12/2016 | Gajewski |
| 2017/0022499 A1 | 1/2017 | Lu |
| 2017/0037416 A1 | 2/2017 | Barrangou |
| 2017/0106026 A1 | 4/2017 | Kovarik |
| 2017/0114351 A1 | 4/2017 | Mahfouz |
| 2017/0143772 A1 | 5/2017 | Mulder |
| 2017/0173085 A1* | 6/2017 | Kovarik ......... C12Y 301/03067 |
| 2017/0174713 A1 | 6/2017 | Du |
| 2017/0175142 A1 | 6/2017 | Zhang |
| 2017/0196225 A1 | 7/2017 | Clube |
| 2017/0246221 A1 | 8/2017 | Clube |
| 2017/0247690 A1 | 8/2017 | Quake |
| 2017/0304443 A1 | 10/2017 | Lebwohl |
| 2017/0327582 A1 | 11/2017 | Bissonnette |
| 2017/0340733 A1 | 11/2017 | Cao |
| 2018/0015131 A1 | 1/2018 | Gajewski |
| 2018/0055852 A1 | 3/2018 | Kutok |
| 2018/0064114 A1 | 3/2018 | Clube |
| 2018/0064115 A1 | 3/2018 | Clube |
| 2018/0070594 A1 | 3/2018 | Clube |
| 2018/0084785 A1 | 3/2018 | Clube |
| 2018/0084786 A1 | 3/2018 | Clube |
| 2018/0140698 A1 | 5/2018 | Clube |
| 2018/0146681 A1 | 5/2018 | Clube |
| 2018/0147221 A1 | 5/2018 | Von Maltzahn et al. |
| 2018/0155721 A1 | 6/2018 | Lu |
| 2018/0155729 A1 | 6/2018 | Beisel |
| 2018/0161368 A1 | 6/2018 | Odegard |
| 2018/0179547 A1 | 6/2018 | Zhang |
| 2018/0200342 A1 | 7/2018 | Bikard |
| 2018/0273940 A1 | 9/2018 | Sommer |
| 2018/0303934 A1 | 10/2018 | Clube |
| 2018/0326057 A1 | 11/2018 | Clube |
| 2018/0371405 A1 | 12/2018 | Barrangou |
| 2019/0015441 A1 | 1/2019 | Shachar |
| 2019/0021343 A1 | 1/2019 | Barrangou |
| 2019/0070233 A1* | 3/2019 | Yeung ............... C12N 15/86 |
| 2019/0117709 A1 | 4/2019 | Kovarik |
| 2019/0133135 A1 | 5/2019 | Clube |
| 2019/0134194 A1 | 5/2019 | Clube |
| 2019/0136230 A1 | 5/2019 | Sather |
| 2019/0142881 A1 | 5/2019 | Turner et al. |
| 2019/0160120 A1 | 5/2019 | Haaber |
| 2019/0230936 A1 | 8/2019 | Clube |
| 2019/0240325 A1 | 8/2019 | Clube |
| 2019/0240326 A1 | 8/2019 | Clube |
| 2019/0255084 A1 | 8/2019 | Schentag |
| 2019/0256900 A1 | 8/2019 | Zhang |
| 2019/0298779 A1 | 10/2019 | Falb |
| 2019/0321468 A1 | 10/2019 | Clube et al. |
| 2019/0321469 A1* | 10/2019 | Clube ............ A61K 39/3955 |
| 2019/0321470 A1 | 10/2019 | Clube |
| 2019/0359933 A1 | 11/2019 | Swee |
| 2020/0030444 A1 | 1/2020 | Clube |
| 2020/0046773 A1 | 2/2020 | Borody |
| 2020/0085066 A1 | 3/2020 | Clube |
| 2020/0087660 A1 | 3/2020 | Sommer |
| 2020/0102551 A1 | 4/2020 | Barrangou |
| 2020/0115716 A1 | 4/2020 | Martinez |
| 2020/0121787 A1* | 4/2020 | Clube ............... A61P 35/00 |
| 2020/0157237 A1 | 5/2020 | Regev |
| 2020/0164070 A1 | 5/2020 | Clube |
| 2020/0179460 A1 | 6/2020 | Kovarik |
| 2020/0337313 A1 | 10/2020 | Clube |
| 2020/0354690 A1 | 11/2020 | Garofolo |
| 2021/0009996 A1 | 1/2021 | Sommer |
| 2021/0113689 A1 | 4/2021 | Clube |
| 2021/0198665 A1 | 7/2021 | Sommer et al. |

FOREIGN PATENT DOCUMENTS

| | | |
|---|---|---|
| EP | 2840140 A1 | 2/2015 |
| EP | 3461337 A1 | 4/2019 |
| EP | 3132035 B1 | 1/2020 |
| EP | 3132036 B1 | 1/2020 |
| EP | 3630975 A1 | 4/2020 |
| EP | 3633032 A2 | 4/2020 |
| EP | 3634442 A1 | 4/2020 |
| EP | 3634473 A1 | 4/2020 |
| RU | 2531343 C2 | 10/2014 |
| WO | 2005046579 A2 | 5/2005 |
| WO | 2005046579 A3 | 8/2005 |
| WO | 2007025097 A2 | 3/2007 |
| WO | 2007025097 A3 | 7/2007 |
| WO | 2008108989 A2 | 9/2008 |
| WO | 2008108989 A3 | 3/2009 |
| WO | 2010011961 A2 | 1/2010 |
| WO | 2010011961 A3 | 6/2010 |

(56) References Cited

FOREIGN PATENT DOCUMENTS

| | | |
|---|---|---|
| WO | 2010075424 A2 | 7/2010 |
| WO | 2010075424 A3 | 9/2010 |
| WO | 2012079000 A1 | 6/2012 |
| WO | 2012079000 A4 | 8/2012 |
| WO | 2012164565 A1 | 12/2012 |
| WO | 2013063361 A1 | 5/2013 |
| WO | 2013176772 A1 | 11/2013 |
| WO | 2014012001 A2 | 1/2014 |
| WO | 2014018423 A2 | 1/2014 |
| WO | 2014018423 A3 | 1/2014 |
| WO | 2014093595 A1 | 6/2014 |
| WO | 2014093661 A2 | 6/2014 |
| WO | 2014093661 A3 | 8/2014 |
| WO | 2014124226 A1 | 8/2014 |
| WO | 2014093661 A9 | 10/2014 |
| WO | 2014204725 A1 | 12/2014 |
| WO | 2015034872 A2 | 3/2015 |
| WO | 2014012001 A3 | 4/2015 |
| WO | 2015034872 A3 | 4/2015 |
| WO | 2015058018 A1 | 4/2015 |
| WO | 2015069682 A2 | 5/2015 |
| WO | 2015070083 A1 | 5/2015 |
| WO | 2015071474 A2 | 5/2015 |
| WO | 2015075688 A1 | 5/2015 |
| WO | 2015088643 A1 | 6/2015 |
| WO | 2015089351 A1 | 6/2015 |
| WO | 2015069682 A3 | 7/2015 |
| WO | 2015071474 A3 | 8/2015 |
| WO | 2015136541 A2 | 9/2015 |
| WO | 2015148680 A1 | 10/2015 |
| WO | 2015153940 A1 | 10/2015 |
| WO | 2015155686 A2 | 10/2015 |
| WO | 2015159068 A1 | 10/2015 |
| WO | 2015159086 A1 | 10/2015 |
| WO | 2015159087 A1 | 10/2015 |
| WO | 2015136541 A3 | 11/2015 |
| WO | 2015155686 A3 | 12/2015 |
| WO | 2016044745 A1 | 3/2016 |
| WO | 2016063263 A2 | 4/2016 |
| WO | 2016063263 A3 | 6/2016 |
| WO | 2016084088 A1 | 6/2016 |
| WO | 2016196361 A1 | 12/2016 |
| WO | 2016196605 A1 | 12/2016 |
| WO | 2016205276 A1 | 12/2016 |
| WO | 2017009399 A1 | 1/2017 |
| WO | 2017042347 A1 | 3/2017 |
| WO | 2017058751 A1 | 4/2017 |
| WO | 2017112620 A1 | 6/2017 |
| WO | 2017118598 A1 | 7/2017 |
| WO | 2017211753 A1 | 12/2017 |
| WO | 2018064165 A2 | 4/2018 |
| WO | 2018081502 A1 | 5/2018 |
| WO | 2018115519 A1 | 6/2018 |
| WO | 2018217351 A1 | 11/2018 |
| WO | 2018217981 A1 | 11/2018 |
| WO | 2018222969 A1 | 12/2018 |
| WO | 2018226853 A1 | 12/2018 |
| WO | 2018064165 A3 | 6/2019 |
| WO | 2020072248 A1 | 4/2020 |
| WO | 2020072250 A1 | 4/2020 |
| WO | 2020072253 A1 | 4/2020 |
| WO | 2020072254 A1 | 4/2020 |
| WO | 2020152369 A1 | 7/2020 |

OTHER PUBLICATIONS

Ang, Y.L.E. et al. (2015). "Best Practice in the Treatment of Advanced Squamous Cell Lung Cancer," Ther. Adv. Respir. Dis. 9(5):224-235.

Arnold, I.C. et al. (Apr. 8, 2015, e-pub. Mar. 4, 2015). "Helicobacter Hepaticus Infection in BALB/c Mice Abolishes Subunit-Vaccine-Induced Protection Against M. Tuberculosis," Vaccine 33(15):1808-1814.

Arslan, Z. et al. (May 7, 2013). "RcsB-BgIJ-Mediated Activation of Cascade Operon Does Not Induce the Maturation of CRISPR RNAs in *E. coli* K12," RNA Biology 10(5):708-715.

Arumugam et al. (May 12, 2011). "Enterotypes of the human gut microbiome," Nature 473(7346):174-180, 16 pages.

Bae, T. et al. (2006). "Prophages of *Staphylococcus aureus* Newman and Their Contribution to Virulence," Molecular Microbiology pp. 1-13.

Barrangou, R. et al. (Mar. 2007). "CRISPR Provides Acquired Resistance Against Viruses in Prokaryotes," Science, 315:1709-1712.

Beisel, C.L. et al. (2014). "A CRISPR Design for Next-Generation Antimicrobials," Genome Biology 15:516, 4 pages.

Belizario, J.E. et al. (Oct. 6, 2015). "Human Microbiomes and Their Roles in Dysbiosis, Common Diseases, and Novel Therapeutic Approaches," Frontiers in Microbiology 6(1050):1-16.

Bikard, D. et al. (2013, e-pub. Jun. 12, 2013). "Programmable Repression and Activation of Bacterial Gene Expression Using an Engineered CRISPR-Cas System," Nucleic Acids Research 41(15):7429-7437.

Bikard, D. et al. (2017, e-pub. Sep. 6, 2017). "Using CRISPR-Cas Systems as Antimicrobials," Current Opinion in Microbiology 37:155-160.

Bikard, D. et al. (Aug. 16, 2012). "CRISPR Interference Can Prevent Natural Transformation and Virulence Acquisition during In Vivo Bacterial Infection," Cell Host & Microbe 12(2):177-186.

Bikard, D. et al. (Nov. 2014). "Development of Sequence-Specific Antimicrobials Based on Programmable CRISPR-Cas Nucleases," Nature Biotechnology 32(11):1146-1151, 16 pages.

Broaders, E. et al. (Jul./Aug. 2013). "Mobile Genetic Elements of the Human Gastrointestinal Tract," Gut Microbes 4(4):271-280.

Brouns, S.J.J. et al. (Aug. 15, 2008). Supplemental Material for "Small CRISPR RNAs Guide Antiviral Defense in Prokaryotes," Science 321:960-964.

Brouns, S.J.J. et al. (Aug. 15, 2008). "Small CRISPR RNAs Guide Antiviral Defense in Prokaryotes," Science 321:960-964.

Bryksin, A. V. et al. (Oct. 8, 2010). "Rational Design of a Plasmid Origin That Replicates Efficiently in Both Gram-Positive and Gram-Negative Bacteria," PloS One 5(10):e13244, 9 pages.

Bugrysheva, J.V et al. (Jul. 2011, E-Pub. Apr. 29, 2011). "The Histone-Like Protein Hlp is Essential for Growth of *Streptococcus pyogenes*: Comparison of Genetic Approaches to Study Essential Genes," Appl. Environ. Microbiol. 77(13):4422-4428.

Bullman, S. et al. (Nov. 23, 2017). "Analysis of Fusobacterium Persistence and Antibiotic Response in Colorectal Cancer," Science pp. 1443-1448, 10 pages.

Chan, B.K. et al. (2013). "Phage Cocktails and the Future of Phage Therapy," Future Microbiol. 8(6):769-783.

Chan, C.T.Y. et al. (Dec. 2015). "'Deadman' and 'Passcode' Microbial Kill Switches for Bacterial Containment," Nat. Chem. Biol. 12(2):82-86.

Cheadle, E.J. et al. (2012). "Chimeric Antigen Receptors for T-Cell Based Therapy," Methods Mol. Biol. 907:645-666, 36 pages.

Citorik, R.J. et al. (Nov. 2014, e-pub Sep. 21, 2014). "Sequence-Specific Antimicrobials Using Efficiently Delivered RNA-Guided Nucleases," Nat. Biotechnol. 32(11):1141-1145, 18 pages.

Cochrane, K. et al. (2016, e-pub. Nov. 3, 2015). "Complete Genome Sequences and Analysis of the Fusobacterium nucleatum Subspecies Animalis 7-1 Bacteripophage Φfunu1 and Φfunu2," Anaerobe 38:125-129. Abstract Only.

Cong, L. et al. (Feb. 15, 2013, e-pub. Oct. 11, 2013). "Multiplex Genome Engineering Using CRISPR/Cas Systems," Science 339(6121):819-823, 9 pages.

Consumer Updates (2019). "Combating Antibiotic Resistance," retrieved from https://www.fda.gov/ForConsumers/ConsumerUpdates/ucm092810.htm, last visited Jan. 28, 2019.

Coyne, M.J. et al. (2014). "Evidence of Extensive DNA Transfer between Bacteroidales Species Within the Human Gut," mBio 5(3):e01305-14, 12 pages.

Cui, L. et al. (2016, e-pub. Apr. 8, 2016). "Consequences of Cas9 Cleavage in the Chromosome of *Escherichia coli*," Nucleic Acids Research 44(9):4243-4251.

(56) References Cited

OTHER PUBLICATIONS

Daillere, R. et al. (Oct. 18, 2016). "Enterococcus hirae and Bamesiella intestinihominis Facilitate Cyclophosphamide-Induced Therapeutic Immunomodulatory Effects," Immunity 95:931-943.
De Filippo, C. et al. (Aug. 33, 2010). "Impact of Diet in Shaping Gut Microbiota Revealed by a Comparative Study in Children From Europe and Rural Africa," Proc. Natl. Acad. Sci. USA 107(33):14691-14696, 6 pages.
De Paepe, M. et al. (Mar. 28, 2014). "Bacteriophages: An Underestimated Role in Human and Animal Health?" Frontiers in Cellular and Infection Microbiology 4(39):1-11.
Deeks, E.D. (2014, e-pub. Jul. 15, 2014). "Nivolumab: A Review of its Use in Patients With Malignant Melanoma," Drugs 74:1233-1239.
Deghorain, M. et al. (Nov. 23, 2012). "The Staphylococci Phages Family: An Overview," Viruses 4:3316-3335.
Denham, J.D. et al. (2018). "Case Report: Treatment of Enteropathogenic *Escherichia coli* Diarrhea in Cancer Patients: A Series of Three Cases," Case Reports in Infectious Diseases Article ID 8438701: 1-3.
Dhar, A.D. (Jul. 20, 2018). "Overview of Bacterial Skin Infections," Merck Manual retrieved from https://www.merckmanuals.com/home/skin-disorders/bacterial-skin-infections/overview-of-bacterial-skin-infections, last visited Jul. 20, 2018, 3 pages.
Dickson, R.P. et al. (Jan./Feb. 2017). "Bacterial Topography of the Healthy Human Lower Respiratory Tract," American Society for Microbiology 8(1):e02287-6, 12 pages.
Diez-Villasenor, C. et al. (May 2013). "CRISPR-Spacer Integration Reporter Plasmids Reveal Distinct Genuine Acquisition Specificities Among CROSPR-Cas 1-E Variants of *Escherichia coli*," RNA Biology 10(5):792-802.
Dutilh, B.E. et al. (Jul. 24, 2014). "A Highly Abundant Bacteriophage Discovered in the Unknown Sequences of Human Faecal Metagenomes," Nature Communications 5(4498):1-10.
Edgar et al. (Dec. 2010). "The *Escherichia coli* CRISPR System Protects From λ Lysogenization, Lysogens, and Prophage Induction," Journal of Bacteriology 192(23):6291-6294, Supplemental Material, 2 pages.
Edgar et al. (Dec. 2010). "The *Escherichia coli* CRISPR System Protects From λ Lysogenization, Lysogens, and Prophage Induction," Journal of Bacteriology 192(23):6291-6294.
Ex Parte Re-Exam, mailed Dec. 10, 2018, for U.S. Appl. No. 90/014,184, filed Aug. 10, 2018, for Reexamination U.S. Pat. No. 9,701,964 102 pages.
Fact Sheet (Oct. 2010). "Antimicrobial Resistance," National Institutes of Health, 1-2.
Foca, A. et al. (2015, e-pub. Apr. 7, 2015). Gut Inflammation and Immunity: What is the Role of the Human Gut Virome? Mediators of Inflammation 2015(326032):1-7.
Galperin, M.Y. (Dec. 2013). "Genome Diversity of Spore-Forming Firmicutes," Microbiology Spectrum 1(2):TBS-0015-2012, 27 pages.
Garon, E.B. et al. (Oct. 2015). "Current Perspectives in Immunotherapy for Non-Small Cell Lung Cancer," Seminars in Oncology 42(5 Supp. 2):S11-S18.
Garrett W.S et al. (Oct. 5, 2007). "Communicable Ulcerative Colitis Induced by T-Bet Deficiency in the Innate Immune System," Cell 131(1):33-45, 23 pages.
Geller, L.T. et al. (Sep. 15, 2017). "Potential Role of Intratumor Bacteria in Mediating Tumor Resistance to the Chemotherapeutic Drug Gemcitabine," Cancer, 1156-1160, 6 pages.
Golubovskaya, V. et al. (Mar. 15, 2016). "Different Subsets of T Cells, Memory, Effector Functions, and CAR-T Immunotherapy," Cancers 8(36), 12 pages.
Gomaa et al. (Jan. 28, 2014). "Programmable Removal of Bacterial Strains by Use of Genome-Targeting CRISPR-Cas Systems," mBio, 5(1):e000928-13.
Gomaa, A.A. et al. (Jan./Feb. 2014). Supplemental Material to "Programmable Removal of Bacterial Strains by Use of GenomeTargeting CRISPR-Cas Systems," American Society for Microbiology 5(1):1-9.

Goodall, E.C.A. et al. (Feb. 20, 2018). "The Essential Genome of *Escherichia coli* K-12," Am. Society for Microbiology—mBio 9(1):e02096-17, 18 pages.
Gopalakrishnan, V. et al. (Jan. 5, 2018). "Gut Microbiome Modulates Response to Anti-PD-1 Immunotherapy in Melanoma Patients," Science 359:97-103, 20 pages.
Green, J. (Jul. 20, 2018). Colgate https://www.colgate.com/en-us/oral-health/conditions/mouth-sores-and-infections/eight-common-oral-infections-0615, last visited Jul. 20, 2018, 4 pages.
Gudbergsdottir, S. et al. (2011, e-pub. Nov. 18, 2010). "Dynamic Properties of the Sulfolobus CRISPR/Das and CRISPR/Cmr Systems When Challenged With Vector-Bome Viral and Plasmid Genes and Protospacers," Molecular Microbiology 79(1):35-49.
Guedan, S. et al. (Aug. 14, 2014). "ICOS-Based Chimeric Antigen Receptors Program Bipolar TH17/TH1 Cells," Blood 124(7):1070-1080.
Hargreaves, K.R. et al. (Aug. 26, 2014). "Abundant and Diverse Clustered Regularly Interspaced Short Palindromic Repeat Spacers in Clostridium difficile Strains and Prophages Target Multiple Phage Types within This Pathogen," mBio 5(5):e01045-13.
Harrington, L.E. (Nov. 2005, e-pub. Oct. 2, 2005). "Interleukin 17-producing CD4+ Effector T Cells Develop Via a Lineage Distinct From the T Helper Type 1 and 2 Lineages," Nat. Immunol. 6(11):1123-1132.
Hartland, E.L. et al. (Apr. 30, 2013). "Enteropathogenic and Enterohemorrhagic *E. coli*: Ecology, Pathogenesis, and Evolution," Frontiers in Cellular and Infection Microbiology 3(15):1-3.
Healthline (2019). "Cystic Fibrosis," retrieved from https://www.healthline.conn/health/cystic-fibrosis#prevention, last visited Aug. 5, 2019, 14 pages.
Hooper, L.V. et al. (Jun. 8, 2012). "Interactions Between the Microbiota and the Immune System," Science 336 (6086):1268-1273, 16 pages.
Horvath, P. et al. (2008, e-pub. Dec. 7, 2007). "Diversity, Activity, and Evolution of CRISPR Loci in *Streptococcus thermophiles*," Journal of Bacteriology 190(4):1401-1412.
Huddleston, J.R. (Jun. 20, 2014). "Horizontal Gene Transfer in the Human Gastrointestinal Tract Potential Spread of Antibiotic Resistance Genes," Infection and Drug Resistance 7:167-176.
International Search Report and the Written Opinion of the International Searching Authority for PCT/EP2018/066954, dated Oct. 23, 2018, filed Jun. 25, 2018, 14 pages.
International Search Report and the Written Opinion of the International Searching Authority for PCT/EP2019/057453, dated Aug. 16, 2019, filed Mar. 25, 2019, 21 pages.
International Search Report for PCT/EP2016/059803, dated Jun. 30, 2016, filed May 3, 2016, 6 pages.
International Search Report for PCT/EP2018/082053, dated Mar. 14, 2019, filed Nov. 21, 2018, 9 pages.
Ivanov, I.I. et al. (May 2010). "Segmented Filamentous Bacteria Take the Stage," Muscosal Immunol. 3(3):209-212, 7 pages.
Jiang, W. et al. (Jan. 29, 2013). "RNA-Guided Editing of Bacterial Genomes Using CRISPR-Cas Systems," Nat. Biotechnology 31:233-241.
Jiang, W. et al. (Mar. 2013, e-pub. Sep. 1, 2013). "CRISPR-Assisted Editing of Bacterial Genomes," Nat. Biotechnol. 31(3):233-239.
Jiang, W. et al. (Nov. 2013). "Demonstiation of CRISPR/Cas9/sgRNA-Mediated Targeted Gene Modification in *Arabidopsis*, Tobacco, Sorghum and Rice," Nucleic Acids Research 41(20):e188, 12 pages.
Jin, Y. et al. (2019, e-pub. Apr. 23, 2019). "The Diversity of Gut Microbiome is Associated With Favorable Responses to Anti-Programmed Death 1 Immunotherapy in Chinese Patients With NSCLC," Journal of Thoracic Oncology 14(8):11378-1389.
Jinek et al. (Aug. 17, 2012). "A Programmable Dual-RNA-Guided DNA Endonuclease in Adaptive Bacterial Immunity," Science 337(6096):816-821.
Kaulich, M. et al. (2015, e-pub. Jan. 13, 2015). "Efficient CRISPR-rAAV Engineering of Endogenous Genes to Study Protein Function by Allele-Specific RNAi," Nucleic Acids Research 43(7):e45, 8 pages.
Khoja, L. et al. (2015). "Pembrolizumab," Journal for ImmunoTherapy of Cancer 3(36):11-13.

(56) References Cited

OTHER PUBLICATIONS

Kochenderfer, J.N. et al. (Sep. 2009). "Construction and Pre-clinical Evaluation of an Anti-CD19 Chimeric Antigen Receptor," J. Immunother. 32(7):689-702, 26 pages.
Kosiewicz, M.M. et al. (2014, e-pub. Mar. 26, 2014). "Relationship Between Gut Microbiota and Development of T Cell Associated Disease," FEBS Lett. 588:4195-4206.
Krom, R.J. et al. (Jul. 5, 2015). "Engineered Phagemids for Nonlytic, Targeted Antibacterial Therapies," Nano Letters 15(7):4808-4813.
Lopez-Sanchez, M.-J. et al. (2012, e-pub. Jul. 27, 2012). "The Highly Dynamic CRISPR1 System of *Streptococcus agalactiae* Controls the Diversity of its Mobilome," Molecular Microbiology 85(6):1057-1071.
Ludwig, E.S. et al. (1985). "The Phylogenetic Position of *Streptococcus* and Enterococcus," Journal of General Microbiology 131:543-551.
Luo, M.L. et al. (2015, e-pub. Oct. 17, 2014). "Repurposing Endogenous Type I CRISPR-Cas Systems for Programmable Gene Repression," Nucleic Acids Research 43(1):674-681.
López, P. et al. (Apr. 5, 2016). "Th17 Responses and Natural IgM Antibodies are Related to Gut Microbiota Composition in Systemic Lupus Erythematosus Patients," Sci. Rep. 6:24072, 12 pages.
Macon, B.L. et al. (Jan. 2, 2018). "Acute Nephrities," retrieved from healthline, https://www.healthline.com/health/acute-nephritic-syndrome#types, last visited Jul. 20, 2018, 13 pages.
Magee, M.S. et al. (Nov. 2014). "Challenges to Chimeric Antigen Receptor (CAR)-T Cell Therapy for Cancer," Discov. Med. 18(100):265-271, 6 pages.
Mahoney, K.M. et al. (2015). "The Next Immune-Checkpoint Inhibitors: PD-1/PD-L1 Blockade in Melanoma," Clinical Therapeutics 37(4):764-782.
Mali, P. et al. (Oct. 2013). "Cas9 as a Versatile Tool for Engineering Biology," Nat. Methods 10(10):957-963, 16 pages.
Mancha-Agresti, P. et al. (Mar. 2017). "A New Broad Range Plasmid for DNA Delivery in Eukaryotic Cells Using Lactic Acid Bacteria: In Vitro and In Vivo Assays," Molecular Therapy: Methods & Clinical Development 4:83-91.
Marraffini, L.A et al. (Dec. 19, 2008). "CRISPR Interference Limits Horizontal Gene Transfer in Staphylococci by Targeting DNA," Science 322(5909):1843-1845, 12 pages.
Mayo Clinic (2019). "Pulmonary Embolism," retrieved from https://www.nnayoclinic.org/diseases-conditions/pulnnonary-ennbolisnn/synnptonns-causes/syc-20354647, last visited Aug. 5, 2019, 8 pages.
Mayo Clinic (2020). "Infectious Diseases," retrieved from https://www.nnayoclinic.org/diseases-conditions/infectious-diseases/diagnosis-treatnnent/drc-20351179, last visited Jan. 17, 2020, 5 pages.
Mayo Clinic (2020). "Malaria," retrieved from https://www.nnayoclinic.org/diseases-conditions/nnalaria/diagnosis-treatnnent/drc-20351190, last visited Jan. 17, 2020, 3 pages.
Mayo Clinic (2020). "Sexually Transmitted Diseases (STDs)," retrieved from https://www.nnayoclinic.org/diseases-conditions/sexually-transnnitted-diseases-stds/diagnosis-treatnnent/drc-20351246, last visited Jan. 17, 2020, 5 pages.
Mayo Clinic (Jul. 20, 2018). "Bacterial Vaginosis," retrieved from https://www.mayoclinic.org/diseases-conditions/bacterial-vaginosis/symptoms-causes/syc-20352279, last visited Jul. 20, 2018, 3 pages.
Mayo Clinic (Jul. 20, 2018). "Cystitis," retrieved from https://www.mayoclinic.org/diseases-conditions/cystitis/symptoms-causes/syc-20371306, last visited Jul. 20, 2018, 10 pages.
Mayo Clinic (Jul. 20, 2018). "Meningitis," retrieved from https://www.mayoclinic.org/diseases-conditions/meningitis/symptoms-causes/syc-20350508, last visited Jul. 20, 2018, 6 pages.
Mayo Clinic (Jul. 20, 2018). "Pneumonia," retrieved from https://www.mayoclinic.org/diseases-conditions/pneumonia/symptoms-causes/syc-20354204, last visited Jul. 20, 2018, 5 pages.
Mayo Clinic (Mar. 29, 2020). "Liver Disease," retrieved from https://www.mayoclinic.org/diseases-conditions/liver-problems/diagnosis-treatment/drc-20374507, last visited Mar. 29, 2020, 8 pages.
Medina-Aparicio, L. et al. (May 2011, e-pub. Mar. 11, 2011). "The CRI SPR/Cas Immune System is an Operon Regulated by LeuO, H-NS, and Leucine-Responsive Regulatory Protein in *Salmonella enterica* Serovar Typhi," Journal of Bacteriology 193(10):2396-2407.
Mei, J.-M. et al. (1997). "Identification of *Staphylococcus aureus* Virulence Genes in a Murine Model of Bacteraemia Using Signature-Tagged Mutagenesis," Molecular Microbiology 26(2):399-407.
Mercenier, A. (1990). "Molecular Genetics of *Streptococcus thermophiles*," FEMS Microbiology Letters 87(1-2):61-77.
Mick, E. et al. (May 2013). "Holding a Grudge: Persisting Anti-Phage CRISPR Immunity in Multiple Human Gut Microbiomes," RNA Biology 10(5):900-906.
Mills, S. et al. (Jan./Feb. 2013). "Movers and Shakers: Influence of Bacteriophages in Shaping the Mammalian Gut Microbiota," Gut Microbes 4(1):4-16.
Nakamura, S. et al. (Nov. 2008). "Metagenomic Diagnosis of Bacterial Infections," Emerging Infectious Diseases 14(11):1784-1786.
Nale, J.Y. et al. (2012). "Diverse Temperate Bacteriophage Carriage in Clostridium Difficile 027 Strains," PloS One 7(5):e37263, 9 pages.
Navarre, L. et al. (2007). "Silencing of Xenogeneic DNA by H-NS—Facilitation of Lateral Gene Transfer in Bacteria by a Defense System That Recognizes Foreign DNA," Genes & Development 21:1456-1471.
Nelson, M.H. et al. (2015). "Harnessing the Microbiome to Enhance Cancer Immunotherapy," Journal of Immunology Research 2015:Article 368736, 12 pages.
News (May 22, 2018). "UK Government and Bill & Melinda Gates Foundation Join Carb-X Partnership in Fight Against Superbugs: Millions Earmarked to Boost Research Into New Life-Saving Products to Address the Global Rise of Drug-Resistant Bacteria," Combating Antibiotic Resistant Bacteria, 7 pages.
Norris, J.S. et al. (2000). "Prokaryotic Gene Therapy to Combat Multidrug Resistant Bacterial Infection," Gene Therapy 7:723-725.
Notice of Intent to Issue Ex Parte Reexamination Certificate, mailed Aug. 12, 2019, for U.S. Appl. No. 90/014,184, filed Aug. 10, 2018, 26 pages.
Nowak, P. et al. (Nov. 28, 2015). "Gut Microbiota Diversity Predicts Immune Status in HIV-1 Infection," AIDS 29(18):2409-2418.
Park, H. et al. (2005). "A Distinct Lineage of CD4 T Cells Regulates Tissue Inflammation by Producing Interleukin 17," Nat. Immunol. 6(11):1133-1141, 24 pages.
Patterson, A.G. et al. (2017, e-pub. Mar. 27, 2017). "Regulation of CRISPR-Cas Adaptive Immune Systems," Current Opinion in Microbiology 37:1-7.
Patterson, A.G. et al. (Dec. 15, 2016). "Quorum Sensing Controls Adaptive Immunity Through the Regulation of Multiple CRISPR-Cas Systems," Mol. Cell 64(6):1102-1108.
Pawluk, A. et al. (Apr. 15, 2014). "A New Group of Phage Anti-CRISPR Genes Inhibits the Type I-E CRISPR-Cas System of Pseudomonas aeruginosa," mBio. 5(2):e00896.
Pires, D.P. et al. (Sep. 2016, e-pub. Jun. 1, 2016). "Genetically Engineered Phages: A Review of Advances Over the Last Decade," Microbiology and Molecular Biology Reviews 80(3):523-543.
Ramalingam, S.S. et al. (2014). "LB2-Metastatic Non-Small Cell Lung Cancer: Phase II Study of Nivolumab (Anti-PD-1, BMS-936558, ONO-4538) in Patients With Advanced, Refractory Squamous Non-Small Cell Lung Cancer," International Journal of Radiation Oncology Biology Physics Late Breaking Abstract (LB2).
Ran, F.A. et al. (Apr. 9, 2015). "In Vivo Genome Editing Using *Staphylococcus aureus* Cas9," Nature 570(7546):186-191, 28 pages.
Rashid, T. et al. (2013). "The Role of Klebsiella in Crohn's Disease With a Potential for the Use of Antimicrobial Measures," International Journal of Rheumatology 2013(Article ID 610393):1-9.
Request for Ex Parte Reexamination mailed Aug. 10, 2018, for U.S. Appl. No. 15/160,405, now U.S. Pat. No. 9,701,964, 42 pages.
Request for Ex Parte Reexamination mailed Nov. 1, 2018, for U.S. Appl. No. 15/160,405, now U.S. Pat. No. 9,701,964, 35 pages.

(56) References Cited

OTHER PUBLICATIONS

Richter, C. et al. (2012, e-pub. Oct. 19, 2012). "Function and Regulation of Clustered Regularly Interspaced Short Palindromic Repeats (CRISPR) / CRISPR Associated (Cas) Systems," Viruses 4(12):2291-2311.
Ridaura, V.K. et al. (Sep. 6, 2013). "Cultured Gut Microbiota From Twins Discordant for Obesity Modulate Adiposity and Metabolic Phenotypes in Mice," Science 341(6150):1241214, 22 pages.
Roberts, A.P. et al. (Jun. 2009, e-pub. May 20, 2009). "A Modular Master on the Move: The Tn916 Family of Mobile Genetic Elements," Trends Microbiol. 17(6):251-258. Abstract Only.
Rong, Z. et al. (Mar. 14, 2014). "Homologous Recombination in Human Embryonic Stem Cells Using CRISPR/Cas9 Nickase and a Long DNA Donor Template," Protein & Cell 5(4):258-260.
Routy, B. et al. (Jan. 5, 2018, e-pub. Nov. 2, 2017). "Gut Microbiome Influences Efficacy of PD-1-Based Immunotherapy Against Epithelial Tumors," Science 359(6371):91-97.
Samaržija, D. et al. (2001). "Taxonomy, Physiology and Growth of Lactococcus Lactisi: A Review," Mljekarstvo 51(1):35-48.
Sapranauskas, R. et al. (Nov. 1, 2011, e-pub. Aug. 3, 2011). "The *Streptococcus thermophilus* CRISPR/Cas System Provides Immunity in *Escherichia coli*," Nucleic Acids Research 39(21):9275-9282.
Schnabi, B.G. (2020), "The Role of Enterococcus Faecalis in Alcoholic Liver Disease," retrieved from https://grantome.com/grant/NIH/O01-BX004594-01A2, last visited Oct. 20, 2020, 2 pages.
Seed et al. (Feb. 27, 2013). "A Bacteriophage Encodes its Own CRISPR/Cas Adaptive Response to Evade Host Innate Immunity," Nature 494(7438):489-491.
Selle et al. (Apr. 1, 2015). "Harnessing CRISPR-Cas Systems for Bacterial Genome Editing," Trends in Microbiology 23(4):225-232.
Sepsis Alliance, (Dec. 14, 2017). "What Are Vaccines," Retrieved from https://www.sepsis.org/sepsisand/prevention-vaccinations/; last visited Jul. 8, 2019, 3 pages.
Sepsis Alliance; (Jul. 8, 2019). "Prevention," Retrieved from https://www.sepsis.org/sepsisand/prevention/;accessed last visited Jul. 8, 2019, 5 pages.
Shoemaker, N.B. et al. (Feb. 2001). "Evidence for Extensive Resistance Gene Transfer Among Bacteroides spp. and Among Bacteroides and Other Genera in the Human Colon," Appl. Environ. Microbiol. 67(2):561-68.
Sivan, A. et al. (Nov. 27, 2015, e-pub Nov. 5, 2015). "Commensal Bifidobacterium Promotes Antitumor Immunity and Facilitates Anti-PD-L1 Efficacy," Science 350(6264):1084-1089, 13 pages.
Skennerton, C.T. et al. (May 2011). "Phage Encoded H-NS: A Potential Achilles Heel in the Bacterial Defence System," PLoS ONE 6(5):e20095.
Somkuti, G. A. et al. (Apr. 1988). "Genetic Transformation of *Streptococcus thermophilus* by Electroporation," Biochimie 70(4):579-585. Abstract Only.
Sorg, R. A. et al. (2014). "Gene Expression Platform for Synthetic Biology in the Human Pathogen *Streptococcus pneumoniae*," ACS Synthetic Biology 4(3):228-239. Abstract Only.
Soutourina, O.A. et al. (May 9, 2013). "Genome-Wide Identification of Regulatory RNAs in the Human Pathogen Clostridium difficile," PLos Genet. 9(5):e1003493, 20 pages.
Stern, A. et al. (2012). "CRISPR Targeting Reveals a Reservoir of Common Phages Associated With the Human Gut Microbiome," Genome Research 22(10):1985-1994.
Stern, A. et al. (Aug. 2010), Self-Targeting by CRISPR: Gene Regulation or Autoimmunity? Trends Genet. 26(8):335-340, 10 pages.
Stiefel, U. et al. (Aug. 2014, e-pub. May 27, 2014). "Gastrointestinal Colonization With a Cephalosporinase-Producing Bacteroides Species Preserves Colonization Resistance Against Vancomycin-Resistant Enterococcus and Clostridium Difficile In Cephalosporin-Treated Mice," Antimicrob. Agents Chemother. 58(8):4535-4542.
Stoebel, D.M. et al. (2008). "Anti-Silencing: Overcoming H-NS-Mediated Repression of Transcription in Gramnegative Enteric Bacteria," Microbiology 154:2533-2545.
Suvorov, A. (1988). "Transformation of Group A Streptococci by Electroporation," FEMS Microbiology Letters 56(1):95-100.
Takaishi, H. et al. (2008). "Imbalance in Intestinal Microflora Constitution Could Be Involved in the Pathogenesis of Inflammatory Bowel Disease," Int. J. Med. Microbiol.298:463-472.
Takeda, T. et al. (2011). "Distribution of Genes Encoding Nucleoid-Associated Protein Homologs in Plasmids," International Journal of Evolutionary Biology 2001:685015, 31 pages.
Tan, J. (Dec. 17, 2015). "Immunotherapy Meets Microbiota," Cell 163:1561.
Topalian, S.L. et al. (Jun. 28, 2012). "Safety, Activity, and Immune Correlates of Anti-PD-1 Antibody in Cancer," N. Engl. J. Med. 366(26):2443-2454, 19 pages.
Turnbaugh, P.J. et al. (Dec. 2006). "An Obesity-Associated Gut Microbiome With Increased Capacity for Energy Harvest," Nature 444:1027-1131.
U.S. Appl. No. 16/201,736, filed Nov. 27, 2018, for Martinez et al. (Not Submitted herewith pursuant to the waiver of 37 C.F.R. 1.98(a)(2)(iii) issued by the Office on Sep. 21, 2004).
U.S. Appl. No. 62/168,355, filed May 29, 2015, Barrangou, R. et al.(Not submitted herewith pursuant to the waiver of 37 C.F.R. 1.98(a)(2)(iii) issued by the Office on Sep. 21, 2004).
Uchiyama, J. et al. (2013, e-pub. Mar. 8, 2013). "Characterization of Helicobacter pylori Bacteriophage KHP30," Applied and Environmental Microbiology 79(10):3176-3184.
USPTO Interference 106,123—Declaration to Declare Interference Jun. 11, 2020, 11 pages.
USPTO Interference 106,123—Junior Party Annotated Claims Jul. 9, 2020, 31 pages.
USPTO Interference 106,123—Junior Party List of Motions Jul. 16, 2020, 6 pages.
USPTO Interference 106,123—Redeclaration Jul. 21, 2020, 6 pages.
USPTO Interference 106,123—Rockefeller Clean Claims Jun. 25, 2020, 7 pages.
USPTO Interference 106,123—Rockefeller Motion 2 (Indefiniteness), Oct. 16, 2020, 24 pages.
USPTO Interference 106,123—Rockefeller Notice of Lead and Backup Counsel Jun. 25, 2020, 3 pages.
USPTO Interference 106,123—Rockefeller Notice of Real Party in Interest Jun. 25, 2020, 3 pages.
USPTO Interference 106,123—Rockefeller Notice of Related Proceedings Jun. 25, 2020, 3 pages.
USPTO Interference 106,123—Rockefeller Power of Attorney Jun. 25, 2020, 3 pages.
USPTO Interference 106,123—Rockefeller Request for File Copies Jun. 25, 2020, 10 pages.
USPTO Interference 106,123—Rockefeller Revised List of Proposed Motions Aug. 13, 2020, 4 pages.
Veeranagouda, Y. et al. (Jun. 4, 2014). "Identification of Genes Required for the Survival of B. fragilis Using Massive Parallel Sequencing of a Saturated Transposon Mutant Library," BMC Genomics 15:429, 11 pages.
Vega, N.M. et al. (Oct. 2014). "Collective Antibiotic Resistence: Mechanisms and Implications," Curr. Opin. Microbiol. 21:28-34, 14 pages.
Vercoe, R.B. et al. (Apr. 18, 2013). "Cytotoxic Chromosomal Targeting by CRISPR/Cas Systems Can Reshape Bacterial Genomes and Expel or Remodel Pathogenicity Islands," PLOS Genetics 9(4):e1003454, 13 pages.
Villarino, N.F. et al. (Feb. 23, 2016, e-pub. Feb. 8, 2016). "Composition of the Gut Microbiota Modulates the Severity of Malaria," Proc. Natl. Acad. Sci. USA 113(8):2235-2240.
Vétizou, M. et al. (Nov. 27, 2015, e-pub Nov. 5, 2015). "Anticancer Immunotherapy by CTLA-4 Blockade Relies on the Gut Microbiota," Science 350(6264):1079-1084, 13 pages.
Walters, W.A. et al. (Nov. 17, 2014). "Meta-Analyses of Human Gut Microbes Associated With Obesity and IBD," FEBS Letters 588(22):4223-4233, 34 pages.
Wegmann, U. et al. (2007). "Complete Genome Sequence of the Prototype Lactic Acid Bacterium Lactococcus Lactis Subsp. Cremoris MG1363," Journal of Bacteriology, 189(8):3256-3270.

(56) References Cited

OTHER PUBLICATIONS

Wei, Y. et al. (2015, e-pub. Jan. 14, 2015). "Sequences Spanning the Leader-Repeat Junction Mediate CRISPR Adaptation to Phage in *Streptococcus thermophiles*," Nucleic Acids Research 43(3):1749-1758.
Westra, E.R. et al. (Sep. 1, 2010, e-pub. Aug. 18, 2010). "H-NS-Mediated Repression of CRISPR-Based Immunity in *Escherichia coli* K12 Can Be Relieved by the Transcription Activator LeuO," Molecular Microbiology 77(6):1380-1393.
Westwater, C. et al. (Apr. 2003). "Use of Genetically Engineered Phage to Deliver Antimicrobial Agents to Bacterial an Alternative Therapy for Treatment of Bacterial Infections," Antimicrobial Agents and Chemotherapy 47(4):1301-1307.
Wexler, H.M. (Oct. 2007). "Bacteroidesi the Good, the Bad, and the Nitty-Gritty," Clinical Microbiology Reviews 20(4):593-621.
Written Opinion for PCT Application No. PCT/EP2016/059803, dated Jun. 30, 2016, filed May 3, 2016, 6 pages.
Written Opinion for PCT/EP2018/082053, dated Mar. 14, 2019, filed Nov. 21, 2018, 6 pages.
Xie, Z. et al. (2013, e-pub. Aug. 9, 2013). "Development of a Tunable Wide-Range Gene Induction System Useful for the Study of Streptococcal Toxin-Antitoxin Systems," Applied and Environmental Microbiology 79(20):6375-6384.
Xu, T. et al. (Jul. 2015). "Efficient Genome Editing in Clostridium cellulolyticum via CRISPR-Cas9 Nickase," Applied and Environmental Microbiology 81(13):4423-4431.
Yang, Y. et al. (Jun. 5, 2014, e-pub. Apr. 13, 2014). "Focused Specificity of Intestinal Th17 Cells Towards Commensal Bacterial Antigens," Nature 510(7503):152-156, 29 pages.
Yao, J. et al. (2016, e-pub. May 9, 2016). "A Pathogen-Selective Antibiotic Minimizes Disturbance to the Microbiome," Antimicrob. Agents Chemother., 24 pages.
Yosef, I. et al. (2011). "High-Temperature Protein G Is Essential for Activity of the *Escherichia coli* Clustered Regularly Interspaced Palindromic Repeats (CRISPR)/Cas System," Proc. Natl. Acad. Sci. USA 108(50):20136-20141.
Yosef, I. et al. (Jun. 9, 2015). "Temperate and Lytic Bacteriophages Programmed to Sensitize and Kill Antibiotic-Resistant Bacteria," Proc. Natl. Acad. Sci. USA 112(23):7267-7272.
YourGenome: CRISPR/CAS9, retrieved from https://www.yourgenonne.org/facts/what-is-crispr-cas9, last visited Jan. 6, 2020, 8 pages.
Yu, Z. et al. (Mar. 21, 2014). "Various Applications of TALEN- and CRISPR/Cas9-Mediated Homologous Recombination to Modify the *Drosophila* Genome," Biology Open 3(4):271-280.
Zhang, R. et al. (2009, e-pub. Oct. 30, 2008). "DEG 5.0, A Database of Essential Genes in Both Prokaryotes and Eukaryotes," Nucleic Acids Research 37:D455-D458.
Zhang, T. et al. (Sep. 24, 2016). "The Efficacy and Safety of Anti-PD-1/PD-L1 Antibodies for Treatment of Advanced or Refractory Cancers: A Meta-Analysis," Oncotarget 7(45):73068-73079.
Zhang, X.Z. (2011). "Simple, Fast and High-Efficiency Transformation System for Directed Evolution of Cellulase in Bacillus Subtilis," Microbial Biotechnology 4(1):98-105.
Zitvogel, L. et al. (Jan. 2015), "Cancer and The Gut Microbiota: An Unexpected Link," Sci. Transl. Med. 7(271):271ps1, 10 pages.
Abedon, S.T. et al. (Dec. 2003). "Experimental Examination of Bacteriophage Latent-Period Evolution as a Response to Bacterial Availability," Applied and Environmental Microbiology 69(12):7499-7506.
Anonymous (Apr. 2016). "Checkpoint Inhibition: A Promising Immunotherapeutic Approach for Colorectal Cancer," Oncology, 5(3):1-5, retrieved from http//www.personalizedmedonc.com/publications/prno/april-2016-vol-5-no-3/checkpoint-inhibition-a-prornising-irmunotherapeutic-approach-for-colorectal-cancer-2/, last visited Aug. 27, 2019, 5 pages.
Burns, M.B. et al. (2015). "Virulence Genes Are a Signature of the Microbiome in the Colorectal Tumor Microenvironment," Genome Medicine 7:55, 12 pages.

Catalao, M.J. et al. (Jul. 2013, e-pub Nov. 8, 2012). "Diversity in Bacterial Lysis Systems: Bacteriophages Show the Way," FEMS Microbiology Reviews 37(4):554-571.
Chen, Z. et al. (Aug. 7, 2020). "Akkermansia muciniphila Enhances the Antitumor Effect of Cisplatin in Lewis Lung Cancer Mice," Journal of Immunology Research 2020(2969287):1-13.
Cronan, J.E. (Jan. 2013). "Improved Plasmid-Based System for Fully Regulated off-to-on Gene Expression in *Escherichia coli*: Application to Production of Toxic Proteins," Plasmid 69(1):81-89, 17 pages.
Datsenko, K.A. et al. (Jul. 10, 2012). "Molecular Memory of Prior Infections Activates the CRISPR/Cas Adaptive Bacterial Immunity System," Nature Communication 3:945, 7 pages.
Esvelt, K.M. et al. (Nov. 2013). "Orthogonal Cas9 Proteins for RNA-Guided Gene Regulation and Editing," Nature Methods 10(11):1116-1123.
European Office Action, dated Jun. 29, 2021, for European Patent Application No. 16719873.8, 24 pages.
Ex Parte Re-Exam, mailed Apr. 21, 2021, for U.S. Appl. No. 90/014,705, filed Mar. 26, 2021, for Reexamination U.S. Pat. No. 10,953,090, 15 pages.
Ex Parte Re-Exam, mailed Apr. 30, 2021, for U.S. Appl. No. 90/014,681, filed Feb. 16, 2021, for Reexamination U.S. Pat. No. 10,920,222, 25 pages.
Ex Parte Re-Exam, mailed Feb. 22, 2021, for U.S. Appl. No. 16/700,856, filed Dec. 2, 2019, for Reexamination U.S. Pat. No. 10,920,222, 459 pages.
Ex Parte Re-Exam, mailed Mar. 23, 2021, for U.S. Appl. No. 16/453,604, filed Jun. 26, 2019, for Reexamination U.S. Pat. No. 10,953,090, 235 pages.
Ex Parte Re-Exam, mailed Mar. 24, 2021, for U.S. Appl. No. 90/014,681, filed Mar. 24, 2021, for Reexamination U.S. Pat. No. 10,920,222, 18 pages.
Extended European Search Report, dated Jul. 27, 2020, for European Patent Application No. 20155001.9, 9 pages.
Extended European Search Report, dated Sep. 24, 2020, for European Patent Application No. 20154858.3, 12 pages.
Garneau, J. E. et al. (Nov. 4, 2010). "The CRISPR/Cas Bacterial Immune System Cleaves Phage and Plasmid DNA," Nature 468(7320):67-71, 28 pages.
Gauer, R.L. et al. (Jul. 1, 2013). "Early Recognition and Management of Sepsis in Adults: The First Six Hours," American Family Physician 88(1):44-53.
Guglielmi, G. (2021). "How Gut Bacteria Boost Cancer Immunotherapy," retrieved from the Internet https://microbiomepost.com/how-gut-bacteria-boost-cancer-immunotherapy/, last visited Jul. 25, 2021, 3 pages.
Gupta, R. et al. (2011). "P-27/HP Endolysin as Antibacterial Agent for Antibiotic Resistant *Staphylococcus aureus* of Human Infections," Curr. Microbiol. 63:39-45.
Hansen, J.J. et al. (Mar. 2015). "Therapeutic Manipulation of the Microbiome in IBD: Current Results and Future Approaches," Curr. T. Options Gastroentrol. 13(1 ):1-18.
Hotta, K. et al. (2011, e-pub. Sep. 20, 2011). "Prognostic Significance of CD45RO+ Memory T Cells in Renal Dell Carcinoma," British Journal of Cancer 105:1191-1196.
Huo, Y. et al. (Sep. 2014). "Structures of CRISPR Cas3 Offer Mechanistic Insights Into Cascade-Activated DNA Unwinding and Degradations," Nat. Struct Mol. Biol. 21(9):771-777, 21 pages.
Kaiser, J. (Nov. 2, 2017). "Your Gut Bacteria Could Determine How You Respond to Cutting-Edge Cancer Drugs," Science retrieved from Internet https://www.sciencemag.org/news/2017/11/your-gut-bacteria-could-dtermine-how-you-respond-cutting-edge-cancer-drugs, last visited Jul. 25, 2021, 4 pages.
Keskin, H. et al. (Nov. 20, 2014). "Transcript-RNA-Templated DNA Recombination and Repair," Nature 515:436-439.
Koonin, E.V. et al. (2017, e-pub. Jun. 9, 2017). "Diversity, Classification and Evolution of CRISPR-Cas Systems," Current Opinion in Microbiology 37:67-78.
Kostic, A.D. et al. (Aug. 14, 2013). "Fusobacterium nucleatum Potentiates Intestinal Tumorigenesis and Modulates the Tumor-Immune Microenvironment," Cell Host Microbe. 14(2):207-215, 18 pages.

(56) References Cited

OTHER PUBLICATIONS

Kugelberg, E. et al. (Aug. 2005). "Establishment of a Superficial Skin Infection Model in Mice by Using *Staphylococcus aureus* and *Streptococcus pyogenes*," Antimicrob Agents Chemother 49(8):3435-3441.
La Scola, B. et al. (Sep. 4, 2008). "The Virophage as a Unique Parasite of the Giant Mimivirus," Nature Letters 455:100-104.
Leshem, A. et al. (Sep. 29, 2020). "The Gut Microbiome and Individual-Specific Responses to Diet," mSystems 5(5):e00665-20, 12 pages.
Lu, T.K. et al. (Jul. 3, 2007). "Dispersing Biofilms With Engineered Enzymatic Bacteriophage," PNAS 104(27):11197-11202.
Makarova, K.S. et al. (Jun. 2011). "Evolution and Classification of the CRISPR-Cas Systems," Nat. Rev. Microbiol. 9(6):467-477, 23 pages.
Manica, A. et al. (2011, e-pub. Mar. 8, 2011). "In vivo Activity of CRISPR-Mediated Virus Defence in a Hyperthermophilic Archaeon," Molecular Microbiology 80(2):481-491.
Martel, B. et al. (2014, e-pub. Jul. 24, 2014). "CRISPR-Cas: An Efficient Tool for Genome Engineering of Virulent Bacteriophages," Nucleic Acids Research 42(14):9504-9513.
Martinez, R.M. et al. (Aug. 12, 2016). "Bloodstream Infections," Microbial Spectrum 4(4):DMIH2-0031-2016, 34 pages.
Mitsuhashi, K. et al. (Mar. 13, 2015). "Association of Fusobacterium Species in Pancreatic Cancer Tissues With Molecular Features and Prognosis," Oncotarget 6(9):7209-7220.
Noonan, K.A. et al. (May 20, 2015). "Adoptive Transfer of Activated Marrow-Infiltrating Lymphocytes Induces Measurable Antitumor Immunity in the Bone Marrow in Multiple Myeloma," Science Translational Medicine (228):288ra78, 14 pages.
Park, A. (Oct. 18, 2011). "A Surprising Link Between Bacteria and Colon Cancer," Cancer retrieved from http://healthlande.time.com/2011/10/18/a-surprising-link-between-bacteria-and-colon-cancer/, last visited Aug. 27, 2019, 3 pages.
Pastagia, N. et al. (Feb. 2011). "A Novel Chimeric Lysin Shows Superiority to Mupirocin for Skin Decolonization of Methicillin-Resistant and -Sensitive *Staphylococcus aureus* Strains," Antimicrobial Agents and Chemotherapy 55(2):738-744.
Perez-Chanona, E. et al. (2016, e-pub. Jan. 26, 2016). "The Role of Microbiota in Cancer Therapy," Current Opinion in Immunology 39:75-81.
Pul, Ü. et al. (2010, e-pub. Feb. 17, 2010). "Identification and Characterization of *E. coli* CRISPR-cas Promoters and Their Silencing by H-NS," Molecular Microbiology 75(6):1495-1512.
Ray, K. (Jan. 2020). "Manipulating the Gut Microbiota to Combat Alcoholic Hepatitis," Nature Reviews Gastroenterology & Hepatology 17:3, 1 page.
Rea, K. et al. (2020, e-pub. Nov. 14, 2019). "Gut Microbiota: A Perspective for Psychiatrists," Neuropsychobiology 79:50-62.
Rogers, L. et al. (2016). "*Escherichia coli* and Other Enterobacteriaceae: Occurrence and Detection," Encyclopedia of Food and Health pp. 545-551.
Saito, H. et al. (Jun. 15, 2016, e-pub. Apr. 12, 2016). "Adoptive Transfer of CD8+ T Cells Generated From Inducted Pluripotent Stem Cells Triggers Regressions of Large Tumors Along With Immunological Memory," Cancer Research 76(12):3473-3483.
Sivan, A. et al. (Nov. 6, 2014). "Evidence Implicating the Commensal Microbiota in Shaping Anti-Tumor Immunity in Melanoma," Journal for ImmunoTherapy of Cancer 2(Suppl. 3):O11, 1 page.
Sorek, R. et al. (2013, e-pub. Mar. 11, 2013). "CRISPR-Mediated Adaptive Immune Systems in Bacteria and Archaea," Annual Review of Biochemistry 82:237-266.
Svenningsen, S.L. et al. (Mar. 22, 2005). "On the Role of Cro in λ Prophage Induction," PNAS 102(12):4465-4469.
Tlaskalová-Hogenová, H. et al. (2011, e-pub. Jan. 31, 2011). "The Role of Gut Microbiota (Commensal Bacteria) and the Mucosal Barrier in the Pathogenesis of Inflammatory and Autoimmune Diseases and Cancer Contribution of Germ-Free and Gnotobiotic Animal Models of Human Diseases," Cellular & Molecular Immunology 8:110-120.
Todar, K. (2012). "The Normal Bacterial Flora of Humans," Todays Online Textbook of Bacteriology, 8 pages.
U.S. Appl. No. 62/296,853, filed Feb. 18, 2016, Barrangou, R et al.(Not submitted herewith pursuant to the waiver of 37 C.F.R. 1 98(a)(2)(iii) issued by the Office on Sep. 21, 2004).
USPTO Interference 106,123—Senior Party List of Proposed Motions Jul. 16, 2020, 5 pages.
USPTO Interference 106,123—SNIPR Clean Copy of Claims Jun. 25, 2020, 27 pages.
USPTO Interference 106,123—SNIPR Motion 2 (Lack of Enablement and Written Description), Oct. 16, 2020, 32 pages.
USPTO Interference 106,123—SNIPR Motion 4 (Deny Benefit to Count 1), Oct. 16, 2020, 16 pages.
USPTO Interference 106,123—SNIPR Motion 5 (Substitute Count), Oct. 16, 2020, 41 pages.
USPTO Interference 106,123—SNIPR Motion 6 (Motion to Designate Claims as Not Corresponding to Count 1 or Proposed Count 2), Oct. 16, 2020, 24 pages.
USPTO Interference 106,123—SNIPR Notice of Lead and Backup Counsel Jun. 25, 2020, 4 pages.
USPTO Interference 106,123—SNIPR Notice of Related Proceedings Jun. 25, 2020, 4 pages.
USPTO Interference 106,123—SNIPR Real Party in Interest Jun. 25, 2020, 3 pages.
USPTO Interference 106,123—SNIPR Request for File Copies Jun. 25, 2020, 10 pages.
USPTO Interference 106,123—Standing Order Jun. 11, 2020, 81 pages.
USPTO Interference 106,123—Joint Stipulated Extension of Time, Sep. 4, 2020, 4 pages.
USPTO Interference 106,123—Junior Party Revised List of Motions Aug. 13, 2020, 6 pages.
USPTO Interference 106,123—Memorandum, Jan. 19, 2021, 6 pages.
USPTO Interference 106,123—Notice of Cross Examination-van der Oost, Dec. 1, 2020, 3 pages.
USPTO Interference 106,123—Order Additional Applications 37 C.F.R. § 41.104(a), Sep. 3, 2020, 6 pages.
USPTO Interference 106,123—Order Authorizing Motions and Setting Times 37 C.F.R. 11.104(c) and 121 Aug. 24, 2020, 10 pages.
USPTO Interference 106,123—Order—Additional Applications, Jan. 13, 2021, 6 pages.
USPTO Interference 106,123—Order—Bd.R. 109(b)—Authorizing Copies of Office Records Jul. 21, 2020, 3 pages.
USPTO Interference 106,123—Order-Video Dispositions 37 C.F.R. § 41.104(a), Sep. 25, 2020, 3 pages.
USPTO Interference 106,123—Rockefeller List of Exhibits, Oct. 16, 2020, 4 pages.
USPTO Interference 106,123—Rockefeller List of Exhibits, Nov. 13, 2020, 4 pages.
USPTO Interference 106,123—Rockefeller List of Exhibits, Feb. 19, 2021, 5 pages.
USPTO Interference 106,123—Rockefeller Motion 1 (Lack of Written Description), Oct. 16, 2020, 30 pages.
USPTO Interference 106,123—Rockefeller Motion 3 (To Add A Claim), Nov. 13, 2020, 36 pages.
USPTO Interference 106,123—Rockefeller Notice of Settlement Discussions, Oct. 21, 2020, 3 pages.
USPTO Interference 106,123—Rockefeller Order—Responsive Motion 37 C.F.R. § 41.121(a)(2), Nov. 2, 2020, 2 pages.
USPTO Interference 106,123—Rockefeller Reply 1, Feb. 19, 2021, 51 pages.
USPTO Interference 106,123—Rockefeller Reply 2, Feb. 19, 2021, 37 pages.
USPTO Interference 106,123—Rockefeller Reply 3, Feb. 19, 2021, 48 pages.
USPTO Interference 106,123—Rockefeller Updated Notice of Related Proceedings, Nov. 13, 2020, 3 pages.
USPTO Interference 106,123—SNIPR Exhibit List, Oct. 16, 2020, 7 pages.

(56) References Cited

OTHER PUBLICATIONS

USPTO Interference 106,123—SNIPR Exhibit List, Feb. 19, 2021, 8 pages.
USPTO Interference 106,123—SNIPR Motion 1 (Terminate Interference as Contrary to AIA), Oct. 16, 2020, 20 pages.
USPTO Interference 106,123—SNIPR Request for Oral Argument, Mar. 12, 2021, 4 pages.
USPTO Interference 106,123—Rockefeller Request for Oral Argument, Mar. 12, 2021, 3 pages.
USPTO Interference 106,123—Rockefeller Updated Notice of Related Proceedings, Jul. 15, 2021, 3 pages.
USPTO Interference 106,123—SNIPR Reply 1, Feb. 19, 2021, 19 pages.
USPTO Interference 106,123—SNIPR Reply 2, Feb. 19, 2021, 42 pages.
USPTO Interference 106,123—SNIPR Reply 4, Feb. 19, 2021, 28 pages.
USPTO Interference 106,123—SNIPR Reply 5, Feb. 19, 2021, 44 pages.
USPTO Interference 106,123—SNIPR Reply 6, Feb. 19, 2021, 27 pages.
Wang, I.-N. et al. (2000). "Holins: The Protein Clocks of Bacteriophage Infections," Annu. Rev. Microbiol. 54:799-825.
Wang, J. et al. (2019). "Core Gut Microbiota Analysis of Feces in Healthy Mouse Model," Supplementary Information, 12 pages.
Wang, J. et al. (Apr. 24, 2019). "Core Gut Bacteria Analysis of Healthy Mice," Frontiers in Microbiology 10(887):1-14.
Weir, T.L. et al. (Aug. 6, 2013). "Stool Microbiome and Metabolome Differences Between Colorectal Cancer Patients and Healthy Adults," Plos One 8(8):e70803, 10 pages.
Westra, E.R. et al. (Jun. 8, 2012). "CRISPR Immunity Relies on the Consecutive Binding and Degradation of Negatively Supercoiled Invader DNA by Cascade and Cas3," Molecular Cell 46:595-605.
Westwater, C. et al. (2002). "Development of a P1 Phagemid System for the Delivery of DNA Into Gram-Negative Bacteria," Microbiology 148:943-950.
Young, R. et al. (1995). "Holins: Form and Function in Bacteriophage Lysis," FEMS Microbiology Reviews 17:191-205.

\* cited by examiner

Commensal gut bacteria

'Relative' of target species

Target species

SELECTIVELY ALTERING MICROBIOTA FOR IMMUNE MODULATION

CROSS REFERENCE TO RELATED APPLICATION

This application is a Continuation Application of U.S. patent application Ser. No. 16/453,598, filed Jun. 26, 2019, which is a Continuation Application of U.S. patent application Ser. No. 16/192,752, which was filed on Nov. 15, 2018 (now U.S. Pat. No. 10,363,308), which is a Continuation Application of U.S. patent application Ser. No. 15/820,296, which was filed on Nov. 21, 2017 (now U.S. Pat. No. 10,195,273), which is a Continuation Application under 35 U.S.C. § 120 of International Patent Application No. PCT/EP2017/063593, which was filed on Jun. 4, 2017, which claims priority benefit to United Kingdom Patent Application No. GB1609811.3, which was filed on Jun. 5, 2016, the contents of each of which are incorporated herein by reference in their entirety.

The content of the following submission on ASCII text file is incorporated herein by reference in its entirety: a computer readable form (CRF) of the Sequence Listing (file name: 786212000232SEQLIST.TXT, date recorded: Aug. 26, 2020, size: 8 KB).

FIELD OF THE INVENTION

The invention relates to methods of modulating immune cells in a patient (endogenous cells of the patient and/or administered cells, such as via adoptive cell therapy) by altering microbiota of the patient. The invention also relates to methods of modulating treatments or therapies in a subject organism by altering microbiota of the subject. The invention also relates cell populations, systems, kits and other means for effecting this. In an example, advantageously selective targeting of a particular species in a human gut microbiota using guided nucleic acid modification is carried out to effect the alteration.

BACKGROUND OF THE INVENTION

One approach to immunotherapy involves engineering patients' own (or a donor's) immune cells to express cell-surface antigen receptors (CARs) that recognise and attack tumours. Although this approach, called adoptive cell transfer (ACT), has been restricted to small clinical trials so far, treatments using these engineered immune cells have generated some remarkable responses in patients with advanced cancer.

The Chimeric Antigen Receptor (CAR) consists of an antibody-derived targeting domain fused with T-cell signaling domains that, when expressed by a T-cell, endows the T-cell with antigen specificity determined by the targeting domain of the CAR. CARs can potentially redirect the effector functions of a T-cell towards any protein and non-protein target expressed on the cell surface as long as an antibody-based targeting domain is available. This strategy thereby avoids the requirement of antigen processing and presentation by the target cell and is applicable to non-classical T-cell targets like carbohydrates. This circumvention of HLA-restriction means that the CAR T-cell approach can be used as a generic tool broadening the potential of applicability of adoptive T-cell therapy. See, eg, Methods Mol Biol. 2012; 907:645-66. doi: 10.1007/978-1-61779-974-7_36, "Chimeric antigen receptors for T-cell based therapy", Cheadle E J et al.

The first CAR-T construct was described in a 1989 paper by immunotherapy pioneer Zelig Eshhar in PNAS. The structure of the CAR now comprises a transmembrane polypeptide chain which is a chimaera of different domains from different cellular proteins. For example, the CAR has an extracellular part joined (often by a linker and/or a hinge region) to an intracellular part, with a transmembrane portion of the CAR embedding the receptor in the membrane of an immune cell, normally a T-cell. The extracellular moiety includes an antibody binding site (usually in the form of an scFv, such as derived from a mouse mAb) that recognizes a target antigen, that commonly is a tumour associated antigen (TAA) on the surface of cancer cells. Antigen recognition in this way dispenses with the need to rely on TCRs that require MHC-restricted antigen presentation, and where binding affinities may be relatively low. The intracellular moiety of the CAR typically includes a CD3-zeta (CD3) domain for intracellular signaling when antigen is bound to the extracellular binding site. Later generation CARs also include a further domain that enhances T-cell mediated responses, which often is a 4-1BB (CD137) or CD28 intracellular domain. On encountering the cognate antigen ligand for the CAR binding site, the CAR can activate intracellular signaling and thus activation of the CAR T-cell to enhance tumour cell killing.

Most CAR-Ts expand in vivo so dose titration in a conventional sense is difficult, and in many cases the engineered T-cells appear to be active "forever"—i.e., the observation of on-going B-cell aplasia seen in most of the CD19 CAR-T clinical studies to date. This poses a serious problem for CAR T-cell approaches. Some observed risks are discussed in Discov Med. 2014 November; 18(100):265-71, "Challenges to chimeric antigen receptor (CAR)-T cell therapy for cancer", Magee M S & Snook A E, which explains that the first serious adverse event following CAR-T cell treatment occurred in a patient with colorectal cancer metastatic to the lung and liver (Morgan et al., 2010). This patient was treated with T cells expressing a third-generation CAR targeting epidermal growth factor receptor 2 (ERBB2, HER2). The CAR contained an scFv derived from the 4D5 antibody (trastuzumab) that is FDA approved for the treatment of HER2-positive breast cancers (Zhao et al., 2009). The patient developed respiratory distress within 15 minutes of receiving a single dose of 1010 CAR-T cells, followed by multiple cardiac arrests over the course of 5 days, eventually leading to death. Serum analysis four hours after treatment revealed marked increases in the cytokines IFNγ, GM-CSF, TNFα, IL-6, and IL-10. CAR-T cells were found in the lung and abdominal and mediastinal lymph nodes, but not in tumour metastases. The investigators attributed toxicity to recognition of HER2 in lung epithelium resulting in inflammatory cytokine release producing pulmonary toxicity and cytokine release syndrome (CRS) causing multi-organ failure (Morgan et al., 2010). Trials utilizing second-generation HER2-targeted CARs derived from a different antibody (FRP5) following conservative dose-escalation strategies are currently underway for a variety of HER2+ malignancies by other investigators (clinicaltrials.gov identifiers NCT01109095, NCT00889954, and NCT00902044).

A variation on the CAR T-cell theme are antibody-coupled T-cell receptor (ACTR) therapeutics, which use CD16A (FCγRIIIA) to bind to Fc regions of tumour-specific IgG (see eg, WO2015/058018, US2015139943). The aim is to enable more control of CAR T-cell activity in vivo by titrating IgG administered to patients. The CD16 binding sites of the CAR-T-cells may be free, however, to also bind to endogenous IgG of the patients and this reduces the attractiveness of the approach. The approach also needs to consider the inherently long half-life of IgG in the body (around 20 days for IgG in man), which may limit control of CAR-cell activity. Ongoing studies may assess the risk of this.

It would be desirable to provide an alternative way to modulate (downregulate or upregulate) immune cell-based therapies, like CAR-T-cell approaches and other cell-based approaches. It would also be desirable to provide a way to address diseases and conditions mediated by endogenous immune cells, such as autoimmune, inflammatory and infectious diseases and conditions.

STATEMENTS OF INVENTION

The invention provides guided nucleases, host cell modifying (HM)-CRISPR/Cas systems, gRNAs, HM-arrays, HM-crRNA, HM-Cas, HM-TALENs, HM-meganucleases, HM-zinc fingers and methods as set out in the claims herein.

Medical practice often involves the administration of antibiotics to patients. Such treatments can typically involve administration of broad-spectrum antibiotics, or antibiotics that target many gram-positive bacterial species or many gram-negative species without discrimination. Similarly, use of broad-spectrum antibiotics in farming and agriculture, for example, raise environmental concerns, including entry of such antibiotics into the human and animal food chain which may be deleterious to health and may add to development of microbial resistance. Rather, the invention involves selective targeting of a first microbiota species or strain. As shown in the worked examples herein, selective targeting of a particular bacterial species has been achieved using guided nuclease targeting of the genome of the selected species, whilst at the same time sparing phylogenetically related species and strains. Furthermore, the invention realises the role that microbiota bacteria and archaea play in shaping immune function in humans and animals, as discussed further below.

Thus, the invention relates to methods of modulating immune cells in a patient (endogenous cells of the patient and/or administered cells, such as via adoptive cell therapy) by altering microbiota of the patient. In an example, advantageously selective targeting of a species in a microbiota (eg, gut microbiota) is carried out to effect the alteration. Selective targeting may, for example, avoid targeting of related species or strains, such as species of the same phylum or such as a different strain of the same species.

For example, the invention provides for modulating immune cell-based or other therapy of diseases and conditions in patients and subjects by altering microbiota, as well as systems, kits and other means for effecting this.

For example, the invention provides for treating or reducing diseases and conditions in patients by altering microbiota, wherein the diseases and conditions are those mediated by immune cells (eg, T-cells) or addressed by altering immune cell activities or populations in patients. Embodiments are cancers, autoimmune diseases or conditions, inflammatory diseases or conditions, viral infections (eg, HIV infection of human patients), or diseases or conditions mediated or caused by viral infections.

The invention also relates to methods of modulating treatments or therapies in a subject organism (eg, a plant, yeast, human or animal patient) by altering microbiota of the subject. Examples of therapies are adoptive cell therapy, antibody therapy (eg, immune checkpoint inhibition), radiation therapy, chemotherapy, eg, for treatment or prevention of a disease or condition in a patient.

In a first configuration the invention provides
A method of modulating a therapy of a disease or condition in a patient, the method comprising
a. Carrying out the therapy in the patient; and
b. Causing gut bacterial microbiota dysbiosis in the patient, whereby said dysbiosis modulates the therapy in the patient by modulating immune cells in the patient.

In another aspect, the first configuration the invention provides
A method of modulating a therapy of a disease or condition in a human or animal patient, the method comprising
a. Carrying out the therapy in the patient; and
b. Causing bacterial (eg, gut bacterial) microbiota dysbiosis in the patient, whereby said dysbiosis modulates the therapy in the patient by modulating immune cells in the patient;
wherein the therapy comprises adoptive immune cell therapy (eg, adoptive T-cell therapy, eg, CAR-T cell administration to the patient).

In another aspect, the first configuration the invention provides
A method of modulating a therapy of a disease or condition in a human or animal patient, the method comprising
a. Carrying out the therapy in the patient; and
b. Causing bacterial (eg, gut bacterial) microbiota dysbiosis in the patient, whereby said dysbiosis modulates the therapy in the patient;
wherein the therapy comprises administering an immune checkpoint inhibitor (eg, an anti-PD-L1, anti-PD-1, anti-CTLA4 or anti-TIM3 inhibitor, eg, an antibody) to the patient.

In another aspect, the first configuration the invention provides
A method of modulating a therapy of a disease or condition in a human or animal patient, the method comprising
a. Carrying out the therapy in the patient; and
b. Causing bacterial (eg, gut bacterial) microbiota dysbiosis in the patient, whereby said dysbiosis modulates the therapy in the patient;
wherein the therapy comprises administering an antibody (eg, an anti-PD-L1, anti-PD-1, anti-CTLA4 or anti-TIM3 antibody; or an anti-TNFa superfamily member antibody, eg, an anti-TNFa, TNFR1 or BAFF antibody; or, an anti-IL6R or anti-IL-4Ra antibody; or an anti-PCSK9 antibody) to the patient.

In another aspect, the first configuration the invention provides
A method of modulating a treatment in a subject, the method comprising
a. Carrying out the treatment in the subject; and
b. Causing microbiota dysbiosis in the subject, whereby said dysbiosis modulates the treatment in the subject.

In an example, the subject or patient is a human. In an example, the subject or patient is a non-human animal. In an example, the subject is a plant, and optionally the treatment is a plant growth-promoting treatment, growth-inhibiting treatment, pesticide treatment, nitrogen fixing promotion treatment, herbicidal treatment or fertilizer treatment. In an example, the subject is a yeast, and optionally the treatment is a yeast growth-promoting treatment or growth-inhibiting treatment.

In an example, the modulating augments, upregulates, downregulates, inhibits, enhances or potentiates the treatment or therapy of the subject or patient. In an example, the treatment or therapy is effective in the subject or patient, wherein the treatment or therapy is not effective or has reduced or increased efficacy in the subject, patient or a control subject or patient that has not been subject to the modulation. The control is of the same species as the subject or patient, and optionally the same age and/or sex. In an example, bacterial or archaeal host cells are killed or growth thereof is inhibited in the subject or patient using a method of an invention, wherein the control comprises cells of the same bacterial or archaeal species and the cells are not killed or growth inhibited by a method of the invention.

In an example, steps (a) and (b) are carried out simultaneously. In an example, step (a) is carried out before step (b). In an example, step (b) is carried out before step (a), and optionally step (b) is performed again after (a).

In an embodiment, the invention provides

A method of modulating a treatment in a plant or yeast, the method comprising a. Carrying out the treatment in the plant or yeast; and
b. Causing bacterial microbiota dysbiosis in the plant or yeast, whereby said dysbiosis modulates the treatment in the subject;
wherein the treatment is a growth-promoting treatment, growth-inhibiting treatment, pesticide treatment, nitrogen fixing promotion treatment, herbicidal treatment or fertilizer treatment.

Causing microbial dysbiosis in the subject, patient, plant or yeast is, in an example comprises causing microbial dysbiosis on a surface of the subject, patient, plant or yeast, eg, on a leaf surface (when the subject is a plant) or on skin, lung, ocular or mucosal surface (when the subject or patient is a human or animal).

Instead of or additionally to causing bacterial dysbiosis, the invention comprises in step (b) causing archaeal microbiota dysbiosis in said subject, patient, plant or yeast.

For example, the disease or condition is an autoimmune disease or condition (eg, SLE) and the therapy is a treatment therefor, eg, administration of a tumor necrosis factor ligand superfamily member antagonist, eg, an anti-B-cell activating factor (BAFF) antibody, such as BENLYSTA® (belimumab) or a generic version thereof. For example, the disease or condition is an inflammatory disease or condition (eg, rheumatoid arthritis, IBD, Crohn's disease, colitis or psoriasis) and the therapy is a treatment therefor, eg, administration of sarilumab, dupilumab, a tumor necrosis factor ligand superfamily member antagonist, eg, an anti-TNF alpha antibody or trap, such as HUMIRA® (adalimumab), REMICADE® (infliximab), SIMPONI® (golimumab) or ENBREL® (etanercept) or a generic version thereof. For example, the disease or condition is a viral infection or mediated by a viral infection (eg, HIV infection) and the therapy is a treatment therefor, eg, administration of an anti-retroviral medicament or an anti-HIV vaccine. For example, the disease or condition is a cancer (eg, melanoma, NSCLC, breast cancer or pancreatic cancer) and the therapy is a treatment therefor, eg, administration of a chemotherapeutic agent, eg, a checkpoint inhibitor or agonist antibody such as an anti-CTLA4, PD-1, PD-L1, PD-L2, LAG3, OX40, CD28, BTLA, CD137, CD27, HVEM, KIR, TIM-3, VISTA, ICOS, GITR, TIGIT or SIRPa antibody. In an example, the antibody is a bispecific antibody that specifically binds first and second targets selected from CTLA4, PD-1, PD-L1, PD-L2, LAG3, OX40, CD28, BTLA, CD137, CD27, HVEM, KIR, TIM-3, VISTA, ICOS, GITR, TIGIT and SIRPa, eg, wherein the first target is CTLA4 and the second target is LAG3 or PD-1. Optionally, the antibody is a human gamma-1 antibody and/or may be enhanced for ADCC or CDC. For example, the therapy is a vaccine therapy, eg, a cancer vaccine therapy or a vaccine therapy for treating or preventing an infection or infectious disease, such as malaria, HIV infection, tuberculosis infection, cholera, *Salmonella typhimurium* infection, *C difficile* infection, *Bordetella pertussis* infection or *chlamydia* infection.

An embodiment of the first configuration provides

A method of modulating a cell therapy of a disease or condition in a patient, the method comprising a. Carrying out cell therapy in the patient, comprising administering a population of cells to the patient, wherein administration of said cells is capable of treating the disease or condition in the patient; and
b. Causing gut bacterial microbiota dysbiosis in the patient, whereby said dysbiosis modulates the cell therapy in the patient.

In an example the cell therapy is an adoptive immune cell therapy, such as CAR-T or TILs therapy for the treatment of a cancer.

In a second configuration the invention provides

A method of treating or reducing the risk of a disease or condition in a patient, wherein the disease or condition is mediated by immune cells (eg, T-cells) in the patient, the method comprising causing gut bacterial microbiota dysbiosis in the patient, whereby said dysbiosis modulates immune cells (eg, $T_H17$ cells) in the patient, thereby treating or reducing the risk of said disease or condition in the patient.

For example, the disease or condition is an autoimmune disease or condition (eg, SLE), an inflammatory disease or condition (eg, rheumatoid arthritis, IBD, Crohn's disease, colitis or psoriasis), a viral infection or mediated by a viral infection (eg, HIV infection).

In an example, microbiota dysbiosis is effected by killing one or more target bacterial species in the microbiota or inhibiting growth of a population of said bacteria in the microbiota. In an example, microbiota dysbiosis is effected by killing one or more target archaeal species in the microbiota or inhibiting growth of a population of said archaea in the microbiota.

In a third configuration the invention provides

A method of modulating an adoptive immune cell therapy of a disease or condition in a patient, the method comprising a. Carrying out adoptive immune cell therapy in the patient, comprising administering a population of immune cells to the patient, wherein administration of said immune cells is capable of treating the disease or condition in the patient; and
b. Altering the relative proportion of a sub-population of cells of a first bacterial species or strain, or archaeal species or strain, in a microbiota (eg, gut microbiota) of the patient, thereby producing an altered microbiota that modulates the immune cell therapy in the patient.

In another aspect, the third configuration the invention provides

A method of modulating a therapy of a disease or condition in a human or animal patient, the method comprising a. Carrying out the therapy in the patient; and
b. Altering the relative proportion of a sub-population of cells of a first bacterial species or strain, or archaeal species or strain, in a microbiota (eg, gut microbiota) of the patient, thereby producing an altered microbiota that modulates the therapy in the patient; wherein the therapy comprises administering an immune checkpoint inhibitor (eg, an anti-PD-L1, anti-PD-1, anti-CTLA4 or anti-TIM3 inhibitor, eg, an antibody) to the patient.

In another aspect, the third configuration the invention provides
A method of modulating a therapy of a disease or condition in a human or animal patient, the method comprising
a. Carrying out the therapy in the patient; and
b. Altering the relative proportion of a sub-population of cells of a first bacterial species or strain, or archaeal species or strain, in a microbiota (eg, gut microbiota) of the patient, thereby producing an altered microbiota that modulates the therapy in the patient; wherein the therapy comprises administering an antibody (eg, an anti-PD-L1, anti-PD-1, anti-CTLA4 or anti-TIM3 antibody; or an anti-TNFa superfamily member antibody, eg, an anti-TNFa, TNFR1 or BAFF antibody; or, an anti-IL6R or anti-IL-4Ra antibody; or an anti-PCSK9 antibody) to the patient.

In another aspect, the third configuration the invention provides
A method of modulating a treatment in a subject, the method comprising
a. Carrying out the treatment in the subject; and
b. Altering the relative proportion of a sub-population of cells of a first bacterial species or strain, or archaeal species or strain, in a microbiota of the subject, whereby said dysbiosis modulates the treatment in the subject.

In an example, the subject or patient is a human. In an example, the subject or patient is a non-human animal. In an example, the subject is a plant, and optionally the treatment is a plant growth-promoting treatment, growth-inhibitng treatment, pesticide treatment, nitrogen fixing promotion treatment, herbicidal treatment or fertilizer treatment. In an example, the subject is a yeast, and optionally the treatment is a yeast growth-promoting treatment or growth-inhibiting treatment.

In an example, the modulating augments, upregulates, downregulates, inhibits, enhances or potentiates the treatment or therapy of the subject or patient. In an example, the treatment or therapy is effective in the subject or patient, wherein the treatment or therapy is not effective or has reduced or increased efficacy in the subject, patient or a control subject or patient that has not been subject to the modulation. The control is of the same species as the subject or patient, and optionally the same age and/or sex. In an example, bacterial or archaeal host cells are killed or growth thereof is inhibited in the subject or patient using a method of an invention, wherein the control comprises cells of the same bacterial or archaeal species and the cells are not killed or growth inhibited by a method of the invention.

In an example, steps (a) and (b) are carried out simultaneously. In an example, step (a) is carried out before step (b). In an example, step (b) is carried out before step (a), and optionally step (b) is performed again after (a).

In an embodiment, the invention provides
A method of modulating a treatment in a plant or yeast, the method comprising
a. Carrying out the treatment in the plant or yeast; and
b. Altering the relative proportion of a sub-population of cells of a first bacterial species or strain, or archaeal species or strain, in a microbiota of the plant or yeast, whereby said dysbiosis modulates the treatment in the plant or yeast; wherein the treatment is a growth-promoting treatment, growth-inhibiting treatment, pesticide treatment, nitrogen fixing promotion treatment, herbicidal treatment or fertilizer treatment.

Said altering of the relative proportion of sub-population of cells in the subject, patient, plant or yeast is, in an example comprises causing microbial dysbiosis on a surface of the subject, patient, plant or yeast, eg, on a leaf surface (when the subject is a plant) or on skin, lung, ocular or mucosal surface (when the subject or patient is a human or animal).

The proportion of the first bacteria or archaea sub-population is increased or decreased. In an example, the relative ratio of first and second bacterial species or strains is altered (eg, increased or decreased); or the relative ratio of first and second archaeal species or strains is altered (eg, increased or decreased).

In an example, the adoptive immune cell therapy is CAR-T therapy for the treatment of a cancer. In an example, the adoptive immune cell therapy is a TILs therapy for the treatment of a cancer.

In an example of the first or third configuration, the cells of step (a) are of a first type selected from the group consisting of CD4$^+$ T-cells, CD8$^+$ T-cells, T$_H$1 cells or T$_H$17 cells and step (b) upregulates cells of that type in the patient. This is useful for enhancing the cell based therapy. In another example the cells of step (a) are of a first type selected from the group consisting of CD4$^+$ T-cells, CD8$^+$ T-cells, T$_H$1 cells or T$_H$17 cells and step (b) downregulates cells of that type in the patient. This is useful for dampening down the cell based therapy or a side effect thereof (eg, CRS).

In an embodiment, the disbyosis or step (b) is carried out using selective targeting of a bacterial or archaeal microbiota sub-population using CRISPR/Cas targeting of microbiota (eg, gut microbiota) bacteria and/or archaea. In an example, the method comprises using guided nuclease (eg RNA-guided nuclease) cutting of a respective target sequence in host cells to modify the target sequences, whereby host cells are killed or the host cell population growth is reduced, thereby reducing the proportion of said sub-population in the microbiota. Suitable systems for carrying out the guided nuclease cutting are, for example, engineered CRISPR/Cas systems, TALENs, meganucleases and zinc finger systems.

To this end, the inventors believe that they have demonstrated for the first time inhibition of population growth of a specific bacterial strain in a mixed consortium of bacteria that naturally occur together in gut microbiota with one or more of the following features:—

Population growth inhibition using an engineered CRISPR/Cas system by
  targeting wild-type cells;
  harnessing of wild-type endogenous Cas nuclease activity;
  targeting essential and antibiotic resistance genes;
  wherein the targets are wild-type sequences.

The inventors have demonstrated this in a mixed population of human gut microbiota bacteria with the following features:—
  targeting bacterial growth inhibition in a mixed population of human gut microbiota species;
  wherein the population comprises three different species;
  comprising selective killing of one of those species and sparing cells of the other species;
  targeting cell growth inhibition in the presence of a phylogenetically-close other human gut microbiota species, which is spared such inhibition;
  targeting cell growth inhibition in a mixed population of human gut microbiota bacteria comprising target Firmicutes species and non-Firmicutes species;
  targeting cell growth inhibition of a specific Firmicutes species whilst sparing a different Firmicutes species in a mixed population of human gut microbiota bacteria;

targeting cell growth inhibition of a specific gram positive bacterial strain whilst sparing a different gram positive bacterial species in a mixed population of human gut microbiota bacteria;

targeting a human gut microbiota bacterial species whilst sparing a commensul human gut bacterial species;

targeting a human gut microbiota bacterial species whilst sparing a priobiotic human gut bacterial species;

targeting cell growth inhibition in a mixed population of human gut microbiota bacteria on a surface;

achieving at least a 10-fold growth inhibition of a specific bacterial species alone or when mixed with a plurality of other bacterial species in a consortium of human gut microbiota bacteria; and achieving at least a 10-fold growth inhibition of two different strains of a specific human gut microbiota bacterial species.

The invention provides:

An ex vivo population of immune cells for use in a method of adoptive cell therapy of a patient for treating or preventing a disease or condition in the patient, the method comprising a. Carrying out adoptive immune cell therapy in the patient, comprising administering cells of said population to the patient, wherein administration of said immune cells is capable of treating the disease or condition in the patient; and b. Causing gut bacterial microbiota dysbiosis in the patient, whereby said dysbiosis modulates the immune cell therapy in the patient and said disease or condition is treated or prevented.

The invention provides

An ex vivo population of immune cells for use in a method of adoptive cell therapy of a patient for treating or preventing a disease or condition in the patient, the method comprising a. Carrying out adoptive immune cell therapy in the patient, comprising administering cells of said population to the patient, wherein administration of said immune cells is capable of treating the disease or condition in the patient; and b. Altering the relative proportion of a sub-population of cells of a first bacterial species or strain, or archaeal species or strain, in the gut microbiota of the patient, thereby producing an altered gut microbiota that modulates the immune cell therapy in the patient. The invention also provides CRISPR/Cas systems, arrays, cRNAs and kits for carrying out a method of the invention.

The invention also relates to systems, kits and other means for effecting the method.

Any features on one configuration herein are, in an example, combined with a different configuration of the invention for possible inclusion of such combination in one or more claims herein.

DETAILED DESCRIPTION

Figure 1:
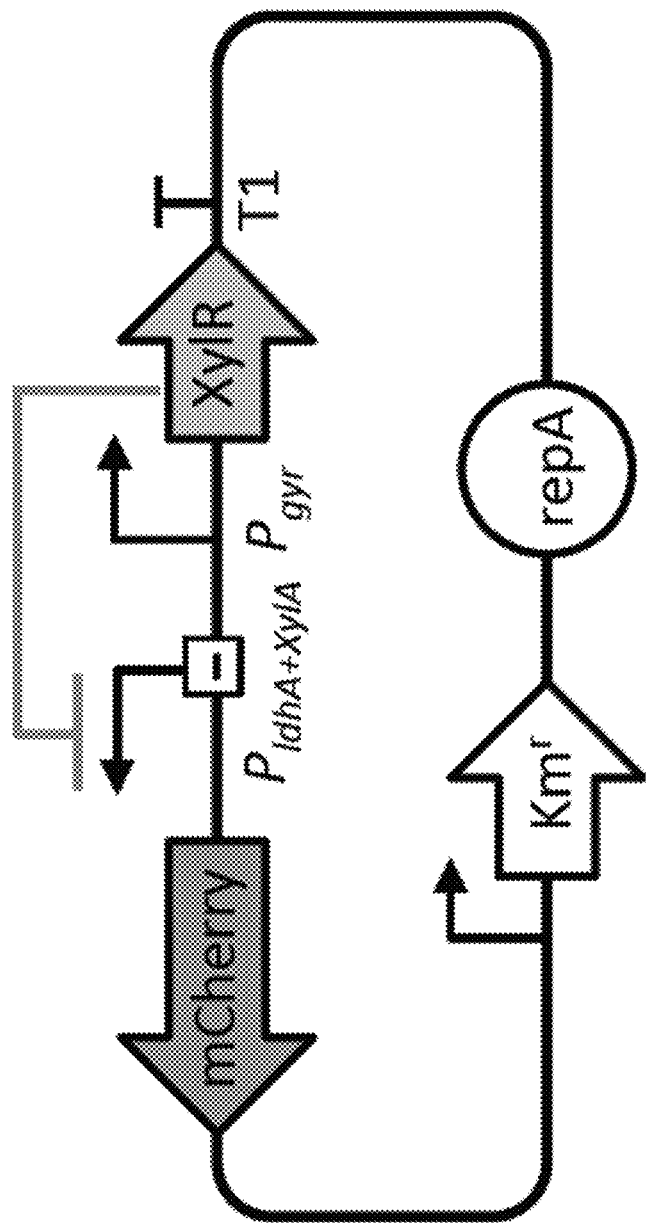
FIG. 1 shows s Xylose inducible system.

In the worked Example below, growth inhibition was addressed in a mixed population of human gut microbiota bacterial species. A >10-fold population growth inhibition in a selectively targeted species (a gram positive Firmicutes population) was achieved, sparing non-targeted commensal bacteria in the consortium. The inventors have realised the useful application of this for altering microbiota, such as gut microbiota, in situ in patients, thereby enabling immune cell modulation in the patient in response to the altered microbiota. The inventors also realised application to modulating treatments in subjects such as plants and yeast that comprise microbiota that can be altered. The inventors furthermore realised the utility for modulating immune cell-based therapies in patients or for treating or preventing immune cell-mediated diseases or conditions in patients, such as autoimmune diseases, inflammatory diseases and viral infections (eg, HIV infection of humans). The inventors realised the utility of causing dysbiosis of gut, skin, vaginal, nasal, ocular, lung, GI tract, rectal, scrotal, ear, skin or hair microbiota for effecting such modulation in a human or animal subject or patient.

As used herein "dysbiosis" refers to a change of the bacterial and/or archaeal balance of the microbiota, eg, gut microbiota. Change is relative to the balance prior to (eg, immediately prior or no more than a day before) carrying out the method. The change can be one or more of (i) an increase in the proportion of a first species (bacterial or archaeal species) or strain in the microbiota (eg, gut microbiota) (eg, B fragalis or thetaiotamicron); (ii) an increase in the relative proportion of first and second species (eg, B fragalis versus C difficile; or S thermophilus v E coli or L lactis), first and second strains of the same species, or first and second phyla which are different from each other (eg, Bacteriodetes versus Firmicutes); (iii) an addition of a species or strain that was not comprised by the microbiota prior to the treatment method; (iv) a decrease in the proportion of a first species (bacterial or archaeal species) or strain in the microbiota (eg, C difficile or S thermophilus); (v) a decrease in the relative proportion of first and second species (eg, B fragalis versus C difficile; or S thermophilus v E coli or L lactis), first and second strains of the same species, or first and second phyla which are different from each other (eg, Bacteriodetes versus Firmicutes); and (vi) a removal of a species or strain that was not comprised by the microbiota prior to the treatment method. Dysbiosis may be effected, for example, using one or more selective antibacterial agents (eg, CRISPR-based or other guided nucleases described herein) of by administering one or more bacterial and/or archaeal transplants to the patient or subject to alter the balance of the microbiota, eg, gut microbiota.

The impact of the immune system on microbiota composition is suggested by several immune deficiencies that alter microbial communities in ways that predispose to disease. For example, Garrett et al. studied mice that lack the transcription factor T-bet (encoded by Tbx21), which governs inflammatory responses in cells of both the innate and the adaptive immune system (Cell. 2007 Oct. 5; 131(1):33-45, "Communicable ulcerative colitis induced by T-bet deficiency in the innate immune system", Garrett W S et al.). When Tbx21-/- mice were crossed onto Rag2-/- mice, which lack adaptive immunity, the Tbx21-/-/Rag2-/- progeny developed ulcerative colitis in a microbiota-dependent manner. Remarkably, this colitis phenotype was transmissible to wild-type mice by adoptive transfer of the Tbx2/-/-/Rag2-/- microbiota. This demonstrated that altered microbiota were sufficient to induce disease. Another example of immune-driven dysbiosis is seen in mice deficient for epithelial cell expression of the inflammasome component NLRP6. These mice develop an altered microbiota with increased abundance of members of the Bacteroidetes phylum associated with increased intestinal inflammatory cell recruitment and susceptibility to chemically-induced colitis.

It has become evident that individual commensal species influence the makeup of lamina propria T lymphocyte subsets that have distinct effector functions. Homeostasis in the gut mucosa is maintained by a system of checks and balances between potentially pro-inflammatory cells, which include $T_H1$ cells that produce interferon-γ, $T_H17$ cells that produce IL-17a, IL-17f, and IL-22, diverse innate lymphoid cells with cytokine effector features resembling $T_H2$ and $T_H17$ cells, and anti-inflammatory Foxp3$^+$ regulatory T cells ($T_{regs}$).

A particular application of the invention is found in the shaping of $T_H17$ cell populations in patients. Such cells have been implicated in autoimmune and inflammatory disorders. These cells were described in: Harrington L E, Hatton R D, Mangan P R, et al., "Interleukin 17-producing CD41 effector T cells develop via a lineage distinct from the T helper type 1 and 2 lineages", Nat Immunol. 2005; 6(11): 1123-1132; and Park H, Li Z, Yang X O, et al., "A distinct lineage of CD4 T cells regulates tissue inflammation by producing interleukin 17", Nat Immunol. 2005; 6(11):1133-1141. In the case of autoimmune disorders, $T_H17$ cell over activation can cause an inappropriate amount of inflammation, like in the case of multiple sclerosis, rheumatoid arthritis, and psoriasis. $T_H17$ cells have also been shown to be necessary for maintenance of mucosal immunity. $T_H17$ cells may contribute to the development of late phase asthmatic response due to increases in gene expression relative to $T_{reg}$ cells.

In HIV, the loss of $T_H17$ cell populations can contribute to chronic infection. The depletion of $T_H17$ cell populations in the intestine disrupts the intestinal barrier, increases levels of movement of bacteria out of the gut through microbial translocation, and contributes to chronic HIV infection and progression to AIDS. Microbial translocation results in bacteria moving from out of the gut lumen, into the lamina propia, to the lymph nodes, and beyond into non-lymphatic tissues. It can cause the constant immune activation seen through the body in the late stages of HIV. Increasing $T_H17$ cell populations in the intestine has been shown to be both an effective treatment as well as possibly preventative. Although all CD4$^+$ T cells gut are severely depleted by HIV, the loss of intestinal $T_H17$ cells in particular has been linked to symptoms of chronic, pathogenic HIV and SIV infection. Microbial translocation is a major factor that contributes to chronic inflammation and immune activation in the context of HIV. In non-pathogenic cases of SIV, microbial translocation is not observed. $T_H17$ cells prevent severe HIV infection by maintaining the intestinal epithelial barrier during HIV infection in the gut. Because of their high levels of CCR5 expression, the coreceptor for HIV, they are preferentially infected and depleted. Thus, it is through $T_H17$ cell depletion that microbial translocation occurs. Additionally, the loss of $T_H17$ cells in the intestine leads to a loss of balance between inflammatory $T_H17$ cells and $T_{reg}$ cells, their anti-inflammatory counterparts. Because of their immunosuppressive properties, they are thought to decrease the anti-viral response to HIV, contributing to pathogenesis. There is more $T_{reg}$ activity compared to $T_H17$ activity, and the immune response to the virus is less aggressive and effective. Revitalizing $T_H17$ cells has been shown to decrease symptoms of chronic infection, including decreased inflammation, and results in improved responses to highly active anti-retroviral treatment (HAART). This is an important finding—microbial translocation generally results in unresponsiveness to HAART. Patients continue to exhibit symptoms and do not show as reduced a viral load as expected. In an SIV-rhesus monkey model, It was found that administering IL-21, a cytokine shown to encourage $T_H17$ differentiation and proliferation, decreases microbial translocation by increasing $T_H17$ cell populations.

In an example of the method, IL-21, IL-15 and/or IL-2 is administered to the patient sequentially or simultaneously with the cell population. This is useful for further modulating immune cell populations in the patient.

Yang et al. observed that the presence of $T_H17$ cells in mice requires colonisation of mice with microbiota. Segmented filamentous bacteria (SFB) were sufficient to induce $T_H17$ cells and promote $T_H17$-dependent autoimmune disease in animal models (Nature, 2014 Jun. 5; 510(7503):152-6. doi: 10.1038/nature13279. Epub 2014 Apr. 13, "Focused specificity of intestinal Th17 cells towards commensal bacterial antigens", Yang Y et al.). SFB appear able to penetrate the mucus layer overlying the intestinal epithelial cells in the terminal ileum, and they interact closely with the epithelial cells, inducing host cell actin polymerization at the site of interaction and, presumably, signaling events that result in a $T_H17$ polarizing environment within the lamina propria.

In an example, the first bacteria are of a species or strain comprising a 16s rDNA sequence that is at least 80, 85, 90, 95, 96, 97, 98 or 99% identical to a 16s rDNA sequence of a segmented filamentous bacterium. In an embodiment, the method increases the proportion of the first bacteria, wherein $T_H17$ cells in the patient are upregulated, eg, wherein the disease is a cancer or a viral infection (eg, HIV). In an embodiment, the method decreases the proportion of the first bacteria, wherein $T_H17$ cells in the patient are downregulated, eg, wherein the disease or condition is an autoimmune or inflammatory disease or condition, or for reducing the risk of CRS in a cancer patient receiving ACT.

In an example, the method treats or prevents an allergic disease or condition, eg, asthma. In an example, the method treats or prevents an IgE-mediated disease or condition, eg, asthma.

In an example, the method reduces autotoxicity in the patient mediated by $T_H2$ cell cytokine release.

López et al. observed that intestinal dysbiosis, characterised by a reduced Firmicutes/Bacteroidetes ratio, has been reported in systemic lupus erythematosus (SLE) patients. In their study, in vitro cultures revealed that microbiota isolated from SLE patient stool samples (SLE-M) promoted lymphocyte activation and $T_H17$ differentiation from naïve CD4+ lymphocytes to a greater extent than healthy control microbiota. Enrichment of SLE-M with $T_{eg}$-inducing bacteria showed that a mixture of two Clostridia strains significantly reduced the $T_H17/T_H1$ balance, whereas *Bifidobacterium bifidum* supplementation prevented CD4+ lymphocyte over-activation. Ex vivo analyses of patient samples showed enlarged $T_H17$ and Foxp3* IL-17+ populations, suggesting a possible $T_{reg}$-$T_H17$ trans-differentiation. Moreover, analyses of faecal microbiota revealed a negative correlation between IL-17+ populations and Firmicutes in healthy controls, whereas in SLE this phylum correlated directly with serum levels of IFNγ, a $T_H1$ cytokine slightly reduced in patients. (Sci Rep. 2016 Apr. 5; 6:24072. doi: 10.1038/srep24072, "Th17 responses and natural IgM antibodies are related to gut microbiota composition in systemic lupus erythematosus patients", Lopez P et al.).

Other bacteria have been shown to enhance the anti-inflammatory branches of the adaptive immune system by directing the differentiation of $T_{regs}$ or by inducing IL-10 expression. For example, colonisation of gnotobiotic mice with a complex cocktail of 46 mouse Clostridial strains, originally isolated from mouse faeces and belonging mainly to cluster IV and XIVa of the *Clostridium* genus, results in the expansion of lamina propria and systemic $T_{regs}$.

*Bacteroides fragilis* polysaccharide-A (PSA) impacts the development of systemic T cell responses. Colonization of germ-free mice with PSA-producing *B. fragilis* results in higher numbers of circulating CD4+ T cells as compared to mice colonized with *B. fragilis* lacking PSA. PSA-producing *B. fragilis* also elicits higher $T_H1$ cell frequencies in the circulation. Together, these findings show that commensal bacteria have a general impact on immunity that reaches well beyond mucosal tissues.

The decrease in *F. prausnitzii* found in IBD patients is of interest because this bacteria is butyrate-producing, and its oral administration reduces the severity of TNBS-induced colitis in mice. In an example, the first species is a butyrate-producing bacterial species (eg, *F. prausnitzii*) and the proportion of the first species in the microbiota is reduced, wherein the method downregulates T-effector and/or T-helper cells in the patient, thereby treating or preventing said disease or condition (eg, an autoimmune or inflammatory disease or condition or CRS).

Archaea have traditionally been divided into five phyla, namely Crenarchaeota, Euryarchaeota, Korarchaeota, Nanoarchaeota and Thaumarchaeota. Based on the increasing wealth of whole genome data (mainly from environmental isolates), the archaeal phylogeny has been revisited recently: the four groups Korarchaeota, Crenarchaeota, Thaumarchaeota and the newly proposed Aigarchaeota have been comprised into one superphylum (the so-called TACK-superphylum) to the exclusion of Euryarchaeota and Nanoarchaeota. The first species in the method of the invention can be any of the archaea mentioned in this paragraph.

T cells mature in the thymus, express TCR (T cell receptor), and can express either CD8 glycoprotein on their surface and are called $CD^{8+}$ T cells (cytotoxic) or CD4 glycoprotein and are then called CD4 cells (helper T cells). $CD^{4+}$ cells differentiate into different subsets: $T_H$ (T helper) 1, $T_H2$, $T_H9$, $T_H17$, $T_H22$, $T_{reg}$ (regulatory T cells) and Tin (follicular helper T cells), which are characterized by different cytokine profiles. These different CD4+ subsets play a critical role in the immune and effector response functions of T cells. All CD4+ $T_H$ subsets are differentiated from naive CD4+ T cells by specific cytokines: $T_H1$ by IL-12 and IFN-y (pro-inflammatory cytokine, with multiple roles such as increase of TLR (Toll-like receptor), induction of cytokine secretion or macrophage activation); $T_H2$ by IL-4; $T_{reg}$ by IL-2 and TGF-beta. Each $T_H$ subset releases specific cytokines that can have either pro- or anti-inflammatory functions, survival or protective functions. For example, $T_H1$ releases IFN-γ and TNF; $T_H2$ releases IL-4 (an important survival factor for B-type lymphocytes), IL-5 and IL-13; $T_H9$ produces IL-9; $T_{reg}$ secretes IL-10 (a cytokine with an immunosuppressive function, maintaining expression of FOXP3 transcription factor needed for suppressive function of $T_{reg}$ on other cells) and TGF-β; $T_H17$ produces IL-17 (a cytokine playing an important role in host defense against bacteria, and fungi).

An embodiment of the invention finds application for modulating CAR-T and other adoptive immune-cell therapies (such as adoptive TILs therapy). Several reports have demonstrated differential roles of different types of cytokines released by $CD4^+$ subsets, an important consideration when assessing CAR-T and other immune cell-based therapies. $T_H 1$ and $T_H 2$ $CD4^+$ T cell subset cytokines were shown to drive different types of cytotoxicity generated by second generation CD28-containing CAR-T. Short-term toxicity was observed with high levels of $T_H1$ cytokines, while high doses of $T_H 2$ type cytokines generated chronic autocytotoxicity in animals that received second generation CD19-specific CAR-T. CAR-T cells engineered to deliver inducible IL-12 modulated tumor stroma to destroy cancer. IL-12 release by engineered CAR-T cells increased anticancer activity by recruiting macrophages. IL-12 released by CAR-T also induced reprogramming of suppressive cells, reversing their inhibitory functions suggesting its evaluation in clinical trials. The persistence of CAR-T therapy was shown to be dependent on the number of $CD4^+$ cells and the number of central memory cells in the infused product. $CD8^+$ clones isolated from central memory T cells but not from $CD8^+$ effector cells persisted long-term in vivo during adoptive T cell transfer in a nonhuman primate model, indicating the importance of specific T cell subset functions for effective adoptive immunotherapy. It has also been shown that the combination of $CD8^+$ subset with $CD4^+$ subset significantly enhanced T cell adoptive transfer. $CD4^+$ cells were shown to support development of $CD8^+$ memory functions, demonstrating the importance of both subsets and combinations in immunotherapy trials. Several preclinical models demonstrated the advantage of different T cell subsets for effective CAR-T therapy: $CD8^+$ $CD45RA^+$ $CCR7^+$ CAR-T cells with closest to the T-memory stem cells phenotype cells produced greater anti-tumor activity of CAR-T cells; both $CD8^+$ and $CD4^+$ subsets expressed synergistic anti-tumor CAR-T activities.

In an example, the administered cell population is a population of CAR-T cells comprising a combination of a $CD8^+$ CAR-T subset with $CD4^+$ CAR-T subset.

In an example of the invention, the cell therapy is an adoptive T-cell therapy and optionally cells selected from the group consisting of $CD4^+$ T-cells, $CD8^+$ T-cells, TH1 cells and TH17 cells are administered to the patient. In an example, cell therapy is enhanced by the method of the invention, eg, immune cell cytotoxicity of cancer cells is enhanced in the patient, or treatment of the disease or condition is enhanced. In an example, cell therapy is reduced by the method of the invention, eg, immune cell cytotoxicity of cancer cells is reduced in the patient, or the risk of CRS is reduced (eg, in a cancer patient). Thus, in an embodiment the method reduces or prevents the risk of cytokine release syndrome (CRS) in the patient. In an embodiment the method reduces or prevents the risk of an unwanted side-effect of the cell therapy (eg, a CAR-T therapy side effect in a human patient, such as CRS).

In an example, the immune cell population comprises CAR-T cells and/or T-cells expressing engineered T-cell receptors (TCRs) and/or tumour infiltrating lymphocytes (TILs, eg, Engineered TILs). WO2013063361, U.S. Pat. No. 9,113,616, US20130109053, US20160081314 and WO2016044745 (whose disclosures are incorporated herein by reference) describe suitable transgenic in vivo platforms for generating CARs and TCRs for use in generating cells for use in the present invention. The immune cell population may comprise engineered autologous or allogeneic immune cells (transplant), eg, T-cells, NK cells and/or TILs, eg, wherein the cells and patient are human. A benefit of autologous cells is that the modulation of the endogenous system is likely to be tuned similarly to modulation of the cell transplanted autologous cells. In an embodiment, the administered cells and patient are of the same species or strain, for example, human or rodent (eg, mouse), for example, HLA or MHC matched donor transplant and recipient patient.

In an example, the T-cells are $CD4^+$ T-cells or $T_H17$ cells. For example, the administered CAR-T cells comprise a chimaeric antigen receptor comprising an ICOS intracellular domain and optionally the cells are $T_H17$ cells. In an embodiment, the administered T-cells are $CD8^+$ $CD45RA^+$ $CCR7^+$ CAR-T cells.

Adoptive transfer experiments in mice indicate that $T_H17$ cells have higher in vivo survival and self-renewal capacity than $T_H1$ polarized cells. In an example, therefore, $T_H17$ cells are modulated in the patient, eg, upregulated, eg, expanded in the patient, or downregulated. These may be endogenous T-cells of the patient and/or cells that have been administered to the patient or progeny thereof. In an embodiment, RORγt-expressing $T_H17$ cells are upregulated, eg, expanded in the patient. In an embodiment expression of one or more $T_H17$-related genes is increased, eg, one or more of Rorc, Il22 and Il26. In an embodiment expression of one or more $T_H1$-related genes is increased, eg, one or more of Ifng, Tnfa and Tbx21 (T-bet). In an embodiment, in this case the disease or condition is a cancer.

In an example, $T_{reg}$ cells are modulated in the patient, eg, upregulated, eg, expanded in the patient, or downregulated. These may be endogenous T-cells of the patient and/or cells that have been administered to the patient or progeny thereof. In an embodiment, in this case the disease or condition is an autoimmune, inflammatory or infectious disease or condition when the $T_{reg}$ cells are upregulated.

In an example, $CD4^+$ cells are modulated in the patient, eg, upregulated, eg, expanded in the patient, or downregulated. These may be endogenous cells of the patient and/or cells that have been administered to the patient or progeny thereof.

In an example, $CD8^+$ cells are modulated in the patient, eg, upregulated, eg, expanded in the patient, or downregulated. These may be endogenous cells of the patient and/or cells that have been administered to the patient or progeny thereof.

In an example, tumour infiltrating lymphocytes (TILs) are modulated in the patient, eg, upregulated, eg, expanded in the patient, or downregulated. These may be endogenous cells of the patient and/or cells that have been administered to the patient or progeny thereof.

In an example, memory cells, such as one or more of central memory T cells ($T_{CM}$), effector memory T cells ($T_{EM}$), stem cell memory cells ($T_{SCM}$) and effector cells ($T_{eff}$), are upregulated in the microbiota or patient, optionally wherein the cells are comprised by the immune cell population administered to the patient and/or are progeny thereof. In an embodiment, the memory cells are $CD45RO^+$ $CD62L^+$ or $CD25^+$ $CD45RA^-$ $CD45RO^+$ $CD127^+$.

Upregulation of a cell population may, for example, be an increase in the population size or proportion of cells of that type (eg, species or strain) in the microbiota or patient or subject and/or an increase in the activity (eg, cytotoxicity, effector function or suppressor function) of cells of that type in the microbiota or patient or subject. Downregulation of a cell population may, for example, be an decrease in the population size or proportion of cells of that type (eg, species or strain) in the microbiota or patient or subject and/or a decrease in the activity (eg, cytotoxicity, effector function or suppressor function) of cells of that type in the microbiota or patient or subject.

In an example, the cell therapy population comprises CAR-T cells (i.e., respectively T-cells engineered to surface-express chimaeric antigen receptors (CARs). Alternatively, the cells are CAR-TIL or CAR-NK cells. A CAR comprises an extracellular receptor domain for binding to a target antigen (eg, a tumour cell antigen), a transmembrane moiety and an intracellular moiety comprising one or more (eg, first and second) signalling domains for signalling in the immune cell (eg, T-cell). Examples of suitable intracellular domains are well known, eg, a combination of a CD3ζ domain and one or more of an ICOS, CD28, OX40 or 4-1BB signalling domain, eg, a combination of an ICOS and CD28; or ICOS and 41-BB; CD28 and 41-BB signalling domain.

Optionally, the cell population is comprised by a transplant that is administered to the patient to treat or prevent a disease (eg, a cancer, autoimmune disease, transplant rejection or GvHD) or the cell or transplant is for such use.

In an example, the patient is a human, eg, is a woman; or a man.

In an example, the patient or human has undergone lymphodepletion before administration of the immune cell (eg, CAR-T cell).

Techniques for producing CARs and CAR T-cells are known and routine in the art, and these can be generally applied to producing cells for use in the invention (eg, see WO2012079000A1; U.S. Pat. Nos. 8,906,682, 8,911,993, 8,916,381, 8,975,071, 9,101,584, 9,102,760, 9,102,761, 9,328,156, 9,464,140, 9,481,728, 9,499,629, 9,518,123, 9,540,445, US20130287748, US20130288368, US20130309258, US20140106449, US20140370017, US20150050729, US20150093822, US20150099299, US20150118202, US20160130355, US20160159907, US20160194404, US20160208012; J Immunother. 2009 September; 32(7): 689-702, doi: 10.1097/CJI.0b013e3181ac6138, "Construction and Pre-clinical Evaluation of an Anti-CD19 Chimeric Antigen Receptor", James N. Kochenderfer et al; also WO2014012001 and US20150290244 for general methods applicable to the present invention). For example, use of electroporation, retroviral vectors or lentiviral vectors—as will be known by the skilled addressee—can be used to introduce nucleotide sequences encoding elements of the CAR into T-cells, NK cells, TILs or other immune cells to produce the CAR-cells. Cells isolated from the patient (autologous cell sample) or from another donor of the same species (allogeneic sample) can be used to provide ancestor cells that are genetically engineered to include the CAR-encoding sequences. Expansion of cells can be used in the process, as known in the art. For example, after engineering CAR-cells, the cell population can be massively expanded using routine techniques to produce a transplant that is administered (eg, transfused) into the patient. The patient can be a human on non-human animal. Nucleotide sequences for one or more of the CAR elements (eg, for one or more of the signalling domains) can be cloned or sequenced using a cell obtained from the patient or from another donor.

For example, the CAR comprises a first intracellular signalling domain, which is a human CD3 domain and the cells administered to the patient are human cells comprising an endogenous nucleotide sequence encoding said human CD3ζ domain. In an example, the CD3 zeta signaling domain comprises SEQ ID NO: 1, i.e., the amino acid sequence of SEQ ID NO: 24 as disclosed in WO2012079000A1, which sequence is explicitly incorporated herein for use in the present invention and possible inclusion in one or more claims herein. In an example, the CD3 zeta signaling domain is encoded by SEQ ID NO: 2, i.e., the nucleic acid sequence of SEQ ID NO: 18 as disclosed in WO2012079000A1, which sequence is explicitly incorporated herein for use in the present invention and possible inclusion in one or more claims herein.

For example, the first signalling domain is a human CD28 domain and the cell population of the invention is a population of human cells each comprising an endogenous nucleotide sequence encoding said human CD28 domain.

For example, the first signalling domain is a human 4-1BB domain and the cell population of the invention is a population of human cells each comprising an endogenous nucleotide sequence encoding said human 4-1BB domain.

For example, the first signalling domain is a human OX40 domain and the cell population of the invention is a population of human cells each comprising an endogenous nucleotide sequence encoding said human OX40 domain.

In an example, the first signalling domain is a CD3 domain, and the first and second intracellular signalling domains do not naturally occur together in a single cell (eg, a human wild-type cell or a cell isolated from the patient), eg, the second domain is a CD28, CD27, OX40 or 4-1BB domain.

In an example, the first intracellular domain is a CD3 domain, CD28 domain or 4-1BB domain.

In an example, the CAR is an engineered single polypeptide comprising (in N- to C-terminal direction) an antigen binding site (eg, an antibody scFv, which may be human); an optional hinge (eg, a human CD8a hinge); a transmembrane domain (eg, a human CD8a or CD28 transmembrane domain); and a human CD3ζ domain. In an example, the CAR is a complex of two or more of said polypeptides. Optionally, the CAR comprises a further intracellular signalling domain (i) between the transmembrane and CD3 domains. Optionally, the CAR comprises a further intracellular signalling domain, wherein the CD3ζ domain is between the further signaling domain and the transmembrane domain. In an example, the further signalling domain is a human CD27 domain, CD28 domain, ICOS domain, OX40 domain, CD40 domain, 4-1BB domain, a FcεRIγ domain, CD64 domain or CD16 domain. In an alternative, instead of a single polypeptide, the CAR comprises an engineered complex of at least 2 polypeptides comprising said domains.

The immune cells may be administered either alone, or as a pharmaceutical composition in combination with diluents and/or with other components such as IL-2 or other cytokines or cell populations.

In an embodiment, the immune cells (eg, CAR cells or cells bearing TCRs) comprise cell surface binding sites (eg, provided by the CAR or TCR) that bind a TAA. Tumour antigens (TAA) are proteins that are produced by tumour cells that elicit an immune response, particularly T-cell mediated immune responses. The selection of the antigen binding specificity will depend on the particular type of cancer to be treated. Tumour antigens are well known in the art and include in the context of an embodiment of the invention, for example, a glioma-associated antigen, carcinoembryonic antigen (CEA), (3-human chorionic gonadotropin, alphafetoprotein (AFP), lectin-reactive AFP, thyroglobulm, RAGE-1, MN-CA IX, human telomerase reverse transcriptase, RU1, RU2 (AS), intestinal carboxyi esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumour antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumour antigen comprises one or more antigenic cancer epitopes associated with a malignant tumour. Malignant tumours express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu ErbB-2. Yet another group of target antigens are onco-foetal antigens such as carcinoembryonic antigen (CEA). In B-cell lymphoma the tumour-specific idiotype immunoglobulin constitutes a truly tumour-specific immunoglobulin antigen that is unique to the individual tumour. B-cell differentiation antigens such as CD I 9, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success. The first antigen or fourth binding moiety can be any of these TAAs or can be an antigenic sequence of any of these TAAs.

Non-limiting examples of TAA antigens in an embodiment of the invention include the following: Differentiation antigens such as MART-1/MelanA (MART-1), g 100 (Pmel 17), tyrosinase, TRP-1, TRP-2 and tumour-specific multi-lineage antigens such as MAGE-1, MAGE-3, BAGE, GAGE-1, GAGE-2, pi 5; overexpressed embryonic antigens such as CEA; overexpressed oncogenes and mutated tumour-suppressor genes such as p53, Ras, HER-2/neu; unique tumour antigens resulting from chromosomal translocations; such as BCR-ABL, E2A-PRL, H4-RET, 1GH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p1 85erbB2, p 1 80erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4(791Tgp72} alpha-fetoprotem, beta-HCG, BCA225, BTAA, CA 125, CA 15-3\CA 27.29\BCAA, CA 195, CA 242, CA-50, CAM43, CD68\ I, CO-029, FGF-5, G250, Ga733VEpCAM, HTgp-175, M344, MA-50, MG7-Ag, MOV 18, NB/70K, NY-CO-1, RCAS 1, SDCCAG16, TA-90\Mac-2 binding proteiiAcyclophilin C-associated protein, TAAL6, TAG72, TLP, and TPS.

In one embodiment, the CAR or TCR comprises a binding site for human CD 19, eg, for a CAR this can be provided by an anti-CD 19 scFV, optionally wherein the anti-CD19 scFV is encoded by SEQ ID NO: 3, i.e., SEQ ID: 14 disclosed in WO2012079000A1. In one embodiment, the anti-CD 19 scFV comprises SEQ ID NO: 4, i.e., the amino acid sequence of SEQ ID NO: 20 disclosed in WO2012079000A1. The sequences in this paragraph appear in WO2012079000A1 and are explicitly incorporated herein for use in the present invention and for possible inclusion in one or more claims herein.

In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD5, CD9, CD16, CD22, CD33, CD37, CD64, CD80, CD86, CD 134, CD137 or CD 154. Alternatively the transmembrane domain may be synthetic, in which case it will comprise predominantly hydrophobic residues such as leucine and valine. Optionally, a triplet of phenylalanine, tryptophan and valine will be found at each end of a synthetic transmembrane domain.

Optionally, a short oligo- or polypeptide linker, preferably between 2 and 10 amino acids in length forms a linkage between the transmembrane domain and the intracellular part of the immune cell transmembrane protein, such as the CAR. A glycine-serine doublet provides a particularly suitable linker (eg, a $(G4S)_n$ linker as disclosed herein).

Optionally, the transmembrane domain is the CD8 transmembrane domain encoded by SEQ ID NO: 5, i.e., the nucleic acid sequence of SEQ ID NO: 16 disclosed in WO2012079000A1. In one embodiment, the CD8 transmembrane domain comprises SEQ ID NO: 6, i.e., the amino acid sequence of SEQ ID NO: 22 disclosed in WO2012079000A1. The sequences in this paragraph appear in WO2012079000A1 and are explicitly incorporated herein for use in the present invention and for possible inclusion in one or more claims herein.

In some instances, the transmembrane domain comprises the CD8 hinge domain encoded by SEQ ID NO: 7, i.e., the nucleic acid sequence of SEQ ID NO: 15 disclosed in WO2012079000A1. In one embodiment, the CD8 hinge domain comprises SEQ ID NO: 8, i.e., the amino acid sequence of SEQ ID NO: 21 disclosed in WO2012079000A1. The sequences in this paragraph appear in WO2012079000A1 and are explicitly incorporated herein for use in the present invention and for possible inclusion in one or more claims herein.

The intracellular part or otherwise the intracellular signaling domain(s) of the transmembrane protein expressed by cells of the cell population administered to the patient is responsible for activation of at least one of the normal effector functions of the immune cell that expresses the transmembrane protein (eg, a T-cell function, such as leading to cytotoxicity (for T-effector cells for example) or suppression (for T-regulatory cells)). The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term "signaling domain" is thus meant to include any truncated portion of the intracellular signaling domain sufficient to transduce the effector function signal. Examples of intracellular signaling domains for use in the transmembrane protein of the administered cells include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling domain) and those that act in an antigen-independent manner to provide a secondary or co-stimulatory signal (secondary cytoplasmic signaling domain). Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

In an example, the first signalling domain is a primary cytoplasmic signaling domain (eg, CD3ζ domain). In an example, the first signalling domain is a secondary cytoplasmic signaling domain (eg, CD28 or 4-1BB domain).

In an example, the first signalling domain comprises one or more ITAMs.

Examples of suitable ITAM containing primary cytoplasmic signaling domains that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the transmembrane protein of the invention comprises a cytoplasmic signaling sequence derived from CD3 zeta.

The intracellular part optionally comprises (eg, as the first signalling domain or a further intracellular domain) a domain of a costimulatory molecule. A costimulatory molecule is a cell surface molecule other than an antigen receptor or their ligands that is required for an efficient response of lymphocytes (eg, T- or NK cells) to an antigen. Examples of such molecules include CD27, CD28, 4-1BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, these and other costimulatory elements are within the scope of the invention for use in the intracellular part of the transmembrane protein.

The intracellular moiety domains may be linked together by one or more linkers, eg, a $(G_4S)_n$ linker as disclosed herein.

In one embodiment, the intracellular moiety comprises the signaling domain of CD3-zeta and the signaling domain of CD28. In another embodiment, the intracellular moiety comprises the signaling domain of CD3-zeta and the signaling domain of 4-1BB. In yet another embodiment, the intracellular moiety comprises the signaling domain of CD3-zeta and the signaling domain of CD28 and 4-1BB.

In one embodiment, the intracellular moiety comprises the signaling domain of 4-1BB and the signaling domain of CD3-zeta, wherein the signaling domain of 4-1BB is encoded by SEQ ID NO: 9, i.e., the nucleic acid sequence set forth in SEQ ID NO: 17 disclosed in WO2012079000A1 and the signaling domain of CD3-zeta is encoded by SEQ ID NO: 2, i.e., the nucleic acid sequence set forth in SEQ ID NO: 18 disclosed in WO2012079000A1. The sequences in this paragraph appear in WO2012079000A1 and are explicitly incorporated herein for use in the present invention and for possible inclusion in one or more claims herein.

In one embodiment, the intracellular moiety comprises the signaling domain of 4-1BB and the signaling domain of CD3-zeta, wherein the signaling domain of 4-1BB comprises SEQ ID NO: 10, i.e., the amino acid sequence of SEQ ID NO: 23 disclosed in WO2012079000A1 and the signaling domain of CD3-zeta comprises SEQ ID NO: 1, i.e., the amino acid sequence of SEQ ID NO: 24 disclosed in WO2012079000A1. The sequences in this paragraph appear in WO2012079000A1 and are explicitly incorporated herein for use in the present invention and for possible inclusion in one or more claims herein.

In one embodiment, the intracellular moiety comprises the signaling domain of 4-1BB and the signaling domain of CD3-zeta, wherein the signaling domain of 4-1BB comprises SEQ ID NO: 10, i.e., the amino acid sequence set forth in SEQ ID NO: 23 as disclosed in WO2012079000A1 and the signaling domain of CD3-zeta comprises SEQ ID NO: 1, i.e., the amino acid sequence set forth in SEQ ID NO: 24 disclosed in WO2012079000A1. The sequences in this paragraph appear in WO2012079000A1 and are explicitly incorporated herein for use in the present invention and for possible inclusion in one or more claims herein.

Sources of T-cells and other immune cells are disclosed in WO2012079000A1, U.S. Pat. Nos. 8,906,682, 8,911,993, 8,916,381, 8,975,071, 9,101,584, 9,102,760, 9,102,761, 9,328,156, 9,464,140, 9,481,728, 9,499,629, 9,518,123, 9,540,445, US20130287748, US20130288368, US20130309258, US20140106449, US20140370017, US20150050729, US20150093822, US20150099299, US20150118202, US20160130355, US20160159907, US20160194404, US20160208012, as well as methods of generating, activating and expanding these. These disclosures are referred to for possible use in working the present invention.

Cancers for Treatment or Prevention by the Method

Cancers that may be treated include tumours that are not vascularized, or not substantially vascularized, as well as vascularized tumours. The cancers may comprise non-solid tumours (such as haematological tumours, for example, leukaemias and lymphomas) or may comprise solid tumours. Types of cancers to be treated with the invention include, but are not limited to, carcinoma, blastoma, and sarcoma, and certain leukaemia or lymphoid malignancies, benign and malignant tumours, and malignancies e.g., sarcomas, carcinomas, and melanomas. Adult tumours/cancers and paediatric tumours/cancers are also included.

Haematologic cancers are cancers of the blood or bone marrow. Examples of haematological (or haematogenous) cancers include leukaemias, including acute leukaemias (such as acute lymphocytic leukaemia, acute myelocytic leukaemia, acute myelogenous leukaemia and myeloblasts, promyeiocytic, myelomonocytic, monocytic and erythroleukaemia), chronic leukaemias (such as chronic myelocytic (granulocytic) leukaemia, chronic myelogenous leukaemia, and chronic lymphocytic leukaemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukaemia and myelodysplasia.

Solid tumours are abnormal masses of tissue that usually do not contain cysts or liquid areas. Solid tumours can be benign or malignant. Different types of solid tumours are named for the type of cells that form them (such as sarcomas, carcinomas, and lymphomas). Examples of solid tumours, such as sarcomas and carcinomas, include fibrosarcoma, myxosarcoma, liposarcoma, chondrosarcoma, osteosarcoma, and other sarcomas, synovioma, mesothelioma, Ewing's tumour, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous eel! carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumour, cervical cancer, testicular tumour, seminoma, bladder carcinoma, melanoma, and CNS tumours (such as a glioma (such as brainstem glioma and mixed gliomas), glioblastoma (also known as glioblastoma multiforme) astrocytoma, CNS lymphoma, germinoma, medu!loblastoma, Schwannoma craniopharyogioma, ependymoma, pineaioma, hemangioblastoma, acoustic neuroma, oligodendroglioma, menangioma, neuroblastoma, retinoblastoma and brain metastases).

In one embodiment, the administered cells express a first antigen binding site (eg, comprised by a CAR) that is designed to treat a particular cancer. For example, it specifically binds to CD19 can be used to treat cancers and disorders, eg, pre-B ALL (paediatric indication), adult ALL, mantle cell lymphoma, diffuse large B-cell lymphoma or for salvage post allogenic bone marrow transplantation. In another embodiment, the first moiety or first binding site specifically binds CD22 to treat diffuse large B-cell lymphoma.

In one embodiment, cancers and disorders include but are not limited to pre-B ALL (paediatric indication), adult ALL, mantle cell lymphoma, diffuse large B-cell lymphoma, salvage post allogenic bone marrow transplantation, and the like can be treated using a combination of bridging agents (or binding moieties or sites comprised by a single agent) that target two or three of: CD19, CD20, CD22, and ROR1 (eg, CD19 and one of the other targets).

In an example, the cells comprises first and second transmembrane proteins (eg, CARs or a CAR and an engineered TCR expressed by a T-cell) that are different, eg that differ in their target antigens (and optionally otherwise are the same). Similarly, the invention may use a mixture of immune cells (eg, a mixture of CAR-cells), eg comprised by the same transplant, wherein the mixture comprises cells comprising transmembrane proteins (eg, CARs or a CAR and an engineered TCR expressed by a T-cell) that are different, eg that differ in their target antigens (and optionally otherwise are the same). This may be useful for reducing resistance to treatment by cancers, for example, or more effectively targeting cell populations such as cancer cells that surface express a plurality of target antigens.

In one embodiment, the antigen binding site specifically binds to mesothelin to treat or prevent mesothelioma, pancreatic cancer or ovarian cancer.

In one embodiment, the antigen binding site specifically binds to CD33/IL3Ra to treat or prevent acute myelogenous leukaemia.

In one embodiment, the antigen binding site specifically binds to c-Met to treat or prevent triple negative breast cancer or non-small cell lung cancer.

In one embodiment, the antigen binding site specifically binds to PSMA to treat or prevent prostate cancer.

In one embodiment, the antigen binding site specifically binds to Glycolipid F77 to treat or prevent prostate cancer.

In one embodiment, the antigen binding site specifically binds to EGFRvIII to treat or prevent gliobastoma.

In one embodiment, the antigen binding site specifically binds to GD-2 to treat or prevent neuroblastoma or melanoma.

In one embodiment, the antigen binding site specifically binds to NY-ESO-1 TCR to treat myeloma, sarcoma or melanoma.

In one embodiment, the antigen binding site specifically binds to MAGE A3 TCR to treat myeloma, sarcoma and melanoma.

Specific antigen binding is binding with a KD of 1 mM or lower (eg, 1 mM or lower, 100 nM or lower, 10 nM or lower, 1 nM or lower, 100 pM or lower, or 10 pM or lower) as determined by Surface Plasmon Resonance (SPR) in vitro at 25 degrees celcius or rtp.

In one example, said treatment using the method reduces progression of the disease or condition or a symptom thereof. In one example, said treatment using the method reduces incidence of the disease or condition or symptom thereof, eg, for at least 1, 2, 3, 4, or 5 years.

In an example, the method is in vivo in a mammal, eg, a human, man or woman, or male child or female child, or a human infant (eg, no more than 1, 2, 3 or 4 years of age). In an example, the patient is an adult human or a paediatric human patient.

The CAR or TCR is engineered, i.e., comprises a non-naturally-occurring combination of moieties and domains. In an example, the cell therapy targets a target cell, wherein the target cell is a cancer cell, eg, a leukemia cell, lymphoma cell, adenocarcinoma cell or cancer stem cell. Optionally, the CAR or TCR of administered immune cells specifically binds to human CD19 (and optionally the target cell is a leukemia or lymphoma cell), EpCAM (and optionally the target cell is a lung cancer cell, gastrointestinal cancer cell, an adenocarcinoma, cancer stem cell), CD20 (and optionally the target cell is a leukemia cell), MCSP (and optionally the target cell is a melanoma cell), CEA, EGFR, EGFRvIII, sialyl Tn, CD133, CD33 (and optionally the target cell is a leukemia cell, eg, AML cell), PMSA, WT1, CD22, L1CAM, ROR-1, MUC-16, CD30, CD47, CD52, gpA33, TAG-72, mucin, CIX, GD2, GD3, GM2, CD123, VEGFR, integrin, cMET, Her1, Her2, Her3, MAGE1, MAGE A3 TCR, NY-ESO-1, IGF1R, EPHA3, CD66e, EphA2,TRAILR1, TRAILR2, RANKL, FAP, Angiopoietin, mesothelin, Glycolipid F77 or tenascin.

Optionally, the CAR comprises the variable domains of an antibody selected from the group consisting of the CD19 binding site of blinatumomab or antibody HD37; EpCAM binding site of Catumaxomab; CD19 binding site of AFM11; CD20 binding site of Lymphomun; Her2 binding site of Ertumaxomab; CEA binding site of AMG211 (MEDI-565, MT111); PSMA binding site of Pasotuxizumab; EpCAM binding site of solitomab; VEGF or angiopoietin 2 binding site of RG7221 or RG7716; Her1 or Her3 binding site of RG7597; Her2 or Her3 binding site of MM111; IGF1R or Her3 binding site of MM141; CD123 binding site of MGD006; gpa33 binding site of MGD007; CEA binding site of TF2; CD30 binding site of AFM13; CD19 binding site of AFM11; and Her1 or cMet binding site of LY3164530.

Optionally, the CAR comprises the variable domains of an antigen binding site of an antibody selected from the group consisting of REOPRO® (Abciximab); RITUXAN® (Rituximab); ZENAPAX® (Daclizumab); SIMULECT® (Basiliximab); SYNAGIS® (Palivizumab); REMICADE® (Infliximab); HERCEPTIN® (Trastuzumab); MYLOTARG® (Gemtuzumab ozogamicin); CAMPATH® (Alemtuzumab); ZEVALIN® (Ibritumomab); HUMIRA® (Adalimumab); XOLAIR® (Omalizumab); BEXXAR® (Tositumomab); RAPTIVA® (Efalizumab); ERBITUX® (Cetuximab); AVASTIN® (Bevacizumab); TYSABRI® (Natalizumab); ACTEMRA® (Tocilizumab); VECTIBIX® (Panitumumab); LUCENTIS® (Ranibizumab); SOLIRIS® (Eculizumab); CIMZIA® (Certolizumab); SIMPONI® (Golimumab); ILARIS® (Canakinumab); STELARA® (Ustekinumab); ARZERRA® (Ofatumumab); PROLIA® (Denosumab); NUMAX® (Motavizumab); AB THRAX® (Raxibacumab); BENLYSTA® (Belimumab); YERVOY® (Ipilimumab); ADCETRIS® (Brentuximab vedotin); PERJETA® (Pertuzumab); KADCYLA® (Ado-trastuzumab); and GAZYVA® (Obinutuzumab).

In an example, the target cell is a blood cell, eg, a stem cell or bone marrow cell of a human or animal. Optionally, the target cell is a B- or T-cell.

In an example, the CAR or TCR comprises an antigen binding site for an autoimmune disease target and the signaling down-regulates cytotoxic activity or proliferation of the immune cells. The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythaematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

Within the overall memory T cell population, several distinct subpopulations have been described and can be recognised by the differential expression of chemokine receptor CCR7 and L-selectin (CD62L). Stem memory $T_{SCM}$ cells, like naive cells, are CD45RO−, CCR7+, CD45RA+, CD62L+ (L-selectin), CD27+, CD28+ and IL-7Ra+, but they also express large amounts of CD95, IL-2Rβ, CXCR3, and LFA-1, and show numerous functional attributes distinctive of memory cells. Central memory $T_{CM}$ cells express L-selectin and the CCR7, they secrete IL-2, but not IFNγ or IL-4. Effector memory $T_{EM}$ cells, however, do not express L-selectin or CCR7 but produce effector cytokines like IFNγ and IL-4. Memory T-cells, such as $T_{SCM}$ may be particularly useful for establishing a sustained population of engineered immune cells in the human.

Any immune cell, target cell or stem cell herein can, in an example, be a $T_{SCM}$, $T_{CM}$ or TEM cell, eg, a human $T_{SCM}$, $T_{CM}$ or TEM cell. In an example, the immune cells of the cell therapy (eg, CAR-T cells) each is a progeny of a cell of a human suffering from an autoimmune disease, an inflammatory disease, a viral infection or a cancer, eg, wherein the human is suffering from lymphoblastic leukaemia, ALL (eg, T-ALL), CLL (eg, B-cell chronic lymphocytic leukaemia) or non-Hodgkin's lymphoma. The human may, for example, be the patient or a relative (eg, sibling or parent) thereof.

In an example, the administered immune cells have been engineered for enhanced signaling, wherein the signaling is selected from CD28, 4-1BB, OX40, ICOS and CD40 signaling.

Optionally, the target cells (eg, tumour cells) are killed. In an example, each target cell is a tumour cell and the method treats or reduces the risk of cancer, or treats or reduces the risk of cancer progression in the human.

Optionally, the human has cancer. In an example, the cancer is a haematological cancer. In an example, the human has a cancer of B-cell origin. In an example, the human has a cancer of T-cell origin. For example the cancer is lung cancer, melanoma, breast cancer, prostate cancer, colon cancer, renal cell carcinoma, ovarian cancer, neuroblastoma, rhabdomyosarcoma, leukaemia and lymphoma. Preferred cancer targets for use with the present invention are cancers of B cell origin, particularly including acute lymphoblastic leukaemia, B-cell chronic lymphocytic leukaemia or B-cell non-Hodgkin's lymphoma. In an example, the cancer is a cancer of T-cell or B-cell origin, eg, lymphoblastic leukaemia, ALL (eg, T-ALL), CLL (eg, B-cell chronic lymphocytic leukaemia) or non-Hodgkin's lymphoma.

Optionally, each administered immune cell (eg, CAR-cells) is a progeny of an immune cell of said human, eg, wherein the human is suffering from lymphoblastic leukaemia, Diffuse Large B-cell Lymphoma (DLBCL), ALL (eg, T-ALL or B-ALL), CLL (eg, B-cell chronic lymphocytic leukaemia) or non-Hodgkin's lymphoma. Optionally, each administered immune cell (eg, CAR-cells) is an autologous cell (eg, T-cell) of said human or is a progeny of such an autologous cell. As used herein, the term "autologous" is meant to refer to any material derived from the same individual to which it is later to be re-introduced into the individual. "Allogeneic" refers to a graft derived from a different animal of the same species.

Optionally, each administered immune cell (eg, CAR-cells) is derived from a blood or tumour sample of the human and activated and expanded in vitro before step (c). "Activation," as used herein, refers to the state of a T-cell or other immune cell that has been sufficiently stimulated to induce detectable cellular proliferation. Activation can also be associated with induced cytokine production, and detectable effector functions. The term "activated T cells" refers to, among other things, T cells that are undergoing cell division.

In an embodiment, the human has an autoimmune disease, wherein the immune cells that are administered (eg, CAR-cells) are anergic, or have reduced proliferation and/or cytotoxic activity when bound to target cells, whereby the cell transplant cells (and/or their progeny) compete with endogenous immune cells of said human that up-regulate said autoimmune disease.

The administration of immune cells in the method may be by cell infusion into the blood of the patient. The immune cells may be expanded to produce an expanded immune cell population that is administered to the patient. The immune cells may be activated produce an activated immune cell population that is administered to the patient. In methods herein, an effective amount of immune cells are administered. An "effective amount" as used herein, means an amount which provides a therapeutic or prophylactic benefit to treat or prevent the disease or condition.

In an embodiment of the method of the invention, the method treats or reduces the risk of cancer in a patient (eg, a human), wherein the patient has undergone lymphodepletion before administration of the immune cells to the patient.

In one embodiment, the human is resistant to at least one chemotherapeutic agent.

In one embodiment, the chronic lymphocytic leukaemia is refractory CD 19+ leukaemia and lymphoma.

The invention also includes a method of generating a persisting population of genetically engineered T cells in a human diagnosed with cancer, wherein the administered cells comprise T-cells and the persisting population comprises progeny thereof. In one embodiment, the method comprises administering to a human a T-cell population (eg, a CAR T-cell population), wherein the persisting population of genetically engineered T-cells persists in the human for at least one month after administration. In one embodiment, the persisting population of genetically engineered T-cells comprises a memory T-cell. In one embodiment, the persisting population of genetically engineered T-cells persists in the human for at least three months after administration. In another embodiment, the persisting population of genetically engineered T-cells persists in the human for at least four months, five months, six months, seven months, eight months, nine months, ten months, eleven months, twelve months, two years, or three years after administration.

In one embodiment, the chronic lymphocytic leukaemia is treated. The invention also provides a method of expanding a population of the engineered T-cells or NK cells in a human diagnosed with cancer, wherein the administered cells comprise T-cells and/or NK cells and the expanded population comprises progeny thereof.

Optionally, autologous lymphocyte infusion is used in the treatment. For example, autologous PBMCs are collected from a patient in need of treatment and CAR-T-cells are engineered to express the CAR transmembrane protein, activated and expanded using the methods known in the art and then infused back into the patient in step (a).

In an example, the administered cells are pluripotent or multipotent.

The stem cell cannot develop into a human. In an embodiment, the stem cell cannot develop into a human embryo or zygote.

In an example, the administered cell population comprises bone marrow stem cells, eg, human autologous or allogeneic cells.

In an example, the administered cell population comprises haematopoietic stem cells, eg, human autologous or allogeneic cells.

Modifying Microbiota

Medical practice often involves the administration of antibiotics to patients. Such treatments can typically involve administration of broad-spectrum antibiotics, or antibiotics that target many gram-positive bacterial species or many gram-negative species without discrimination. Similarly, use of broad-spectrum antibiotics in farming and agriculture, for example, raise environmental concerns, including entry of such antibiotics into the human and animal food chain which may be deleterious to health and may add to development of microbial resistance. Rather, in an example, the invention involves selective targeting of a first microbial (eg, bacterial or archaeal) species or strain of the microbiota. As shown in the worked examples herein, selective targeting of a particular bacterial species has been achieved using guided nuclease targeting of the genome of the selected species, whilst at the same time sparing related species and strains, as well as species that co-reside (in the Examples species that co-reside in human gut microbiota). Thus, in one example, the step of causing dysbiosis or step (b) comprises killing first cells of a microbiota sub-population or inhibiting growth of said sub-population by using guided nuclease (eg, RNA guided nuclease) targeting to the genome of first cells comprised by a microbiota sub-population. Suitable systems for carrying out the guided nuclease targeting are, for example, engineered CRISPR/Cas systems, TALENs, meganucleases and zinc finger systems. By way of example, CRISPR/Cas-mediated guided targeting of a selected human gut microbiota bacterial species in a consortium is demonstrated in the Examples herein. The targeting produces nuclease cutting of target species or strain DNA, for example, which reduces the relative proportion of the species in the mircrobiota or inhibits growth of the sub-population of said species in the microbiota. Selective targeting of species in the method is generally advantageous to enable finer control over change in the relative proportions of bacterial and/or archaeal species in the microbiota. In this way, the invention provides the ability to alter the microbiota with the aim of influencing the upregulation or downregulation of particular immune cell populations, such as $T_H1$, $T_H17$ and/or $T_{reg}$ cells (be these cells endogenous to the patient and/or comprised by adoptive immune cell populations that are administered to the patient), or other outcomes of modulating the microbiota as described herein.

In an example first cell population growth is reduced by at least 5-fold compared to the growth before said dysbiosis or step (b). The method may comprise inhibiting first cell population growth on a gut surface. The method may comprise inhibiting first cell population growth on a plant (eg, leaf and/or stem) surface.

In an alternative, instead of being applied to a subject, the treatment is applied to an environment or soil (eg, the treatment is a fertiliser, plant growth promoting or inhibiting, herbicide or pesticide treatment), wherein the treatment is modulated by the invention.

It will be readily apparent to the skilled addressee how to determine changes in bacteria and archaea in a gut microbiota or other microbiota. For example, this can be done by analyzing a facecal sample of the patient before and after the treatment. One may determine the types of different species or strains in each sample and the proportion of species or strains before and after treatment. Using conventional analysis of 16s ribosomal RNA-encoding DNA (16s rDNA) it is possible to identify species, for example. Additionally or alternatively, standard biochemical test can be used to identify strains or species, eg, also involving one or more of: staining, motility testing, serological testing, phage typing and identification disc testing (eg using a Kirby Baur disc diffusion method). Biochemical testing may involve one or more of: a (a) Catalase test (b) Coagulase test (c) Oxidase test (d) Sugar fermentation test (e) Indole test (f) Citrate test and (g) Urease test. Relative proportions may be determined by growing colonies on agar plates (as in the Examples herein) from each sample and counting colony numbers.

In an example, the dysbiosis or step (b) increases the proportion of *Bacteroides* (eg, *B fragalis* and/or *B thetaiotamicron*) in the microbiota, eg, gut microbiota.

In an example, the dysbiosis or step (b) decreases the proportion of *Bacteroides* (eg, *B fragalis* and/or *B thetaiotamicron*) in the microbiota, eg, gut microbiota. In an example, the dysbiosis or step (b) increases the proportion of Bacteroidetes to Firmicutes in the microbiota, eg, gut microbiota. In an example, the dysbiosis or step (b) decreases the proportion of Bacteroidetes to Firmicutes in the microbiota, eg, gut microbiota.

Accumulating evidence supports the role of commensal strains of *Bifidobacterium* and *Clostridium* spp. belonging to clusters IV and XIVa in the induction of Treg cells. See, eg, Lopez et al. In an example, the dysbiosis or step (b) reduces the proportion of one or more *Clostridium* species or strain (eg, In an example, each species is a cluster IV or XIVa *Clostridium* species) in the gut microbiota. In an example, the dysbiosis or step (b) increases the proportion of one or more *Clostridium* species or strain (eg, In an example, each species is a cluster IV or XIVa *Clostridium* species) in the gut microbiota.

In an example, the dysbiosis or step (b) reduces the proportion of *Bifidobacterium* (eg, *B bifidum*) in the gut microbiota. In an example, the dysbiosis or step (b) increases the proportion of *Bifidobacterium* (eg, *B bifidum*) in the gut microbiota.

For example, by selectively altering the human gut microbiota the invention provides for upregulation of CAR-T or other ACT treatment (eg, wherein the altered microbiota downregulates $T_{reg}$ cells in the patient that has received the CAR-T or ACT administration and/or upregulates $T_H1$ and/or $T_H17$ cells in the patient—such cells being comprised by the CAR-T or ACT transplant for example). Downregulating $T_{reg}$ cells may reduce suppression of T-effectors and/or T-helpers in the patient, thereby enhancing the CAR-T or ACT cytotoxicity or other desirable activity against cancer or other disease-mediating cells. Upregulating $T_H1$ and/or $T_H17$ cells may increase T-effector activity, thereby enhancing the CAR-T or ACT cytotoxicity or other desirable activity against cancer or other disease-mediating cells.

In another example, alteration of the microbiota can be used as a switch to dampen down CAR-T or other ACT treatment (eg, wherein the altered microbiota upregulates $T_{reg}$ cells in the patient that has received the CAR-T or ACT administration and/or downregulates $T_H1$ and/or $T_H17$ cells in the patient—such cells being comprised by the CAR-T or ACT transplant for example). Upregulating $T_{reg}$ cells may increase suppression of T-effectors and/or T-helpers in the patient, thereby reducing the CAR-T or ACT ability to promote cytokine release or other undesirable activity. Downregulating $T_H1$ and/or $T_H17$ cells may decrease T-effector activity, thereby reducing the CAR-T or ACT ability to promote cytokine release or other undesirable activity. This may be useful for limiting the risk of cytokine release syndrome (CRS) in the patient. Subsequent further modification of the gut microbiota of the patient using the method of the invention can be performed to upregulate the CAR-T or ACT treatment when it is desired to use this once more to address the disease or condition at hand (eg, a cancer, such as a haematological cancer). In this instance, memory T-cell CAR-T or ACT populations may be present in the patient from the earlier treatment, and the upregulation using microbiota alteration according to the invention may upregulate memory T-cells to differentiate into effector and/or helper cells to address the disease or condition. Thus, in one example, the cell therapy of the invention comprises administering an immune cell population comprising immune memory cells (eg, memory T-cells, such as central memory T cells ($T_{CM}$) and/or stem cell memory cells ($T_{SCM}$); and/or the administered population comprises cells that spawn such memory cells following the initial microbiota alteration.

Whilst one aspect of the invention recognizes utility for modulating cell-based therapy in a patient, another aspect recognizes utility for modulating (i.e., treating or preventing) cell-mediated diseases and conditions in patients, such as autoimmune and inflammatory diseases and conditions which are mediated, for example by T-cells or other immune cells of the patient. In a further aspect, the invention recognizes utility as a means for modulating (eg, enhancing) another therapy of a disease or condition; for example, for enhancing or effecting therapy with an antibody or anti-viral medicine to treat or prevent the disease or condition. For example, the medicine can be an immune checkpoint antagonist or agonist (eg, for treating or preventing a cancer, such as melanoma or NSCLC). By "effecting therapy" it is contemplated that the patient does not respond or poorly responds to the medicine and the microbiota alteration according to the invention (eg, using selective guided nuclease targeting of a bacterial or archaeal species as described herein) brings about a response (or improved response) to the medicine by the patient. For example, the method of the invention upregulates $T_H17$ cells in a patient suffering from HIV infection. In one aspect, this enhances anti-retroviral therapy or HIV vaccine therapy of the patient. The $T_H17$ cells may be the patient's endogenous cells or cells provided by ACT of the patient. In another example, the method of the invention upregulates $T_H17$ cells in a patient suffering from a cancer (eg, melanoma or lung cancer, such as NSCLC). In one aspect, this enhances immune checkpoint antagonism or agonism therapy of the patient. The $T_H17$ cells may be the patient's endogenous cells or cells provided by ACT of the patient. For example, the therapy is antibody therapy using an antibody selected from ipilimumab (or YERVOY™), tremelimumab, nivolumab (or OPDIVO™), pembrolizumab (or KEYTRUDA™), pidilizumab, BMS-936559, durvalumab and atezolizumab.

The invention relates to guided nuclease systems (eg, engineered CRISPR/Cas systems, TALENs, meganucleases and zinc finger systems), arrays (eg, CRISPR arrays), cRNAs, gRNAs and vectors (eg, phage comprising components of a said system) for use in a method of the invention for targeting the first cells or causing said dysbiosis by inhibiting bacterial or archaeal cell population growth or altering the relative proportion of one or more sub-populations of cells in plant, yeast, environmental, soil, human or animal microbiota, such as for the alteration of the proportion of Bacteroidetes (eg, *Bacteroides*), Firmicutes and/or gram positive or negative bacteria in gut microbiota of a human. The invention, for example, involves modifying (eg, cutting and/or mutating) one or more target genomic or episomal nucleotide sequences of a host bacterial cell, eg, a Bacteroidetes cell or Firmicutes cell, or a host archaeal cell. In an example, the first bacteria are pathogenic gut bacteria.

There have been a number of studies pointing out that the respective levels of the two main intestinal phyla, the Bacteroidetes and the Firmicutes, are linked to obesity, both in humans and in germ-free mice. The authors of the studies deduce that carbohydrate metabolism is the important factor. They observe that the microbiota of obese individuals are more heavily enriched with bacteria of the phylum Firmicutes and less with Bacteroidetes, and they surmise that this bacterial mix may be more efficient at extracting energy from a given diet than the microbiota of lean individuals (which have the opposite proportions). In some studies, they found that the relative abundance of Bacteroidetes increases as obese individuals lose weight and, further, that when the microbiota of obese mice are transferred to germfree mice, these mice gain more fat than a control group that received microbiota from lean mice. See, eg, Turnbaugh, P. J., R. E. Ley, M. A. Mahowald, V. Magrini, E. R. Mardis, and J. I. Gordon. 2006, "An obesity-associated gut microbiome with increased capacity for energy harvest", Nature 444:1027-1131. In a further aspect, the invention recognizes utility as a means for enhancing an anti-obesity therapy of a patient, eg, by increasing the ratio of Bacteroidetes versus Firmicutes in the microbiota.

Optionally the first cells are in the presence of cells of a different strain or species, wherein the different cells are Enterobacteriaceae or bacteria that are probiotic, commensal or symbiotic with humans (eg, in the human gut). In an example, each first cell is a Firmicutes, eg, *Streptococcus*, cell.

In an example, the invention is able to selectively kill or downregulate the target microbes in the microbiota whilst not targeting a second related strain of the same species or a different species that is nevertheless phylogenetically related (as indicated by 16s rDNA). For example, the microbiota comprises cells of a second bacterial species or strain, or archaeal species or strain, wherein the second species or strain has a 16s ribosomal RNA-encoding DNA sequence that is at least 80, 85, 90, 95, 96, 97, 98 or 99% identical to an 16s ribosomal RNA-encoding DNA sequence of the first cell species or strain, wherein the growth of the second cells in the microbiota is not inhibited by said method. In an embodiment, the growth of second strain or species is not inhibited; or the growth of said first cells is inhibited by at least 2×, 3×, 4×, 5×, 6×, 7×, 8×, 9×, 10×, 50×, 100× or 1000× the growth inhibition of the second cells.

In one aspect of the method, causing the dysbiosis or step (b) comprises altering the proportion of a sub-population of first cells (host cells) in the microbiota, eg, gut microbiota, of the patient, thereby producing an altered gut microbiota that modulates the immune cell therapy in the patient, wherein the sub-population comprises host cells of said first species or strain, the method comprising using guided nuclease (eg RNA-guided nuclease) cutting of a respective target sequence in host cells to modify the target sequences, whereby host cells are killed or the host cell population growth is reduced, thereby reducing the proportion of said sub-population in the microbiota. Suitable systems for carrying out the guided nuclease cutting are, for example, engineered CRISPR/Cas systems, TALENs, meganucleases and zinc finger systems. By way of example, CRISPR/Cas-mediated guided cutting of a selected human gut microbiota bacterial species in a consortium is demonstrated in the Examples herein.

In an example, the target sequence modification is carried out by
 a. combining the microbiota with multiple copies of engineered nucleic acid sequences encoding host modifying (HM) crRNAs, and
 b. expressing HM-crRNAs in host cells,
wherein each engineered nucleic acid sequence is operable with a Cas nuclease in a respective host cell to form a HM-CRISPR/Cas system and the engineered sequence comprises
 (i) spacer and repeat sequences encoding a HM-crRNA;
 (ii) the HM-crRNA comprising a sequence that is capable of hybridizing to a host cell target sequence to guide Cas nuclease to the target sequence in the host cell; and optionally the HM-system comprises a tracrRNA sequence or a DNA sequence expressing a tracrRNA sequence;
whereby HM-crRNAs guide Cas modification of host target sequences in host cells, whereby host cells are killed or the host cell population growth is reduced, thereby reducing the proportion of said sub-population in the microbiota.

In an alternative, HM-crRNA and tracrRNA are comprised by a single guide RNA (gRNA). In an example, each engineered nucleic acid sequence is comprised by a respective vector, wherein each vector is optionally a plasmid (eg, a conjugative plasmid capable of transfer into a host cell), phage, phagemid or prophage. The phage is capable of infecting a said host cell.

In an example, endogenous Cas nuclease of host cells is used for modification of target nucleotide sequences. In an embodiment, therefore, each vector lacks a Cas (eg, a Cas9) nuclease-encoding sequence. By harnessing endogenous Cas nuclease, embodiments of the invention use endogenous Cas nuclease activity (i.e., without the need for prior genetic modification of the host cell to activate or enhance the nuclease activity). Thus, in an example, the Cas nuclease is encoded by a wild-type gene of the host cell. In an example, the nuclease is active to achieve the cell killing or growth reduction without inhibition of an endogenous Cas nuclease (or Cas nuclease gene) repressor in the host cell. Thus, the invention can address wild-type bacterial populations without the need for prior manipulation to make bring about effective Cas-mediated cell killing or growth reduction. Thus, the population can be exposed to the cRNA when the population is in its wild-type environment (such as comprised by a plant, yeast, environmental, soil, human or animal microbiome).

In an example, the cRNA or gRNA is for administration to (or administered to) a human or non-human animal patient by mucosal, gut, oral, intranasal, intrarectal or buccal administration.

Optionally said Cas nuclease is provided by an endogenous Type II CRISPR/Cas system of each first cell. Optionally, the tracrRNA sequence or DNA sequence expressing a tracrRNA sequence is endogenous to each host cell. Optionally, each target sequence is comprised by an antibiotic resistance gene, virulence gene or essential gene of the respective host cell, for example the target sequences are identical between the host cells. Optionally, the engineered nucleic acid sequences are comprised by an antibiotic composition, wherein the sequences are in combination with an antibiotic agent (first antibiotic), and in an example the target sequences are comprised by an antibiotic resistance gene wherein the antibiotic is said first antibiotic. The antibiotic composition is administered to the patient or subject to effect said dysbiosis or step (b).

Optionally, each host cell comprises a deoxyribonucleic acid strand with a free end (HM-DNA) encoding a HM-sequence of interest and/or wherein the method comprising into the host cells such a sequence encoding the HM-DNA, wherein the HM-DNA comprises a sequence or sequences that are homologous respectively to a sequence or sequences in or flanking the target sequence for inserting the HM-DNA into the host genome (eg, into a chromosomal or episomal site).

The invention also provides vectors for introducing into first cells (host cells) for carrying out the treatment or prevention method of the invention, wherein each vector is:
An engineered nucleic acid vector for modifying a bacterial or archaeal host cell comprising an endogenous CRISPR/Cas system, the vector comprising nucleic acid sequences for expressing a plurality of different crRNAs (eg, gRNAs) for use in causing the dysbiosis or for use in step (b) of the method; and optionally lacking a nucleic acid sequence encoding a Cas nuclease, wherein a first of said crRNAs is capable of hybridising to a first nucleic acid sequence in said host cell; and a second of said crRNAs is capable of hybridising to a second nucleic acid sequence in said host cell, wherein said second sequence is different from said first sequence; and a. the first sequence is comprised by an antibiotic resistance gene (or RNA thereof) and the second sequence is comprised by an antibiotic resistance gene (or RNA thereof); optionally wherein the genes are different;
b. the first sequence is comprised by an antibiotic resistance gene (or RNA thereof) and the second sequence is comprised by an essential or virulence gene (or RNA thereof);
c. the first sequence is comprised by an essential gene (or RNA thereof) and the second sequence is comprised by an essential or virulence gene (or RNA thereof); or
d. the first sequence is comprised by a virulence gene (or RNA thereof) and the second sequence is comprised by an essential or virulence gene (or RNA thereof).

Each vector may be as described above, eg, a phage capable of infecting a host cell or conjugative plasmid capable of introduction into a host cell. In an example, the vectors are in combination with an antibiotic agent (eg, a beta-lactam antibiotic).

Each first cell (host cell) may be a *Staphylococcus, Streptococcus, Pseudomonas, Salmonella, Listeria, E coli, Desulfovibrio* or *Clostridium* host cell. In an example, each first cell (host cell) is a Firmicutes cell, eg, a *Staphylococcus, Streptococcus, Listeria* or *Clostridium* cell.

In an example, each engineered nucleic acid sequence comprises a sequence R1-S1-R1' for expression and production of the respective crRNA (eg, comprised by a single guide RNA) in the host cell, (i) wherein R1 is a first CRISPR repeat, R1' is a second CRISPR repeat, and R1 or R1' is optional; and (ii) Si is a first CRISPR spacer that comprises or consists of a nucleotide sequence that is 95% or more identical to said target sequence.

In an example, R1 and R1' are at least 95% identical respectively to the first and second repeat sequences of a CRISPR array of the host cell species. In an example, R1 and R1' are at least 95% (eg, 96, 97, 98, 99 or 100%) identical respectively to the first (5'-most) and second (the repeat immediately 3' of the first repeat) repeat sequences of a CRISPR array of said species, eg, of a said host cell of said species. In an example, R1 and R1' are functional with a Type II Cas9 nuclease (eg, a *S thermophilus, S pyogenes* or *S aureus* Cas9) or Type I Cas3 to modify the target in a said host cell.

In one aspect, the method involves the following use, as demonstrated by the worked experimental Example:

The use of wild-type endogenous Cas nuclease activity of the first cell (host cell) population to inhibit growth of the population, wherein each host cell has an endogenous CRISPR/Cas system having wild-type Cas nuclease activity, the use comprising transforming host cells of the population, wherein each transformed host cell is transformed with an engineered nucleotide sequence for providing host modifying (HM) cRNA or guide RNA (gRNA) in the host cell, the HM-cRNA or gRNA comprising a sequence that is capable of hybridising to a host cell target protospacer sequence for guiding endogenous Cas to the target, wherein the cRNA or gRNA is cognate to an endogenous Cas nuclease of the host cell that has said wild-type nuclease activity and following transformation of the host cells growth of the population is inhibited.

By "cognate to" it is intended that the endogenous Cas is operable with crRNA or gRNA sequence to be guided to the target in the host cell. The skilled addressee will understand that such Cas guiding is generally a feature of CRISPR/Cas activity in bacterial and archaeal cells, eg, wild-type CRISPR/Cas activity in bacterial or archaeal cells having endogenous active wild-type CRISPR/Cas systems.

By "wild-type" Cas activity it is intended, as will be clear to the skilled addressee, that the endogenous Cas is not an engineered Cas or the cell has not been engineered to de-repress the endogenous Cas activity. This is in contrast to certain bacteria where Cas nuclease activity is naturally repressed (i.e., there is no wild-type Cas nuclease activity or none that is useful for the present invention, which on the contrary is applicable to addressing wild-type host cells in situ for example where the endogenous Cas activity can be harnessed to effect cell population growth inhibition).

In the worked Examples below, inhibition was addressed in a bacterial population (a gram positive Firmicutes) on a solid surface. A >10-fold inhibition of host cell population growth was achieved. Targeting was directed to an antibiotic resistance gene and an essential gene. The demonstration of the invention's ability to inhibit host cell growth on a surface is important and desirable in embodiments where the invention is for treating or preventing diseases or conditions mediated or caused by microbiota as disclosed herein in a human or animal subject. Such microbiota are typically in contact with tissue of the subject (eg, gut, tissue) and thus we believe that the demonstration of activity to inhibit growth of a microbiota bacterial species (exemplified by *Streptococcus*) on a surface supports this utility. Targetig microbiota on plant surfaces is also a desired application.

In an example, inhibition of first cell (host cell) population growth is at least 2, 3, 4, 5, 6, 7, 8, 9 or 10-fold compared to the growth of cells of the same species or strain not exposed to said engineered nucleotide sequence. For example, growth inhibition is indicated by a lower bacterial colony number of a first sample of host cells (alone or in a mixed bacterial population, eg, a microbiota or faecal sample of the patient after treatment) by at least 2, 3, 4, 5, 6, 7, 8, 9 or 10-fold compared to the colony number of a second sample of the host cells (alone or in a mixed bacterial population, eg, a microbiota or faecal sample of the patient before treatment), wherein the first cells have been transformed by said engineered nucleotide sequence but the second sample has not been exposed to said engineered nucleotide sequence. In an embodiment, the colony count is determined 12, 24, 36 or 48 hours after the first sample has been exposed to the engineered sequence. In an embodiment, the colonies are grown on solid agar in vitro (eg, in a petri dish). It will be understood, therefore, that growth inhibition can be indicated by a reduction (<100% growth compared to no treatment, i.e., control sample growth) in growth of first (host) cells or populations, or can be a complete elimination of such growth. In an example, growth of the host cell population is reduced by at least 10, 20, 30, 40, 50, 60, 70, 80, 90 or 95%, i.e., over a predetermined time period (eg, 24 hours or 48 hours following combination with the cRNA or gRNA, TALEN, meganuclease, zinc finger etc in the host cells), i.e., growth of the host cell population is at least such percent lower than growth of a control host cell population that has not been exposed to said cRNA or gRNA etc but otherwise has been kept in the same conditions for the duration of said predetermined period. In an example, percent reduction of growth is determined by comparing colony number in a sample of each population at the end of said period (eg, at a time of mid-exponential growth phase of the control sample). For example, after exposing the test population to the crRNA or gRNA etc at time zero, a sample of the test and control populations is taken and each sample is plated on an agar plate and incubated under identical conditions for said predetermined period. At the end of the period, the colony number of each sample is counted and the percentage difference (i.e., test colony number divided by control colony number and then times by 100, and then the result is subtracted from 100 to give percentage growth reduction). The fold difference is calculated by dividing the control colony number by the test colony number.

Inhibition of population growth can be indicated, therefore, by a reduction in proliferation of first (host) cell number in the population. This may be due to cell killing by the nuclease and/or by downregulation of host cell proliferation (division and/or cell growth) by the action of the nuclease on the target protospacer sequence. In an embodiment of a treatment or prevention as disclosed herein, host cell burden of the human or animal subject is reduced, whereby the disease or condition is treated (eg, reduced or eliminated) or prevented (i.e., the risk of the subject developing the disease or condition) is reduced or eliminated.

In an example, wild-type host cell endogenous Cas9 or cfp1 activity is used. In an example, wild-type host cell endogenous Cas3 and/or CASCADE activity is used The engineered nucleotide sequence may not be in combination with an exogenous Cas nuclease-encoding sequence. Optionally, said Cas nuclease is a nickase.

In an example, the formation of bacterial colonies of said host cells is inhibited following said dysbiosis or step (b). In an example, proliferation of host cells is inhibited following said dysbiosis or step (b). In an example, host cells are killed following said dysbiosis or step (b).

In another aspect, the method comprises producing ex vivo a medicament for administration to the patient for causing said dysbiosis or step (b) for treating or preventing the disease or condition, wherein the medicament comprises a modified mixed bacterial population (eg, obtained from faeces or gut microbiota of one or more human donors or said patient), wherein the modified population is administered to the patient to cause said dysbiosis or in step (b) to alter the balance of species or strains in the patient's gut microbiota, thereby altering the proportion of the first cells in the gut microbiota. The modified mixed population can be produced ex vivo using guided nuclease modification techniques as described herein. Thus, for example, the method can be used to reduce the proportion of a specific Firmicutes sub-population and spare Bacteroidetes in the mixed population, eg, for producing a medicament for treating or preventing a metabolic or GI condition or disease disclosed herein. In this way, the invention can use a modified bacterial transplant (eg, a modified faecal transplant) medicament for such use or for said treatment or prevention in a human or animal. For example, the method can be used to modify one or more microbiota in vitro to produce a modified collection of bacteria for administration to a human or animal for medical use (eg, treatment or prevention of a metabolic condition (such as obesity or diabetes) or a GI tract condition (eg, any such condition mentioned herein) or a cancer (eg, a GI tract cancer). In an example, the transformation of bacterial cells with phage or plasmid vectors comprising engineered nucleic acid sequences as described herein is carried out in vitro, or the engineered nucleotide sequence is comprised by nucleic acid that is electroporated into host cells. In an example, the nucleic acid are RNA (eg, copies of the gRNA). In another example, the nucleic acid are DNA encoding the crRNA or gRNA for expression thereof in host cells.

Thus, in an example, the invention provides an engineered nucleotide sequence for providing host cell modifying (HM) cRNA or guide RNA (gRNA) in a population of wild-type bacterial host cells comprised by a microbiota of a plant, yeast, environmental, soil, human or animal subject for use in the method of the invention, the cRNA or gRNA comprising a sequence that is capable of hybridising to a host cell target protospacer sequence for guiding Cas to the target, wherein the cRNA or gRNA is cognate to an endogenous host cell Cas nuclease that has wild-type nuclease activity, wherein following transformation of host cells growth of the population is inhibited and the disease or condition is treated or prevented, or the therapy or treatment is modulated.

In an example, the engineered nucleotide sequence comprises a HM-CRISPR array. In an example, the engineered nucleotide sequence encodes a single guide RNA. In an example, the engineered nucleotide sequence is a guide RNA (eg, a single guide RNA) or crRNA. In an example, the engineered sequence is comprised by a bacteriophage that is capable of infecting the host cells, wherein the transformation comprises transduction of the host cells by the bacteriophage. The bacteriophage can be a phage as described herein. In an example, the engineered nucleotide sequence is comprised by a plasmid (eg, a conjugative plasmid) that is capable of transforming host cells. The plasmid can be a plasmid as described herein. In an example, the engineered nucleotide sequence is comprised by a transposon that is capable of transfer into and/or between host cells. The transposon can be a transposon as described herein.

Any method of the invention can comprise transforming host cells with nucleic acid vectors for producing cRNA or gRNA in the cells. For example, the vectors or nucleic acid comprising the engineered nucleotide sequence are administered orally, intravenously, topically, ocularly, intranasally, by inhalation, by rectal administration, or by any other route of administration disclosed herein or otherwise to the patient, wherein the administration transforms the first (host) cells with the vectors or nucleic acid.

In an example, the first are mixed with second bacteria in the microbiota of the patient or subject. Optionally, the second bacteria species is *E coli, L lactis* or *S thermophilus*, as shown in the worked Example below, such are strains that co-exist symbiotically in human and animal gut microbiota. The Example also addresses targeting in a mixed gram positive and gram negative bacterial population. Additionally, the Example addresses a population of Firmicutes (*S thermophilus*) and a population of Enterobacteriaceae (*E coli*), both of which are found in human microbiota. Other examples of Enterobacteriaceae are *Salmonella, Yersinia pestis, Klebsiella, Shigella, Proteus, Enterobacter, Serratia*, and *Citrobacter*.

In an example, the condition or disease is a metabolic or gastrointestinal disease or condition, eg, obesity, IBD, IBS, Crohn's disease or ulcerative colitis. In an example, the condition or disease is a cancer, eg, a solid tumour or a GI cancer (eg, stomach cancer), liver cancer or pancreatic cancer. In an example, the condition is resistance or reduced responsiveness to an antibiotic (eg, any antibiotic disclosed herein).

In an example, each first (host) cell comprises an endogenous RNase III that is operable with the engineered sequence in the production of said HM-crRNA in the cell. In an alternative, one or more of the vectors comprises a nucleotide sequence encoding such a RNase III for expression of the RNase III in the host cell.

In an example, the essential gene (comprising the target) encodes a DNA polymerase of the cell. This is exemplified below.

In an example, the cRNA or gRNA comprises a sequence that is capable of hybridising to a host cell target protospacer sequence that is a adjacent a NGG, NAG, NGA, NGC, NGGNG, NNGRRT or NNAGAAW protospacer adjacent motif (PAM), eg, a AAAGAAA or TAAGAAA PAM (these sequences are written 5' to 3'). In an embodiment, the PAM is immediately adjacent the 3' end of the protospacer sequence. In an example, the Cas is a *S aureus*, *S thermophilus* or *S pyogenes* Cas. In an example, the Cas is Cpf1 and/or the PAM is TTN or CTA.

In an example, each engineered nucleotide sequence or vector comprises a said CRISPR array or a sequence encoding a said crRNA or gRNA and further comprises an antibiotic resistance gene (eg, kanamycin resistance), wherein the HM-crRNA or gRNA does not target the antibiotic resistance gene. In an example, the target sequence is comprised by an antibiotic resistance gene of the host cell, wherein the antibiotic is different from the first antibiotic (eg, kanamycin). In this way, the engineered sequence or vector is able to target the host without targeting itself. By exposing the host cells to the first antibiotic (eg, by orally or intravenously administering it to the patient), one can promote retention of the engineered sequence or vector therein by positive selection pressure since cells containing the first antibiotic resistance gene will have a survival advantage in the presence of the first antibiotic (when host cells that are not transformed by the engineered sequence or vectors are not resistant to the first antibiotic). Thus, an example provides: The method of the invention comprising exposing the first (host) cell population to said antibiotic (eg, kanamycin) and said engineered sequence or vector(s), for promoting maintenance of cRNA or gRNA-encoding sequences in host cells; or the engineered sequence, array or vector of the invention is in combination with said antibiotic.

In an example the sequence encoding the cRNA or gRNA is under a constitutive promoter (eg, a strong promoter) operable in the host cell species, or an inducible promoter.

In an example, the or each first (host) cell is a gram positive cell. In another example, the or each first (host) cell is a gram positive cell.

The invention also provides: An ex vivo mixed population of microbiota bacteria obtainable by the method by isolation of a gut microbiota sample from the patient after carrying out the method, or by isolation of a faecal sample of the patient after carrying out the method. In an example, the mixed population is in a container for medical or nutritional use. For example, the container is a sterilised container, eg, an inhaler, intranasal delivery device or connected to a syringe or IV needle. In an example, the mixed population is useful for administration to a human or animal to populate a microbiome thereof for treating a disease or condition (eg, a disease or condition disclosed herein).

Herein, in an example the *Bacteroides* is a species selected from *caccae, capillosus, cellulosilyticus, coprocola, coprophilus, coprosuis, distasonis, dorei, eggerthii, faecis, finegoldii, fluxus, fragalis, intestinalis, melaninogenicus, nordii, oleiciplenus, oralis, ovatus, pectinophilus, plebeius, stercoris, thetaiotaomicron, uniformis, vulgatus* and *xylanisolvens*. For example, the *Bacteroides* is *thetaiotaomicron*. In an example, the first (host cell) population or second bacteria comprise a plurality of different Bacteroidetes species, or a plurality of *Bacteroides* species (eg, comprising *B thetaiotaomicron* and *B fragalis*), or *Bacteroides* and *Prevotella* species. Herein, in an example, the *Prevotella* is a species selected from *bergensis, bivia, buccae, buccalis, copri, melaninogenica, oris, ruminicola, tannerae, timonensis* and *veroralis*. In an alternative, the first (host) cells or second bacteria are Firmicutes cells, for example comprising or consisting of one or more Firmicutes selected from *Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira,Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter* and *Weisella*. In an example, the first (host) cells or second bacteria comprise or consist of *Clostridium* (eg, *dificile*) cells (and optionally the other sub-population consists of *Bacteroides* (eg, *thetaiotaomicron*) cells). In an example, the first (host) cells or second bacteria comprise or consist of *Enterococcus* cells (and optionally the other cells consist of *Bacteroides* (eg, *thetaiotaomicron*) cells). In an example, the first (host) cells or second bacteria comprise or consist of *Ruminococcus* cells (and optionally the other cells consist of *Bacteroides* (eg, *thetaiotaomicron*) cells). In an example, the first (host) cells or second bacteria comprise or consist of *Streptococcus* cells (and optionally the other cells consist of *Bacteroides* (eg, *thetaiotaomicron*) cells). In an example, the first (host) cells or second bacteria comprise or consist of *Faecalibacterium* cells (and optionally the other cells consist of *Bacteroides* (eg, *thetaiotaomicron*) cells). For example, the *Faecalibacterium* is a *Faecalibacterium prausnitzii* (eg, A2-165, L2-6, M21/2 or SL3/3).

In an example, the first (host) cells or second bacteria consist of *Streptococcus* cells (optionally *S thermophilus* and/or *pyogenes* cells) and the second bacteria consists of *Bacteroides* (eg, *thetaiotaomicron*) and/or Enterobacteriaceae (eg, *E coli*) cells.

In an example, the first (host) cells are infectious disease pathogens of humans, an animal (eg, non-human animal) or a plant.

In an example, the first (host) cells are selected from a species of *Escherichia* (eg, *E coli* O157:H7 or O104: H4), *Shigella* (eg, *dysenteriae*), *Salmonella* (eg, *typhi* or *enterica*, eg, serotype *typhimurium*, eg, DT 104), *Erwinia, Yersinia* (eg, *pestis*), *Bacillus, Vibrio, Legionella* (eg, *pneumophilia*), *Pseudomonas* (eg, *aeruginosa*), *Neisseria* (eg, *gonnorrhoea* or *meningitidis*), *Bordetella* (eg, *pertussus*), *Helicobacter* (eg, *pylori*), *Listeria* (eg, *monocytogenes*), *Agrobacterium, Staphylococcus* (eg, *aureus*, eg, MRSA), *Streptococcus* (eg, *pyogenes* or *thermophilus*), *Enterococcus, Clostridium* (eg, *dificile* or *botulinum*), *Corynebacterium* (eg, *amycolatum*), *Mycobacterium* (eg, *tuberculosis*), *Treponema, Borrelia* (eg, *burgdorferi*), *Francisella, Brucella, Campylobacter* (eg, *jejuni*), *Klebsiella* (eg, *pneumoniae*), *Frankia, Bartonella, Rickettsia, Shewanella, Serratia, Enterobacter, Proteus, Providencia, Brochothrix, Bifidobacterium, Brevibacterium, Propionibacterium, Lactococcus, Lactobacillus, Pediococcus, Leuconostoc, Vibrio* (eg, *cholera*, eg, O139, or *vulnificus*), *Haemophilus* (eg, *influenzae*), *Brucella* (eg, *abortus*), *Franciscella, Xanthomonas, Erlichia* (eg, *chaffeensis*), *Chlamydia* (eg, *pneumoniae*), *Parachlamydia, Enterococcus* (eg, *faecalis* or *faceim*, eg, linezolid-resistant), *Oenococcus* and *Acinetoebacter* (eg, *baumannii*, eg, multiple drug resistant).

In an example, the first (host) cells are *Staphylococcus aureus* cells, eg, resistant to an antibiotic selected from methicillin, vancomycin-resistant and teicoplanin.

In an example, the first (host) cells are *Pseudomonas aeruginosa* cells, eg, resistant to an antibiotic selected from cephalosporins (eg, ceftazidime), carbapenems (eg, imipenem or meropenem), fluoroquinolones, aminoglycosides (eg, gentamicin or tobramycin) and colistin.

In an example, the first (host) cells are *Klebsiella* (eg, *pneumoniae*) cells, eg, resistant to carbapenem.

In an example, the first (host) cells are Streptoccocus (eg, *pneumoniae* or *pyogenes*) cells, eg, resistant to an antibiotic selected from erythromycin, clindamycin, beta-lactam, macrolide, amoxicillin, azithromycin and penicillin.

In an example, the first (host) cells are *Salmonella* (eg, serotype *Typhi*) cells, eg, resistant to an antibiotic selected from ceftriaxone, azithromycin and ciprofloxacin.

In an example, the first (host) cells are *Shigella* cells, eg, resistant to an antibiotic selected from ciprofloxacin and azithromycin.

In an example, the first (host) cells are *Mycobacterium tuberculosis* cells, eg, resistant to an antibiotic selected from Resistance to isoniazid (INH), rifampicin (RMP), fluoroquinolone, amikacin, kanamycin and capreomycin.

In an example, the first (host) cells are *Enterococcus* cells, eg, resistant to vancomycin.

The method of claim 13, wherein all of the host cells are Enterobacteriaceae cells, eg, resistant to an antibiotic selected from a cephalosporin and carbapenem.

In an example, the first (host) cells are *E. coli* cells, eg, resistant to an antibiotic selected from trimethoprim, itrofurantoin, cefalexin and amoxicillin.

In an example, the first (host) cells are *Clostridium* (eg, dificile) cells, eg, resistant to an antibiotic selected from fluoroquinolone antibiotic and carbapenem.

In an example, the first (host) cells are *Neisseria* gonnorrhoea cells, eg, resistant to an antibiotic selected from cefixime (eg, an oral cephalosporin), ceftriaxone (an injectable cephalosporin), azithromycin and tetracycline.

In an example, the first (host) cells are *Acinetoebacter baumannii* cells, eg, resistant to an antibiotic selected from beta-lactam, meropenem and a carbapenem.

In an example, the first (host) cells are *Campylobacter* cells, eg, resistant to an antibiotic selected from ciprofloxacin and azithromycin.

In an example, the second species or strain is a human gut commensal species or strain and/or a human gut probiotic species or strain.

In an example, the second species or strain is a Bacteroidetes (eg, *Bacteroides*) and optionally the host cells are gram positive bacterial cells.

In an example, the first cells are Firmicutes cells.

In an example, causing said dysbiosis or step (b) is carried out by targeting the sub-population of first cells by administering thereto an anti-bacterial or anti-archaeal agent simultaneously or sequentially with said immune cell population, whereby first cells are killed or the sub-population growth is reduced, thereby reducing the proportion of said sub-population in the gut microbiota of the patient.

In an example, the method reduces first (host) cell population growth by at least 5, 10, 20, 50 or 100-fold compared to the growth of a control population of host cells that have not received said guided nuclease (eg, Cas) modification.

In an example, the method inhibits host cell population growth on a gut surface.

In an example, for each host cell the system comprises components according to (i) to (iv):—
(i) at least one nucleic acid sequence encoding a Cas nuclease;
(ii) an engineered HM-CRISPR array comprising a spacer sequence and repeats encoding a HM-crRNA, the HM-crRNA comprising a sequence that hybridises to a host cell target sequence to guide said Cas to the target in the host cell to modify the target sequence;
(iii) an optional tracrRNA sequence or a DNA sequence expressing a tracrRNA sequence;
(iv) wherein said components of the system are split between the host cell and at least one nucleic acid vector that transforms the host cell, whereby the HM-crRNA guides Cas to the target to modify the host target sequence in the host cell; and
wherein the target sequence is modified by the Cas whereby the host cell is killed or host cell growth is reduced;
the method comprising introducing the vectors of (iv) into host cells and expressing said HM-crRNA in the host cells, allowing HM-cRNA to hybridise to host cell target sequences to guide Cas to the targets in the host cells to modify target sequences, whereby host cells are killed or host cell growth is reduced, thereby altering the proportion of said sub-population in the microbiota.

In an example, component (i) is endogenous to each host cell.

In an example, each vector is a virus or phage.

In an example, each target sequence is adjacent a NNA-GAAW or NGGNG protospacer adjacent motif (PAM).

In an example, alternatively HM-crRNA and tracrRNA are comprised by a single guide RNA (gRNA), the method comprising introducing said gRNA into host cells or expressing the gRNA in host cells.

In an example, the microbiota comprises a second bacterial or archaeal species, wherein each of the first and second species is a respective species of the same phylum (eg, both Firmicutes species) and the growth of the second bacteria is not inhibited by the HM-system; or wherein the microbiota comprises a second bacterial or archaeal strain, wherein each of the first and second bacteria or archaea is a respective strain of the same species and the growth of the second bacteria or archaea is not inhibited by the HM-system.

In an example, the microbiota comprises a second bacterial species, wherein each of the first and second species is a respective gram-positive species and the growth of the second bacteria is not inhibited by the HM-system.

In an example, each target sequence is comprised by an antibiotic resistance gene, virulence gene or essential gene of the host cell.

In an example, each first cell is a *Staphylococcus, Streptococcus, Pseudomonas, Salmonella, Listeria, E coli, Desulfovibrio, Vibrio* or *Clostridium* cell.

In an example, the dysbiosis or step (b) comprises stimulating Paneth cells of the patient by gut *Bacteroides* (eg, *B thetaiotamicron*), wherein the altered microbiota produced by the dysbiosis or step (b) comprises an increased proportion of *Bacteroides* first bacteria compared with the microbiota before the dysbiosis or step (b), whereby Paneth cells are stimulated and the cell therapy is modulated.

*Bacteroides* can affect expression of Paneth cell proteins. Small intestinal crypts house stem cells that serve to constantly replenish epithelial cells that die and are lost from the villi. Paneth cells (immune systems cells similar to neutrophils), located adjacent to these stem cells, protect them against microbes by secreting a number of antimicrobial molecules (defensins) into the lumen of the crypt, and it is possible that their protective effect even extends to the mature cells that have migrated onto the villi. In animal models, *B. thetaiotaomicron* can stimulate production of an antibiotic Paneth cell protein (Ang4) that can kill certain pathogenic organisms (eg, *Listeria monocytogenes*). *Listeria monocytogenes* is a strong $T_H1$ cell inducer, and thus by stimulating Paneth cells in certain aspects of the invention, this may be useful to skew immunity from TH1 to other cell types, such as $T_H17$. This may be useful for increasing or enhancing the immune cell therapy of the invention. For example, this may be useful when the invention comprises administering $T_H17$-based cell therapy (eg, CAR-$T_H17$ cells) to the patient.

In an example, the dysbiosis or step (b) comprises developing an immune response in the patient to gut *Bacteroides* (eg, *B thetaiotamicron*), wherein the altered microbiota produced by the dysbiosis or step (b) comprises an increased proportion of *Bacteroides* first bacteria compared with the microbiota before the dysbiosis or step (b), whereby the cell therapy is modulated.

In an example, the dysbiosis or step (b) comprises altering the relative proportion of a or said sub-population of first cells in the gut microbiota of the patient, thereby producing an altered gut microbiota that modulates the immune cell therapy in the patient, wherein the dysbiosis or step (b) comprises killing first cells of said sub-population or inhibiting growth of said sub-population by using guided nuclease targeting to the genome of first cells comprised by the sub-population.

The invention also provides: A bacterial or archaeal transplant for administration to a patient for therapy of a disease or condition in the patient using the method of the invention. Optionally the transplant comprises cells of said first species. Optionally the transplant comprises cells of said second species (and eg, does not comprise cells of the first species).

The invention also provides: A bacterial or archaeal transplant for administration to a subject (eg, a plant or yeast) or to soil or an environment for modulating a treatment thereof using the method of the invention. Optionally the transplant comprises cells of said first species. Optionally the transplant comprises cells of said second species (and eg, does not comprise cells of the first species).

In an example, the yeast comprises a population of yeast cells of the same species or strain. For example, the yeast is comprised by the microbiota, eg, the yeast comprises a sub-population of cells of the microbiota, such as where the targeted cells are bacteria or archaea cells also comprised by the microbiota. In an embodiment, the method kills the targeted cells (eg, bacteria) or reduces growth of the target cell sub-population comprised by the microbiota, wherein release of (or the concentration of) one or more chemicals or messengers by target cells in the microbiota is reduced. For example, the one or more chemicals or messengers that mediate quorum sensing in microbes (eg, bacteria) of the microbiota is reduced. This may be useful to shape the growth of target cell and/or other microbial cell populations in the microbiota. In an example, the one or more chemicals or messengers inhibit growth of the yeast or kill the yeast, and thus reduction of the release or concentration of the chemical or messenger(s) in the microbiota is advantageous to promote growth and/or maintenance of the yeast in the microbiota. In an embodiment of these examples, the treatment is nutrition of the yeast or treatment of the yeast with a growth promoter (eg, wherein the yeast are for foodstuff or beverage production, or for production of a biotechnology or medical product, such as an antibody eg, the yeast is *Saccharaomyces*). In another example, the chemical or messenger(s) promote yeast growth, wherein the yeast treatment is treatment with a yeast killing agent (eg, an fungicide). This is useful to promote efficacy of the killing treatment when the yeast are undesirable (eg, an undesirable mould). In an example when the subject is a plant, the one or more chemicals or messengers inhibit growth of the plant or kill the plant, and thus reduction of the release or concentration of the chemical or messenger(s) in the microbiota is advantageous to promote growth of the plant and/or inhibit killing of the plant. In an embodiment of these examples, the treatment is nutrition of the plant or treatment of the yeast with afertilizer or nitrogen fixing agent. In an embodiment, the treatment is a pesticide treatment of the plant, such as a treatment that is inhibited or reduced in the presence of the targeted microbiota cells.

In an example, the plant is a crop plant (eg, wheat, barley, cereal or livestock fodder plant), fruit plant (eg, apple, orange, citrus, lime, lemon, raspberry, strawberry, berry or banana plant), legume plant, sugar cane plant, spice plant, garden plant, vegetable plant, grass, tree or flowering plant. For example, the plant is a tuber plant, eg, a potato or a sweet potato (eg, and the first, host or targeted bacteria are *Pectobacterium atrosepticum* cells, optionally wherein the treatment is storage (eg, cold storage), washing, a pesticide or herbicide treatment, fertilising or hydrating of the plant of a crop thereof (eg, a potato crop)). For example, the plant is a tobacco plant (eg, and the first, host or targeted bacteria are *Ralstonia solanacearum* cells, optionally wherein the treatment is storage (eg, cold storage), washing, a pesticide or herbicide treatment, fertilising or hydrating of the plant of a crop thereof (eg, a tobacco leaf crop)).

In an example, the subject is a protozoa. In an example, the subject or patient is a fish. In an example, the subject or patient is a bird. In an example, the subject or patient is a reptile. In an example, the subject or patient is an arachnid. In an example, the subject is a yeast cell (eg, a *Saccharomyces* cell). In an example, the subject or patient is an animal (eg, a rodent, mouse or rat). In an example, the subject or patient is a human (eg, an embryo or not an embryo). In an example, the subject or patient is a companion pet animal (eg, a bird, horse, dog, cat or rabbit). In an example, the subject or patient is an insect (an insect at any stage of its lifecycle, eg, egg, larva or pupa, eg, a fly or crawling insect or a beetle). In an example, the subject or patient is a cephalopod or nematode. In an example, the subject or patient is a plant or animal pest. In an example, the treatment of an animal or human may be a nutritional treatment, therapy of a disease or condition, prophylais of a disease or condition, ocular treatment, pesticide treatment, dental treatment, topical treatment or digestion treatment. In an example, the method enhances immunity of the subject or patient against a pathogen (eg a pathogenic parasite, protozoan, virus or bacteria). In an example, the treatment or therapy is a combination treatment or therapy practised on the human or animal, wherein the human or animal is administered a first medicament in combination with a second medicament or radiation. The first and/or second medicament may be an antibody therapy or immune cell transplant (eg, CAR-T or TILs transplant) therapy (and the immune modulation aspect of the invention may be advantageous for modulating such therapies). In an example, each medicament or treatment is selected from Table 2.

In an example, the disease or condition is diabetes (eg, Type I or II diabetes, insulin-resistant diabetes (eg, insulin-resistant Type II diabetes), onset of insulin resistance in a diabetic or pre-diabetic patient or reduction in insulin responsiveness in a diabetic or pre-diabetic patient. Optionally additionally in this example, the first or host cells that are targeted are *Prevotella copri* or *Bacteroides* vulgatus cells. In an embodiment, both *Prevotella copri* and *Bacteroides* vulgatus cells are targeted (i.e., killed and/or population growth reduced, or reduced in the microbiota following administration of a transplant as described herein) in the patient, wherein said disease or condition is treated or prevented.

The invention also provides: the HM-CRISPR/Cas system, HM-array or HM-crRNA for administration to a patient for therapy of a disease or condition in the patient using the method of the invention.

The invention also provides: A kit comprising an ex vivo population of immune cells for adoptive cell therapy of a patient, wherein the kit further comprises the transplant, system, array or crRNA, optionally wherein the immune cells are selected from CAR-T cells, T-cells expressing engineered T-cell receptors (TCRs), tumour infiltrating lymphocytes (TILs) and NK cells.

Mobile Genetic Elements (MGEs)

In an example, each vector is a nucleic acid vector comprising or consisting of a mobile genetic element (MGE), wherein the MGE comprises an origin of transfer (oriT) and a CRISPR array for modifying a target sequence of the genome of a host cell or the genome of a virus (eg, prophage) in a host cell. Examples of MGEs are ICEs, transposons, plasmids and bacteriophage. An origin of transfer (oriT) is a short sequence (eg, up to 500 bp) that is necessary for transfer of the DNA that contains it from a bacterial host to recipient during conjugation. The oriT is cis-acting—it is found on the same DNA that is being transferred, and it is transferred along with the DNA. A typical origin of transfer comprises three functionally defined domains: a nicking domain, a transfer domain, and a termination domain.

Reference is made to the ICEberg database (http://db-mml.sjtu.edu.cn/ICEberg/), which provides examples of suitable ICEs for the invention and sources for suitable oriT. In an example, the ICE is a member of an ICE family comprising an ICE selected from the group 1 to 28, or the oriT is an oriT of a member of such a family: 1=SXT/R391; 2=Tn916; 3=Tn4371; 4=CTnDOT/ERL; 5=ICEclc; 6=ICEBs1; 7=ICEHin1056; 8=PAPI-1; 9=ICEM1Sym (R7A); 10=ICESt1; 11=SPI-7; 12=ICE6013; 13=ICEKp1; 14=TnGBS1; 15=Tn5253; 16=ICESa2603; 17=ICEYe1; 18=10270-RD.2; 19=Tn1207.3; 20=Tn1806; 21=ICEA5632; 22=ICEF-I/II; 23=ICEAPG2; 24=ICEM; 25=10270-RD.1; 26=Tn5801; 27=PPI-1; 28=ICEF-III. Family descriptions are found in the ICEberg database. For example, the Tn916 family was defined by Roberts et al (2009) (Trends Microbiol. 2009 June; 17(6):251-8. doi: 10.1016/j.tim.2009.03.002. Epub 2009 May 20; "A modular master on the move: the Tn916 family of mobile genetic elements", Roberts A, Mullany P). Elements belonging to the Tn916 family are defined by the following criteria: they must have the general organization shown in Roberts et al, and they must have a core region (conjugation and regulation module) that is similar in sequence and structure to the original Tn916 at the DNA level. Exceptions are some conjugative transposons, such as Tn1549 which have been previously classified in this family and those with a high degree of protein similarity as described in corresponding references. Optionally, the ICE is a transposon, eg, a conjugative transposon. In an example, the MGE is a mobilisable transposon that is mobilisable in the presence of a functional helper element, optionally wherein the transposon is in combination with a said helper element.

Optionally the vector is a plasmid, optionally wherein the MGE is a transposon comprised by the plasmid. For example, the transposon is a conjugative transposon. In an example the transposon is a mobilisable transposon (eg, mobilisable using one or more factors encoded by the plasmid, eg, by genes outside the transposon sequence of the plasmid). Optionally, the transposon is a Type I transposon. Optionally, the transposon is a Type II transposon. Optionally, the vector oriT is an oriT of a Bacteroidetes (eg, *Bacteroidales* or *Bacteroides*) or *Prevotella* transposon. This useful when the first (host) cells are Bacteroidetes (eg, *Bacteroidales* or *Bacteroides*) or *Prevotella* respectively. Optionally, the vector oriT is a CTnDot, CTnERL SXT/R391, Tn916 or Tn4371 family transposon oriT.

Optionally, the method comprises exposing the patient's microbiota to a vector or MGE (eg, one described above) that comprises a toxin-antioxin module that comprises an antitoxin gene that is operable in the second bacteria, but is not operable or has reduced operation in first (host) cells. Thus, first cells are killed and second bacteria are spared, thereby altering the proportion of first cells in the patient's microbiota.

Split CRISPR/Cas System

In one aspect, endogenous Cas of the first (host) cells is harnessed and operates with the engineered sequences comprised by vectors (eg, phage) that are introduced into host cells. This aspect is advantageous to free up space in vectors, for example viruses or phage that have restricted capacity for carrying exogenous sequence. By freeing up space, one is able to include more targeting spacers or arrays, which is useful for evading host resistance. It is advantageous, for example to harness the endogenous Cas endonuclease rather than encode it in the vector—especially for bulky Cas sequences such as sp or saCas9. Additionally, there is not chance of inferior compatibility as may be seen with some exogenous Cas from non-host sources. The ability to reduce virus, eg, phage genome size, may also be beneficial for promoting host cell uptake (infection and/or maintenance of the virus in host cells). In some examples, an advantage is that invasion of the host by the vector (eg, phage) may upregulate host CRISPR/Cas activity, including increased expression of host Cas nucleases—in an attempt of the host to combat invading nucleic acid. This, however, is also useful to provide endogenous Cas for use with the invention when these use cRNA or gRNA that are recognised by the host Cas. In the case where the invention involves cRNA or gRNA targeting a host CRISPR array, this then promotes inactivation of the host CRISPR array itself, akin to a "suicidal" host cell which then uses its own Cas nuclease to inactivate its own CRISPR systems.

Thus, the vectors may lack a Cas nuclease (eg, aCas9)-encoding sequence.

Optionally, the endogenous first (host) cell system is a CRISPR/Cas9 system. Optionally, the nuclease is a Type I Cas nuclease. Optionally, the nuclease is a Type II Cas nuclease (eg, a Cas9). Optionally, the nuclease is a Type III Cas nuclease.

To save even more space, optionally a tracrRNA sequence is not provided by the vectors, but is a tracrRNA sequence of an endogenous host cell CRISPR/Cas system, wherein the tracrRNA is capable of hybridising with the HM-crRNA in the cell for subsequent processing into mature crRNA for guiding Cas to the target in the host cell.

Generally Applicable Features

The following features apply to any configuration (eg, in any of its aspects, embodiments, concepts, paragraphs or examples) of the invention:—

In an example, the target sequence is a chromosomal sequence, an endogenous host cell sequence, a wild-type host cell sequence, a non-viral chromosomal host cell sequence and/or a non-phage sequence (i.e., one more or all of these), eg, the sequence is a wild-type host chromosomal cell sequence such as antibiotic resistance gene or essential gene sequence comprised by a host cell chromosome. In an example, the sequence is a host cell plasmid sequence, eg, an antibiotic resistance gene sequence.

In an example, at least two target sequences are modified by Cas, for example an antibiotic resistance gene and an essential gene. Multiple targeting in this way may be useful to reduce evolution of escape mutant host cells.

In an example, the Cas is a wild-type endogenous host cell Cas nuclease. In an example, each host cell has constitutive Cas nuclease activity, eg, constitutive wild-type Cas nuclease activity. In an example, the host cell is a bacterial cell; in another example the host cell is an archael cell. Use of an endogenous Cas is advantageous as this enables space to be freed in vectors cRNA or gRNA. For example, Type II Cas9 nucleotide sequence is large and the use of endogenous Cas of the host cell instead is advantageous in that instance when a Type II CRISPR/Cas system is used for host cell modification in the present invention. The most commonly employed Cas9, measuring in at 4.2 kilobases (kb), comes from *S pyogenes*. While it is an efficient nuclease, the molecule's length pushes the limit of how much genetic material a vector can accommodate, creating a barrier to using CRISPR in the tissues of living animals and other settings described herein (see F. A. Ran et al., "In vivo genome editing using *Staphylococcus aureus* Cas9," Nature, doi:10.1038/nature14299, 2015). Thus, in an embodiment, the vector of the invention is a AAV vector or has an exogenous DNA insertion capacity no more than an AAV vector, and the Cas is an endogenous Cas of the host cell, wherein the cell is a bacterial or archaeal cell. *S thermophilus* Cas9 (UniProtKB-G3ECR1 (CAS9_STRTR)) nucleotide sequence has a size of 1.4 kb.

In an example, the vector is a viral vector. Viral vectors have a particularly limited capacity for exogenous DNA insertion, thus virus packaging capacity needs to be considered. Room needs to be left for sequences encoding vital viral functions, such as for expressing coat proteins and polymerase. In an example, the vector is a phage vector or an AAV or lentiviral vector. Phage vectors are useful where the host is a bacterial cell.

By use of the term "engineered" it will be readily apparent to the skilled addressee that the array, sequence, vector, cRNA, gRNA, MGE or any other configuration, concept, aspect, embodiment, paragraph or example etc of the invention is non-naturally occurring. For example, the MGE, vector, sequence or array comprises one or more sequences or components not naturally found together with other sequences or components of the MGE, vector, sequence or array. For example, the array or sequence is recombinant, artificial, synthetic or exogenous (i.e., non-endogenous or not wild-type) to the or each host cell.

In an example, the array or sequence of the invention is an engineered version of an array or sequence isolated, for example isolated from a host cell. In an example, the engineered array or sequence is not in combination with a Cas endonuclease-encoding sequence that is naturally found in a cell.

Studies suggest that *Bacteroides* have a role in preventing infection with *Clostridium difficile*. The development of the immune response that limits entry and proliferation of potential pathogens is profoundly dependent upon *B fragilis*. Also, Paneth cell proteins may produce antibacterial peptides in response to stimulation by *B thetaiotomicron*, and these molecules may prevent pathogens from colonizing the gut. In addition, *B thetaiotomicron* can induce Paneth cells to produce a bactericidal lectin, RegIII, which exerts its antimicrobial effect by binding to the peptidoglycan of gram-positive organisms. Thus, the use of the invention in any of its configurations for increasing the proportion of *Bacteroides* (eg, thetaiotomicron and/or fragalis) in the patient's microbiota is useful for limiting pathogenic bacterial colonisation of the population or a gut of a human or non-human animal.

Hooper et al demonstrated that *B thetaiotomicron* can modify intestinal fucosylation in a complex interaction mediated by a fucose repressor gene and a signaling system. Using transcriptional analysis it was demonstrated that *B thetaiotaomicron* can modulate expression of a variety of host genes, including those involved in nutrient absorption, mucosal barrier fortification, and production of angiogenic factors.

Optionally, the host (or first and/or second bacteria) is a gram negative bacterium (eg, a *spirilla* or *vibrio*). Optionally, the host (or first and/or second bacteria) is a gram positive bacterium. Optionally, the host (or first and/or second bacteria) is a *mycoplasma*, chlamydiae, spirochete or *mycobacterium*. Optionally, the host (or first and/or second bacteria) is a *Streptococcus* (eg, *pyogenes* or *thermophilus*) host. Optionally, the host (or first and/or second bacteria) is a *Staphylococcus* (eg, *aureus*, eg, MRSA) host. Optionally, the host (or first and/or second bacteria) is an *E. coli* (eg, O157: H7) host, eg, wherein the Cas is encoded by the vecor or an endogenous host Cas nuclease activity is de-repressed. Optionally, the host (or first and/or second bacteria) is a *Pseudomonas* (eg, *aeruginosa*) host. Optionally, the host (or first and/or second bacteria) is a Vibro (eg, *cholerae* (eg, O139) or *vulnificus*) host. Optionally, the host (or first and/or second bacteria) is a *Neisseria* (eg, *gonnorrhoeae* or *meningitidis*) host. Optionally, the host (or first and/or second bacteria) is a *Bordetella* (eg, pertussis) host. Optionally, the host (or first and/or second bacteria) is a *Haemophilus* (eg, *influenzae*) host. Optionally, the host (or first and/or second bacteria) is a *Shigella* (eg, *dysenteriae*) host. Optionally, the host (or first and/or second bacteria) is a *Brucella* (eg, *abortus*) host. Optionally, the host (or first and/or second bacteria) is a *Francisella* host. Optionally, the host (or first and/or second bacteria) is a *Xanthomonas* host. Optionally, the host (or first and/or second bacteria) is a *Agrobacterium* host. Optionally, the host (or first and/or second bacteria) is a *Erwinia* host. Optionally, the host (or first and/or second bacteria) is a *Legionella* (eg, *pneumophila*) host. Optionally, the host (or first and/or second bacteria) is a *Listeria* (eg, *monocytogenes*) host. Optionally, the host (or first and/or second bacteria) is a *Campylobacter* (eg, *jejuni*) host. Optionally, the host (or first and/or second bacteria) is a *Yersinia* (eg, *pestis*) host. Optionally, the host (or first and/or second bacteria) is a *Borelia* (eg, *burgdorferi*) host. Optionally, the host (or first and/or second bacteria) is a *Helicobacter* (eg, *pylori*) host. Optionally, the host (or first and/or second bacteria) is a *Clostridium* (eg, *dificile* or *botulinum*) host. Optionally, the host (or first and/or second bacteria) is a *Erlichia* (eg, *chaffeensis*) host. Optionally, the host (or first and/or second bacteria) is a *Salmonella* (eg, *typhi* or *enterica*, eg, serotype *typhimurium*, eg, DT 104) host. Optionally, the host (or first and/or second bacteria) is a *Chlamydia* (eg, *pneumoniae*) host. Optionally, the host (or first and/or second bacteria) is a Parachlamydia host. Optionally, the host (or first and/or second bacteria) is a *Corynebacterium* (eg, *amycolatum*) host. Optionally, the host (or first and/or second bacteria) is a *Klebsiella* (eg, *pneumoniae*) host. Optionally, the host (or first and/or second bacteria) is a *Enterococcus* (eg, *faecalis* or faecim, eg, linezolid-resistant) host. Optionally, the host (or first and/or second bacteria) is a *Acinetobacter* (eg, *baumannii*, eg, multiple drug resistant) host.

A tracrRNA sequence may be omitted from a array or vector of the invention, for example for Cas systems of a Type that does not use tracrRNA.

In an example, the Cas guided to the target is an exonuclease. Optionally a nickase as mentioned herein is a double nickase. An example of a nickase is a Cas9 nickase, i.e., a Cas9 that has one of the two nuclease domains inactivated— either the RuvC and/or HNH domain.

Mention herein of using vector DNA can also in an alternative embodiment apply mutatis mutandis to vector RNA where the context allows. For example, where the vector is an RNA vector. All features of the invention are therefore in the alternative disclosed and to be read as "RNA" instead of "DNA" when referring to vector DNA herein when the context allows. In an example, the or each vector also encodes a reverse transcriptase.

In an example, the or each array or engineered nucleotide sequence is provided by a nanoparticle vector or in liposomes.

In an example, the Cas is a Cas nuclease for cutting, dead Cas (dCas) for interrupting or a dCas conjugated to a transcription activator for activating the target.

In an example, the or each array or engineered sequence comprises an exogenous promoter functional for transcription of the crRNA or gRNA in the host.

In an embodiment the array or engineered sequence is contained in a virophage vector and the host is alternatively a virus which can infect a cell. For example, the host is a large virus that may have infected an amoeba cell. For example, the host is a Sputnik virus, Pithovirus, mimivirus, mamavirus, Megavirus or Pandoravirus, eg, wherein the host virus is in water. In an example of this embodiment, the invention is for water or sewage treatment (eg, purification, eg, waterway, river, lake, pond or sea treatment).

In an embodiment the or each vector or engineered sequence is or is comprised by a ΦNM1 phage, eg, wherein the host cell(s) is a *S. aureus* (eg, MRSA) cell.

For example the method is practised on a mammalian subject, eg, a human, rodent, mouse or rat. For example the method is practised on a vertebrate, reptile, bird or fish.

The cell population can be administered to the patient in one or more doses. For example, the method comprises administering an antibacterial agent to cause said dysbiosis, or administering a bacterial transplant to the patient to cause said dysbiosis.

Wherein the method reduces the cell therapy, the therapy can be downregulated, dampened or switched off, eg, to reduce or prevent an unwanted side-effect of the cell therapy (eg, a CAR-T therapy side effect in a human patient, such as CRS). Wherein the method increases the cell therapy, the therapy can be upregulated, enhance or switched on, eg, to enhance cytotoxicity against one target cells.

The method treats or prevents (i.e., reduces the risk of) the disease or condition. This may be complete or partial treatment or prevention, i.e., a reduction but not complete reduction of the disease/condition or symptoms thereof; or a reducing of the risk but not total prevention of the disease/condition or a symptom thereof. Similarly, the method treats or prevents (i.e., reduces the risk of) an undesirable symptom of the disease or condition or the therapy (eg, CRS).

Concepts:

1. A method of modulating an adoptive immune cell therapy of a disease or condition in a patient, the method comprising a. Carrying out adoptive immune cell therapy in the patient, comprising administering a population of immune cells to the patient, wherein administration of said immune cells is capable of treating the disease or condition in the patient; and b. Causing bacterial microbiota (eg, gut microbiota) dysbiosis in the patient, whereby said dysbiosis modulates the immune cell therapy in the patient.

2. A method of modulating an adoptive immune cell therapy of a disease or condition in a patient, the method comprising a. Carrying out adoptive immune cell therapy in the patient, comprising administering a population of immune cells to the patient, wherein administration of said immune cells is capable of treating the disease or condition in the patient; and b. Altering the relative proportion of a sub-population of cells of a first bacterial species or strain, or archaeal species or strain, in a microbiota (eg, gut microbiota) of the patient, thereby producing an altered microbiota that modulates the immune cell therapy in the patient.

3. The method of concept 2, wherein step (b) is carried out by targeting the sub-population of first cells by administering thereto an anti-bacterial or anti-archaeal agent simultaneously or sequentially with said immune cell population, whereby first cells are killed or the sub-population growth is reduced, thereby reducing the proportion of said sub-population in the microbiota of the patient.

4. The method of any preceding concept, wherein the cell therapy is an adoptive T-cell therapy.

5. The method of concept 4, wherein cells selected from the group consisting of CD4$^+$ T-cells, CD8$^+$ T-cells, $T_H1$ cells and $T_H17$ cells are administered to the patient in step (a).

6. The method of concept 4 or 5, wherein $T_H17$ cells are modulated in the patient.

7. The method of concept 4, 5 or 6, wherein $T_{reg}$ cells are modulated in the patient.

8. The method of any preceding concept, wherein the cell therapy is enhanced.

9. The method of any preceding concept wherein $T_H17$ cells are upregulated in the patient and/or $T_{reg}$ cells are downregulated in the patient.

10. The method of any preceding concept, wherein CD4$^+$ T-cells are upregulated in the patient.

11. The method of any preceding concept, wherein CD8$^+$ T-cells are upregulated in the patient.

12. The method of any preceding concept, wherein one or more of central memory T cells ($T_{CM}$), effector memory T cells ($T_{EM}$), stem cell memory cells ($T_{SCM}$) and effector cells ($T_{eff}$) are upregulated in the patient, wherein the cells are comprised by the immune cell population administered in step (a) and/or are progeny thereof.

13. The method of any one of concepts 1 to 7, wherein the cell therapy is reduced.

14. The method of concept 13, wherein the method reduces or prevents the risk of cytokine release syndrome (CRS) in the patient.

15. The method of any one of concepts 1 to 7, 13 and 14, wherein, $T_H17$ cells are downregulated in the patient and/or $T_{reg}$ cells are upregulated in the patient.

16. The method of any one of concepts 1 to 7 and 13 to 15, wherein CD4$^+$ T-cells are downregulated in the patient.

17. The method of any one of concepts 1 to 7 and 13 to 16, wherein CD8$^+$ T-cells are downregulated in the patient.

18. The method of any one of concepts 1 to 7 and 13 to 17, wherein one or more of central memory T cells ($T_{CM}$), effector memory T cells (TEM), stem cell memory cells ($T_{SCM}$) and effector cells ($T_{eff}$) are downregulated in the patient, wherein the cells are comprised by the immune cell population administered in step (a) and/or are progeny thereof.

19. The method of any preceding concept, wherein the immune cell population comprises CAR-T cells and/or T-cells expressing engineered T-cell receptors (TCRs) and/or tumour infiltrating lymphocytes (TILs).

20. The method of any preceding concept, wherein the immune cell population comprises engineered autologous or allogeneic immune cells, eg, T-cells, NK cells and/or TILs.

21. The method of concept 19 or 20, wherein the T-cells are CD4$^+$ T-cells or $T_H17$ cells.

22. The method of any preceding concept, wherein step (b) increases the proportion of *Bacteroides* (eg, *B fragalis* and/or *B thetaiotamicron*) in the microbiota.

23. The method of any one of concepts 1 to 21, wherein step (b) decreases the proportion of *Bacteroides* (eg, *B fragalis* and/or *B thetaiotamicron*) in the microbiota.

24. The method of any preceding concept, wherein step (b) increases the proportion of Bacteroidetes to Firmicutes in the microbiota.

25. The method of any one of concepts 1 to 23, wherein step (b) decreases the proportion of Bacteroidetes to Firmicutes in the microbiota.

26. The method of any preceding concept, wherein step (b) reduces the proportion of one or more *Clostridium* species or strain (eg, wherein each species is a cluster IV or XIVa *Clostridium* species) in the microbiota.

27. The method of any one of concepts 1 to 25, wherein step (b) increases the proportion of one or more *Clostridium* species or strain (eg, wherein each species is a cluster IV or XIVa *Clostridium* species) in the microbiota.

28. The method of any preceding concept, wherein step (b) reduces the proportion of *Bifidobacterium* (eg, *B bifidum*) in the microbiota.

29. The method of any one of concepts 1 to 27, wherein step (b) increases the proportion of *Bifidobacterium* (eg, *B bifidum*) in the microbiota.

30. The method of any preceding concept, wherein step (b) comprises altering the relative proportion of a or said sub-population of first cells in the microbiota of the patient, thereby producing an altered microbiota that modulates the immune cell therapy in the patient, wherein the sub-population comprises host cells of said first species or strain, the method comprising
   a. combining the microbiota with multiple copies of engineered nucleic acid sequences encoding host modifying (HM) crRNAs, and
   b. expressing HM-crRNAs in host cells,
wherein each engineered nucleic acid sequence is operable with a Cas nuclease in a respective host cell to form a HM-CRISPR/Cas system and the engineered sequence comprises
   (iii) spacer and repeat sequences encoding a HM-crRNA;
   (iv) the HM-crRNA comprising a sequence that is capable of hybridizing to a host cell target sequence to guide Cas nuclease to the target sequence in the host cell; and optionally the HM-system comprises a tracrRNA sequence or a DNA sequence expressing a tracrRNA sequence;
whereby HM-crRNAs guide Cas modification of host target sequences in host cells, whereby host cells are killed or the host cell population growth is reduced, thereby reducing the proportion of said sub-population in the microbiota.

31. The method of concept 30, comprising using endogenous Cas nuclease of host cells for modification of target nucleotide sequences.

32. The method of concept 30 or 31, comprising reducing host cell population growth by at least 5-fold compared to the growth of a control population of host cells that have not received said Cas modification.

33. The method of any one of concepts 30 to 32, comprising inhibiting host cell population growth on a gut surface.

34. The method of any one of concepts 30 to 33, wherein the microbiota comprises cells of a second bacterial species or strain, or archaeal species or strain, wherein the second species or strain has a 16s ribosomal RNA-encoding DNA sequence that is at least 80% identical to an 16s ribosomal RNA-encoding DNA sequence of the host cell species or strain, wherein the growth of the second cells in the microbiota is not inhibited by said HM-system.

35. The method of concept 34, wherein the second species or strain is a human gut commensal species or strain and/or a human gut probiotic species or strain.

36. The method of concept 34 or 35, wherein the second species or strain is a Bacteroidetes (eg, *Bacteroides*) and optionally the host cells are gram positive bacterial cells.

37. The method of any one of concepts 30 to 36, wherein the first cells are Firmicutes cells.

38. The method of any one of concepts 30 to 37, wherein for each host cell the system comprises components according to (i) to (iv):—
   (i) at least one nucleic acid sequence encoding a Cas nuclease;
   (ii) an engineered HM-CRISPR array comprising a spacer sequence and repeats encoding a HM-crRNA, the HM-crRNA comprising a sequence that hybridises to a host cell target sequence to guide said Cas to the target in the host cell to modify the target sequence;
   (iii) an optional tracrRNA sequence or a DNA sequence expressing a tracrRNA sequence;
   (iv) wherein said components of the system are split between the host cell and at least one nucleic acid vector that transforms the host cell, whereby the HM-crRNA guides Cas to the target to modify the host target sequence in the host cell; and wherein the target sequence is modified by the Cas whereby the host cell is killed or host cell growth is reduced;
the method comprising introducing the vectors of (iv) into host cells and expressing said HM-crRNA in the host cells, allowing HM-cRNA to hybridise to host cell target sequences to guide Cas to the targets in the host cells to modify target sequences, whereby host cells are killed or host cell growth is reduced, thereby altering the proportion of said sub-population in the microbiota.

39. The method of concept 38, wherein component (i) is endogenous to each host cell.

40. The method of concept 38 or 39, wherein each vector is a virus or phage.

41. The method of any one of concepts 30 to 40, wherein each target sequence is adjacent a NNAGAAW or NGGNG protospacer adjacent motif (PAM).

42. The method of any one of concepts 30 to 41, wherein alternatively HM-crRNA and tracrRNA are comprised by a single guide RNA (gRNA), the method comprising introducing said gRNA into host cells or expressing the gRNA in host cells.

43. The method of any one of concepts 30 to 35 and 37 to 42, wherein the microbiota comprises a second bacterial or archaeal species, wherein each of the first and second species is a respective species of the same phylum (eg, both Firmicutes species) and the growth of the second bacteria is not inhibited by the HM-system; or wherein the microbiota comprises a second bacterial or archaeal strain, wherein each of the first and second bacteria or archaea is a respective strain of the same species and the growth of the second bacteria or archaea is not inhibited by the HM-system.

44. The method of any one of concepts 30 to 43, wherein the microbiota comprises a second bacterial species, wherein each of the first and second species is a respective gram-positive species and the growth of the second bacteria is not inhibited by the HM-system.

45. The method of any one of concepts 30 to 44, wherein each target sequence is comprised by an antibiotic resistance gene, virulence gene or essential gene of the host cell.

46. The method of any preceding concept, wherein each first cell is a *Staphylococcus, Streptococcus, Pseudomonas, Salmonella, Listeria, E coli, Desulfovibrio, Vibrio* or *Clostridium* cell.

47. The method of any preceding concept, wherein step (b) comprises stimulating Paneth cells of the patient by gut *Bacteroides* (eg, *B thetaiotamicron*), wherein the altered microbiota produced by step (b) comprises an increased proportion of *Bacteroides* first bacteria compared with the microbiota before step (b), whereby Paneth cells are stimulated and the cell therapy is modulated.

48. The method of any preceding concept, wherein step (b) comprises developing an immune response in the patient to gut *Bacteroides* (eg, *B thetaiotamicron*), wherein the altered microbiota produced by step (b) comprises an increased proportion of *Bacteroides* first bacteria compared with the microbiota before step (b), whereby the cell therapy is modulated.

49. The method of any preceding concept, wherein step (b) comprises altering the relative proportion of a or said sub-population of first cells in the microbiota of the patient, thereby producing an altered microbiota that modulates the immune cell therapy in the patient, wherein step (b) comprises killing first cells of said sub-population or inhibiting growth of said sub-population by using guided nuclease targeting to the genome of first cells comprised by the sub-population.

50. A bacterial or archaeal transplant for administration to a patient for therapy of a disease or condition in the patient using the method of any preceding concept, optionally wherein the transplant comprises cells of said first species.

51. A HM-CRISPR/Cas system, HM-array or HM-crRNA as recited in any one of concepts 30 to 45 for administration to a patient for therapy of a disease or condition in the patient using the method of any one of concepts 1 to 49.

52. A kit comprising an ex vivo population of immune cells for adoptive cell therapy of a patient, wherein the kit further comprises a transplant, system, array or crRNA of concept 50 or 51, optionally wherein the immune cells are selected from CAR-T cells, T-cells expressing engineered T-cell receptors (TCRs), tumour infiltrating lymphocytes (TILs) and NK cells.

Aspects:

1. An ex vivo population of immune cells for use in a method of adoptive cell therapy of a patient for treating or preventing a disease or condition in the patient, the method comprising
    a. Carrying out adoptive immune cell therapy in the patient, comprising administering cells of said population to the patient, Wherein administration of said immune cells is capable of treating the disease or condition in the patient; and
    b. Causing gut bacterial microbiota dysbiosis in the patient, whereby said dysbiosis modulates the immune cell therapy in the patient and said disease or condition is treated or prevented.

2. An ex vivo population of immune cells for use in a method of adoptive cell therapy of a patient for treating or preventing a disease or condition in the patient, the method comprising
    a. Carrying out adoptive immune cell therapy in the patient, comprising administering cells of said population to the patient, wherein administration of said immune cells is capable of treating the disease or condition in the patient; and
    b. Altering the relative proportion of a sub-population of cells of a first bacterial species or strain, or archaeal species or strain, in the gut microbiota of the patient, thereby producing an altered gut microbiota that modulates the immune cell therapy in the patient.

3. The immune cell population of Aspect 2, wherein step (b) is carried out by targeting the sub-population of first cells by administering thereto an anti-bacterial or anti-archaeal agent (eg, a guided nuclease) simultaneously or sequentially with said immune cell population, whereby first cells are killed or the sub-population growth is reduced, thereby reducing the proportion of said sub-population in the gut microbiota of the patient.

4. The immune cell population of any preceding Aspect, wherein the cell therapy is an adoptive T-cell therapy.

5. The immune cell population of Aspect 4, wherein cells selected from the group consisting of CD4$^+$ T cells, CD8$^+$ T-cells, T$_H$1 cells and T$_H$17 cells are administered to the patient in step (a).

6. The immune cell population of Aspect 4 or 5, wherein T$_H$17 cells are modulated in the patient.

7. The immune cell population of Aspect 4, 5 or 6, wherein T$_{reg}$ cells are modulated in the patient.

8. The immune cell population of any preceding Aspect, wherein the cell therapy is enhanced.

9. The immune cell population of any preceding Aspect wherein T$_{11}$17 cells are upregulated in the patient and/or T$_{reg}$ cells are downregulated in the patient.

10. The immune cell population of any preceding Aspect, wherein CD4$^+$ T-cells are upregulated in the patient.

11. The immune cell population of any preceding Aspect, wherein CD8$^+$ T-cells are upregulated in the patient.

12. The immune cell population of any preceding Aspect, wherein one or more of central memory T cells (T$_{CM}$), effector memory T cells (T$_{EM}$), stem cell memory cells (T$_{SCM}$) and effector cells (T$_{eff}$) are upregulated in the patient, wherein the cells are comprised by the immune cell population administered in step (a) and/or are progeny thereof.

13. The immune cell population of any one of Aspects 1 to 7, wherein the cell therapy is reduced.

14. The immune cell population of Aspect 13, wherein the method reduces or prevents the risk of cytokine release syndrome (CRS) in the patient.

15. The immune cell population of any one of Aspects 1 to 7, 13 and 14, wherein, T$_H$7 cells are downregulated in the patient and/or T$_{reg}$ cells are upregulated in the patient.

16. The immune cell population of any one of Aspects 1 to 7 and 13 to 15, wherein CD4$^+$ T cells are downregulated in the patient.

17. The immune cell population of any one of Aspects 1 to 7 and 13 to 16, wherein CD8$^+$ T-cells are downregulated in the patient.
18. The immune cell population of any one of Aspects 1 to 7 and 13 to 17, wherein one or more of central memory T cells ($T_{CM}$), effector memory T cells ($T_{EM}$), stem cell memory cells ($T_{SCM}$) and effector cells ($T_{eff}$) are downregulated in the patient, wherein the cells are comprised by the immune cell population administered in step (a) and/or are progeny thereof.
19. The immune cell population of any preceding Aspect, wherein the immune cell population comprises or consists of CAR-T cells and/or T-cells expressing engineered T-cell receptors (TCRs) and/or tumour infiltrating lymphocytes (TILs).
20. The immune cell population of any preceding Aspect, wherein the immune cell population comprises or consists of engineered autologous or allogeneic immune cells, eg, T-cells, NK cells and/or TILs.
21. The immune cell population of Aspect 19 or 20, wherein the T-cells are CD4$^+$ T-cells or $T_H17$ cells.
22. The immune cell population of any preceding Aspect, wherein step (b) increases the proportion of *Bacteroides* (eg, *B fragalis* and/or *B thetaiotamicron*) in the gut microbiota.
23. The immune cell population of any one of Aspects 1 to 21, wherein step (b) decreases the proportion of *Bacteroides* (eg, *B fragalis* and/or *B thetaiotamicron*) in the gut microbiota.
24. The immune cell population of any preceding Aspect, wherein step (b) increases the proportion of Bacteroidetes to Firmicutes in the gut microbiota.
25. The immune cell population of any one of Aspects 1 to 23, wherein step (b) decreases the proportion of Bacteroidetes to Firmicutes in the gut microbiota.
26. The immune cell population of any preceding Aspect, wherein step (b) reduces the proportion of one or more *Clostridium* species or strain (eg, wherein each species is a cluster IV or XIVa *Clostridium* species) in the gut microbiota.
27. The immune cell population of any one of Aspects 1 to 25, wherein step (b) increases the proportion of one or more *Clostridium* species or strain (eg, wherein each species is a cluster IV or XIVa *Clostridium* species) in the gut microbiota.
28. The immune cell population of any preceding Aspect, wherein step (b) reduces the proportion of *Bifidobacterium* (eg, *B bifidum*) in the gut microbiota.
29. The immune cell population of any one of Aspects 1 to 27, wherein step (b) increases the proportion of *Bifidobacterium* (eg, *B bifidum*) in the gut microbiota.
30. The immune cell population of any preceding Aspect, wherein step (b) comprises altering the relative proportion of a or said sub-population of first cells in the gut microbiota of the patient, thereby producing an altered gut microbiota that modulates the immune cell therapy in the patient, wherein the sub-population comprises host cells of said first species or strain, the method comprising
    a. combining the microbiota with multiple copies of engineered nucleic acid sequences encoding host modifying (HM) crRNAs, and
    b. expressing HM-crRNAs in host cells,
wherein each engineered nucleic acid sequence is operable with a Cas nuclease in a respective host cell to form a HM-CRISPR/Cas system and the engineered sequence comprises
    (i) spacer and repeat sequences encoding a HM-crRNA;
    (ii) the HM-crRNA comprising a sequence that is capable of hybridizing to a host cell target sequence to guide Cas nuclease to the target sequence in the host cell; and optionally the HM-system comprises a tracrRNA sequence or a DNA sequence expressing a tracrRNA sequence;
whereby HM-crRNAs guide Cas modification of host target sequences in host cells, whereby host cells are killed or the host cell population growth is reduced, thereby reducing the proportion of said sub-population in the microbiota.
31. The immune cell population of Aspect 30, comprising using endogenous Cas nuclease of host cells for modification of target nucleotide sequences.
32. The immune cell population of Aspect 30 or 31, comprising reducing host cell population growth by at least 5-fold compared to the growth of a control population of host cells that have not received said Cas modification.
33. The immune cell population of any one of Aspects 30 to 32, comprising inhibiting host cell population growth on a gut surface.
34. The immune cell population of any one of Aspects 30 to 33, wherein the microbiota comprises cells of a second bacterial species or strain, or archaeal species or strain, wherein the second species or strain has a 16s ribosomal RNA-encoding DNA sequence that is at least 80% identical to an 16s ribosomal RNA-encoding DNA sequence of the host cell species or strain, wherein the growth of the second cells in the microbiota is not inhibited by said HM-system.
35. The immune cell population of Aspect 34, wherein the second species or strain is a human gut commensal species or strain and/or a human gut probiotic species or strain.
36. The immune cell population of Aspect 34 or 35, wherein the second species or strain is a Bacteroidetes (eg, *Bacteroides*) and optionally the host cells are gram positive bacterial cells.
37. The immune cell population of any one of Aspects 30 to 36, wherein the first cells are Firmicutes cells.
38. The immune cell population of any one of Aspects 30 to 37, wherein for each host cell the system comprises components according to (i) to (iv):—
    (i) at least one nucleic acid sequence encoding a Cas nuclease;
    (ii) an engineered HM-CRISPR array comprising a spacer sequence and repeats encoding a HM-crRNA, the HM-crRNA comprising a sequence that hybridises to a host cell target sequence to guide said Cas to the target in the host cell to modify the target sequence;
    (iii) an optional tracrRNA sequence or a DNA sequence expressing a tracrRNA sequence;
    (iv) wherein said components of the system are split between the host cell and at least one nucleic acid vector that transforms the host cell, whereby the HM-crRNA guides Cas to the target to modify the host target sequence in the host cell; and wherein the target sequence is modified by the Cas whereby the host cell is killed or host cell growth is reduced;
    the method comprising introducing the vectors of (iv) into host cells and expressing said HM-crRNA in the host cells, allowing HM-cRNA to hybridise to host cell target sequences to guide Cas to the targets in the host cells to modify target sequences, whereby host cells are killed or host cell growth is reduced, thereby altering the proportion of said sub-population in the microbiota.
39. The immune cell population of Aspect 38, wherein component (i) is endogenous to each host cell.

40. The immune cell population of Aspect 38 or 39, wherein each vector is a virus or phage.
41. The immune cell population of any one of Aspects 30 to 40, wherein each target sequence is adjacent a NNA-GAAW or NGGNG protospacer adjacent motif (PAM).
42. The immune cell population of any one of Aspects 30 to 41, wherein alternatively HM-crRNA and tracrRNA are comprised by a single guide RNA (gRNA), the method comprising introducing said gRNA into host cells or expressing the gRNA in host cells.
43. The immune cell population of any one of Aspects 30 to 35 and 37 to 42, wherein the microbiota comprises a second bacterial or archaeal species, wherein each of the first and second species is a respective species of the same phylum (eg, both Firmicutes species) and the growth of the second bacteria is not inhibited by the HM-system; or wherein the microbiota comprises a second bacterial or archaeal strain, wherein each of the first and second bacteria or archaea is a respective strain of the same species and the growth of the second bacteria or archaea is not inhibited by the HM-system.
44. The immune cell population of any one of Aspects 30 to 43, wherein the microbiota comprises a second bacterial species, wherein each of the first and second species is a respective gram-positive species and the growth of the second bacteria is not inhibited by the HM-system.
45. The immune cell population of any one of Aspects 30 to 44, wherein each target sequence is comprised by an antibiotic resistance gene, virulence gene or essential gene of the host cell.
46. The method of any preceding Aspect, wherein each first cell is a *Staphylococcus, Streptococcus, Pseudomonas, Salmonella, Listeria, E coli, Desulfovibrio, Vibrio* or *Clostridium* cell.
47. The immune cell population of any preceding Aspect, wherein step (b) comprises stimulating Paneth cells of the patient by gut *Bacteroides* (eg, *B thetaiotamicron*), wherein the altered microbiota produced by step (b) comprises an increased proportion of *Bacteroides* first bacteria compared with the microbiota before step (b), whereby Paneth cells are stimulated and the cell therapy is modulated.
48. The immune cell population of any preceding Aspect, wherein step (b) comprises developing an immune response in the patient to gut *Bacteroides* (eg, *B thetaiotamicron*), wherein the altered microbiota produced by step (b) comprises an increased proportion of *Bacteroides* first bacteria compared with the microbiota before step (b), whereby the cell therapy is modulated.
49. The immune cell population of any preceding Aspect, wherein step (b) comprises altering the relative proportion of a or said sub-population of first cells in the gut microbiota of the patient, thereby producing an altered gut microbiota that modulates the immune cell therapy in the patient, wherein step (b) comprises killing first cells of said sub-population or inhibiting growth of said sub-population by using guided nuclease targeting to the genome of first cells comprised by the sub-population.
50. A bacterial or archaeal transplant for administration to a patient for therapy of a disease or condition in the patient using the method recited in any preceding Aspect, optionally wherein the transplant comprises cells of said first species.
51. A HM-CRISPR/Cas system, HM-array or HM-crRNA as recited in any one of Aspects 30 to 45 for administration to a patient for therapy of a disease or condition in the patient using the method recited in any one of Aspects 1 to 49.
52. A kit comprising an ex vivo population of immune cells according to any one of Aspects 1 to 49 for adoptive cell therapy of a patient to treat said disease or condition, wherein the kit further comprises a transplant, system, array or crRNA of Aspect 50 or 51, optionally wherein the immune cells are selected from CAR-T cells, T-cells expressing engineered T-cell receptors (TCRs), tumour infiltrating lymphocytes (TILs) and NK cells.

Optionally, the host cell(s), first cell(s), second cell(s) or mixed bacterial population is comprised by a human or a non-human animal subject, eg, the population is comprised by a gut microbiota, skin microbiota, oral cavity microbiota, throat microbiota, hair microbiota, armpit microbiota, vaginal microbiota, rectal microbiota, anal microbiota, ocular microbiota, nasal microbiota, tongue microbiota, lung microbiota, liver microbiota, kidney microbiota, genital microbiota, penile microbiota, scrotal microbiota, mammary gland microbiota, ear microbiota, urethra microbiota, labial microbiota, organ microbiota or dental microbiota. Optionally, the mixed bacterial population is comprised by a plant (eg, a tobacco, crop plant, fruit plant, vegetable plant or tobacco, eg on the surface of a plant or contained in a plant) or by an environment (eg, soil or water or a waterway or acqueous liquid).

Optionally, the disease or condition of a human or animal subject or patient is selected from
(a) A neurodegenerative disease or condition;
(b) A brain disease or condition;
(c) A CNS disease or condition;
(d) Memory loss or impairment;
(e) A heart or cardiovascular disease or condition, eg, heart attack, stroke or atrial fibrillation;
(f) A liver disease or condition;
(g) A kidney disease or condition, eg, chronic kidney disease (CKD);
(h) A pancreas disease or condition;
(i) A lung disease or condition, eg, cystic fibrosis or COPD;
(j) A gastrointestinal disease or condition;
(k) A throat or oral cavity disease or condition;
(l) An ocular disease or condition;
(m) A genital disease or condition, eg, a vaginal, labial, penile or scrotal disease or condition;
(n) A sexually-transmissible disease or condition, eg, gonorrhea, HIV infection, syphilis or *Chlamydia* infection;
(o) An ear disease or condition;
(p) A skin disease or condition;
(q) A heart disease or condition;
(r) A nasal disease or condition
(s) A haematological disease or condition, eg, anaemia, eg, anaemia of chronic disease or cancer;
(t) A viral infection;
(u) A pathogenic bacterial infection;
(v) A cancer;
(w) An autoimmune disease or condition, eg, SLE;
(x) An inflammatory disease or condition, eg, rheumatoid arthritis, psoriasis, eczema, asthma, ulcerative colitis, colitis, Crohn's disease or IBD;
(y) Autism;
(z) ADHD;
(aa) Bipolar disorder;
(bb) ALS [Amyotrophic Lateral Sclerosis];
(cc) Osteoarthritis;

(dd) A congenital or development defect or condition;
(ee) Miscarriage;
(ff) A blood clotting condition;
(gg) Bronchitis;
(hh) Dry or wet AMD;
(ii) Neovascularisation (eg, of a tumour or in the eye);
(jj) Common cold;
(kk) Epilepsy;
(ll) Fibrosis, eg, liver or lung fibrosis;
(mm) A fungal disease or condition, eg, thrush;
(nn) A metabolic disease or condition, eg, obesity, anorexia, diabetes, Type I or Type II diabetes.
(oo) Ulcer(s), eg, gastric ulceration or skin ulceration;
(pp) Dry skin;
(qq) Sjogren's syndrome;
(rr) Cytokine storm;
(ss) Deafness, hearing loss or impairment;
(tt) Slow or fast metabolism (i.e., slower or faster than average for the weight, sex and age of the subject);
(uu) Conception disorder, eg, infertility or low fertility;
(vv) Jaundice;
(ww) Skin rash;
(xx) Kawasaki Disease;
(yy) Lyme Disease;
(zz) An allergy, eg, a nut, grass, pollen, dust mite, cat or dog fur or dander allergy;
(aaa) Malaria, typhoid fever, tuberculosis or cholera;
(bbb) Depression;
(ccc) Mental retardation;
(ddd) Microcephaly;
(eee) Malnutrition;
(fff) Conjunctivitis;
(ggg) Pneumonia;
(hhh) Pulmonary embolism;
(iii) Pulmonary hypertension;
(jjj) A bone disorder;
(kkk) Sepsis or septic shock;
(lll) Sinusitus;
(mmm) Stress (eg, occupational stress);
(nnn) Thalassaemia, anaemia, von Willebrand Disease, or haemophilia;
(ooo) Shingles or cold sore;
(ppp) Menstruation;
(qqq) Low sperm count.

Neurodegenerative or CNS Diseases or Conditions for Treatment or Prevention by the Method In an example, the neurodegenerative or CNS disease or condition is selected from the group consisting of Alzheimer disease, geriopsychosis, Down syndrome, Parkinson's disease, Creutzfeldt-jakob disease, diabetic neuropathy, Parkinson syndrome, Huntington's disease, Machado-Joseph disease, amyotrophic lateral sclerosis, diabetic neuropathy, and Creutzfeldt Creutzfeldt-Jakob disease. For example, the disease is Alzheimer disease. For example, the disease is Parkinson syndrome.

In an example, wherein the method of the invention is practised on a human or animal subject for treating a CNS or neurodegenerative disease or condition, the method causes downregulation of Treg cells in the subject, thereby promoting entry of systemic monocyte-derived macrophages and/or Treg cells across the choroid plexus into the brain of the subject, whereby the disease or condition (eg, Alzheimer's disease) is treated, prevented or progression thereof is reduced. In an embodiment the method causes an increase of IFN-gamma in the CNS system (eg, in the brain and/or CSF) of the subject. In an example, the method restores nerve fibre and/or reduces the progression of nerve fibre damage. In an example, the method restores nerve myelin and/or reduces the progression of nerve myelin damage. In an example, the method of the invention treats or prevents a disease or condition disclosed in WO2015136541 and/or the method can be used with any method disclosed in WO2015136541 (the disclosure of this document is incorporated by reference herein in its entirety, eg, for providing disclosure of such methods, diseases, conditions and potential therapeutic agents that can be administered to the subject for effecting treatment and/or prevention of CNS and neurodegenerative diseases and conditions, eg, agents such as immune checkpoint inhibitors, eg, anti-PD-1, anti-PD-L1, anti-TIM3 or other antibodies disclosed therein).

Cancers for Treatment or Prevention by the Method

Cancers that may be treated include tumours that are not vascularized, or not substantially vascularized, as well as vascularized tumours. The cancers may comprise non-solid tumours (such as haematological tumours, for example, leukaemias and lymphomas) or may comprise solid tumours. Types of cancers to be treated with the invention include, but are not limited to, carcinoma, blastoma, and sarcoma, and certain leukaemia or lymphoid malignancies, benign and malignant tumours, and malignancies e.g., sarcomas, carcinomas, and melanomas. Adult tumours/cancers and paediatric tumours/cancers are also included.

Haematologic cancers are cancers of the blood or bone marrow. Examples of haematological (or haematogenous) cancers include leukaemias, including acute leukaemias (such as acute lymphocytic leukaemia, acute myelocytic leukaemia, acute myelogenous leukaemia and myeloblasts, promyeiocytic, myelomonocytic, monocytic and erythroleukaemia), chronic leukaemias (such as chronic myelocytic (granulocytic) leukaemia, chronic myelogenous leukaemia, and chronic lymphocytic leukaemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukaemia and myelodysplasia.

Solid tumours are abnormal masses of tissue that usually do not contain cysts or liquid areas. Solid tumours can be benign or malignant. Different types of solid tumours are named for the type of cells that form them (such as sarcomas, carcinomas, and lymphomas). Examples of solid tumours, such as sarcomas and carcinomas, include fibrosarcoma, myxosarcoma, liposarcoma, chondrosarcoma, osteosarcoma, and other sarcomas, synovioma, mesothelioma, Ewing's tumour, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous eel! carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumour, cervical cancer, testicular tumour, seminoma, bladder carcinoma, melanoma, and CNS tumours (such as a glioma (such as brainstem glioma and mixed gliomas), glioblastoma (also known as glioblastoma multiforme) astrocytoma, CNS lymphoma, germinoma, medu!loblastoma, Schwannoma craniopharyogioma, ependymoma, pineaioma, hemangioblastoma, acoustic neuroma, oligodendroglioma, menangioma, neuroblastoma, retinoblastoma and brain metastases).

Autoimmune Diseases for Treatment or Prevention by the Method
- Acute Disseminated Encephalomyelitis (ADEM)
- Acute necrotizing hemorrhagic leukoencephalitis
- Addison's disease
- Agammaglobulinemia
- Alopecia areata
- Amyloidosis
- Ankylosing spondylitis
- Anti-GBM/Anti-TBM nephritis
- Antiphospholipid syndrome (APS)
- Autoimmune angioedema
- Autoimmune aplastic anemia
- Autoimmune dysautonomia
- Autoimmune hepatitis
- Autoimmune hyperlipidemia
- Autoimmune immunodeficiency
- Autoimmune inner ear disease (AIED)
- Autoimmune myocarditis
- Autoimmune oophoritis
- Autoimmune pancreatitis
- Autoimmune retinopathy
- Autoimmune thrombocytopenic purpura (ATP)
- Autoimmune thyroid disease
- Autoimmune urticaria
- Axonal & neuronal neuropathies
- Balo disease
- Behcet's disease
- Bullous pemphigoid
- Cardiomyopathy
- Castleman disease
- Celiac disease
- Chagas disease
- Chronic fatigue syndrome
- Chronic inflammatory demyelinating polyneuropathy (CIDP)
- Chronic recurrent multifocal ostomyelitis (CRMO)
- Churg-Strauss syndrome
- Cicatricial pemphigoid/benign mucosal pemphigoid
- Crohn's disease
- Cogans syndrome
- Cold agglutinin disease
- Congenital heart block
- Coxsackie myocarditis
- CREST disease
- Essential mixed cryoglobulinemia
- Demyelinating neuropathies
- Dermatitis herpetiformis
- Dermatomyositis
- Devic's disease (neuromyelitis optica)
- Discoid lupus
- Dressler's syndrome
- Endometriosis
- Eosinophilic esophagitis
- Eosinophilic fasciitis
- Erythema nodosum
- Experimental allergic encephalomyelitis
- Evans syndrome
- Fibromyalgia
- Fibrosing alveolitis
- Giant cell arteritis (temporal arteritis)
- Giant cell myocarditis
- Glomerulonephritis
- Goodpasture's syndrome
- Granulomatosis with Polyangiitis (GPA) (formerly called Wegener's Granulomatosis)
- Graves' disease
- Guillain-Barre syndrome
- Hashimoto's encephalitis
- Hashimoto's thyroiditis
- Hemolytic anemia
- Henoch-Schonlein purpura
- Herpes gestationis
- Hypogammaglobulinemia
- Idiopathic thrombocytopenic purpura (ITP)
- IgA nephropathy
- IgG4-related sclerosing disease
- Immunoregulatory lipoproteins
- Inclusion body myositis
- Interstitial cystitis
- Juvenile arthritis
- Juvenile diabetes (Type 1 diabetes)
- Juvenile myositis
- Kawasaki syndrome
- Lambert-Eaton syndrome
- Leukocytoclastic vasculitis
- Lichen planus
- Lichen sclerosus
- Ligneous conjunctivitis
- Linear IgA disease (LAD)
- Lupus (SLE)
- Lyme disease, chronic
- Meniere's disease
- Microscopic polyangiitis
- Mixed connective tissue disease (MCTD)
- Mooren's ulcer
- Mucha-Habermann disease
- Multiple sclerosis
- Myasthenia gravis
- Myositis
- Narcolepsy
- Neuromyelitis optica (Devic's)
- Neutropenia
- Ocular cicatricial pemphigoid
- Optic neuritis
- Palindromic rheumatism
- PANDAS (Pediatric Autoimmune Neuropsychiatric Disorders Associated with *Streptococcus*)
- Paraneoplastic cerebellar degeneration
- Paroxysmal nocturnal hemoglobinuria (PNH)
- Parry Romberg syndrome
- Parsonnage-Turner syndrome
- Pars planitis (peripheral uveitis)
- Pemphigus
- Peripheral neuropathy
- Perivenous encephalomyelitis
- Pernicious anemia
- POEMS syndrome
- Polyarteritis *nodosa*
- Type I, II, & III autoimmune polyglandular syndromes
- Polymyalgia rheumatica
- Polymyositis
- Postmyocardial infarction syndrome
- Postpericardiotomy syndrome
- Progesterone dermatitis
- Primary biliary cirrhosis
- Primary sclerosing cholangitis
- Psoriasis
- Psoriatic arthritis
- Idiopathic pulmonary fibrosis
- Pyoderma gangrenosum
- Pure red cell aplasia
- Raynauds phenomenon
- Reactive Arthritis Reflex sympathetic dystrophy
Reiter's syndrome
Relapsing polychondritis
Restless legs syndrome
Retroperitoneal fibrosis
Rheumatic fever
Rheumatoid arthritis
Sarcoidosis
Schmidt syndrome
Scleritis
Scleroderma
Sjogren's syndrome
Sperm & testicular autoimmunity
Stiff person syndrome
Subacute bacterial endocarditis (SBE)
Susac's syndrome
Sympathetic ophthalmia
Takayasu's arteritis
Temporal arteritis/Giant cell arteritis
Thrombocytopenic purpura (TTP)
Tolosa-Hunt syndrome
Transverse myelitis
Type 1 diabetes
Ulcerative colitis
Undifferentiated connective tissue disease (UCTD)
Uveitis
Vasculitis
Vesiculobullous dermatosis
Vitiligo
Wegener's granulomatosis (now termed Granulomatosis with Polyangiitis (GPA).

Inflammatory Diseases for Treatment or Prevention by the Method

Alzheimer's
ankylosing spondylitis
arthritis (osteoarthritis, rheumatoid arthritis (RA), psoriatic arthritis)
asthma
atherosclerosis
Crohn's disease
colitis
dermatitis
diverticulitis
fibromyalgia
hepatitis
irritable bowel syndrome (IBS)
systemic lupus erythematous (SLE)
nephritis
Parkinson's disease
ulcerative colitis.

In an example (eg, in the method of the invention involving a mixed bacterial population), the host cell (or first cell or second cell) genus or species is selected from a genus or species listed in Table 1. In examples of the present invention, the Cas (eg, Cas nuclease such as a Type I, II or III Cas, eg, a Cas3 or 9) is a Cas comprised by bacteria of a genus or species that is selected from a genus or species listed in Table 1, and optionally the host cell (or first cell or second cell) is of the same genus or species. In an example of this, the Cas is endogenous to said host cell (or first or second cell), which is useful for embodiments herein wherein endogenous Cas is used to modify a target sequence. In this case, the HM-array may comprise one or more repeat nucleotide (eg, DNA or RNA) sequences that is at least 90, 95, 96, 97, 98 or 99% identical (or is 100% identical) to a repeat sequence of said cell, genus or species, whereby the Cas is operable with cRNA encoded by the HM-array for modifying one or more target sequences in the cell. In an example, the Cas is a Type I Cas3 and is used with a Type I CASCADE, wherein one or both of the Cas3 and CASCADE are endogenous to the host or first cells, or are vector-borne (i.e., exogenous to the host or first cells).

In an example, the method of the invention selectively kills first cells in the microbiota whilst not targeting second cells, eg, wherein the second cells are (a) of a related strain to the strain of the first species or (b) of a species that is different to the first species and is phylogenetically related to the first species, wherein the second species or strain has a 16s ribosomal RNA-encoding DNA sequence that is at least 80% identical to an 16s ribosomal RNA-encoding DNA sequence of the first cell species or strain. In an embodiment, the first cells are of a first species selected from Table 1 and the second cells are of a different species selected from Table 1. In an example, the species are of the same genus or are of different genera.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications and all US equivalent patent applications and patents are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non limiting Examples.

EXAMPLES

Example 1: Specific Microbiota Bacterial Population Growth Inhibition By Harnessing Wild-Type Endogenous Cas 1. Material and Methods
1.1. Strains The following strains were used in the course of this Example and Examples 2 and 3: *E. coli* MG1655, *E. coli* TOP10, *Streptococcus thermophilus* LMD-9 (ATCC BAA-491, Manassas, Va.), *Streptococcus thermophilus* DSM 20617(T) (DSMZ, Braunschweig, Germany), *Lactococcus lactis* MG1363 and *Streptococcus mutans* Clarke 1924 DSM 20523 (DSMZ, Braunschweig, Germany).

During the course of media selection and testing of the genetic constructs different *Streptoccoci* strains were used. *Streptococcus thermophilus* LMD-9 (ATCC BAA-491) and *Escherichia coli* TOP10 were considered because of their compatible growth requirements. All strains were cultivated in Todd-Hewitt broth (TH) (T1438 Sigma-Aldrich), in aerobic conditions and at 37° C., unless elsewhere indicated. The strains were stored in 25% glycerol at −80° C.

1.2. Differential Growth Media

All strains were grown on TH media at 37° C. for 20 hours. Selective media for *S.thermophilus* was TH media supplemented with 3 g l$^{-1}$ of 2-phenylethanol (PEA). PEA was added to the media and autoclaved at 121° C. for 15 minutes at 15 psi. Agar plates were prepared by adding 1.5% (wt/vol) agar to the corresponding media. When necessary for selection or plasmid maintenance 30 µg ml$^{-1}$ kanamycin was used for both *S. thermophilus* strains and *E. coli*, and 500 µg ml$^{-1}$ for *S.mutans*.

In some cases, depending on the strain and plasmid, a longer incubation, up to 48 hours, may be needed to see growth on media supplemented with PEA. In order to control for the viability of the organisms used, a control TH agar must be done in parallel.

1.3. Cloning

*E. coli* (One Shot® ThermoFischer TOP10 Chemically Competent cells) was used in all subcloning procedures. PCR was carried out using Phusion polymerase. All PCR products were purified with Nucleospin Gel and PCR Clean-up by Macherey-Nagel following the manufacturer's protocol. The purified fragments were digested with restriction enzyme DpnI in 1×FD buffer with 10 enzyme in a total volume of 34 µl. The digested reaction was again purified with Nucleospin Gel and PCR Clean-up by Macherey-Nagel following the manufacturer's protocol. Gibson assembly was performed in 10 µl reactions following the manufacturer's protocol (NewEngland Biolab).

Plasmid DNA was prepared using Qiagen kits according to the manufacturer's instructions. Modifications for Gram-positive strains included growing bacteria in a medium supplemented with 0.5% glycine and lysozyme to facilitate cell lysis.

1.4. Transformation 1.4.1 Electro-Competent *E. coli* Cells and Transformation

Commercially electrocompetent cells were used for cloning and the experiments (One Shot® ThermoFischer TOP10 Chemically Competent *E. coli*). Electroporation was done using standard settings: 1800 V, 25 µF; and 200Ω using an Electro Cell Manipulator (BTX Harvard Apparatus ECM630). Following the pulse, 1 ml LB-SOC media was added and the cells were incubated at 37° C. for 1 hour. The transformed cells were plated in LB-agar containing 50 µg ml$^{-1}$ of kanamycin.

1.4.2 Preparation of Electro-Competent *S. thermophilus* Cells

The electroporation protocol was modified from Somkuti and Steinberg, 1988. An overnight culture of *Streptococcus thermophilus* in TH Broth supplemented with 40 mM DL-threonine (T8375 Sigma-Aldrich) was diluted 100-fold in 5 ml of the same media and grown to an $OD_{600}$ between 0.3-0.5 (approximately 2.5 hours after inoculation). The cells were collected by centrifugation at 10,000×g for 10 min at 4° C. and washed three times with 5 ml of ice cold wash buffer (0.5 M sucrose+10% glycerol). After the cells were washed, they were suspended to an $OD_{600}$ of 15-30 in electroporation buffer (0.5 M sucrose, 10% glycerol and 1 mM $MgCl_2$). The cells in the electroporation buffer may be kept at 4° C. until use (within one hour) or aliquot 50 µl in eppendorf tubes, freezing them in liquid nitrogen and stored at −80° C. for later use.

1.4.3 Electroporation *S. thermophilus* Cells

1 µl of purified plasmid DNA was added to 50 µl of the cell suspension and electroporation was carried out in 2 mm-gap electroporation cuvettes pre-cooled. The electroporation setting were 2500 V, 25 µF; and 200Ω using an Electro Cell Manipulator (BTX Harvard Apparatus ECM630). Immediately after the electric pulse, 1 ml of TH broth was added to the cells and the suspension was kept on ice for 10 minutes, subsequently the cells were incubated for 3 h at 37° C. After allowing time for expression of the resistance gene the cells were plated onto TH-agar plates containing 30 µg ml$^{-1}$ of kanamycin. Depending on the construct, colonies were visible between 12 and 48 h of incubation at 37° C.

1.5. Construction of XylS Plasmid

All the plasmids used in this work were based on pBAV1K-T5, which is a broad-host range expression vector derived from the a cryptic plasmid pWV01 from *Streptococcus cremoris* (Bryksin & Matsumura, 2010), the backbone was amplified using that contain overhangs for assembly with the other fragments using Gibson's method.

The xylose inducible system was constructed by cloning the promoter gyrA in front of the XylR repressor (FIG. 1). The XylR repressor was amplified from *Bacillus Subtilis* strain SCK6 (Zhang et al. 2011) with the a reverse primer that includes an overhang for Gibson assembly and a forward primer, that is an ultramer used to introduce the gyrA promoter (Xie et al. 2013) and the corresponding overhang for assembly into pBAV1KT5 backbone. The resulting fragment was flanked by an mCherry amplified from pCL002 (unpublished work) with an ultramer that include Pldha+PxylA hybrid promoter (Xie et al. 2013). The three resulting PCR products were assembled in a Gibson Master Mix® (NewEngland Biolab) according to manufacturer's instructions. The product was finally transformed in E. coli TOP10 electrocompetent cells. See FIG. 1.

1.6. Design and Construction of CRISPR Array Plasmid

Figure 2:
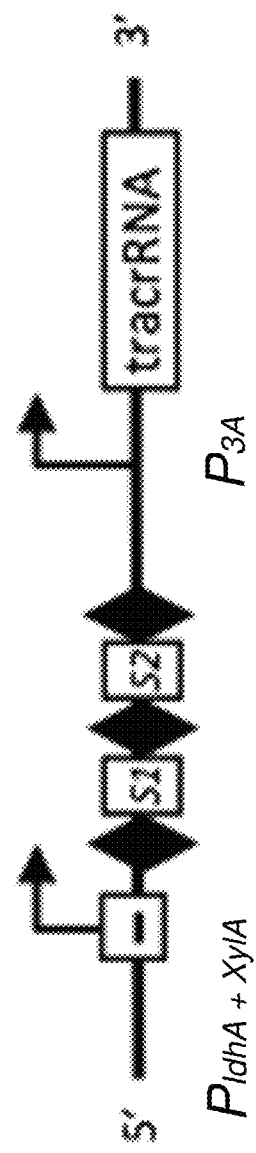
FIG. 2 shows a ST1-CRISPR array.

Streptococcus thermophilus has 4 distinct CRISPR systems (Sapranauskas, et al. 2011), for this work the type II CRISPR1 (ST1-CRISPR) system was chosen. The design of the target sequence was based on the available genome sequence of LMD-9 (GenBank: CP000419.1). The ST1-CRISPR array was designed to contain only the CRISPR array repeats and spacers under a xylose inducible promoter (Xie et al. 2013), followed by the corresponding tracrRNA under a strong constitutive promoter for Streptococci species (Sorg et al. 2014) (FIG. 2).

The tracrRNA plays a role in the maturation of crRNA and it is processed by S. thermophilus endogenous RNase III, forming a complex with crRNA. This complex acts as a guide for the endonuclease ST1-Cas9 (Horvath & Barrangou, 2010). After transcription of the synthetic array from the xylose inducible promoter, the endogenous Cas9 and RNAses will process it into a functional gRNA. The gRNA/Cas9 complex will cause a double stranded break at the target location.

The design of the array used 2 specific target sequences high on GC content and a reduced portion of the tracrRNA (i.e., a less than complete tracrRNA sequence), which has been suggested not to be necessary for proper maturation of crRNA (Horvath & Barrangou, 2010).

The 2 targets were an essential gene (DNA polymerase III subunit alpha) and an antibiotic resistance gene (tetA-like gene).

Primers were used to amplify pBAV1KT5-XylR-PldhA backbone. The CRISPR array gBlock and the backbone with overhangs were assembled in a Gibson Master Mix @ according to manufacturer's instructions (NewEngland Biolabs). The product was finally transformed in E. coli TOP10 electrocompetent cells.

1.7. Characterization of Xylose Inducible System in Streptoccocus thermophilus LMD-9

Overnight stationary-phase cultures were diluted 1:100 into TH broth with corresponding antibiotic. Mid-log cells were induced with different concentration of D-(+)-xylose (0, 0.001, 0.01, 0.1, 0.5 and 1% wt/vol) and the cell cultures were measured either directly in medium to assess the extent of autofluorescence of the media, on the cell suspension or the suspension buffer (PBS buffer). 20p1 samples of the cell cultures were diluted 1/10 on PBS buffer, on 96-well plates with flat bottoms. Fluorescence of cell suspensions or media was read on a plate reader. mCherry fluorescence was measured using an excitation wavelength of 558 nm and emission at 612 nm. Absorbance of the resuspended cells was measured at OD 600 nm. A minimum of three independent biological replicates was done for each experiment.

1.8. Activation of CRISPR Array in S. thermophilus

S. thermophilus LMD-9 and E. coli TOP10 both with the plasmid containing the CRISPR array targeting the DNA polymerase III and tetA of S. thermophilus were grown overnight in 3 ml cultures supplemented with 30 µg ml$^{-1}$ of kanamycin for plasmid maintenance. The next day 96 well deep well plates were inoculated with 500 µl of 1/100 of overnight culture in fresh TH media, supplemented with 30 µg ml$^{-1}$ kanamycin. Mid-log cell cultures were induced with 1% xylose. The killing effect was tested on S.thermophilus and E. coli alone. For each strain and condition tested a negative control was kept without xylose. The cells were grown till ~OD 0.5 and next 10-fold serially diluted in TH media and using a 96-well replicator (Mettler Toledo Liquidator™ 96) 5 µL volume drops were spotted on TH agar and TH agar supplemented with g l$^{-1}$ PEA plates. The plates were incubated for 24H at 37° C. and the colony forming units (CFU) were calculated from triplicate measurements.

2. Results 2.1 Growth Condition and Selective Media

Figure 3:
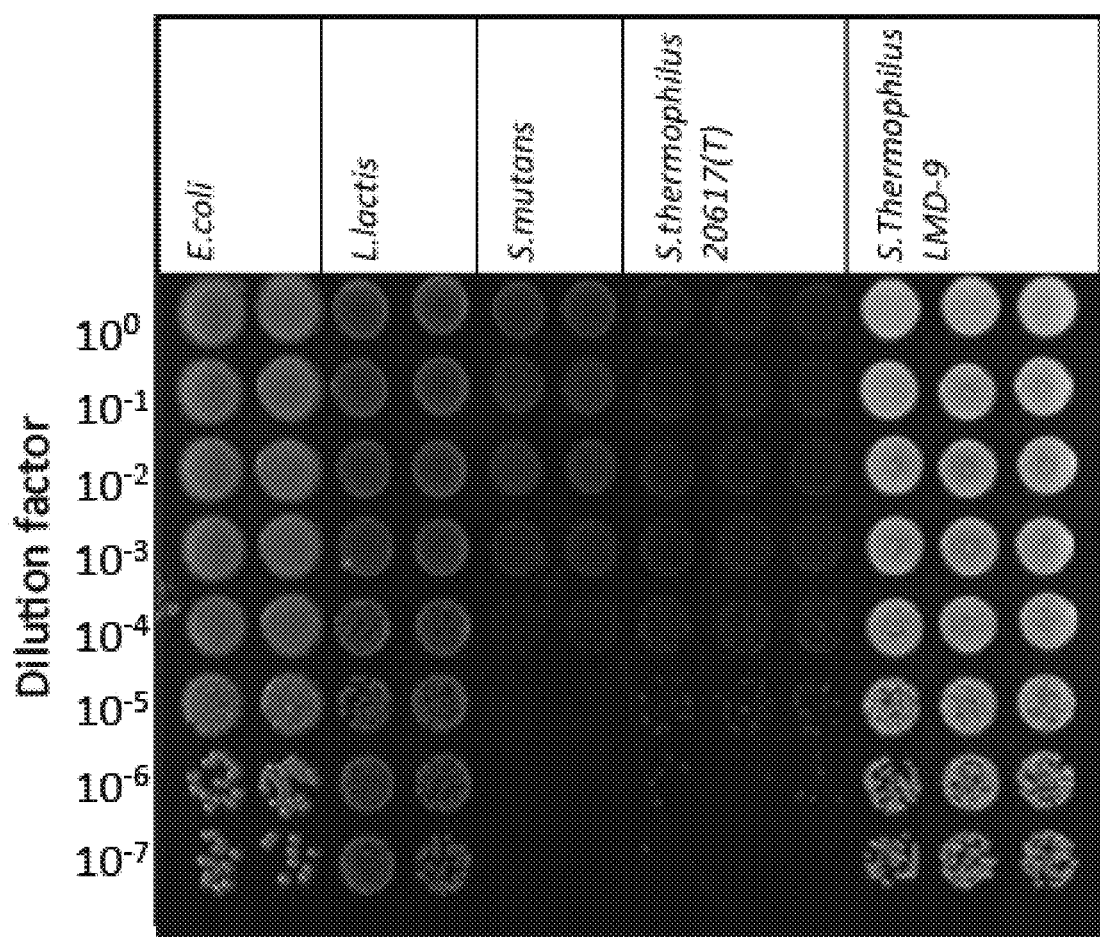
FIG. 3 shows a spot assay on TH-agar of the strains used in this work. All strains were grown on TH-agar at 37° C. for 20 hours. Serial dilutions of overnight cultures were done in duplicate for E. coli, L Lactis and S. mutans, and triplicate for both strains of S. thermophilus in order to count individual colonies.

We first set out to establish the bacterial strains and cultivation protocol that would support growth for all strains we planned to use for the co-cultivation experiments. We used S. thermophilus strain LMD-9 which was able to support a similar growth as E. coli in TH broth at 37° C. (FIG. 3).

Distinguishing the different bacteria from a mixed culture is important in order to determine cell number of the different species. With MacConkey agar is possible to selectively grow E. coli, however there is no specific media for selective growth of S.thermophilus. PEA agar is a selective medium that is used for the isolation of gram-positive (S.thermophilus) from gram-negative (E. coli). Additionally, we found that different concentrations of PEA partially inhibit the growth of other gram positives, which allow for selection between the other gram-positive bacteria used in this work (FIG. 4). 3 g l$^{-1}$ of PEA proved to selectively grow S. thermophilus LMD-9 while limiting growth of E. coli.

2.2 Design and Validation of Inducible System

An induction system for Streptococcus species was previously developed based on the Bacillus megaterium xylose operon (FIG. 5) by creating a heterologous xylose induction cassette (Xyl-S). The xylR and xylA promoters were replaced with S. mutans' constitutively expressed gyrA and ldh promoters respectively. This expression cassette for Streptococcus species showed differences in sensitivity and expression levels between different species, however the system was not tested in S. thermophilus (Xie et al. 2013). Therefore we first set out to validate the xylose induction cassette in S. thermophilus.

Figure 5:
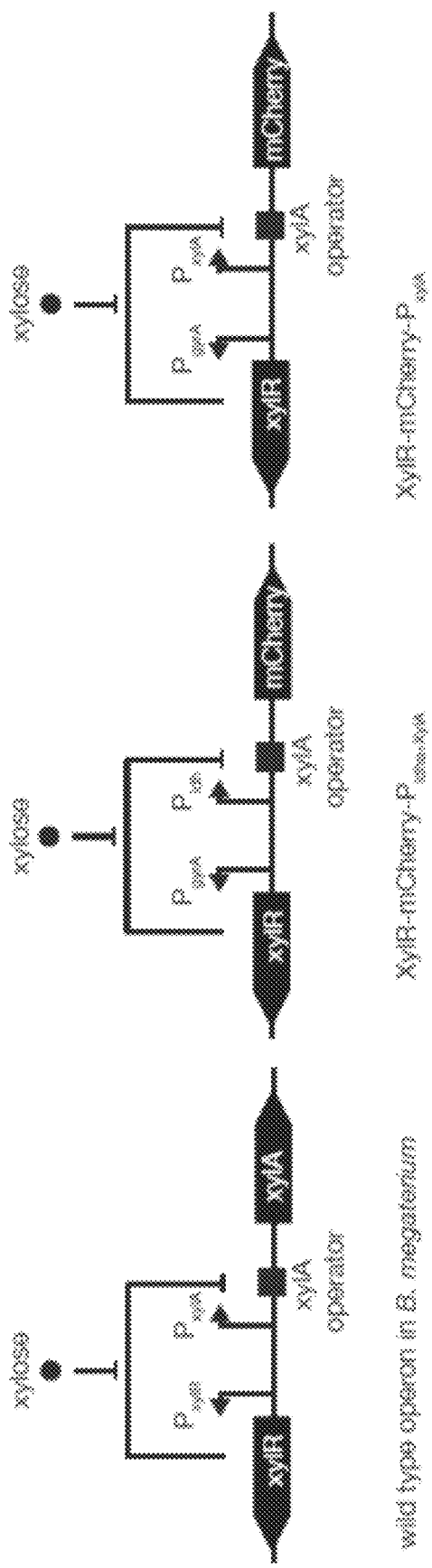
FIG. 5 illustrates construction of two xylose induction cassettes.

An alternative version of the induction cassette was constructed by only replacing the xylR promoter with the S. mutans' gyrA promoter but left the endogenous B. megaterium xylA promoter intact. During the design of the xylose inducible system we considered both versions of the inducible promoter, the natural $P_{XylA}$ promoter found in Bacillus megaterium and a hybrid promoter of the highly conserved promoter $P_{ldha}$ fused with the repressor binding sites of $P_{XylA}$ promoter (FIG. 5). Only a few Streptococcus species have been reported to metabolize xylose, and thus the presence of a regulatory machinery to recognize the xylA promoter in the other Streptococcus species is not likely. Therefore we constructed both xylose induction systems but only tested the inducibility of mCherry with the $P_{ldha+XylA}$ system.

Figure 6:
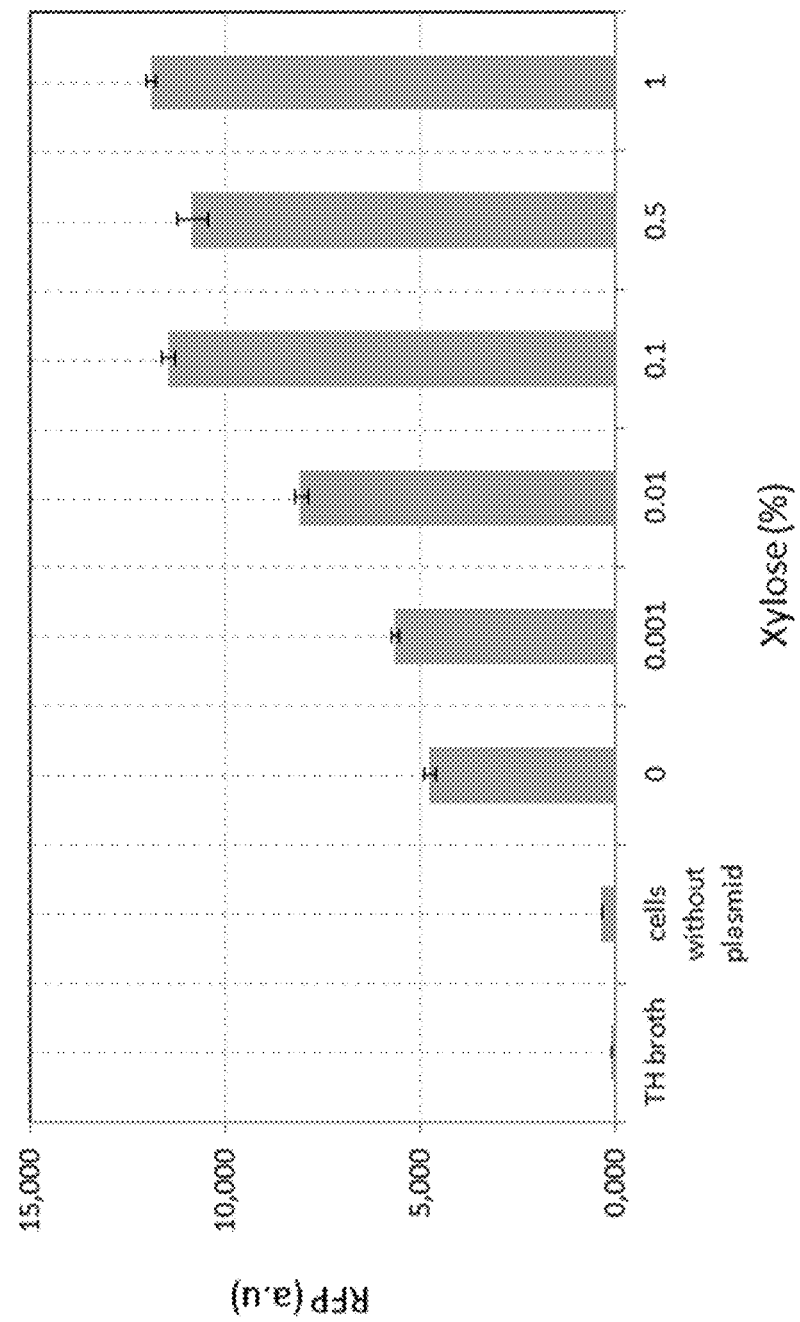
FIG. 6 demonstrated characterization of the xylose inducible cassette in Streptoccocus thermophilus LMD-9 with the plasmid pBAV1KT5-XylR-mCherry-Pldha. A clear response in fluorescence can be observed with increasing amount of xylose.

In order to determine mCherry inducible expression by xylose, mid-log cultures of cells with the plasmid (pBAV1KT5-XylR-mCherry $P_{ldha+XylA}$) were induced with different concentrations of xylose. Six hours after the induction we measured mCherry fluorescence in the cultures, where we observed substantially higher overall expression levels in cells carrying the plasmid (FIG. 6). It is worth noticing that the system showed a substantial level of basal expression even in the cultures where xylose was not added. This means that the system is 'leaky' and in context of the kill-array this can lead to cell death even before the system is induced with xylose. However, in the subsequent course of this study we used both versions of the plasmid (pBAV1KT5-XylR-mCherry-P$_{ldha+XylA}$ and pBAV1KT5-XylR-mCherry-P$_{xylA}$).

2.3 Design of CRISPR/CAS9 Array

Figure 7:
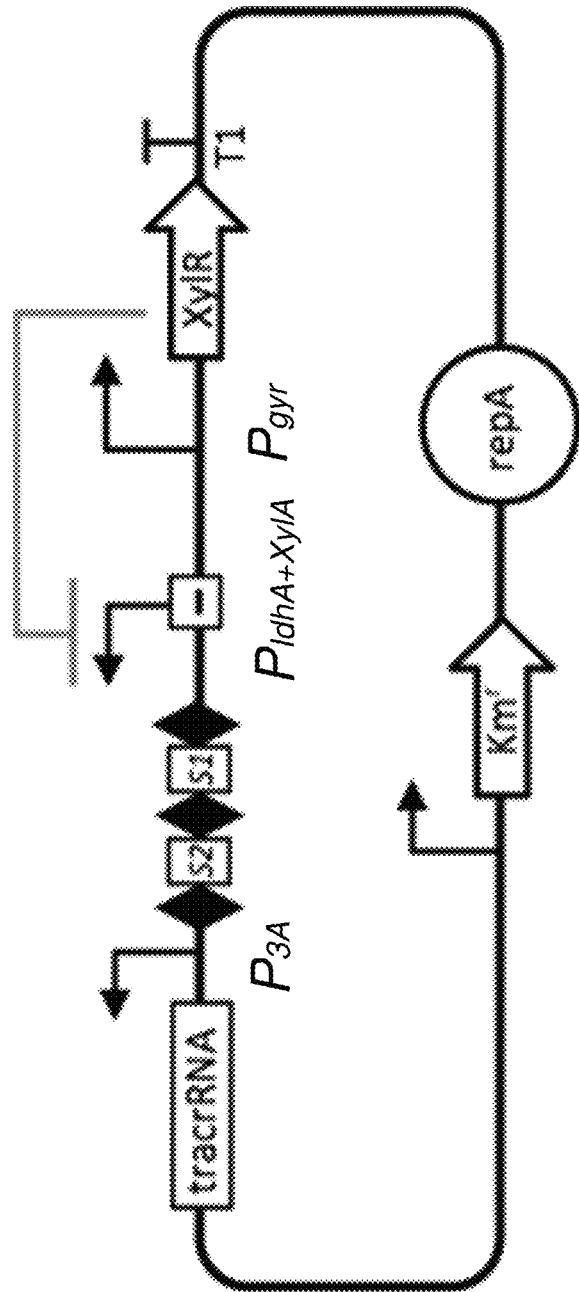
FIG. 7 illustrates the design of CRISPR array in pBAV1KT5-XylR-mCherry-$P_{ldha+XylA}$. The array contains 2 spacer sequences that target S. thermophilus genes under an inducible xylose promoter and a tracrRNA under a strong constitutive promoter P3A.

In order to determine if the genomic targeting spacers in a CRISPR array can cause death in *S.thermophilus* LMD-9, we inserted the CRISPR array we designed into the two xylose inducible systems previously constructed (pBAV1KT5-XylR-mCherry P$_{ldha+XylA}$ and pBAV1KT5-XylR-mCherry-P$_{xylA}$). In these plasmids we replaced mCherry with the gBlock containing the CRISPR array (FIG. 7). The variant with the P$_{ldha+XylA}$ promoter was expected to be stronger and have a higher basal activity than the P$_{xylA}$ (Xie et al. 2013).

2.4 Inhibition of Bacterial Population Growth Using Endogenous Cas9

Figure 8:
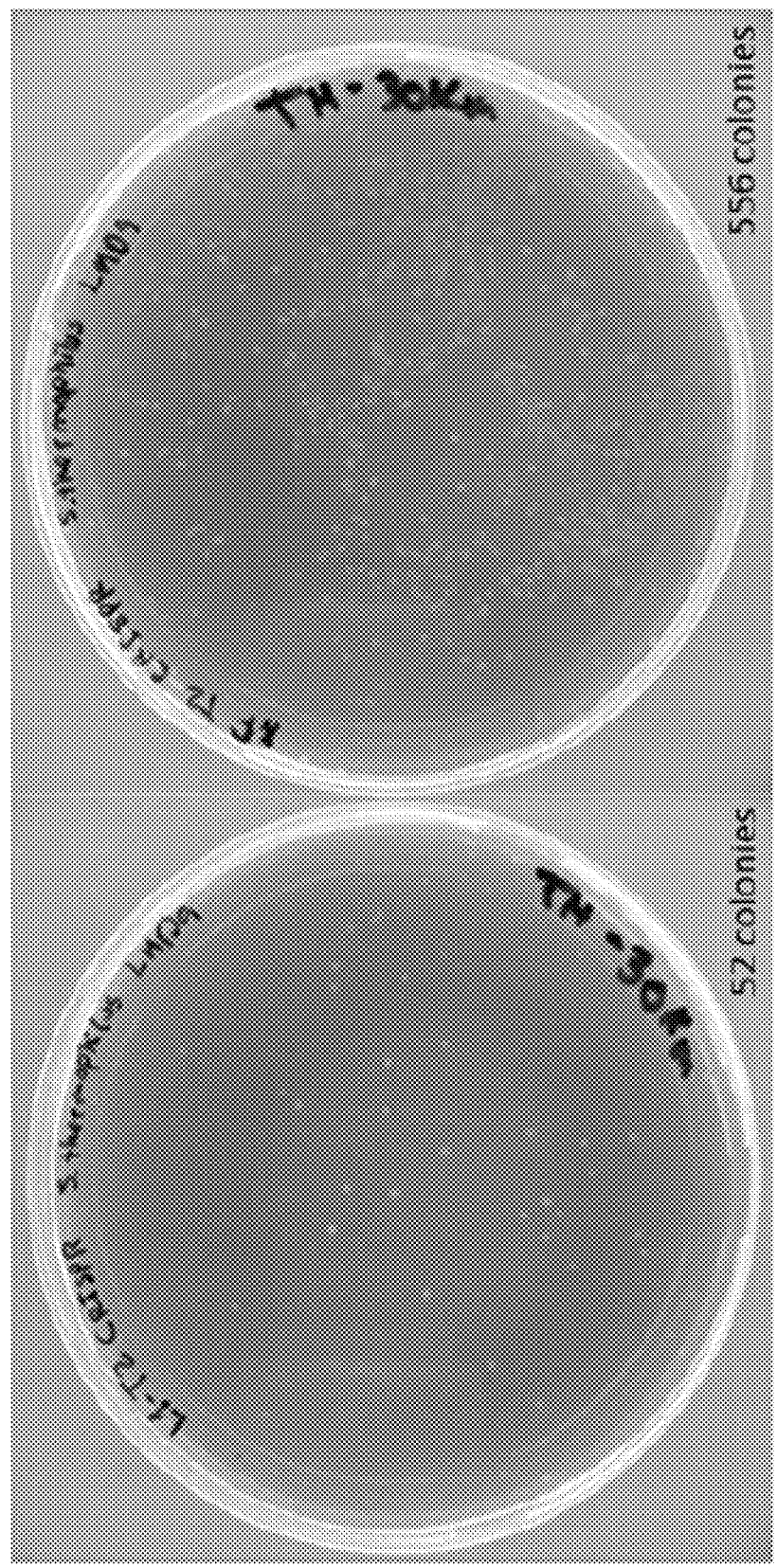
FIG. 8 shows transformation efficiency of Streptoccocus thermophilus LMD-9 with the plasmid pBAV1KT5-XylR-CRISPR-$P_{ldh+XylA}$ and with pBAV1KT5-XylR-CRISPR-$P_{XylA}$.

After we constructed the plasmids in *E. coli*, we transformed the plasmids into *S. thermophilus*. This would allow us to determine if we could cause cell death of a specific bacterial species. Interestingly, bacterial host population size (indicated by growing bacteria and counting colony numbers on agar plates) in *S. thermophilus* exposed to the plasmid containing the strong P$_{ldh+XylA}$ hybrid promoter was 10-fold less when compared to *S. thermophilus* exposed to the plasmid containing the weak, normal P$_{xylA}$ promoter (FIG. 8; 52 colonies with the strong array expression versus 556 colonies with weak array expression, 10.7-fold difference), the 2 strains having been transformed in parallel using the same batch of electrocompetent *S. thermophilus* cells. This suggests to us that the plasmid carrying the CRISPR array targeting *S. thermophilus* genes is able to kill the cells using the endogenous Cas nuclease and RNase III, thereby inhibiting population growth by 10-fold.

We expect that weak array expression in host cells transformed by the plasmid comprising the P$_{xylA}$ promoter led to a degree of cell killing, albeit much less than with the strong promoter plasmid. We expect that population growth inhibition that is greater than the observed 10-fold inhibition would be determined if a comparison of the activity of strong array expression was made with *S thermophilus* that is not exposed to any array-encoding plasmid (such as bacteria directly isolated from gut microbiota). Thus, we believe that array (or single guide RNA) expression in host cells for harnessing endogenous Cas nuclease will be useful for providing effective growth inhibition of target host cells in environmental, medical and other settings mentioned herein. Co-administration of antibiotic may also be useful to enhance the growth inhibition, particularly when one or more antibiotic resistance genes are targeted.

3. Discussion and Outlook

In this study we set out to design a CRISPR-array to specifically kill *S. thermophilus* using the endogenous Cas9 system. In order to gain control over the killing signal we sought to apply an inducible system that can be applied in *S. thermophilus*. The xylose inducible XylR system from *B. megaterium* was previously applied in *S. nutans* (Xie, 2013) but not in *S. thermophilus*. In this study we demonstrated the functionality of the xylR induction system using the designed XylR-mCherry-Pldha circuit in *S. thermophilus*. We found 0.1% wt/vol is sufficient to fully induce the XylR system in *S. thermophilus* (FIG. 6).

Figure 4:
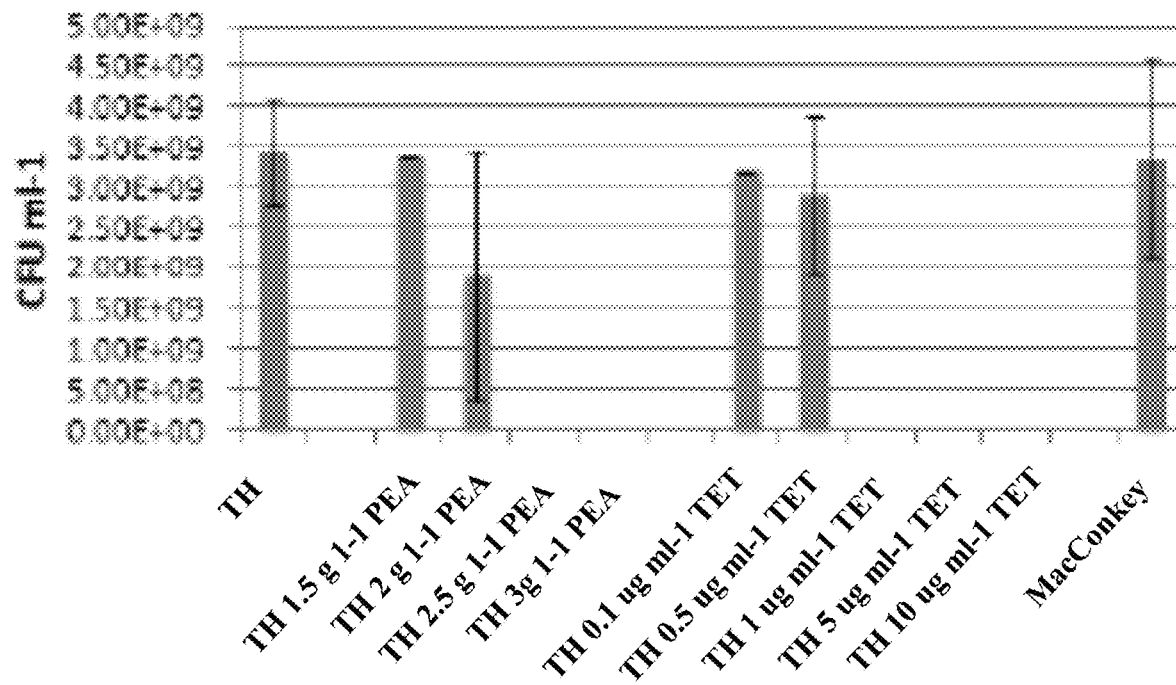
FIG. 4 shows selective growth of S. thermophilus, S. nutans, L. lactis and E. coli under different culture conditions. Tetracycline cannot be used to selectively grown S. thermophilus LMD-9. However, 3 g l$^{-1}$ of PEA proved to selectively grow S. thermophilus LMD-9 while limiting growth of E. coli.
Figure 4:
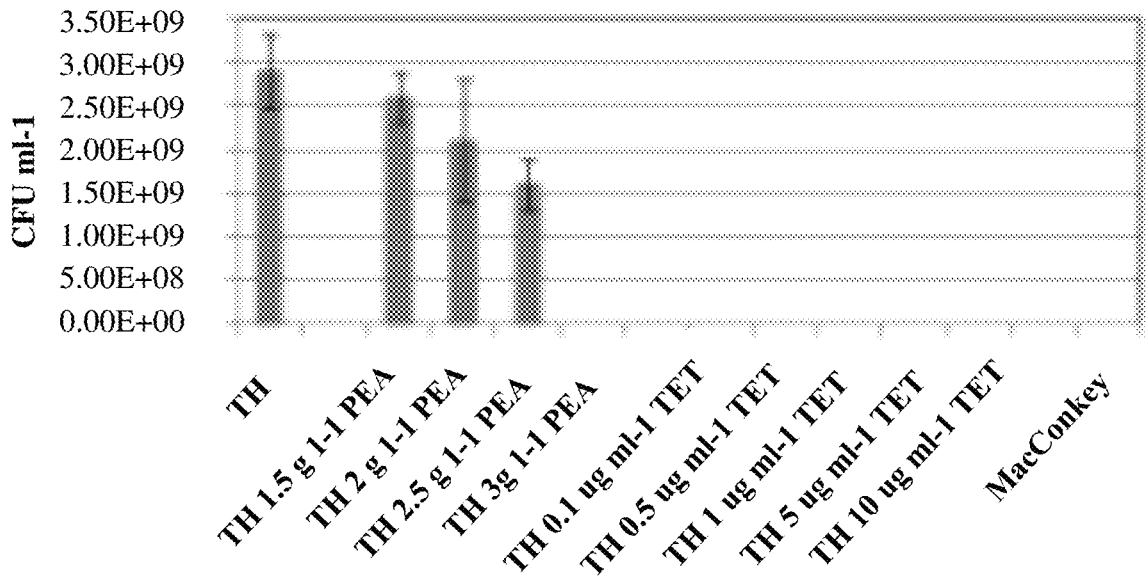
Figure 4:
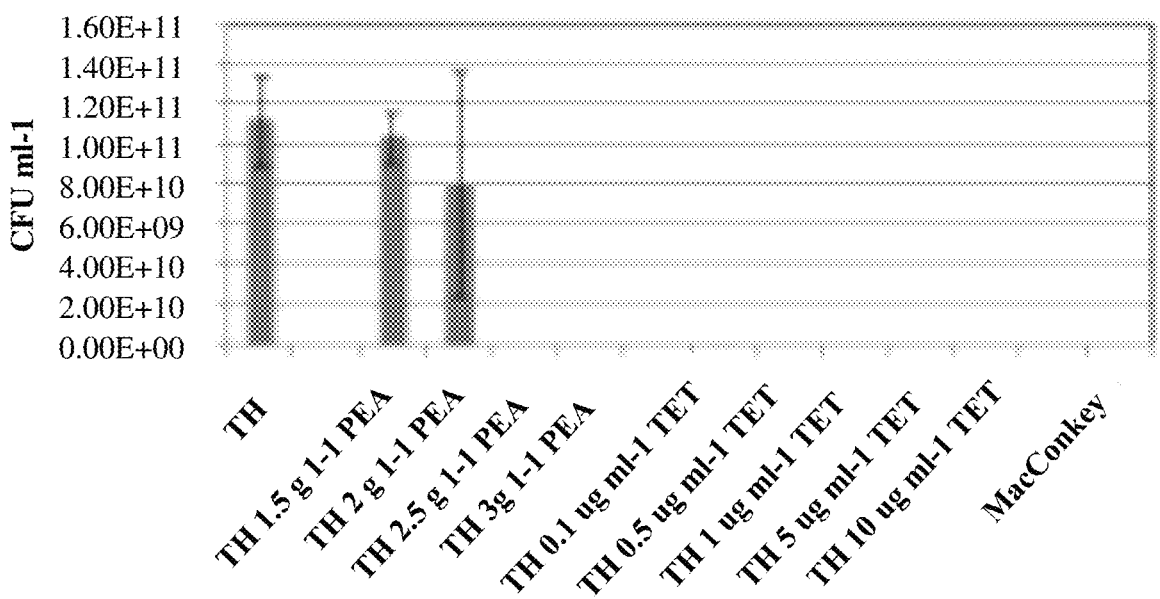
Figure 4:
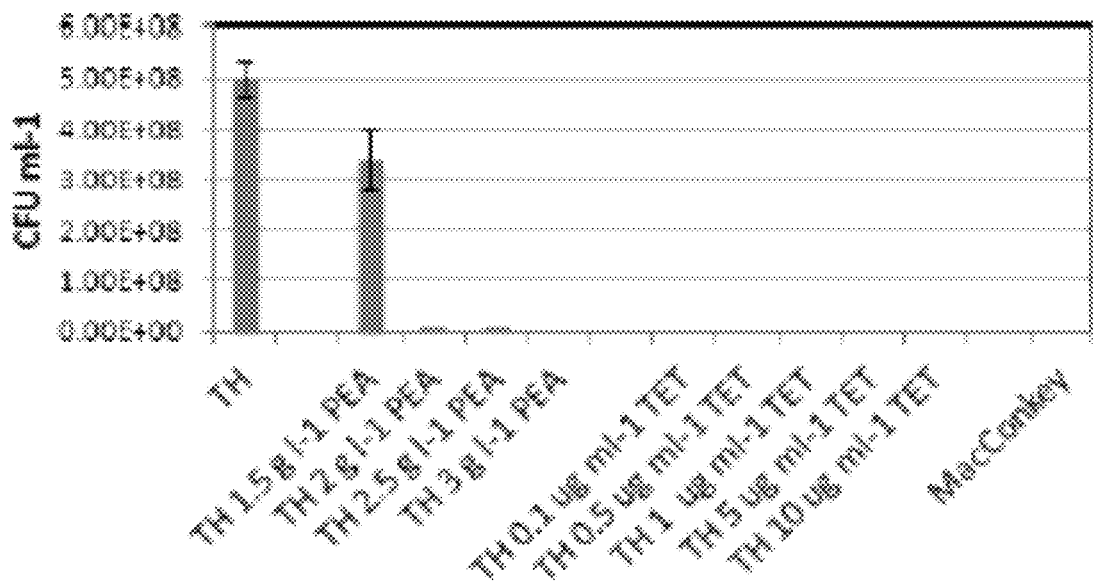
Figure 4:
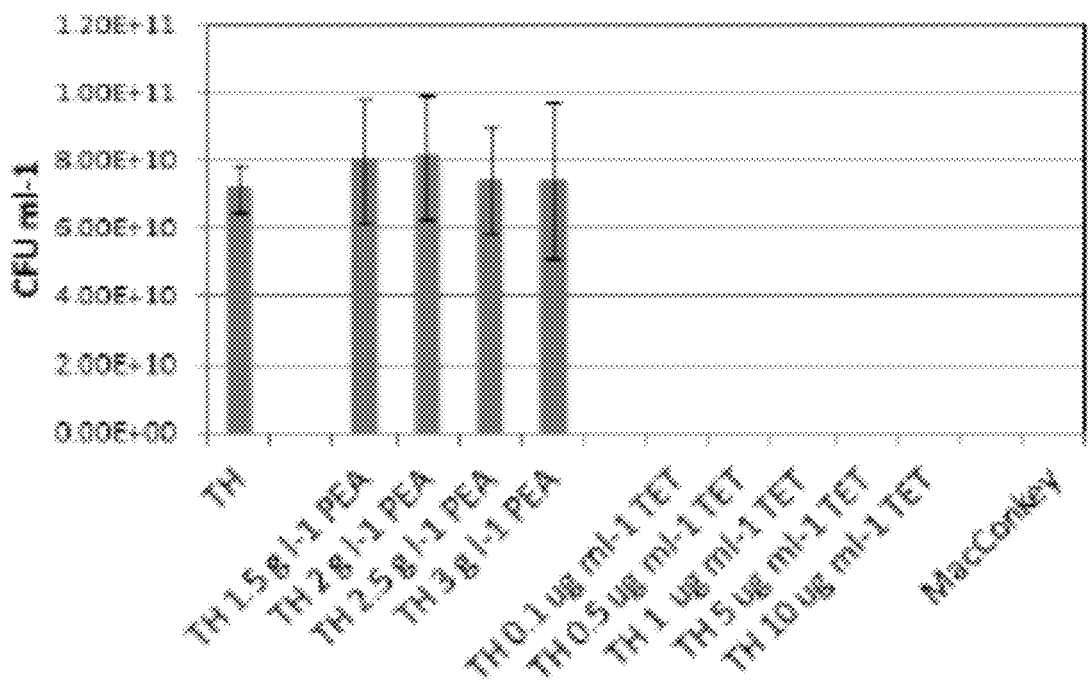

In order to observe abundance when co-culturing *S. thermophilus* and *E. coli* we established that supplementation of the culture media with 3 g l$^{-1}$ of PEA, allows for the selective growth of *S. thermophilus* while limiting the growth of *E. coli* (FIG. 4).

Figure 9:
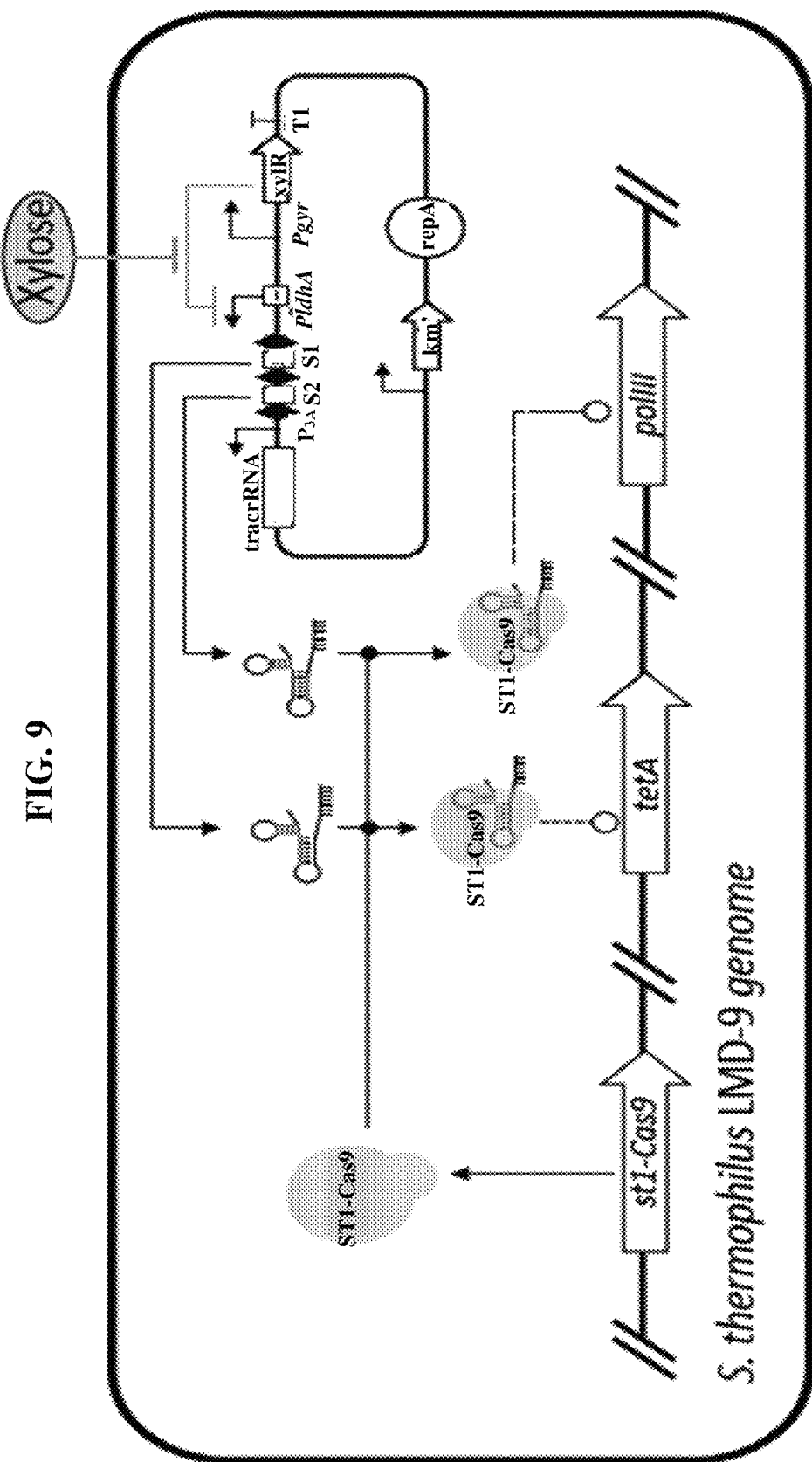
FIG. 9 shows a schematic of the xylose-inducible CRISPR device. Upon induction of xylose the CRISPR array targeting both polIII and tetA on the S. thermophiles LMD-9 genome are expressed. Together with the constitutively expressed tracrRNA a complex is formed with Cas9. This complex will introduce a double stranded break in the tetA and polIII genes in the S. thermophilus LMD-9 genome resulting in limited cell viability.

A ST1-CRISPR array, targeting the DNA polymerase III subunit alpha and a tetA like gene in the *S. thermophilus* LMD-9 genome, was placed under the xylose inducible promoter (Xie et al. 2013). Targeting these regions should lead to a double strand break and thus limit *S. thermophilus* viability (FIG. 9). Since the engineered array was designed to target *S. thermophilus* genome using the endogenous CRISPR/Cas machinery to process the encoded CRISPR array, the array is expected to have no influence on growth of unrelated strains such as *E. coli*, even similar targets could be found on its genome. This was successfully tested in a mixed bacterial population (simulating aspects of a human microbiota) as discussed in Example 3.

The demonstration of the ability to inhibit host cell growth on a surface is important and desirable in embodiments where the invention is for treating or preventing diseases or conditions mediated or caused by microbiota as disclosed herein in a human or animal subject. Such microbiota are typically in contact with tissue of the subject (eg, gut tissue) and thus we believe that the demonstration of activity to inhibit growth of a microbiota bacterial species (exemplified by *Streptococcus*) on a surface supports this utility.

Example 2: Specific Microbiota Bacterial Population Growth Inhibition in Different Strains Example 1 demonstrated specific growth inhibition of *Streptococcus thermophilus* LMD-9. Here we demonstrate growth inhibition can also be obtained in a second strain: *Streptococcus thermophilus* DSM 20617. Methods described in Example 1 were, therefore, applied to the latter strain (except that selective media for *S.thermophilus* DSM 20617 was TH media supplemented with 2.5 g l$^{-1}$ of 2-phenylethanol (PEA)).

Figure 10:
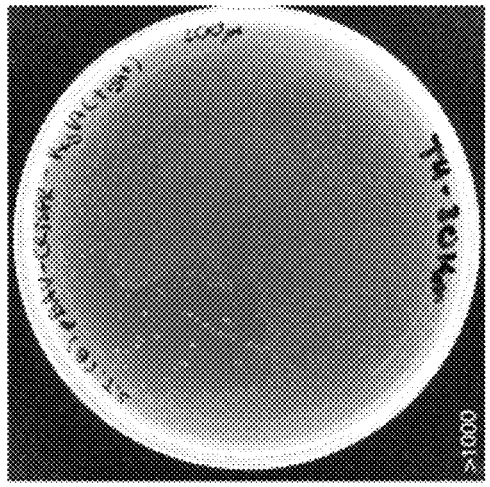
FIG. 10 shows growth inhibition of Streptoccocus thermophilus DSM 20617(T) with the plasmid pBAV1KT5-XylR-CRISPR-PXylA or pBAV1KT5-XylR-CRISPR-PldhA+XylA, not induced and induced. Picture taken after 63H of incubation. Colony counts in bottom left corner (top row: >1000, >1000, bottom row: 336, 113).
Figure 10:
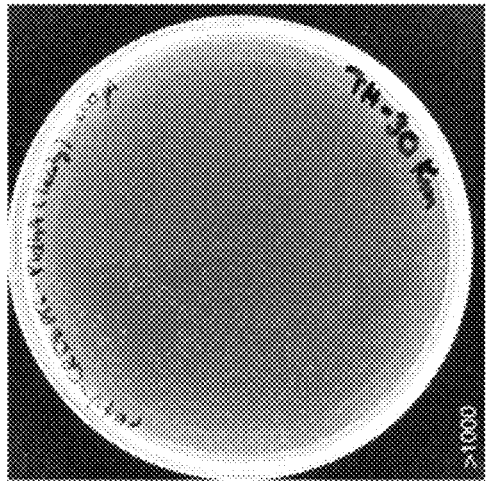
Figure 10:
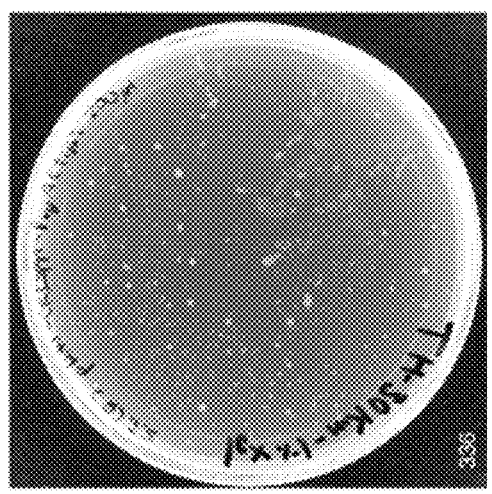
Figure 10:
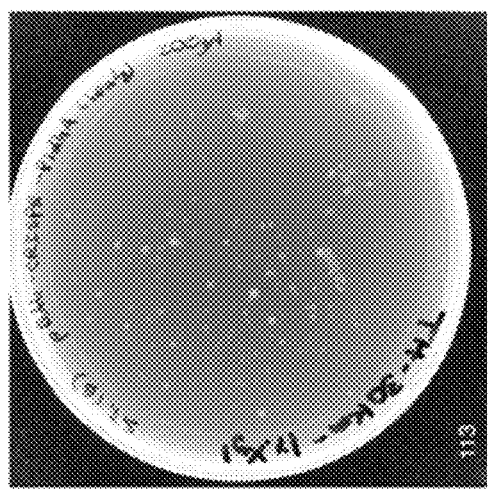

*Streptococcus thermophilus* DSM 20617 transformed with the CRISPR array plasmids were incubated for recovery in liquid media for a period of 3 hours at 37° C. that would allow for expression of kanamycin resistance. After a recovery period, cells were plated in different selection media in presence of 1% xylose in order to induce cell death, and without xylose as a control (FIG. 10). It is evident that; (1) by xylose induction the growth of *S. thermophilus* can be inhibited (around 10-fold for the 'strong' promoter plasmid versus control), (2) the 'strong' system (pBAV1KT5-XylR-CRISPR-P$_{ldhA}$) results in more growth reduction than the 'weak' system (pBAV1KT5-XylR-CRISPR-P$_{xylA}$)

Example 3: Selective Bacterial Population Growth Inhibition in a Mixed Consortium of Different Microbiota Species We next demonstrated selective growth inhibition of a specific bacterial species in a mixed population of three species. We selected species found in gut microbiota of humans and animals (*S thermophilus* DSM 20617(T), *Lactobacillus lactis* and *E coli*). We included two gram-positive species (the *S thermophilus* and *L lactis*) to see if this would affect the ability for selective killing of the former species; furthermore to increase difficulty (and to more closely simulate situations in microbiota) *L lactis* was chosen as this is a phylogenetically-related species to *S thermophilus* (as indicated by high 16s ribosomal RNA sequence identity between the two species). The *S thermophilus* and *L lactis* are both Firmicutes. Furthermore, to simulate microbiota, a human commensal gut species (*E coli*) was included.

1. Materials & Methods

Methods as set out in Example 1 were used (except that selective media was TH media supplemented with 2.5 g l$^{-1}$ of 2-phenylethanol (PEA)).

1.1 Preparation of Electro-Competent *L. lactis* Cells

Overnight cultures of *L. lactis* in TH media supplemented with 0.5 M sucrose and 1% glycine were diluted 100-fold in 5 ml of the same media and grown at 30° C. to an OD$_{600}$ between 0.2-0.7 (approximately 2 hours after inoculation). The cells were collected at 7000×g for 5 min at 4° C. and washed three times with 5 ml of ice cold wash buffer (0.5 M sucrose+10% glycerol). After the cells were washed, they were suspended to an OD$_{600}$ of 15-30 in electroporation buffer (0.5 M sucrose, 10% glycerol and 1 mM MgCl$_2$). The cells in the electroporation buffer were kept at 4° C. until use (within one hour) or aliquot 50 µl in eppendorf tubes, freezing them in liquid nitrogen and stored at −80° C. for later use.

Electroporation conditions for all species were as described in Example 1.

1.2 Activation of CRISPR Array: Consortium Experiments.

*S. thermophilus* DSM 20617, *L. lactis* MG1363 and *E. coli* TOP10 were genetically transformed with the plasmid containing the CRISPR array targeting the DNA polymerase III and tetA of *S. thermophilus*. After transformation all cells were grown alone and in co-culture for 3 hours at 37° C. allowing for recovery to develop the antibiotic resistance encoded in the plasmid. We decided to use transformation efficiency as a read out of CRISPR-encoded growth inhibition. Therefore, after allowing the cells for recovery the cultures were plated in TH media, TH supplemented with PEA and MacConkey agar all supplemented with Kanamycin, and induced by 1% xylose.

2. Results 2.0 Phylogenetic Distance Between *L. lactis*, *E. Coli* and *S. thermophilus*

Figure 11:
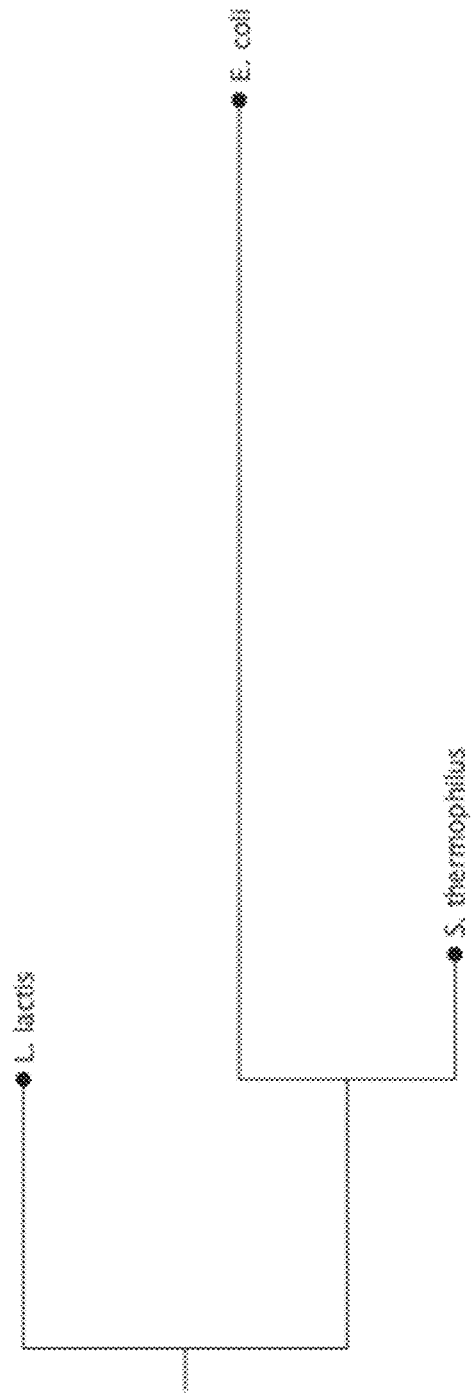
FIG. 11 shows a maximum-likelihood phylogenetic tree of 16S sequences from S. thermophilus, L. lactis and E. coli.

The calculated sequence similarity in the 16S rRNA-encoding DNA sequence of the *S. thermophilus* and *L. lactis* was determined as 83.3%. The following 16S sequences were used: *E. coli*: AB030918.1, *S. thermophilus*: AY188354.1, *L. lactis*: AB030918. The sequences were aligned with needle (http://www.ebi.ac.uk/Tools/psdemboss_needle/nucleotide.html) with the following parameters: -gapopen 10.0-gapextend 0.5-endopen 10.0-endextend 0.5-aformat3 pair -snucleotide1 -snucleotide2. FIG. 11 shows the maximum-likelihood phylogenetic tree of 16S sequences from *S. thermophilus*, *L. lactis* and *E. coli*.

2.1 Growth Condition and Selective Media

*S. thermophilus* and *L. lactis* are commonly used in combination in many fermented foods and yoghurt. We chose these strains since they are commonly known to be gut microbes that form an intimate association with the host and previous characterizations of the 16S ribosomal RNA region of *S. thermophilus* and *L. lactis* have shown that these organisms are phylogenetically closely related (Ludwig et al., 1995). In parallel we also evaluated the growth of *E. coli* for our mixed population co-culture experiments, since this organism is also commonly found in gut microbe communities. We first set out to establish the bacterial strains and cultivation protocol that would support growth for all strains we planned to use for the co-cultivation experiments. We found that all strains were able to support growth in TH broth at 37° C. (FIG. 3).

Distinguishing the different bacteria from a mixed culture is important in order to determine cell number of the different species. With MacConkey agar is possible to selectively grow *E. coli*, however there is no specific media for selective growth of *S. thermophilus*. PEA agar is a selective medium that is used for the isolation of gram-positive (*S. thermophilus*) from gram-negative (*E. coli*). Additionally, different concentrations of PEA partially inhibit the growth of the different grams positive species and strains, which allow for selection between the other gram-positive bacteria used in this work. Using 2.5 g l$^{-1}$ of PEA proved to selectively grow *S. thermophilus* while limiting growth of *L. lactis* and *E. coli*.

All strains were transformed with a plasmid that used the vector backbone of pBAV1KT5 that has a kanamycin selection marker; we found that using media supplemented with 30 ug ml$^{-1}$ of kanamycin was enough to grow the cells while keeping the plasmid.

2.3 Transformation & Selective Growth Inhibition in a Mixed Population

We transformed *S. thermophilus*, *L. lactis* and *E. coli* with plasmid containing the CRISPR array and cultured them in a consortium of all the bacterial species combined in equal parts, which would allow us to determine if we could cause cell death specifically in *S.thermophilus*. We transformed all the species with either the pBAV1KT5-XylR-CRISPR-P$_{XylA}$ or pBAV1KT5-XylR-CRISPR-P$_{ldha+XylA}$ plasmid.

Figure 12:
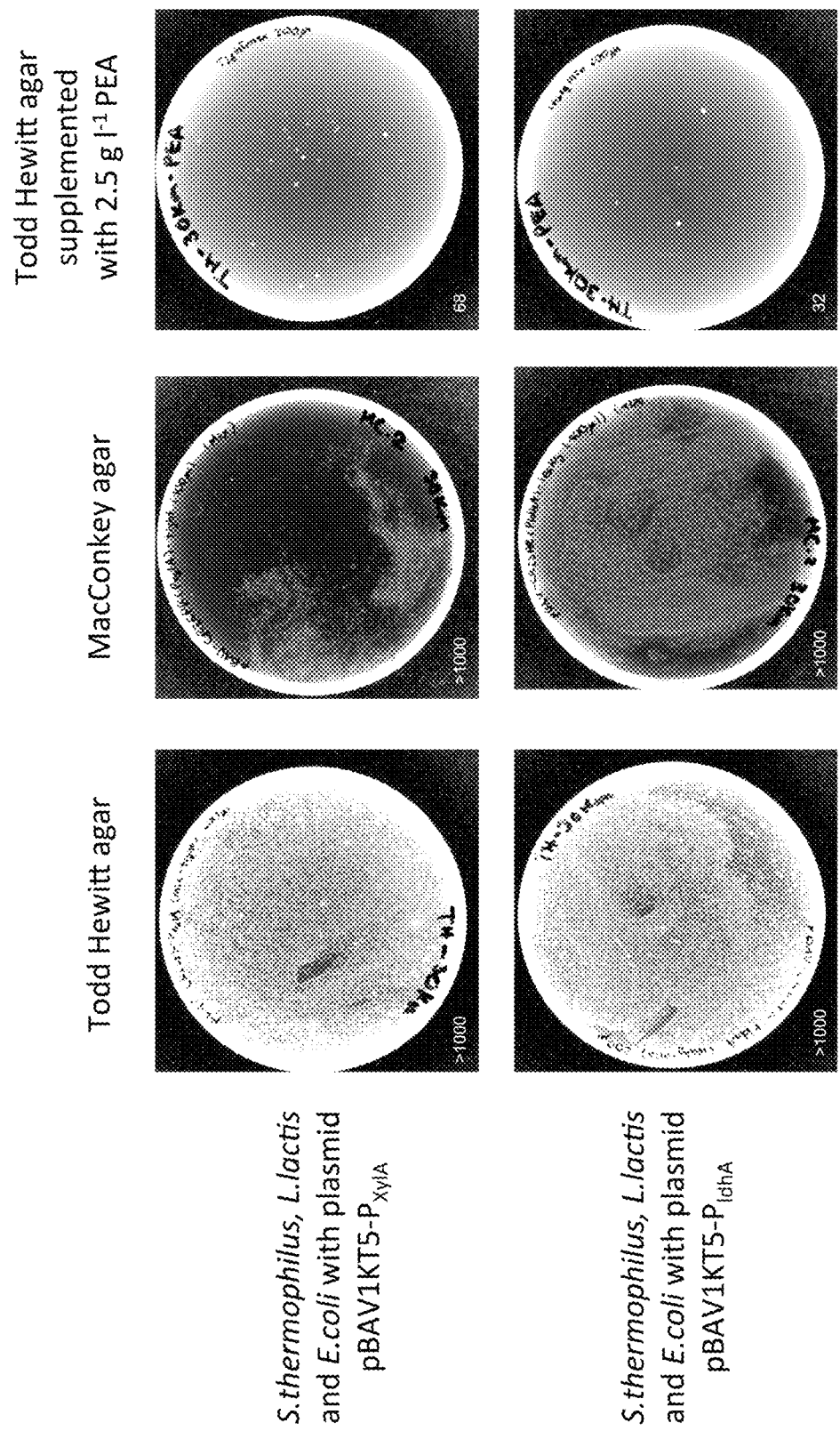
FIG. 12 shows the selective S thermophilus growth inhibition in a co-culture of E. coli, L. lactis and S. thermophiles harboring either the pBAV1KT5-XylR-CRISPR-PxylA or the pBAV1KT5-XylR-CRISPR-PldhA+XylA plasmid. No growth difference is observed between E. coli harboring the pBAV1KT5-XylR-CRISPR-PxylA or the pBAV1KT5-XylR-CRISPR-PldhA+XylA plasmid. However, S. thermophiles (selectively grown on TH agar supplemented with 2.5 gl-1 PEA) shows a decrease in transformation efficiency between the pBAV1KT5-XylR-CRISPR-PxylA (strong) or the pBAV1KT5-XylR-CRISPR-PldhA+XylA (weak) plasmid as we expected. We thus demonstrated a selective growth inhibition of the target S. thermophilus sub-population in the mixed population of cells. Colony counts in bottom left corner (top row: >1000, >1000, 68, bottom row: >1000, >1000, 32).

'FIG. 12 shows the selective *S thermophilus* growth inhibition in a co-culture of *E. coli*, *L. lactis* and *S. thermophilus* harboring either the pBAV1KT5-XylR-CRISPR-P$_{xylA}$ or the pBAV1KT5-XylR-CRISPR-P$_{ldhA+xylA}$ plasmid. No growth difference is observed between *E. coli* harboring the pBAV1KT5-XylR-CRISPR-P$_{xylA}$ or the pBAV1KT5-XylR-CRISPR-P$_{ldnA+xylA}$ plasmid (middle column). However, *S. thermophilus* (selectively grown on TH agar supplemented with 2.5 gl$^{-1}$ PEA, last column) shows a decrease in transformation efficiency between the pBAV1KT5-XylR-CRISPR-P$_{xylA}$ (strong) or the pBAV1KT5-XylR-CRISPR-P$_{ldhA+xylA}$ (weak) plasmid as we expected. We thus demonstrated a selective growth inhibition of the target *S thermophilus* sub-population in the mixed population of cells.

REFERENCES

1. Barrangou, R., Fremaux, C., Deveau, H., Richards, M., Patrick Boyaval, Moineau, S., . . . Horvath, P. (2007). CRISPRProvides Acquired Resistance Against Viruses in Prokaryotes. *Science*, 315(March), 1709-1712.
2. Bryksin, A. V, & Matsumura, I. (2010). Rational design of a plasmid origin that replicates efficiently in both gram-positive and gram-negative bacteria. *PloS One*, 5(10), e13244.
3. Chan C T Y, Lee J W, Cameron D E, Bashor C J, Collins J J: "Deadman" and "Passcode" microbial kill switches for bacterial containment. *Nat Chem Biol* 2015, 12(December): 1-7.
4. Horvath, P., Romero, D. A., Coûté-Monvoisin, A.-C., Richards, M., Deveau, H., Moineau, S., . . . Barrangou, R. (2008). Diversity, activity, and evolution of CRISPR loci in *Streptococcus thermophilus*. *Journal of Bacteriology*, 190(4), 1401-12.
5. Ludwig, E. S., Klipper, R., Magrum L., Wose C., & Stackebrandt, E. (1985). The phylogenetic position of *Streptococcus* and *Enterococcus*. *Journal of Gencwl Microhiologj.*, 131, 543-551.
6. Mercenier, A. (1990). Molecular genetics of *Streptococcus thermophilus*. *FEMS Microbiology Letters*, 87(1-2), 61-77. \

7. Samaržlija, D., Antunac, N., & Havranek, J. (2001). Taxonomy, physiology and growth of *Lactococcus lactis*: a review. *Mljekarstvo,* 51(1), 35-48. Retrieved from
8. Sapranauskas, R., Gasiunas, G., Fremaux, C., Barrangou, R., Horvath, P., & Siksnys, V. (2011). The *Streptococcus thermophilus* CRISPR/Cas system provides immunity in *Escherichia coli*. *Nucleic Acids Research,* 39(21), 9275-9282.
9. Somkuti, G. A., & Steinberg, D. H. (1988). Genetic transformation of *Streptococcus thermophilus* by electroporation. *Biochimie,* 70(4), 579-585
10. Sorg, R. A., Kuipers, O. P., & Veening, J.-W. (2014). Gene expression platform for synthetic biology in the human pathogen *Streptococcus pneumoniae*. *ACS Synthetic Biology,* 4(3), 228-239.
11. Suvorov, a. (1988). Transformation of group A streptococci by electroporation. *FEMS Microbiology Letters,* 56(1), 95-99.
12. Xie, Z., Qi, F., & Merritt, J. (2013). Development of a tunable wide-range gene induction system useful for the study of streptococcal toxin-antitoxin systems. *Applied and Environmental Microbiology,* 79(20), 6375-84.
13. Zhang, X. Z., & Zhang, Y. H. P. (2011). Simple, fast and high-efficiency transformation system for directed evolution of cellulase in *Bacillus subtilis*. *Microbial Biotechnology,* 4(1), 98-105.

Example 4: Altering the Ratio of *Clostridium dificile* in a Mixed Gut Microbiota Population Alteration of the ratio of bacteria will be performed according to the present example, which is described by reference to knocking-down *Clostridium dificile* bacteria in a mixed gut microbiota sample. The sample will contain *Bacteroides* and metronidazole (MTZ)-resistant *C dificile* strain 630 sub-populations. Ex vivo the mixed population is combined with a population of carrier bacteria (*Lactobacillus acidophilus* La-14 and/or La-5) that have been engineered to contain CRISPR arrays.

Each CRISPR array is comprised on a plasmid that is compatible with the carrier bacterium and *C dificile* cells. The array is comprised by a *Bacteroides* thetaiotamicron CTnDot transposon that also comprises oriT, an intDOT sequence, a tetQ-rteA-rteB operon, rteC and the operon xis2c-xis2d-orf3-exc. In one experiment, mob and tra operons are excluded (instead relying on these supplied by *Bacteroides* cells to which the transposons are transferred in the mixture combined with the carrier bacteria). In another experiment, the mob and tra operons are included in the transposons.

Protein translocation across the cytoplasmic membrane is an essential process in all bacteria. The Sec system, comprising at its core an ATPase, SecA, and a membrane channel, SecYEG, is responsible for the majority of this protein transport. A second parallel Sec system has been described in a number of Gram-positive species. This accessory Sec system is characterized by the presence of a second copy of the energizing ATPase, SecA2; where it has been studied, SecA2 is responsible for the translocation of a subset of Sec substrates. In common with many pathogenic Gram-positive species, *Clostridium difficile* possesses two copies of SecA. Export of the S-layer proteins (SLPs) and an additional cell wall protein (CwpV) is dependent on SecA2. Accumulation of the cytoplasmic precursor of the SLPs SlpA and other cell wall proteins is observed in cells expressing dominant-negative secA1 or secA2 alleles, concomitant with a decrease in the levels of mature SLPs in the cell wall. Furthermore, expression of either dominant-negative allele or antisense RNA knockdown of SecA1 or SecA2 dramatically impairs growth, indicating that both Sec systems are essential in *C. difficile*.

*C. difficile* Strain 630 (epidemic type X) has a single circular chromosome with 4,290,252 bp (G+C content=29.06%) and a circular plasmid with 7,881 bp (G+C content=27.9%). The whole genome has been sequenced and found that 11% of the genome consists of mobile genetic elements such as conjugative transposons. These elements provide *C. difficile* with the genes responsible for its antimicrobial resistance, virulence, host interaction and the production of surface structures. For example, the cdeA gene of *C. difficile* produces a multidrug efflux pump which was shown to be homologous to known efflux transporters in the multidrug and toxic compound extrusion (MATE) family. The protein facilitates energy-dependent and sodium-coupled efflux of drugs from cells. In addition, the cme gene in *C. difficile* has been shown to provide multidrug resistance in other bacteria.

The array comprises a 121-S1-R1' CRISPR unit (spacer flanked by two CRISPR repeats) for targeting a sequence in an essential gene (SecA2) of *C dificile* cells. In another experiment, targeting is to the cdeA gene in the presence of MTZ and optionally one or more other anti-*C dificile* antibiotics. Each spacer (S) comprises a 20 mer nucleotide sequence of the SecA or cdeA gene, wherein the sequence comprises a PAM of a *C dificile* strain 630 CRISPR/Cas system that is cognate to the repeat sequences. Each repeat is identical to a *C dificile* strain 630 repeat.

The repeats function with Cas that is endogenous to the *C dificile* cells in the mixed population. The mixed population of bacteria is retrieved as an ex vivo sample from a stool sample of a human patient suffering from *C dificile* infection. The mixed population is mixed with the carrier bacteria in vitro and incubated at 37 degrees centigrade under anaerobic conditions to simulate gut conditions in the presence of tetracycline. It is expected that transposons containing the CRISPR arrays will be transferred to *Bacteroides* and *C dificile* cells in the mixture. Furthermore, it is expected that the target sites in the latter cells will be cut by Cas nuclease action, thus reducing the proportion of *C dificile* in the mixed population (and increasing the ratio of *Bacteroides* versus *C dificile*).

In a follow-on experiment, a drink is produced comprising the carrier bacteria and this is consumed by the human patient once or twice for several consecutive days with or without an ant-acid. The patient is also administered with tetracycline during the treatment period. It is expected that stool analysis will reveal that the proportion of *C difficile* in the stool samples will reduce (and the ratio of *Bacteroides* versus *C difficile* will increase).

Example 5: Vector-Encoded System for Selective Species & Strain Growth Inhibition in a Mixed Bacterial Consortium In Example 3 we surprisingly established the possibility of harnessing endogenous Cas nuclease activity in host bacteria for selective population growth inhibition in a mixed consortium of different species. We next explored the possibility of instead using vector-encoded Cas activity for selective population growth inhibition in a mixed consortium of different species. We demonstrated selective growth inhibition of a specific bacterial species in a mixed population of three different species, and further including a strain alternative to the target bacteria. We could surprisingly show selective growth inhibition of just the target strain of the predetermined target species. Furthermore, the alternative strain was not targeted by the vector-encoded CRISPR/Cas system, which was desirable for establishing the fine specificity of such vector-borne systems in a mixed bacterial consortium that mimicked human or animal gut microbiota elements.

We selected species found in gut microbiota of humans and animals (*Bacillus subtilis, Lactobacillus lactis* and *E coli*). We included two strains of the human commensal gut species, *E coli*. We thought it of interest to see if we could distinguish between closely related strains that nevertheless had sequence differences that we could use to target killing in one strain, but not the other. This was of interest as some strains of *E coli* in microbiota are desirable, whereas others may be undesirable (eg, pathogenic to humans or animals) and thus could be targets for Cas modification to knockdown that strain.

1. Material and Methods 1.1. Plasmids and Strains

See Tables 7 and 8. All strains were cultivated in Todd-Hewitt broth (TH) (T1438 Sigma-Aldrich), in aerobic conditions and at 37° C., unless elsewhere indicated. The strains were stored in 25% glycerol at −80° C.

The self-targeting sgRNA-Cas9 complex was tightly regulated by a theophylline riboswitch and the AraC/$P_{BAD}$ expression system respectively. Tight regulation of Cas9 is desired in order to be carried stably in *E. coli*. The plasmid contained the exogenous Cas9 from *Streptococcus pyogenes* with a single guide RNA (sgRNA) targeting *E. coli*'s K-12 strains. Therefore K-12 derived strains TOP10 was susceptible to double strand self-cleavage and consequent death when the system was activated. *E. coli* strains like Nissle don't have the same target sequence therefore they were unaffected by the sgRNA-Cas9 activity. See Tables 9-11 below, which show sequences used in Example 9. We chose a target sequence (ribosomal RNA-encoding sequence) that is conserved in the target cells and present in multiple copies (7 copies), which increased the chances of cutting host cell genomes in multiple places to promote killing using a single gRNA design.

Figure 13:
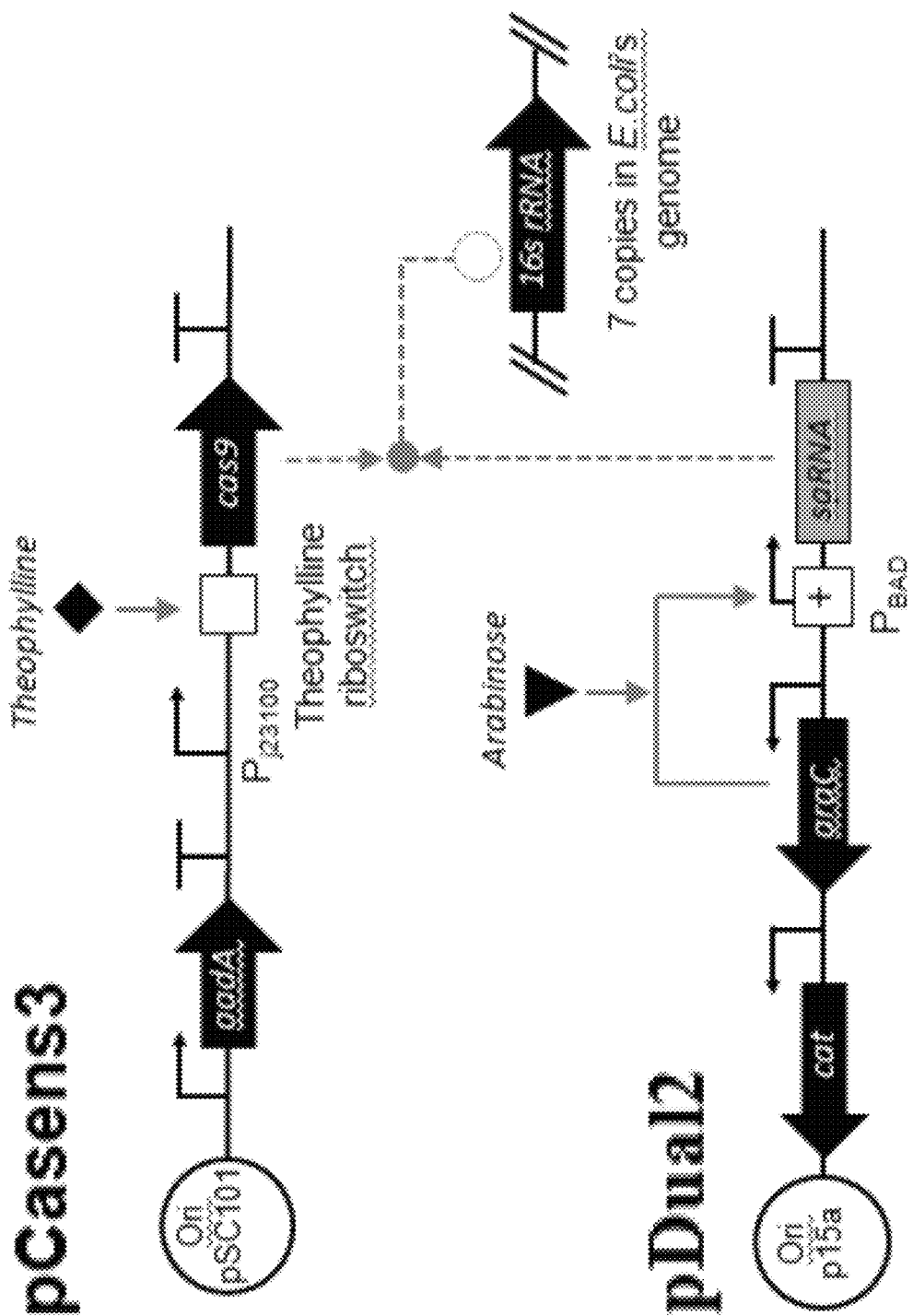
FIG. 13 shows regulators controlling the expression of spCas9 and the self-targeting sgRNA targeting the ribosomal RNA subunit 16s.

FIG. 13 shows regulators controlling the expression of spCas9 and the self-targeting sgRNA targeting the ribosomal RNA subunit 16s.

1.2. Differential Growth Media

All strains were grown on TH media at 37° C. for 20 hours. Selective media for *B.subtilis* was TH media supplemented with 2.5 g l$^{-1}$ of 2-phenylethanol (PEA). PEA was added to the media and autoclaved at 121° C. for 15 minutes at 15 psi. Agar plates were prepared by adding 1.5% (wt/vol) agar to the corresponding media.

1.3. Cloning

*E. coli* (One Shot® ThermoFischer TOP10 Chemically Competent cells) was used in all subcloning procedures. PCR was carried out using Phusion™ polymerase. All PCR products were purified with Nucleospin™ Gel and PCR Clean-up by Macherey-Nagel™ following the manufacturer's protocol. The purified fragments were digested with restriction enzyme DpnI in 1×FD buffer with 1 µl enzyme in a total volume of 34 µl. The digested reaction was again purified with Nucleospin Gel and PCR Clean-up by Macherey-Nagel following the manufacturer's protocol. Gibson assembly was performed in 10 µl reactions following the manufacturer's protocol (NewEngland Biolab).

Plasmid DNA was prepared using Qiagen kits according to the manufacturer's instructions. Modifications for Gram-positive strains included growing bacteria in a medium supplemented with 0.5% glycine and lysozyme to facilitate cell lysis.

1.4. Transformation 1.4.1 Electro-Competent *E. coli* Cells and Transformation

Commercially electrocompetent cells were used for cloning and the experiments (One Shot® ThermoFischer TOP10 electrompetent *E. coli*). Electroporation was done using standard settings: 1800 V, 25 µF; and 200Ω using an Electro Cell Manipulator (BTX Harvard Apparatus ECM630). Following the pulse, 1 ml LB-SOC media was added and the cells were incubated at 37° C. for 1 hour. The transformed cells were plated in LB-agar containing the corresponding antibiotics.

1.5. Activation of sgRNA-Cas9 in *E. coli* and Consortium Experiments.

*E. coli* TOP10 and Nissle both with the plasmid containing the sgRNA targeting the ribosomal RNA-encoding sequence of K-12 derived strains and the other bacteria were grown overnight in 3 ml of TH broth. The next day the cells were diluted to ~OD 0.5 and next 10-fold serially diluted in TH media and using a 96-well replicator (Mettler Toledo Liquidator™ 96) 4 µL volume drops were spotted on TH agar, TH agar with inducers (1% arabinose and 2 mM theophylline), TH agar supplemented with 2.5 g l$^{-1}$ PEA and MacConkey agar supplemented with 1% maltose. The plates were incubated for 20h at 37° C. and the colony forming units (CFU) were calculated from triplicate measurements.

2. Results 2.1 Specific Targeting of *E. coli* Strains Using an Exogenous CRISPR-Cas9 System We first tested if the system could differentiate between two *E. coli* strains by introducing the killing system in both *E. coli* TOP10 and Nissle.

2.1 Targeting of *E. coli* Using an Exogenous CRISPR-Cas9 System in a Mixed Culture Serial dilutions of overnight cultures were done in duplicate for both *E. coli* strains, *B.subtilis*, *L.lactis*, and in triplicate for the mixed cultures. All strains were grown at 37° C. for 20 hours in selective plates with and without the inducers. Induction of the system activates the sgRNA-Cas9 targeting K-12 derived strains, while leaving intact the other bacteria.

Distinguishing the different bacteria from a mixed culture is important in order to determine cell numbers of the different species and determine the specific removal of a species. MacConkey agar selectively grows *E. coli*, PEA agar is a selective medium that is used for the isolation of gram-positive (*B.subtilis*) from gram-negative (*E. coli*). Additionally, we found that different concentrations of PEA partially inhibit the growth of other gram positives. 2.5 g l$^{-1}$ of PEA proved to selectively grow *B.subtilis* while limiting growth of *E. coli* and *L.lactis*.

Figure 14:
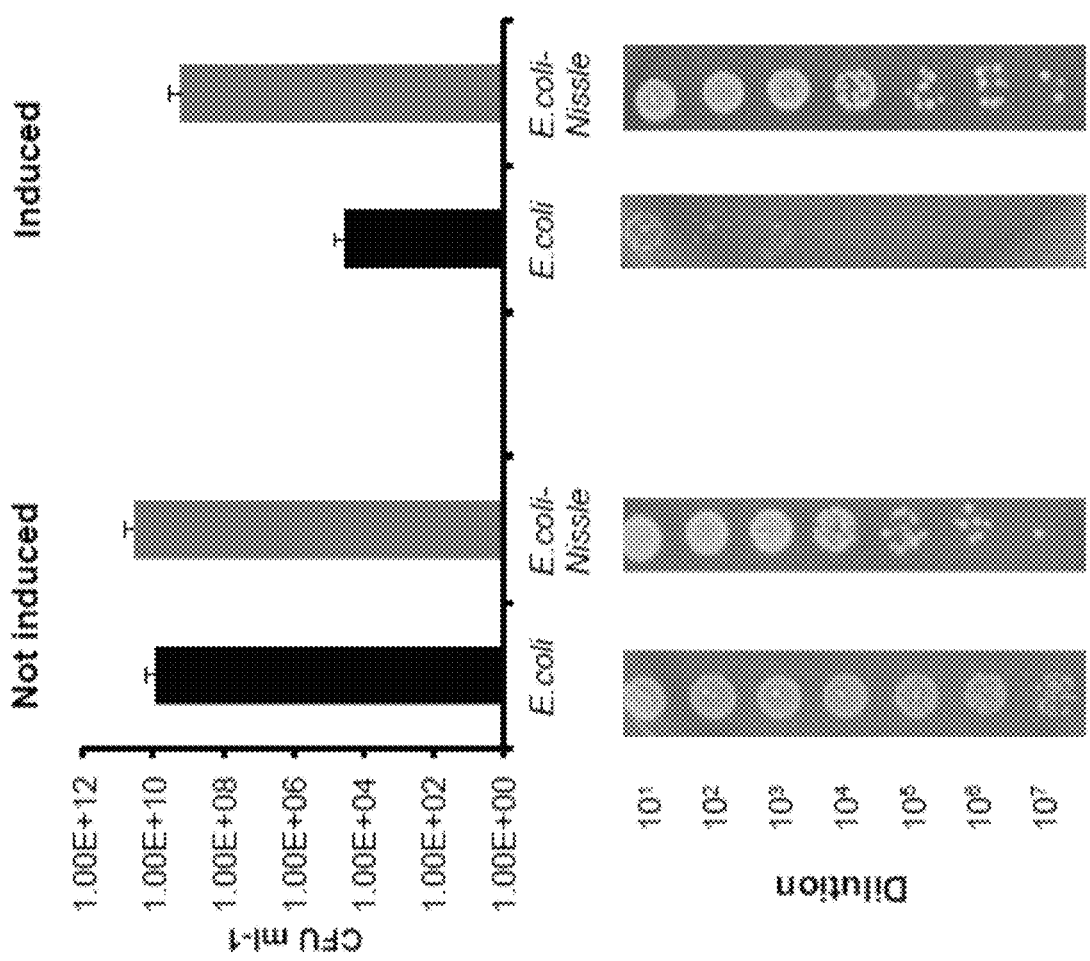
FIG. 14 shows specific targeting of E. coli strain by an exogenous CRISPR-Cas system. The sgRNA target the genome of K-12 derived E. coli strains, like E. coli TOP10, while the other strain tested was unaffected.

FIG. 14 shows specific targeting of *E. coli* strain by the inducibe, exogenous, vector-borne CRISPR-Cas system. The sgRNA target the genome of K-12 derived *E. coli* strain *E. coli* TOP10, while the other *E. coli* strain tested was unaffected.

Figure 15:
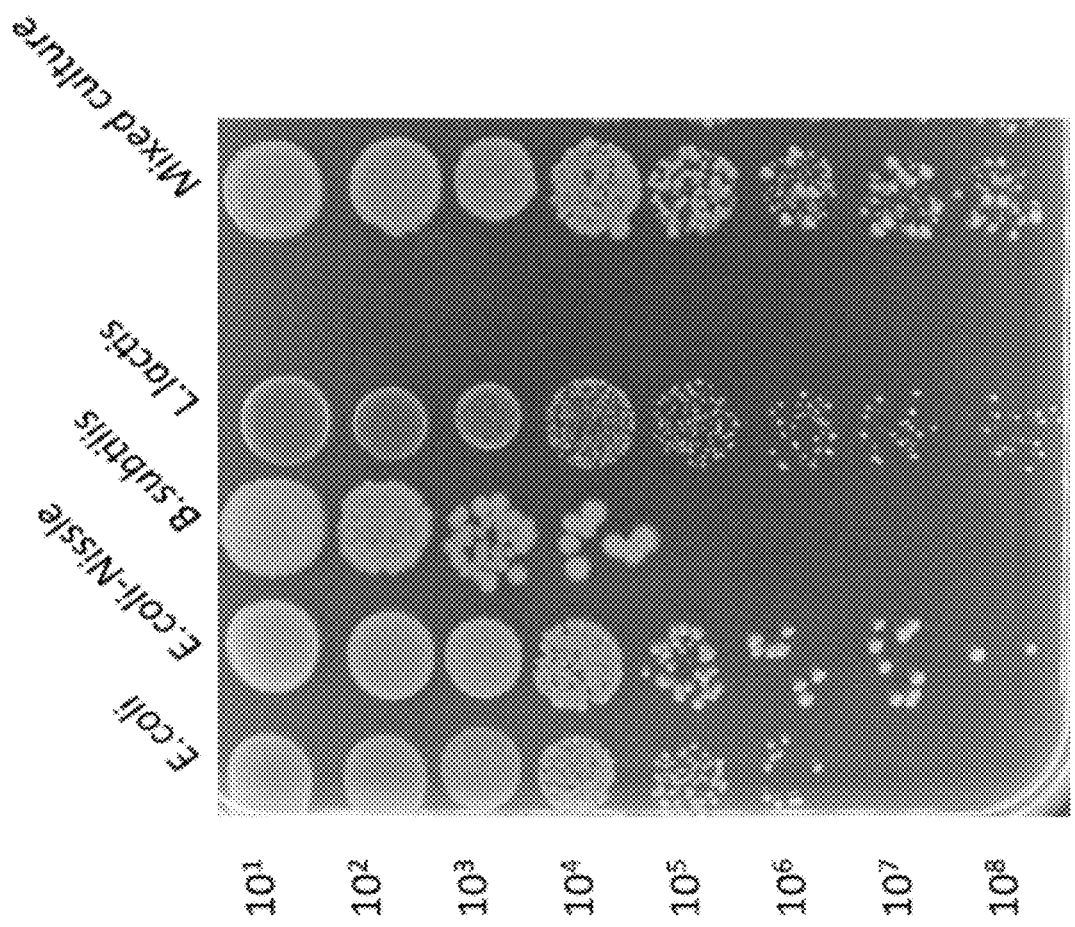
FIG. 15 shows spot assay with serial dilutions of individual bacterial species used in this study and mixed culture in TH agar without induction of CRISPR-Cas9 system.

FIG. 15 shows spot assay with serial dilutions of individual bacterial species used in this study and mixed culture in TH agar without induction of the CRISPR-Cas9 system.

Figure 16:
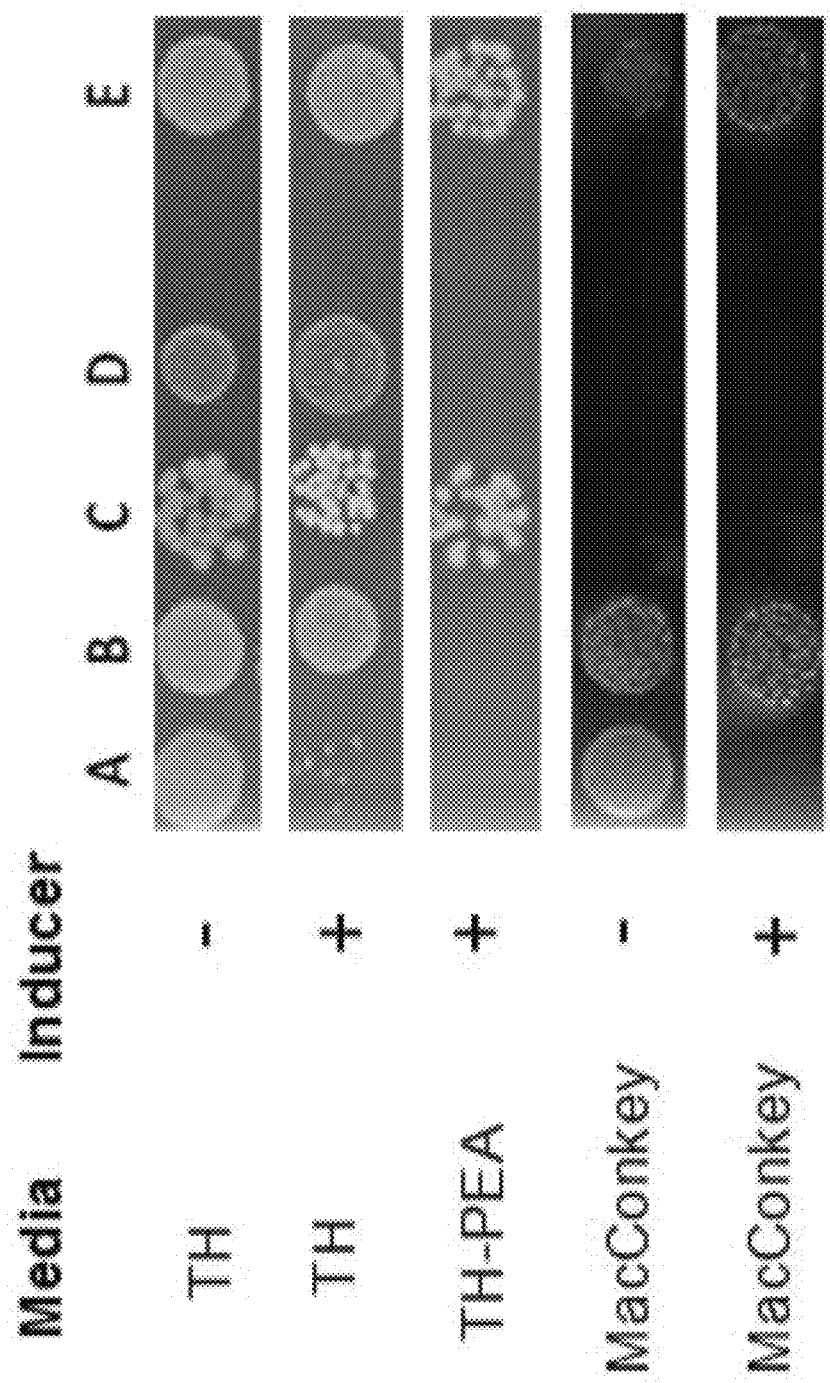
FIG. 16 shows spot assay of the dilution $10^3$ on different selective media. TH with 2.5 g l$^{-1}$ PEA is a selective media for B. subtilis alone. MacConkey supplemented with maltose is a selective and differential culture medium for bacteria designed to selectively isolate Gram-negative and enteric bacilli and differentiate them based on maltose fermentation. Therefore TOP10 ΔmalK mutant makes white colonies on the plates while Nissle makes pink colonies; A is E coli ΔmalK, B is E coli Nissile, C is B subtilis, D is L lactis, E is mixed culture; the images at MacConkey-/B and E appear pink; the images at MacConkey+/B and E appear pink.
Figure 17:
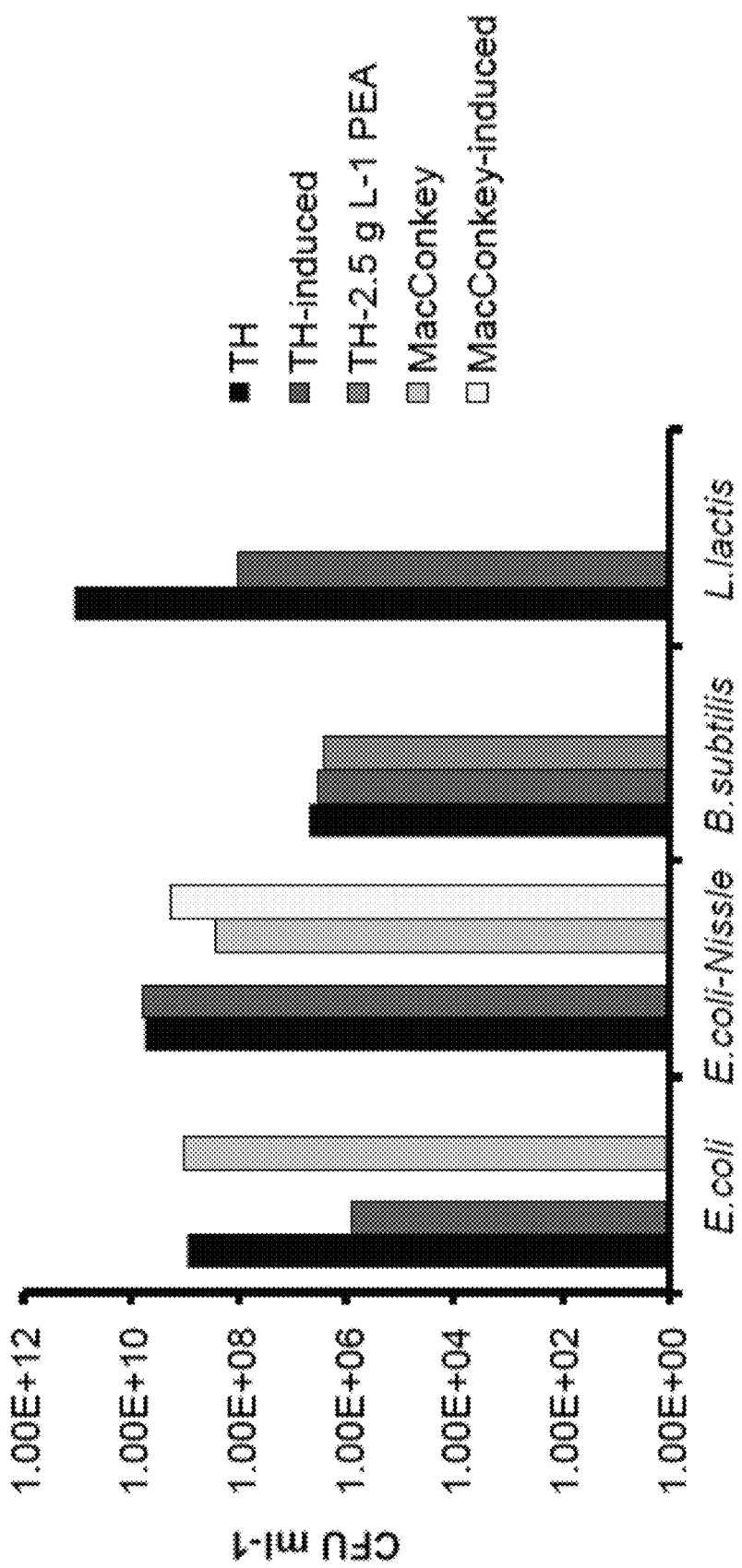
FIG. 17 shows selective growth of the bacteria used in this study on different media and selective plates.

FIG. 16 shows a spot assay of the dilution 10$^3$ on different selective media. TH with 2.5 g l$^{-1}$ PEA is a selective media for *B.subtilis* alone. MacConkey supplemented with maltose is a selective and differential culture medium for bacteria designed to selectively isolate Gram-negative and enteric bacilli and differentiate them based on maltose fermentation. Therefore TOP10 ΔmalK mutant makes white colonies on the plates while Nissle makes pink colonies; A is *E coli* ΔmalK, B is *E coli* Nissile, C is *B subtilis*, D is *L lactis*, E is mixed culture; the images at MacConkey-/B and E appear pink; the images at MacConkey+/B and E appear pink. FIG. 17 shows selective growth of the bacteria used in this study on different media and selective plates. It can be seen that we clearly, selectively killed the target *E coli* strain ("*E coli*" on x-axis in FIG. 17) in the mixed population, whereas the other related strain ("*E coli*-Nissle") was not similarly killed. Killing of the target strain in the mixed population was 1000-fold in this experiment.

REFERENCES

1. Zhang, X. Z., & Zhang, Y. H. P. (2011). Simple, fast and high-efficiency transformation system for directed evolution of cellulase in *Bacillus subtilis*. *Microbial Biotechnology*, 4(1), 98-105. http://doi.org/10.1111/j.1751-7915.2010.00230.x
2. Wegmann, U., O'Connell-Motherway, M., Zomer, A., Buist, G., Shearman, C., Canchaya, C., . . . Kok, J. (2007). Complete genome sequence of the prototype lactic acid bacterium *Lactococcus lactis* subsp. *cremoris* MG1363. *Journal of Bacteriology*, 189(8), 3256-70. http://doi.org/10.1128/JB.01768-06

TABLE 1

EXAMPLE BACTERIA

| | | | | |
|---|---|---|---|---|
| Abiotrophia | Acidocella | Actinomyces | Alkalilimnicola | Aquaspirillum |
| Abiotrophia defectiva | Acidocella aminolytica | Actinomyces bovis Actinomyces denticolens | Alkalilimnicola ehrlichii Alkaliphilus | Aquaspirillum polymorphum Aquaspirillum |
| Acaricomes | Acidocella facilis | Actinomyces | Alkaliphilus | putridiconchylium |
| Acaricomes phytoseiuli | Acidomonas Acidomonas | europaeus Actinomyces | oremlandii Alkaliphilus | Aquaspirillum serpens |
| Acetitomaculum | methanolica | georgiae | transvaalensis | Aquimarina |
| Acetitomaculum ruminis | Acidothermus Acidothermus | Actinomyces gerencseriae | Allochromatium Allochromatium | Aquimarina latercula |
| Acetivibrio cellulolyticus | cellulolyticus Acidovorax | Actinomyces hordeovulneris | vinosum Alloiococcus | Arcanobacterium Arcanobacterium |
| Acetivibrio ethanolgignens | Acidovorax anthurii | Actinomyces howellii | Alloiococcus otitis Allokutzneria | haemolyticum Arcanobacterium |
| Acetivibrio multivorans | Acidovorax caeni Acidovorax | Actinomyces hyovaginalis | Allokutzneria albata Altererythrobacter | pyogenes Archangium |
| Acetoanaerobium | cattleyae | Actinomyces | Altererythrobacter | Archangium |
| Acetoanaerobium noterae | Acidovorax citrulli Acidovorax | israelii Actinomyces | ishigakiensis Altermonas | gephyra Arcobacter |
| Acetobacter | defluvii | johnsonii | Altermonas | Arcobacter butzleri |
| Acetobacter aceti | Acidovorax | Actinomyces | haloplanktis | Arcobacter |
| Acetobacter cerevisiae | delafieldii Acidovorax facilis | meyeri Actinomyces | Altermonas macleodii | cryaerophilus Arcobacter |
| Acetobacter | Acidovorax | naeslundii | Alysiella | halophilus |
| cibinongensis | konjaci | Actinomyces neuii | Alysiella crassa | Arcobacter |
| Acetobacter estunensis | Acidovorax temperans | Actinomyces odontolyticus | Alysiella filiformis Aminobacter | nitrofigilis Arcobacter |
| Acetobacter | Acidovorax | Actinomyces oris | Aminobacter | skirrowii |
| fabarum | valerianellae | Actinomyces | aganoensis | Arhodomonas |
| Acetobacter ghanensis | Acinetobacter Acinetobacter | radingae Actinomyces | Aminobacter aminovorans | Arhodomonas aquaeolei |
| Acetobacter | baumannii | slackii | Aminobacter | Arsenophonus |
| indonesiensis | Acinetobacter | Actinomyces | niigataensis | Arsenophonus |
| Acetobacter lovaniensis | baylyi Acinetobacter | turicensis Actinomyces | Aminobacterium Aminobacterium | nasoniae Arthrobacter |
| Acetobacter | bouvetii | viscosus | mobile | Arthrobacter agilis |
| malorum | Acinetobacter | Actinoplanes | Aminomonas | Arthrobacter albus |
| Acetobacter | calcoaceticus | Actinoplanes | Aminomonas | Arthrobacter |
| nitrogenifigens | Acinetobacter | auranticolor | paucivorans | aurescens |
| Acetobacter oeni | gerneri | Actinoplanes | Ammoniphilus | Arthrobacter |
| Acetobacter | Acinetobacter | brasiliensis | Ammoniphilus | chlorophenolicus |
| orientalis | haemolyticus | Actinoplanes | oxalaticus | Arthrobacter |
| Acetobacter | Acinetobacter | consettensis | Ammoniphilus | citreus |
| orleanensis | johnsonii | Actinoplanes | oxalivorans | Arthrobacter |
| Acetobacter | Acinetobacter junii | deccanensis | Amphibacillus | crystallopoietes |
| pasteurianus | Acinetobacter | Actinoplanes | Amphibacillus | Arthrobacter |
| Acetobacter | lwoffi | derwentensis | xylanus | cumminsii |
| pomorum | Acinetobacter | Actinoplanes | Amphritea | Arthrobacter |
| Acetobacter | parvus | digitatis | Amphritea balenae | globiformis |
| senegalensis | Acinetobacter | Actinoplanes | Amphritea japonica | Arthrobacter |
| Acetobacter | radioresistens | durhamensis | Amycolatopsis | histidinolovorans |
| xylinus | Acinetobacter | Actinoplanes | Amycolatopsis alba | Arthrobacter ilicis |
| Acetobacterium | schindleri | ferrugineus | Amycolatopsis | Arthrobacter luteus |
| Acetobacterium | Acinetobacter soli | Actinoplanes | albidoflavus | Arthrobacter |
| bakii | Acinetobacter | globisporus | Amycolatopsis | methylotrophus |
| Acetobacterium | tandoii | Actinoplanes | azurea | Arthrobacter |
| carbinolicum | Acinetobacter | humidus | Amycolatopsis | mysorens |
| Acetobacterium | tjernbergiae | Actinoplanes | coloradensis | Arthrobacter |
| dehalogenans | Acinetobacter | italicus | Amycolatopsis | nicotianae |
| Acetobacterium | towneri Acinetobacter | Actinoplanes | lurida | Arthrobacter |

TABLE 1-continued

EXAMPLE BACTERIA

| | | | | |
|---|---|---|---|---|
| fimetarium | ursingii | liguriensis | Amycolatopsis | nicotinovorans |
| Acetobacterium | Acinetobacter | Actinoplanes | mediterranei | Arthrobacter |
| malicum | venetianus | lobatus | Amycolatopsis | oxydans |
| Acetobacterium | Acrocarpospora | Actinoplanes | rifamycinica | Arthrobacter |
| paludosum | Acrocarpospora | missouriensis | Amycolatopsis | pascens |
| Acetobacterium | corrugata | Actinoplanes | rubida | Arthrobacter |
| tundrae | Acrocarpospora | palleronii | Amycolatopsis | phenanthrenivorans |
| Acetobacterium | macrocephala | Actinoplanes | sulphurea | Arthrobacter |
| wieringae | Acrocarpospora | philippinensis | Amycolatopsis | polychromogenes |
| Acetobacterium | pleiomorpha | Actinoplanes | tolypomycina | Atrhrobacter |
| woodii | Actibacter | rectilineatus | Anabaena | protophormiae |
| Acetofilamentum | Actibacter | Actinoplanes | Anabaena cylindrica | Arthrobacter |
| Acetofilamentum | sediminis | regularis | Anabaena flosaquae | psychrolactophilus |
| rigidum | Actinoalloteichus | Actinoplanes | Anabaena variabilis | Arthrobacter |
| Acetohalobium | Actinoalloteichus | teichomyceticus | Anaeroarcus | ramosus |
| Acetohalobium | cyanogriseus | Actinoplanes | Anaeroarcus | Arthrobacter |
| arabaticum | Actinoalloteichus | utahensis | burkinensis | sulfonivorans |
| Acetomicrobium | hymeniacidonis | Actinopolyspora | Anaerobaculum | Arthrobacter |
| Acetomicrobium | Actinoalloteichus | Actinopolyspora | Anaerobaculum | sulfureus |
| faecale | spitiensis | halophila | mobile | Arthrobacter |
| Acetomicrobium | Actinobaccillus | Actinopolyspora | Anaerobiospirillum | uratoxydans |
| flavidum | Actinobacillus | mortivallis | Anaerobiospirillum | Arthrobacter |
| Acetonema | capsulatus | Actinosynnema | succiniciproducens | ureafaciens |
| Acetonema longum | Actinobacillus | Actinosynnema | Anaerobiospirillum | Arthrobacter |
| Acetothermus | delphinicola | mirum | thomasii | viscosus |
| Acetothermus | Actinobacillus | Actinotalea | Anaerococcus | Arthrobacter |
| paucivorans | hominis | Actinotalea | Anaerococcus | woluwensis |
| Acholeplasma | Actinobacillus | fermentans | hydrogenalis | Asaia |
| Acholeplasma | indolicus | Aerococcus | Anaerococcus | Asaia bogorensis |
| axanthum | Actinobacillus | Aerococcus | lactolyticus | Asanoa |
| Acholeplasma | lignieresii | sanguinicola | Anaerococcus | Asanoa ferruginea |
| brassicae | Actinobacillus | Aerococcus urinae | prevotii | Asticcacaulis |
| Acholeplasma | minor | Aerococcus | Anaerococcus | Asticcacaulis |
| cavigenitalium | Actinobacillus | urinaeequi | tetradius | biprosthecium |
| Acholeplasma | muris | Aerococcus | Anaerococcus | Asticcacaulis |
| equifetale | Actinobacillus | urinaehominis | vaginalis | excentricus |
| Acholeplasma | pleuropneumoniae | Aerococcus | Anaerofustis | Atopobacter |
| granularum | Actinobacillus | viridans | Anaerofustis | Atopobacter |
| Acholeplasma | porcinus | Aeromicrobium | stercorihominis | phocae |
| hippikon | Actinobacillus | Aeromicrobium | Anaeromusa | Atopobium |
| Acholeplasma | rossii | erythreum | Anaeromusa | Atopobium fossor |
| laidlawii | Actinobacillus | Aeromonas | acidaminophila | Atopobium |
| Acholeplasma | scotiae | Aeromonas | Anaeromyxobacter | minutum |
| modicum | Actinobacillus | allosaccharophila | Anaeromyxobacter | Atopobium |
| Acholeplasma | seminis | Aeromonas | dehalogenans | parvulum |
| morum | Actinobacillus | bestiarum | Anaerorhabdus | Atopobium rimae |
| Acholeplasma | succinogenes | Aeromonas caviae | Anaerorhabdus | Atopobium vaginae |
| multilocale | Actinobaccillus | Aeromonas | furcosa | Aureobacterium |
| Acholeplasma | suis | encheleia | Anaerosinus | Aureobacterium |
| oculi | Actinobacillus | Aeromonas | Anaerosinus | barkeri |
| Acholeplasma | ureae | enteropelogenes | glycerini | Aurobacterium |
| palmae | Actinobaculum | Aeromonas | Anaerovirgula | Aurobacterium |
| Acholeplasma | Actinobaculum | eucrenophila | Anaerovirgula | liquefaciens |
| parvum | massiliense | Aeromonas | multivorans | Avibacterium |
| Acholeplasma | Actinobaculum | ichthiosmia | Ancalomicrobium | Avibacterium avium |
| pleciae | schaalii | Aeromonas | Ancalomicrobium | Avibacterium |
| Acholeplasma | Actinobaculum | jandaei | adetum | gallinarum |
| vituli | suis | Aeromonas media | Ancylobacter | Avibacterium |
| Achromobacter | Actinomyces | Aeromonas | Ancylobacter | paragallinarum |
| Achromobacter | urinale | popoffii | aquaticus | Avibacterium |
| denitrificans | Actinocatenispora | Aeromonas sobria | Aneurinibacillus | volantium |
| Achromobacter | Actinocatenispora | Aeromonas veronii | Aneurinibacillus | Azoarcus |
| insolitus | rupis | Agrobacterium | aneurinilyticus | Azoarcus indigens |
| Achromobacter | Actinocatenispora | Agrobacterium | Aneurinibacillus | Azoarcus |
| piechaudii | thailandica | gelatinovorum | migulanus | tolulyticus |
| Achromobacter | Actinocatenispora | Agrococcus | Aneurinibacillus | Azoarcus |
| ruhlandii | sera | Agrococcus | thermoaerophilus | toluvorans |
| Achromobacter | Actinocorallia | citreus | Angiococcus | Azohydromonas |
| spanius | Actinocorallia | Agrococcus | Angiococcus | Azohydromonas |
| Acidaminobacter | aurantiaca | jenensis | disciformis | australica |
| Acidaminobacter | Actinocorallia | Agromonas | Angulomicrobium | Azohydromonas |
| hydrogenoformans | aurea | Agromonas | Angulomicrobium | lata |
| Acidaminococcus | Actinocorallia | oligotrophica | tetraedrale | Azomonas |
| Acidaminococcus | cavernae | Agromyces | Anoxybacillus | Azomonas agilis |
| fermentans | Actinocorallia | Agromyces | Anoxybacillus | Azomonas insignis |
| Acidaminococcus | glomerata | fucosus | pushchinoensis | Azomonas |
| intestini | Actinocorallia | Agromyces | Aquabacterium | macrocytogenes |
| Acidicaldus | herbida | hippuratus | Aquabacterium | Azorhizobium |

TABLE 1-continued

EXAMPLE BACTERIA

| | | | | |
|---|---|---|---|---|
| *Acidicaldus organivorans* | *Actinocorallia libanotica* | *Agromyces luteolus* | *commune* | *Azorhizobium caulinodans* |
| *Acidimicrobium* | *Actinocorallia longicatena* | *Agromyces mediolanus* | *Aquabacterium parvum* | *Azorhizophilus* |
| *Acidimicrobium ferrooxidans* | *Actinomadura* | *Agromyces ramosus* | | *Azorhizophilus paspali* |
| *Acidiphilium* | *Actinomadura alba* | *Agromyces rhizospherae* | | *Azospirillum* |
| *Acidiphilium acidophilum* | *Actinomadura atramentaria* | *Akkermansia* | | *Azospirillum brasilense* |
| *Acidiphilium angustum* | *Actinomadura bangladeshensis* | *Akkermansia muciniphila* | | *Azospirillum halopraeferens* |
| *Acidiphilium cryptum* | *Actinomadura catellatispora* | *Albidiferax* | | *Azospirillum irakense* |
| *Acidiphilium multivorum* | *Actinomadura chibensis* | *Albidiferax ferrireducens* | | *Azotobacter* |
| *Acidiphilium organovorum* | *Actinomadura chokoriensis* | *Albidovulum* | | *Azotobacter beijerinckii* |
| *Acidiphilium rubrum* | *Actinomadura citrea* | *Albidovulum inexpectatum* | | *Azotobacter chroococcum* |
| *Acidisoma* | *Actinomadura coerulea* | *Alcaligenes* | | *Azotobacter nigricans* |
| *Acidisoma sibiricum* | *Actinomadura echinospora* | *Alcaligenes denitrificans* | | *Azotobacter salinestris* |
| *Acidisoma tundrae* | *Actinomadura fibrosa* | *Alcaligenes faecalis* | | *Azotobacter vinelandii* |
| *Acidisphaera* | *Actinomadura formosensis* | *Alcanivorax* | | |
| *Acidisphaera rubrifaciens* | *Actinomadura hibisca* | *Alcanivorax borkumensis* | | |
| *Acidithiobacillus* | *Actinomadura kijaniata* | *Alcanivorax jadensis* | | |
| *Acidithiobacillus albertensis* | *Actinomadura latina* | *Algicola* | | |
| *Acidithiobacillus caldus* | *Actinomadura livida* | *Algicola bacteriolytica* | | |
| *Acidithiobacillus ferrooxidans* | *Actinomadura luteofluorescens* | *Alicyclobacillus* | | |
| *Acidithiobacillus thiooxidans* | *Actinomadura macra* | *Alicyclobacillus disulfidooxidans* | | |
| *Acidobacterium* | *Actinomadura madurae* | *Alicyclobacillus sendaiensis* | | |
| *Acidobacterium capsulatum* | *Actinomadura oligospora* | *Alicyclobacillus vulcanalis* | | |
| | *Actinomadura pelletieri* | *Alishewanella* | | |
| | *Actinomadura rubrobrunea* | *Alishewanella fetalis* | | |
| | *Actinomadura rugatobispora* | *Alkalibacillus* | | |
| | *Actinomadura umbrina* | *Alkalibacillus haloalkaliphilus* | | |
| | *Actinomadura verrucosospora* | | | |
| | *Actinomadura vinacea* | | | |
| | *Actinomadura viridilutea* | | | |
| | *Actinomadura viridis* | | | |
| | *Actinomadura yumaensis* | | | |

| | | | | |
|---|---|---|---|---|
| *Bacillus* [see below] | *Bacteroides* | *Bibersteinia* | *Borrelia* | *Brevinema* |
| *Bacteriovorax* | *Bacteroides caccae* | *Bibersteinia trehalosi* | *Borrelia afzelii* | *Brevinema andersonii* |
| *Bacteriovorax stolpii* | *Bacteroides coagulans* | *Bifidobacterium* | *Borrelia americana* | *Brevundimonas* |
| | *Bacteroides eggerthii* | *Bifidobacterium adolescentis* | *Borrelia burgdorferi* | *Brevundimonas alba* |
| | *Bacteroides fragilis* | *Bifidobacterium angulatum* | *Borrelia carolinensis* | *Brevundimonas aurantiaca* |
| | *Bacteroides galacturonicus* | *Bifidobacterium animalis* | *Borrelia coriaceae* | *Brevundimonas diminuta* |
| | *Bacteroides helcogenes* | *Bifidobacterium asteroides* | *Borrelia garinii* | *Brevundimonas intermedia* |
| | *Bacteroides ovatus* | *Bifidobacterium bifidum* | *Borrelia japonica* | *Brevundimonas subvibrioides* |
| | *Bacteroides pectinophilus* | *Bifidobacterium boum* | *Bosea* | *Brevundimonas vancanneytii* |
| | | *Bifidobacterium breve* | *Bosea minatitlanensis* | *Brevundimonas* |
| | | *Bifidobacterium catenulatum* | *Bosea thiooxidans* | |
| | | | *Brachybacterium* | |
| | | | *Brachybacterium alimentarium* | |

TABLE 1-continued

EXAMPLE BACTERIA

| | | | |
|---|---|---|---|
| *Bacteroides pyogenes* | *Bifidobacterium choerinum* | *Brachybacterium faecium* | *variabilis* |
| *Bacteroides salyersiae* | *Bifidobacterium coryneforme* | *Brachybacterium paraconglomeratum* | *Brevundimonas vesicularis* |
| *Bacteroides stercoris* | *Bifidobacterium cuniculi* | *Brachybacterium rhamnosum* | *Brochothrix campestris* |
| *Bacteroides suis* | *Bifidobacterium dentium* | *Brachybacterium tyrofermentans* | *Brochothrix thermosphacta* |
| *Bacteroides tectus* | *Bifidobacterium gallicum* | *Brachyspira* | *Brucella* |
| *Bacteroides thetaiotaomicron* | *Bifidobacterium gallinarum* | *Brachyspira alvinipulli* | *Brucella canis* |
| *Bacteroides uniformis* | *Bifidobacterium indicum* | *Brachyspira hyodysenteriae* | *Brucella neotomae* |
| *Bacteroides ureolyticus* | *Bifidobacterium longum* | *Brachyspira innocens* | *Bryobacter* |
| *Bacteroides vulgatus* | *Bifidobacterium magnumBifidobacterium merycicum* | *Brachyspira murdochii* | *Bryobacter aggregatus* |
| *Balnearium* | *Bifidobacterium minimum* | *Brachyspira pilosicoli* | *Burkholderia* |
| *Balnearium lithotrophicum* | *Bifidobacterium pseudocatenulatum* | *Bradyrhizobium* | *Burkholderia ambifaria* |
| *Balneatrix* | *Bifidobacterium pseudolongum* | *Bradyrhizobium canariense* | *Burkholderia andropogonis* |
| *Balneatrix alpica* | *Bifidobacterium pullorum* | *Bradyrhizobium elkanii* | *Burkholderia anthina* |
| *Balneola* | *Bifidobacterium ruminantium* | *Bradyrhizobium japonicum* | *Burkholderia caledonica* |
| *Balneola vulgaris* | *Bifidobacterium saeculare* | *Bradyrhizobium liaoningense* | *Burkholderia caryophylli* |
| *Barnesiella* | *Bifidobacterium subtile* | *Brenneria* | *Burkholderia cenocepacia* |
| *Barnesiella viscericola* | *Bifidobacterium thermophilum* | *Brenneria alni* | *Burkholderia cepacia* |
| *Bartonella* | *Bilophila* | *Brenneria nigrifluens* | *Burkholderia cocovenenans* |
| *Bartonella alsatica* | *Bilophila wadsworthia* | *Brenneria quercina* | *Burkholderia dolosa* |
| *Bartonella bacilliformis* | *Biostraticola* | *Brenneria quercina* | *Burkholderia fungorum* |
| *Bartonella clarridgeiae* | *Biostraticola tofi* | *Brenneria salicis* | *Burkholderia glathei* |
| *Bartonella doshiae* | *Bizionia* | *Brevibacillus* | *Burkholderia glumae* |
| *Bartonella elizabethae* | *Bizionia argentinensis* | *Brevibacillus agri* | *Burkholderia graminis* |
| *Bartonella grahamii* | *Blastobacter* | *Brevibacillus borstelensis* | *Burkholderia kururiensis* |
| *Bartonella henselae* | *Blastobacter capsulatus* | *Brevibacillus brevis* | *Burkholderia multivorans* |
| *Bartonella rochalimae* | *Blastobacter denitrificans* | *Brevibacillus centrosporus* | *Burkholderia phenazinium* |
| *Bartonella vinsonii* | *Blastococcus* | *Brevibacillus choshinensis* | *Burkholderia plantarii* |
| *Bavariicoccus* | *Blastococcus aggregatus* | *Brevibacillus invocatus* | *Burkholderia pyrrocinia* |
| *Bavariicoccus seileri* | *Blastococcus saxobsidens* | *Brevibacillus laterosporus* | *Burkholderia silvatlantica* |
| *Bdellovibrio* | *Blastochloris* | *Brevibacillus parabrevis* | *Burkholderia stabilis* |
| *Bdellovibrio bacteriovorus* | *Blastochloris viridis* | *Brevibacillus reuszeri* | *Burkholderia thailandensis* |
| *Bdellovibrio exovorus* | *Blastomonas* | *Brevibacterium* | *Burkholderia tropica* |
| *Beggiatoa* | *Blastomonas natatoria* | *Brevibacterium abidum* | *Burkholderia unamae* |
| *Beggiatoa alba* | *Blastopirellula* | *Brevibacterium album* | *Burkholderia vietnamiensis* |
| *Beijerinckia* | *Blastopirellula marina* | *Brevibacterium aurantiacum* | *Buttiauxella* |
| *Beijerinckia derxii* | *Blautia* | *Brevibacterium celere* | *Buttiauxella agrestis* |
| *Beijerinckia fluminensis* | *Blautia coccoides* | *Brevibacterium epidermidis* | *Buttiauxella brennerae* |
| *Beijerinckia indica* | *Blautia hansenii* | *Brevibacterium frigoritolerans* | *Buttiauxella ferragutiae* |
| *Beijerinckia mobilis* | *Blautia producta* | *Brevibacterium halotolerans* | *Buttiauxella gaviniae* |
| *Belliella* | *Blautia wexlerae* | *Brevibacterium iodinum* | *Buttiauxella izardii* |
| *Belliella baltica* | *Bogoriella* | *Brevibacterium linens* | *Buttiauxella* |
| *Bellilinea* | *Bogoriella caseilytica* | *Brevibacterium lyticum* | |
| *Bellilinea caldifistulae* | *Bordetella* | *Brevibacterium mcbrellneri* | |
| *Belnapia* | *Bordetella avium* | *Brevibacterium* | |
| *Belnapia moabensis* | *Bordetella bronchiseptica* | | |
| *Bergeriella* | *Bordetella hinzii* | | |
| *Bergeriella denitrificans* | *Bordetella holmesii* | | |
| | *Bordetella parapertussis* | | |
| | *Bordetella pertussis* | | |
| | *Bordetella petrii* | | |
| | *Bordetella trematum* | | |

TABLE 1-continued

EXAMPLE BACTERIA

| | | | | |
|---|---|---|---|---|
| *Beutenbergia* | | *otitidis* | *noackiae* | |
| *Beutenbergia* | | *Brevibacterium* | *Buttiauxella* | |
| *cavernae* | | *oxydans* | *warmboldiae* | |
| | | *Brevibacterium* | *Butyrivibrio* | |
| | | *paucivorans* | *Butyrivibrio* | |
| | | *Brevibacterium* | *fibrisolvens* | |
| | | *stationis* | *Butyrivibrio* | |
| | | | *hungatei* | |
| | | | *Butyrivibrio* | |
| | | | *proteoclasticus* | |

*Bacillus*
| | | | | |
|---|---|---|---|---|
| B. acidiceler | B. aminovorans | B. glucanolyticus | B. taeanensis | B. lautus |
| B. acidicola | B. amylolyticus | B. gordonae | B. tequilensis | B. lehensis |
| B. acidiproducens | B. andreesenii | B. gottheilii | B. thermantarcticus | B. lentimorbus |
| B. acidocaldarius | B. aneurinilyticus | B. graminis | B. thermoaerophilus | B. lentus |
| B. acidoterrestris | B. anthracis | B. halmapalus | B. thermoamylovorans | B. licheniformis |
| B. aeolius | B. aquimaris | B. haloalkaliphilus | B. thermocatenulatus | B. ligniniphilus |
| B. aerius | B. arenosi | B. halochares | B. thermocloacae | B. litoralis |
| B. aerophilus | B. arseniciselenatis | B. halodenitrificans | B. thermocopriae | B. locisalis |
| B. agaradhaerens | B. arsenicus | B. halodurans | B. thermodenitrificans | B. luciferensis |
| B. agri | B. aurantiacus | B. halophilus | B. thermoglucosidasius | B. luteolus |
| B. aidingensis | B. arvi | B. halosaccharovorans | B. thermolactis | B. luteus |
| B. akibai | B. aryabhattai | B. hemicellulosilyticus | B. thermoleovorans | B. macauensis |
| B. alcalophilus | B. asahii | B. hemicentroti | B. thermophilus | B. macerans |
| B. algicola | B. atrophaeus | B. herbersteinensis | B. thermoruber | B. macquariensis |
| B. alginolyticus | B. axarquiensis | B. horikoshii | B. thermosphaericus | B. macyae |
| B. alkalidiazotrophicus | B. azotofixans | B. horneckiae | B. thiaminolyticus | B. malacitensis |
| B. alkalinitrilicus | B. azotoformans | B. horti | B. thioparans | B. mannanilyticus |
| B. alkalisediminis | B. badius | B. huizhouensis | B. thuringiensis | B. marisflavi |
| B. alkalitelluris | B. barbaricus | B. humi | B. tianshenii | B. marismortui |
| B. altitudinis | B. bataviensis | B. hwajinpoensis | B. trypoxylicola | B. marmarensis |
| B. alveayuensis | B. beijingensis | B. idriensis | B. tusciae | B. massiliensis |
| B. alvei | B. benzoevorans | B. indicus | B. validus | B. megaterium |
| B. amyloliquefaciens | B. beringensis | B. infantis | B. vallismortis | B. mesonae |
| B.a. subsp. *amyloliquefaciens* | B. berkeleyi | B. infernus | B. vedderi | B. methanolicus |
| B.a. subsp. *plantarum* | B. beveridgei | B. insolitus | B. velezensis | B. methylotrophicus |
| B. dipsosauri | B. bogoriensis | B. invictae | B. vietnamensis | B. migulanus |
| B. drentensis | B. boroniphilus | B. iranensis | B. vireti | B. mojavensis |
| B. edaphicus | B. borstelensis | B. isabeliae | B. vulcani | B. mucilaginosus |
| B. ehimensis | B. brevis Migula | B. isronensis | B. wakoensis | B. muralis |
| B. eiseniae | B. butanolivorans | B. jeotgali | B. weihenstephanensis | B. murimartini |
| B. enclensis | B. canaveralius | B. kaustophilus | B. xiamenensis | B. mycoides |
| B. endophyticus | B. carboniphilus | B. kobensis | B. xiaoxiensis | B. naganoensis |
| B. endoradicis | B. cecembensis | B. kochii | B. zhanjiangensis | B. nanhaiensis |
| B. farraginis | B. cellulosilyticus | B. kokeshiiformis | B. peoriae | B. nanhaiisediminis |
| B. fastidiosus | B. centrosporus | B. koreensis | B. persepolensis | B. nealsonii |
| B. fengqiuensis | B. cereus | B. korlensis | B. persicus | B. neidei |
| B. firmus | B. chagannorensis | B. kribbensis | B. pervagus | B. neizhouensis |
| B. flexus | B. chitinolyticus | B. krulwichiae | B. plakortidis | B. niabensis |
| B. foraminis | B. chondroitinus | B. laevolacticus | B. pocheonensis | B. niacini |
| B. fordii | B. choshinensis | B. larvae | B. polygoni | B. novalis |
| B. formosus | B. chungangensis | B. laterosporus | B. polymyxa | B. oceanisediminis |
| B. fortis | B. cibi | B. salexigens | B. popilliae | B. odysseyi |
| B. fumarioli | B. circulans | B. saliphilus | B. pseudalcalophilus | B. okhensis |
| B. funiculus | B. clarkii | B. schlegelii | B. pseudofirmus | B. okuhidensis |
| B. fusiformis | B. clausii | B. sediminis | B. pseudomycoides | B. oleronius |
| B. galactophilus | B. coagulans | B. selenatarsenatis | B. psychrodurans | B. oryzaecorticis |
| B. galactosidilyticus | B. coahuilensis | B. selenitireducens | B. psychrophilus | B. oshimensis |
| B. galliciensis | B. cohnii | B. seohaeanensis | B. psychrosaccharolyticus | B. pabuli |
| B. gelatini | B. composti | B. shacheensis | B. psychrotolerans | B. pakistanensis |
| B. gibsonii | B. curdlanolyticus | B. shackletonii | B. pulvifaciens | B. pallidus |
| B. ginsengi | B. cycloheptanicus | B. siamensis | B. pumilus | B. pallidus |
| B. ginsengihumi | B. cytotoxicus | B. silvestris | B. purgationiresistens | B. panacisoli |
| B. ginsengisoli | B. daliensis | B. simplex | B. pycnus | B. panaciterrae |
| B. globisporus | B. decisifrondis | B. siralis | B. qingdaonensis | B. pantothenticus |
| (eg, B.g. subsp. | B. decolorationis | B. smithii | B. qingshengii | B. parabrevis |
| *Globisporus*; | B. deserti | B. soli | B. reuszeri | B. paraflexus |
| or B.g. subsp. | | B. solimangrovi | B. rhizosphaerae | B. pasteurii |
| *Marinus*) | | B. solisalsi | B. rigui | B. patagoniensis |
| | | B. songklensis | B. ruris | |
| | | B. sonorensis | B. safensis | |
| | | B. sphaericus | B. salarius | |
| | | B. sporothermodurans | | |
| | | B. stearothermophilus | | |
| | | B. stratosphericus | | |
| | | B. subterraneus | | |
| | | B. subtilis | | |

TABLE 1-continued

EXAMPLE BACTERIA (eg, B.s. subsp. *Inaquosorum*; or B.s. subsp. *Spizizeni*; or B.s. subsp. *Subtilis*)

| | | | | |
|---|---|---|---|---|
| *Caenimonas* | *Campylobacter* | *Cardiobacterium* | *Catenuloplanes* | *Curtobacterium* |
| *Caenimonas koreensis* | *Campylobacter coli* | *Cardiobacterium hominis* | *Catenuloplanes atrovinosus* | *Curtobacterium albidum* |
| *Caldalkalibacillus* | *Campylobacter concisus* | *Carnimonas* | *Catenuloplanes castaneus* | *Curtobacterium citreus* |
| *Caldalkalibacillus uzonensis* | *Campylobacter curvus* | *Carnimonas nigrificans* | *Catenuloplanes crispus* | |
| *Caldanaerobacter* | *Campylobacter fetus* | *Carnobacterium* | *Catenuloplanes indicus* | |
| *Caldanaerobacter subterraneus* | *Campylobacter gracilis* | *Carnobacterium alterfunditum* | *Catenuloplanes japonicus* | |
| *Caldanaerobius* | *Campylobacter helveticus* | *Carnobacterium divergens* | *Catenuloplanes nepalensis* | |
| *Caldanaerobius fijiensis* | *Campylobacter hominis* | *Carnobacterium funditum* | *Catenuloplanes niger* | |
| *Caldanaerobius polysaccharolyticus* | *Campylobacter hyointestinalis* | *Carnobacterium gallinarum* | *Chryseobacterium* | |
| *Caldanaerobius zeae* | *Campylobacter jejuni* | *Carnobacterium maltaromaticum* | *Chryseobacterium balustinum* | |
| *Caldanaerovirga* | *Campylobacter lari* | *Carnobacterium mobile* | *Citrobacter* | |
| *Caldanaerovirga acetigignens* | *Campylobacter mucosalis* | *Carnobacterium viridans* | *C. amalonaticus* | |
| *Caldicellulosiruptor* | *Campylobacter rectus* | *Caryophanon* | *C. braakii* | |
| *Caldicellulosiruptor bescii* | *Campylobacter showae* | *Caryophanon latum* | *C. diversus* | |
| *Caldicellulosiruptor kristjanssonii* | *Campylobacter sputorum* | *Caryophanon tenue* | *C. farmeri* | |
| *Caldicellulosiruptor owensensis* | *Campylobacter upsaliensis* | *Catellatospora* | *C. freundii* | |
| | *Capnocytophaga* | *Catellatospora citrea* | *C. gillenii* | |
| | *Capnocytophaga canimorsus* | *Catellatospora methionotrophica* | *C. koseri* | |
| | *Capnocytophaga cynodegmi* | *Catenococcus* | *C. murliniae* | |
| | *Capnocytophaga gingivalis* | *Catenococcus thiocycli* | *C. pasteurii*[1] | |
| | *Capnocytophaga granulosa* | | *C. rodentium* | |
| | *Capnocytophaga haemolytica* | | *C. sedlakii* | |
| | *Capnocytophaga ochracea* | | *C. werkmanii* | |
| | *Capnocytophaga sputigena* | | *C. youngae* | |
| | | | *Clostridium* (see below) | |
| | | | *Coccochloris* | |
| | | | *Coccochloris elabens* | |
| | | | *Corynebacterium* | |
| | | | *Corynebacterium flavescens* | |
| | | | *Corynebacterium variabile* | |

*Clostridium*
*Clostridium absonum, Clostridium aceticum, Clostridium acetireducens, Clostridium acetobutylicum, Clostridium acidisoli, Clostridium aciditolerans, Clostridium acidurici, Clostridium aerotolerans, Clostridium aestuarii, Clostridium akagii, Clostridium aldenense, Clostridium aldrichii, Clostridium algidicarni, Clostridium algidixylanolyticum, Clostridium algifaecis, Clostridium algoriphilum, Clostridium alkalicellulosi, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium autoethanogenum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium colletant, Clostridium colicanis, Clostridium colinum, Clostridium collagenovorans, Clostridium cylindrosporum, Clostridium difficile, Clostridium diolis, Clostridium disporicum, Clostridium drakei, Clostridium durum, Clostridium estertheticum, Clostridium estertheticum estertheticum, Clostridium estertheticum laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium gasigenes, Clostridium ghonii, Clostridium glycolicum, Clostridium glycyrrhizinilyticum, Clostridium grantii, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogeniformans, Clostridium hydroxybenzoicum, Clostridium hylemonae, Clostridium jejuense, Clostridium indolis, Clostridium innocuum, Clostridium intestinale, Clostridium irregulare, Clostridium isatidis, Clostridium josui, Clostridium kluyveri, Clostridium lactatifermentans, Clostridium lacusfryxellense, Clostridium*

TABLE 1-continued

EXAMPLE BACTERIA

*laramiense, Clostridium lavalense, Clostridium lentocellum, Clostridium lentoputrescens, Clostridium leptum, Clostridium limosum, Clostridium litorale, Clostridium lituseburense, Clostridium ljungdahlii, Clostridium lortetii, Clostridium lundense, Clostridium magnum, Clostridium malenominatum, Clostridium mangenotii, Clostridium mayombei, Clostridium methoxybenzovorans, Clostridium methylpentosum, Clostridium neopropionicum, Clostridium nexile, Clostridium nitrophenolicum, Clostridium novyi, Clostridium oceanicum, Clostridium orbiscindens, Clostridium oroticum, Clostridium oxalicum, Clostridium papyrosolvens, Clostridium paradoxum, Clostridium paraperfringens* (Alias: *C. welchii*), *Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polysaccharolyticum, Clostridium populeti, Clostridium propionicum, Clostridium proteoclasticum, Clostridium proteolyticum, Clostridium psychrophilum, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium scatologenes, Clostridium schirmacherense, Clostridium scindens, Clostridium septicum, Clostridium sordellii, Clostridium sphenoides, Clostridium spiroforme, Clostridium sporogenes, Clostridium sporosphaeroides, Clostridium stercorarium, Clostridium stercorarium leptospartum, Clostridium stercorarium stercorarium, Clostridium stercorarium thermolacticum, Clostridium sticklandii, Clostridium straminisolvens, Clostridium subterminale, Clostridium sufflavum, Clostridium sulfidigenes, Clostridium symbiosum, Clostridium tagluense, Clostridium tepidiprofundi, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium villosum, Clostridium vincentii, Clostridium viride, Clostridium xylanolyticum, Clostridium xylanovorans*

| | | | |
|---|---|---|---|
| *Dactylosporangium* | *Deinococcus* | *Delftia* | *Echinicola* |
| *Dactylosporangium aurantiacum* | *Deinococcus aerius* | *Delftia acidovorans* | *Echinicola pacifica* |
| *Dactylosporangium fulvum* | *Deinococcus apachensis* | *Desulfovibrio* | *Echinicola vietnamensis* |
| *Dactylosporangium matsuzakiense* | *Deinococcus aquaticus* | *Desulfovibrio desulfuricans* | |
| *Dactylosporangium roseum* | *Deinococcus aquatilis* | *Diplococcus* | |
| *Dactylosporangium thailandense* | *Deinococcus caeni* | *Diplococcus pneumoniae* | |
| *Dactylosporangium vinaceum* | *Deinococcus radiodurans* | | |
| | *Deinococcus radiophilus* | | |

| | | | |
|---|---|---|---|
| *Enterobacter* | *Enterobacter kobei* | *Faecalibacterium* | *Flavobacterium* |
| *E. aerogenes* | *E. ludwigii* | *Faecalibacterium prausnitzii* | *Flavobacterium antarcticum* |
| *E. amnigenus* | *E. mori* | *Fangia* | *Flavobacterium aquatile* |
| *E. agglomerans* | *E. nimipressuralis* | *Fangia hongkongensis* | *Flavobacterium aquidurense* |
| *E. arachidis* | *E. oryzae* | *Fastidiosipila* | *Flavobacterium balustinum* |
| *E. asburiae* | *E. pulveris* | *Fastidiosipila sanguinis* | *Flavobacterium croceum* |
| *E. cancerogenous* | *E. pyrinus* | *Fusobacterium* | *Flavobacterium cucumis* |
| *E. cloacae* | *E. radicincitans* | *Fusobacterium nucleatum* | *Flavobacterium daejeonense* |
| *E. cowanii* | *E. taylorae* | | *Flavobacterium defluvii* |
| *E. dissolvens* | *E. turicensis* | | *Flavobacterium degerlachei* |
| *E. gergoviae* | *E. sakazakii* | | *Flavobacterium denitrificans* |
| *E. helveticus* | *Enterobacter soli* | | *Flavobacterium filum* |
| *E. hormaechei* | *Enterococcus* | | *Flavobacterium flevense* |
| *E. intermedius* | *Enterococcus durans* | | *Flavobacterium frigidarium* |
| | *Enterococcus faecalis* | | *Flavobacterium mizutaii* |
| | *Enterococcus faecium* | | *Flavobacterium okeanokoites* |
| | *Erwinia* | | |
| | *Erwinia hapontici* | | |
| | *Escherichia* | | |
| | *Escherichia coli* | | |

TABLE 1-continued

EXAMPLE BACTERIA

| | | | |
|---|---|---|---|
| *Gaetbulibacter* | *Haemophilus* | *Ideonella* | *Janibacter* |
| *Gaetbulibacter saemankumensis* | *Haemophilus aegyptius* | *Ideonella azotifigens* | *Janibacter anophelis* |
| *Gallibacterium* | *Haemophilus* | *Idiomarina* | *Janibacter* |
| *Gallibacterium anatis* | *aphrophilus* | *Idiomarina* | *corallicola* |
| *Gallicola* | *Haemophilus felis* | *abyssalis* | *Janibacter* |
| *Gallicola barnesae* | *Haemophilus* | *Idiomarina* | *limosus* |
| *Garciella* | *gallinariim* | *baltica* | *Janibacter* |
| *Garciella nitratireducens* | *Haemophilus haemolyticus* | *Idiomarina fontislapidosi* | *melonis* *Janibacter* |
| *Geobacillus* | *Haemophilus* | *Idiomarina* | *terrae* |
| *Geobacillus thermoglucosidasius* | *influenzae* *Haemophilus* | *loihiensis* *Idiomarina* | *Jannaschia* *Jannaschia* |
| *Geobacillus stearothermophilus* | *paracuniculus* *Haemophilus* | *ramblicola* *Idiomarina* | *cystaugens* *Jannaschia* |
| *Geobacter* | *parahaemolyticus* | *seosinensis* | *helgolandensis* |
| *Geobacter bemidjiensis* | *Haemophilus parainfluenzae* | *Idiomarina zobellii* | *Jannaschia pohangensis* |
| *Geobacter brememis* | *Haemophilus* | *Ignatzschineria* | *Jannaschia* |
| *Geobacter chapellei* | *paraphrohaemolyticus* | *Ignatzschineria* | *rubra* |
| *Geobacter grbiciae* | *Haemophilus* | *larvae* | *Janthinobacterium* |
| *Geobacter hydrogenophilus* | *parasuis* *Haemophilus* | *Ignavigranum* *Ignavigranum* | *Janthinobacterium agaricidamnosum* |
| *Geobacter lovleyi* | *pittmaniae* | *ruoffiae* | *Janthinobacterium* |
| *Geobacter metallireducens* | *Hafnia* *Hafnia alvei* | *Ilumatobacter* *Ilumatobacter* | *lividum* *Jejuia* |
| *Geobacter pelophilus* | *Hahella* | *fluminis* | *Jejuia* |
| *Geobacter pickeringii* | *Hahella* | *Ilyobacter* | *pallidilutea* |
| *Geobacter sulfurreducens* | *ganghwensis* *Halalkalibacillus* | *Ilyobacter delafieldii* | *Jeotgalibacillus* *Jeotgalibacillus* |
| *Geodermatophilus* | *Halalkalibacillus* | *Ilyobacter* | *alimentarius* |
| *Geodermatophilus obscurus* | *halophilus* *Helicobacter* | *insuetus* *Ilyobacter* | *Jeotgalicoccus* *Jeotgalicoccus* |
| *Gluconacetobacter* | *Helicobacter* | *polytropus* | *halotolerans* |
| *Gluconacetobacter xylinus* | *pylori* | *Ilyobacter tartaricus* | |
| *Gordonia* | | | |
| *Gordonia rubripertincta* | | | |

| | | | | |
|---|---|---|---|---|
| *Kaistia* | *Labedella* | *Listeria ivanovii* | *Micrococcus* | *Nesterenkonia* |
| *Kaistia adipata* | *Labedella gwakjiensis* | *L. marthii* *L. monocytogenes* | *Micrococcus luteus* | *Nesterenkonia holobia* |
| *Kaistia soli* *Kangiella* | *Labrenzia* | *L. newyorkensis* | *Micrococcus* | *Nocardia* |
| *Kangiella aquimarina* | *Labrenzia aggregata* | *L. riparia* *L. rocourtiae* | *lylae* *Moraxella* | *Nocardia argentinensis* |
| *Kangiella koreensis* | *Labrenzia alba* | *L. seeligeri* | *Moraxella bovis* | *Nocardia* |
| *Kerstersia* | *Labrenzia alexandrii* | *L. weihenstephanensis* *L. welshimeri* | *Moraxella nonliquefaciens* | *corallina* *Nocardia* |
| *Kerstersia gyiorum* *Kiloniella* | *Labrenzia marina* | *Listonella* | *Moraxella* | *otitidiscaviarum* |
| *Kiloniella laminariae* | *Labrys* | *Listonella anguillarum* | *osloensis* *Nakamurella* | |
| *Klebsiella* | *Labrys methylaminiphilus* | *Macrococcus* | *Nakamurella* | |
| *K. granulomatis* *K. oxytoca* | *Labrys* | *Macrococcus bovicus* | *multipartita* *Nannocystis* | |
| *K. pneumoniae* | *miyagiensis* | *Marinobacter* | *Nannocystis* | |
| *K. terrigena* *K. variicola* | *Labrys monachus* *Labrys* | *Marinobacter algicola* | *pusilla* *Natranaerobius* | |
| *Kluyvera* | *okinawensis* | *Marinobacter* | *Natranaerobius* | |
| *Kluyvera ascorbata* | *Labrys portucalensis* | *bryozoorum* *Marinobacter* | *thermophilus* *Natranaerobius* | |
| *Kocuria* | *Lactobacillus* | *flavimaris* | *trueperi* | |
| *Kocuria roasea* *Kocuria varians* | [see below] *Laceyella* | *Meiothermus* | *Naxibacter* *Naxibacter* | |
| *Kurthia* | *Laceyella putida* | *Meiothermus ruber* | *alkalitolerans* | |
| *Kurthia zopfii* | *Lechevalieria* *Lechevalieria* | *Methylophilus* *Methylophilus* | *Neisseria* *Neisseria cinerea* | |
| | *aerocolonigenes* *Legionella* | *methylotrophus* *Microbacterium* | *Neisseria denitrificans* | |
| | [see below] *Listeria* | *Microbacterium ammoniaphilum* | *Neisseria gonorrhoeae* | |
| | *L. aquatica* *L. booriae* | *Microbacterium* | *Neisseria* | |
| | *L. cornellensis* | *arborescens* | *lactamica* | |
| | *L. fleischmannii* *L. floridensis* | *Microbacterium liquefaciens* | *Neisseria mucosa* *Neisseria sicca* | |
| | *L. grandensis* | *Microbacterium* | *Neisseria subflava* | |
| | *L. grayi* *L. innocua* | *oxydans* | *Neptunomonas* *Neptunomonas* | |

TABLE 1-continued

EXAMPLE BACTERIA

*japonica*

*Lactobacillus*

| | | | | |
|---|---|---|---|---|
| L. acetotolerans | L. catenaformis | L. mali | L. parakefiri | L. sakei |
| L. acidifarinae | L. ceti | L. manihotivorans | L. paralimentarius | L. salivarius |
| L. acidipiscis | L. coleohominis | L. mindensis | L. paraplantarum | L. sanfranciscensis |
| L. acidophilus | L. collinoides | L. mucosae | L. pentosus | L. satsumensis |
| Lactobacillus agilis | L. composti | L. murinus | L. perolens | L. secaliphilus |
| L. algidus | L. concavus | L. nagelii | L. plantarum | L. sharpeae |
| L. alimentarius | L. coryniformis | L. namurensis | L. pontis | L. siliginis |
| L. amylolyticus | L. crispatus | L. nantensis | L. protectus | L. spicheri |
| L. amylophilus | L. crustorum | L. oligofermentans | L. psittaci | L. suebicus |
| L. amylotrophicus | L. curvatus | L. oris | L. rennini | L. thailandensis |
| L. amylovorus | L. delbrueckii | L. panis | L. reuteri | L. ultunensis |
| L. animalis | subsp. bulgaricus | L. pantheris | L. rhamnosus | L. vaccinostercus |
| L. antri | L. delbrueckii | L. parabrevis | L. rimae | L. vaginalis |
| L. apodemi | subsp. delbrueckii | L. parabuchneri | L. rogosae | L. versmoldensis |
| L. aviarius | L. delbrueckii | L. paracasei | L. rossiae | L. vini |
| L. bifermentans | subsp. lactis | L. paracollinoides | L. ruminis | L. vitulinus |
| L. brevis | L. dextrinicus | L. parafarraginis | L. saerimneri | L. zeae |
| L. buchneri | L. diolivorans | L. homohiochii | L. jensenii | L. zymae |
| L. camelliae | L. equi | L. iners | L. johnsonii | L. gastricus |
| L. casei | L. equigenerosi | L. ingluviei | L. kalixensis | L. ghanensis |
| L. kitasatonis | L. farraginis | L. intestinalis | L. kefiranofaciens | L. graminis |
| L. kunkeei | L. farciminis | L. fuchuensis | L. kefiri | L. hammesii |
| L. leichmannii | L. fermentum | L. gallinarum | L. kimchii | L. hamsteri |
| L. lindneri | L. fornicalis | L. gasseri | L. helveticus | L. harbinensis |
| L. malefermentans | L. fructivorans | | L. hilgardii | L. hayakitensis |
| | L. frumenti | | | |

*Legionella*

| | | | | |
|---|---|---|---|---|
| Legionella adelaidensis | Legionella drancourtii | Legionella jeonii | Candidatus Legionella | Legionella quinlivanii |
| Legionella anisa | Legionella dresdenensis | Legionella jordanis | Legionella lansingensis | Legionella rowbothamii |
| Legionella beliardensis | Legionella drozanskii | Legionella londiniensis | Legionella longbeachae | Legionella rubrilucens |
| Legionella birminghamensis | Legionella dumoffii | Legionella lytica | Legionella maceachernii | Legionella sainthelensi |
| Legionella bozemanae | Legionella erythra | Legionella massiliensis | Legionella micdadei | Legionella santicrucis |
| Legionella brunensis | Legionella fairfieldensis | Legionella monrovica | Legionella moravica | Legionella shakespearei |
| Legionella busanensis | Legionella fallonii | Legionella nagasakiensis | Legionella nautarum | Legionella spiritensis |
| Legionella cardiaca | Legionella feeleii | Legionella norrlandica | Legionella oakridgensis | Legionella steelei |
| Legionella cherrii | Legionella geestiana | Legionella parisiensis | Legionella pittsburghensis | Legionella steigerwaltii |
| Legionella cincinnatiensis | Legionella genomospecies | Legionella pneumophila | Legionella quateirensis | Legionella taurinensis |
| Legionella clemsonensis | Legionella gormanii | | | Legionella tucsonensis |
| Legionella donaldsonii | Legionella gratiana | | | Legionella tunisiensis |
| | Legionella gresilensis | | | Legionella wadsworthii |
| | Legionella hackeliae | | | Legionella waltersii |
| | Legionella impletisoli | | | Legionella worsleiensis |
| | Legionella israelensis | | | Legionella yabuuchiae |
| | Legionella jamestowniensis | | | |

| | | | |
|---|---|---|---|
| Oceanibulbus | Paenibacillus | Prevotella | Quadrisphaera |
| Oceanibulbus indolifex | Paenibacillus thiaminolyticus | Prevotella albensis | Quadrisphaera granulorum |
| Oceanicaulis | Pantoea | Prevotella amnii | Quatrionicoccus |
| Oceanicaulis alexandrii | Pantoea agglomerans | Prevotella bergensis | Quatrionicoccus australiensis |
| Oceanicola | Paracoccus | Prevotella bivia | Quinella |
| Oceanicola batsensis | Paracoccus alcaliphilus | Prevotella brevis | Quinella ovalis |
| Oceanicola | | Prevotella | Ralstonia |

TABLE 1-continued

EXAMPLE BACTERIA

| | | | |
|---|---|---|---|
| granulosus | Paucimonas | bryantii | Ralstonia |
| Oceanicola | Paucimonas | Prevotella buccae | eutropha |
| nanhaiensis | lemoignei | Prevotella | Ralstonia |
| Oceanimonas | Pectobacterium | buccalis | insidiosa |
| Oceanimonas | Pectobacterium | Prevotella copri | Ralstonia |
| baumannii | aroidearum | Prevotella | mannitolilytica |
| Oceaniserpentilla | Pectobacterium | dentalis | Ralstonia |
| Oceaniserpentilla | atrosepticum | Prevotella | pickettii |
| haliotis | Pectobacterium | denticola | Ralstonia |
| Oceanisphaera | betavasculorum | Prevotella disiens | pseudosolanacearum |
| Oceanisphaera | Pectobacterium | Prevotella | Ralstonia syzygii |
| donghaensis | cacticida | histicola | Ralstonia |
| Oceanisphaera | Pectobacterium | Prevotella | solanacearum |
| litoralis | carnegieana | intermedia | Ramlibacter |
| Oceanithermus | Pectobacterium | Prevotella | Ramlibacter |
| Oceanithermus | carotovorum | maculosa | henchirensis |
| desulfurans | Pectobacterium | Prevotella | Ramlibacter |
| Oceanithermus | chrysanthemi | marshii | tataouinensis |
| profundus | Pectobacterium | Prevotella | Raoultella |
| Oceanobacillus | cypripedii | melaninogenica | Raoultella |
| Oceanobacillus caeni | Pectobacterium | Prevotella micans | ornithinolytica |
| Oceanospirillum | rhapontici | Prevotella | Raoultella |
| Oceanospirillum | Pectobacterium | multiformis | planticola |
| linum | wasabiae | Prevotella | Raoultella |
| | Planococcus | nigrescens | terrigena |
| | Planococcus | Prevotella oralis | Rathayibacter |
| | citreus | Prevotella oris | Rathayibacter |
| | Planomicrobium | Prevotella | caricis |
| | Planomicrobium | oulorum | Rathayibacter |
| | okeanokoites | Prevotella pallens | festucae |
| | Plesiomonas | Prevotella salivae | Rathayibacter |
| | Plesiomonas | Prevotella | iranicus |
| | shigelloides | stercorea | Rathayibacter |
| | Proteus | Prevotella | rathayi |
| | Proteus vulgaris | tannerae | Rathayibacter |
| | | Prevotella | toxicus |
| | | timonensis | Rathayibacter |
| | | Prevotella | tritici |
| | | veroralis | Rhodobacter |
| | | Providencia | Rhodobacter |
| | | Providencia | sphaeroides |
| | | stuartii | Ruegeria |
| | | Pseudomonas | Ruegeria |
| | | Pseudomonas | gelatinovorans |
| | | aeruginosa | |
| | | Pseudomonas | |
| | | alcaligenes | |
| | | Pseudomonas | |
| | | anguillispetica | |
| | | Pseudomonas | |
| | | fluorescens | |
| | | Pseudoalteromonas | |
| | | haloplanktis | |
| | | Pseudomonas | |
| | | mendocina | |
| | | Pseudomonas | |
| | | pseudoalcaligenes | |
| | | Pseudomonas | |
| | | putida | |
| | | Pseudomonas | |
| | | tutzeri | |
| | | Pseudomonas | |
| | | syringae | |
| | | Psychrobacter | |
| | | Psychrobacter | |
| | | faecalis | |
| | | Psychrobacter | |
| | | phenylpyruvicus | |
| Saccharococcus | Sagittula | Sanguibacter | Stenotrophomonas | Tatlockia |
| Saccharococcus | Sagittula stellata | Sanguibacter | Stenotrophomonas | Tatlockia |
| thermophilus | Salegentibacter | keddieii | maltophilia | maceachernii |
| Saccharomonospora | Salegentibacter | Sanguibacter | Streptococcus | Tatlockia |
| Saccharomonospora | salegens | suarezii | [also see below] | micdadei |
| azurea | Salimicrobium | Saprospira | Streptomyces | Tenacibaculum |
| Saccharomonospora | Salimicrobium | Saprospira | Streptomyces | Tenacibaculum |
| cyanea | album | grandis | achromogenes | amylolyticum |
| Saccharomonospora | Salinibacter | Sarcina | Streptomyces | Tenacibaculum |

TABLE 1-continued

| EXAMPLE BACTERIA | | | | |
|---|---|---|---|---|
| viridis | Salinibacter ruber | Sarcina maxima | cesalbus | discolor |
| Saccharophagus | Salinicoccus | Sarcina ventriculi | Streptomyces | Tenacibaculum |
| Saccharophagus | Salinicoccus | Sebaldella | cescaepitosus | gallaicum |
| degradans | alkaliphilus | Sebaldella | Streptomyces | Tenacibaculum |
| Saccharopolyspora | Salinicoccus | termitidis | cesdiastaticus | lutimaris |
| Saccharopolyspora | hispanicus | Serratia | Streptomyces | Tenacibaculum |
| erythraea | Salinicoccus roseus | Serratia fonticola | cesexfoliatus | mesophilum |
| Saccharopolyspora | Salinispora | Serratia | Streptomyces | Tenacibaculum |
| gregorii | Salinispora | marcescens | fimbriatus | skagerrakense |
| Saccharopolyspora | arenicola | Sphaerotilus | Streptomyces | Tepidanaerobacter |
| hirsuta | Salinispora tropica | Sphaerotilus | fradiae | Tepidanaerobacter |
| Saccharopolyspora | Salinivibrio | natans | Streptomyces | syntrophicus |
| hordei | Salinivibrio | Sphingobacterium | fulvissimus | Tepidibacter |
| Saccharopolyspora | costicola | Sphingobacterium | Streptomyces | Tepidibacter |
| rectivirgula | Salmonella | multivorum | griseoruber | formicigenes |
| Saccharopolyspora | Salmonella bongori | Staphylococcus | Streptomyces | Tepidibacter |
| spinosa | Salmonella enterica | [see below] | griseus | thalassicus |
| Saccharopolyspora | Salmonella | | Streptomyces | Thermus |
| taberi | subterranea | | lavendulae | Thermus |
| Saccharothrix | Salmonella typhi | | Streptomyces | aquaticus |
| Saccharothrix | | | phaeochromogenes | Thermus |
| australiensis | | | Streptomyces | filiformis |
| Saccharothrix | | | thermodiastaticus | Thermus |
| coeruleofusca | | | Streptomyces | thermophilus |
| Saccharothrix | | | tubercidicus | |
| espanaensis | | | | |
| Saccharothrix | | | | |
| longispora | | | | |
| Saccharothrix mutabilis | | | | |
| Saccharothrix syringae | | | | |
| Saccharothrix tangerinus | | | | |
| Saccharothrix texasensis | | | | |
| | Staphylococcus | | | |
| | S. arlettae | S. equorum | S. microti | S. schleiferi |
| | S. agnetis | S. felis | S. muscae | S. sciuri |
| | S. aureus | S. fleurettii | S. nepalensis | S. simiae |
| | S. auricularis | S. gallinarum | S. pasteuri | S. simulans |
| | S. capitis | S. haemolyticus | S. petrasii | S. stepanovicii |
| | S. caprae | S. hominis | S. pettenkoferi | S. succinus |
| | S. carnosus | S. hyicus | S. piscifermentans | S. vitulinus |
| | S. caseolyticus | S. intermedius | S. pseudintermedius | S. warneri |
| | S. chromogenes | S. kloosii | S. pseudolugdunensis | S. xylosus |
| | S. cohnii | S. leei | S. pulvereri | |
| | S. condimenti | S. lentus | S. rostri | |
| | S. delphini | S. lugdunensis | S. saccharolyticus | |
| | S. devriesei | S. lutrae | S. saprophyticus | |
| | S. epidermidis | S. lyticans | | |
| | | S. massiliensis | | |
| Streptococcus | | | | |
| Streptococcus agalactiae | Streptococcus infantarius | Streptococcus orisratti | Streptococcus thermophilus | |
| Streptococcus anginosus | Streptococcus iniae | Streptococcus parasanguinis | Streptococcus sanguinis | |
| Streptococcus bovis | Streptococcus intermedius | Streptococcus peroris | Streptococcus sobrinus | |
| Streptococcus canis | Streptococcus lactarius | Streptococcus pneumoniae | Streptococcus suis | |
| Streptococcus constellatus | Streptococcus milleri | Streptococcus pseudopneumoniae | Streptococcus uberis | |
| Streptococcus downei | Streptococcus mitis | Streptococcus pyogenes | Streptococcus vestibularis | |
| Streptococcus dysgalactiae | Streptococcus mutans | Streptococcus ratti | Streptococcus viridans | |
| Streptococcus equines | Streptococcus oralis | Streptococcus salivariu | Streptococcus zooepidemicus | |
| Streptococcus faecalis | Streptococcus tigurinus | | | |
| Streptococcus ferus | | | | |
| Uliginosibacterium | Vagococcus | Vibrio | Virgibacillus | Xanthobacter |
| Uliginosibacterium gangwonense | Vagococcus carniphilus | Vibrio aerogenes | Virgibacillus halodenitrificans | Xanthobacter agilis |
| Ulvibacter | Vagococcus | Vibrio aestuarianus | Virgibacillus pantothenticus | Xanthobacter aminoxidans |
| Ulvibacter litoralis | elongatus | Vibrio albensis | Weissella | Xanthobacter |
| Umezawaea | Vagococcus fessus | Vibrio alginolyticus | Weissella cibaria | autotrophicus |
| Umezawaea tangerina | Vagococcus fluvialis | Vibrio campbellii | Weissella confusa | Xanthobacter |
| Undibacterium | Vagococcus lutrae | Vibrio cholerae | Weissella | Xanthobacter flavus |
| Undibacterium pigrum | Vagococcus | Vibrio | halotolerans | Xanthobacter |
| Ureaplasma | salmoninarum | | | |

TABLE 1-continued

EXAMPLE BACTERIA

| | | | | |
|---|---|---|---|---|
| *Ureaplasma urealyticum* | *Variovorax* | *Vibrio cincinnatiensis* | *Weissella hellenica* | *tagetidis* |
| *Ureibacillus* | *Variovorax boronicumulans* | *Vibrio coralliilyticus* | *Weissella kandleri* | *Xanthobacter viscosus* |
| *Ureibacillus composti* | *Variovorax dokdonensis* | *Vibrio cyclitrophicus* | *Weissella koreensis* | *Xanthomonas* |
| *Ureibacillus suwonensis* | *Variovorax paradoxus* | *Vibrio diazotrophicus* | *Weissella minor* | *Xanthomonas albilineans* |
| *Ureibacillus terrenus* | *Variovorax soli* | *Vibrio fluvialis* | *Weissella paramesenteroides* | *Xanthomonas alfalfae* |
| *Ureibacillus thermophilus* | *Veillonella* | *Vibrio furnissii* | *Weissella soli* | *Xanthomonas arboricola* |
| *Ureibacillus thermosphaericus* | *Veillonella atypica* | *Vibrio gazogenes* | *Weissella thailandensis* | *Xanthomonas axonopodis* |
| | *Veillonella caviae* | *Vibrio halioticoli* | *Weissella viridescens* | *Xanthomonas campestris* |
| | *Veillonella criceti* | *Vibrio harveyi* | *Williamsia* | *Xanthomonas citri* |
| | *Veillonella dispar* | *Vibrio ichthyoenteri* | *Williamsia marianensis* | *Xanthomonas codiaei* |
| | *Veillonella montpellierensis* | *Vibrio mediterranei* | *Williamsia maris* | *Xanthomonas cucurbitae* |
| | *Veillonella parvula* | *Vibrio metschnikovii* | *Williamsia serinedens* | *Xanthomonas euvesicatoria* |
| | *Veillonella ratti* | *Vibrio mytili* | *Winogradskyella* | *Xanthomonas fragariae* |
| | *Veillonella rodentium* | *Vibrio natriegens* | *Winogradskyella thalassocola* | *Xanthomonas fuscans* |
| | *Venenivibrio* | *Vibrio navarrensis* | *Wolbachia* | *Xanthomonas gardneri* |
| | *Venenivibrio stagnispumantis* | *Vibrio nereis* | *Wolbachia persica* | *Xanthomonas hortorum* |
| | *Verminephrobacter* | *Vibrio nigripulchritudo* | *Wolinella* | *Xanthomonas hyacinthi* |
| | *Verminephrobacter eiseniae* | *Vibrio ordalii* | *Wolinella succinogenes* | *Xanthomonas perforans* |
| | *Verrucomicrobium* | *Vibrio orientalis* | *Zobellia* | *Xanthomonas phaseoli* |
| | *Verrucomicrobium spinosum* | *Vibrio parahaemolyticus* | *Zobellia galactanivorans* | *Xanthomonas pisi* |
| | | *Vibrio pectenicida* | *Zobellia uliginosa* | *Xanthomonas populi* |
| | | *Vibrio penaeicida* | *Zoogloea* | *Xanthomonas theicola* |
| | | *Vibrio proteolyticus* | *Zoogloea ramigera* | *Xanthomonas translucens* |
| | | *Vibrio shilonii* | *Zoogloea resiniphila* | *Xanthomonas vesicatoria* |
| | | *Vibrio splendidus* | | *Xylella* |
| | | *Vibrio tubiashii* | | *Xylella fastidiosa* |
| | | *Vibrio vulnificus* | | *Xylophilus* |
| | | | | *Xylophilus ampelinus* |
| *Xenophilus* | *Yangia* | *Yersinia mollaretii* | *Zooshikella* | *Zobellella* |
| *Xenophilus azovorans* | *Yangia pacifica* | *Yersinia* | *Zooshikella ganghwensis* | *Zobellella denitrificans* |
| *Xenorhabdus* | *Yaniella* | *Yersinia philomiragia* | *Zunongwangia* | *Zobellella taiwanensis* |
| *Xenorhabdus beddingii* | *Yaniella flava* | *Yersinia pestis* | *Zunongwangia profunda* | *Zeaxanthinibacter* |
| *Xenorhabdus bovienii* | *Yaniella halotolerans* | *Yersinia pseudotuberculosis* | *Zymobacter* | *Zeaxanthinibacter enoshimensis* |
| *Xenorhabdus cabanillasi* | *Yeosuana* | *Yersinia rohdei* | *Zymobacter palmae* | *Zhihengliuella* |
| *Xenorhabdus doucetiae* | *Yeosuana aromativorans* | *Yersinia ruckeri* | *Zymomonas* | *Zhihengliuella halotolerans* |
| *Xenorhabdus griffiniae* | *Yersinia* | *Yokenella* | *Zymomonas mobilis* | *Xylanibacterium* |
| *Xenorhabdus hominickii* | *Yersinia aldovae* | *Yokenella regensburgei* | *Zymophilus* | *Xylanibacterium ulmi* |
| *Xenorhabdus koppenhoeferi* | *Yersinia bercovieri* | *Yonghaparkia* | *Zymophilus paucivorans* | |
| *Xenorhabdus nematophila* | *Yersinia enterocolitica* | *Yonghaparkia alkaliphila* | *Zymophilus raffinosivorans* | |
| *Xenorhabdus poinarii* | *Yersinia entomophaga* | *Zavarzinia* | | |
| *Xylanibacter* | *Yersinia frederiksenii* | *Zavarzinia compransoris* | | |
| *Xylanibacter oryzae* | *Yersinia intermedia* | | | |
| | *Yersinia kristensenii* | | | |

TABLE 2

MEDICAMENTS

ACE inhibitors with calcium channel blocking agents
ACE inhibitors with thiazides
adamantane antivirals
adrenal cortical steroids
adrenal corticosteroid inhibitors
adrenergic bronchodilators
agents for hypertensive emergencies
agents for pulmonary hypertension
aldosterone receptor antagonists
alkylating agents
allergenics
alpha-glucosidase inhibitors
alternative medicines
amebicides
aminoglycosides
aminopenicillins
aminosalicylates
AMPA receptor antagonists
amylin analogs
analgesic combinations
analgesics
androgens and anabolic steroids
angiotensin converting enzyme inhibitors
angiotensin II inhibitors with calcium channel blockers
angiotensin II inhibitors with thiazides
angiotensin receptor blockers
angiotensin receptor blockers and neprilysin inhibitors
anorectal preparations
anorexiants
antacids
anthelmintics
anti-angiogenic ophthalmic agents
anti-CTLA-4 monoclonal antibodies
anti-infectives
Anti-PD-1 monoclonal antibodies
antiadrenergic agents (central) with thiazides
antiadrenergic agents (peripheral) with thiazides
antiadrenergic agents, centrally acting
antiadrenergic agents, peripherally acting
antiandrogens
antianginal agents
antiarrhythmic agents
antiasthmatic combinations
antibiotics/antineoplastics
anticholinergic antiemetics
anticholinergic antiparkinson agents
anticholinergic bronchodilators
anticholinergic chronotropic agents
anticholinergics/antispasmodics
anticoagulant reversal agents
anticoagulants
anticonvulsants
antidepressants
antidiabetic agents
antidiabetic combinations
antidiarrheals
antidiuretic hormones
decongestants
dermatological agents
diagnostic radiopharmaceuticals
diarylquinolines
dibenzazepine anticonvulsants
digestive enzymes
dipeptidyl peptidase 4 inhibitors
diuretics
dopaminergic antiparkinsonism agents
drugs used in alcohol dependence
echinocandins
EGFR inhibitors
estrogen receptor antagonists
estrogens
expectorants
factor Xa inhibitors
fatty acid derivative anticonvulsants
fibric acid derivatives
first generation cephalosporins
fourth generation cephalosporins
functional bowel disorder agents
gallstone solubilizing agents
gamma-aminobutyric acid analogs
gamma-aminobutyric acid reuptake inhibitors
gastrointestinal agents
general anesthetics
genitourinary tract agents
GI stimulants
glucocorticoids
glucose elevating agents
glycopeptide antibiotics
glycoprotein platelet inhibitors
glycylcyclines
gonadotropin releasing hormones
gonadotropin-releasing hormone antagonists
gonadotropins
group I antiarrhythmics
group II antiarrhythmics
group III antiarrhythmics
group IV antiarrhythmics
group V antiarrhythmics
growth hormone receptor blockers
growth hormones
guanylate cyclase-C agonists
*H. pylori* eradication agents
H2 antagonists
hedgehog pathway inhibitors
hematopoietic stem cell mobilizer
heparin antagonists
heparins
HER2 inhibitors
respiratory agents
sex hormones
topical agents
uncategorized agents
vaginal agents
mitotic inhibitors
monoamine oxidase inhibitors
mouth and throat products
mTOR inhibitors
mucolytics
multikinase inhibitors
muscle relaxants
mydriatics
narcotic analgesic combinations
narcotic analgesics
nasal anti-infectives
nasal antihistamines and decongestants
nasal lubricants and irrigations
nasal preparations
nasal steroids
natural penicillins
neprilysin inhibitors
neuraminidase inhibitors
neuromuscular blocking agents
neuronal potassium channel openers
next generation cephalosporins
nicotinic acid derivatives
NK1 receptor antagonists
NNRTIs
non-cardioselective beta blockers
non-iodinated contrast media
non-ionic iodinated contrast media
non-sulfonylureas
nonsteroidal anti-inflammatory agents
NS5A inhibitors
nucleoside reverse transcriptase inhibitors (NRTIs)
nutraceutical products
nutritional products
ophthalmic anesthetics
ophthalmic anti-infectives
ophthalmic anti-inflammatory agents
ophthalmic antihistamines and decongestants
ophthalmic diagnostic agents
ophthalmic glaucoma agents
ophthalmic lubricants and irrigations
ophthalmic preparations
otic agents
renin inhibitors
respiratory agents
respiratory inhalant products
rifamycin derivatives
salicylates
sclerosing agents
second generation cephalosporins
selective estrogen receptor modulators
selective immunosuppressants
selective phosphodiesterase-4 inhibitors
selective serotonin reuptake inhibitors
serotonin-norepinephrine reuptake inhibitors
serotoninergic neuroenteric modulators
sex hormone combinations
sex hormones
SGLT-2 inhibitors
skeletal muscle relaxant combinations
skeletal muscle relaxants
smoking cessation agents
somatostatin and somatostatin analogs
spermicides
statins
sterile irrigating solutions
*streptomyces* derivatives
succinimide anticonvulsants
sulfonamides
sulfonylureas
synthetic ovulation stimulants
tetracyclic antidepressants
tetracyclines
therapeutic radiopharmaceuticals
therapeutic vaccines
thiazide diuretics
thiazolidinediones
thioxanthenes
third generation cephalosporins
thrombin inhibitors
thrombolytics
thyroid drugs
TNF alfa inhibitors
tocolytic agents
topical acne agents
topical agents
topical anesthetics
topical anti-infectives
topical anti-rosacea agents
topical antibiotics
topical antifungals
topical antihistamines
topical antineoplastics
topical antipsoriatics
topical antivirals
topical astringents TABLE 2-continued

MEDICAMENTS antidotes
antiemetic/antivertigo agents
antifungals
antigonadotropic agents
antigout agents
antihistamines
antihyperlipidemic agents
antihyperlipidemic combinations
antihypertensive combinations
antihyperuricemic agents
antimalarial agents
antimalarial combinations
antimalarial quinolines
antimetabolites
antimigraine agents
antineoplastic detoxifying agents
antineoplastic interferons
antineoplastics
antiparkinson agents
antiplatelet agents
antipseudomonal penicillins
antipsoriatics
antipsychotics
antirheumatics
antiseptic and germicides
antithyroid agents
antitoxins and antivenins
antituberculosis agents
antituberculosis combinations
antitussives
antiviral agents
antiviral boosters
antiviral combinations
antiviral interferons
anxiolytics, sedatives, and hypnotics
aromatase inhibitors
atypical antipsychotics
azole antifungals
bacterial vaccines
barbiturate anticonvulsants
barbiturates
BCR-ABL tyrosine kinase inhibitors
benzodiazepine anticonvulsants
benzodiazepines
beta blockers with calcium channel blockers
beta blockers with thiazides
beta-adrenergic blocking agents
beta-lactamase inhibitors
bile acid sequestrants
biologicals
bisphosphonates
bone morphogenetic proteins
bone resorption inhibitors
bronchodilator combinations
bronchodilators
calcimimetics
calcineurin inhibitors
calcitonin
calcium channel blocking agents
carbamate anticonvulsants
carbapenems
carbonic anhydrase inhibitors
herbal products
histone deacetylase inhibitors
hormones
hormones/antineoplastics
hydantoin anticonvulsants
hydrazide derivatives
immune globulins
immunologic agents
immunostimulants
immunosuppressive agents
impotence agents
in vivo diagnostic biologicals
incretin mimetics
inhaled anti-infectives
inhaled corticosteroids
inotropic agents
insulin
insulin-like growth factor
integrase strand transfer inhibitor
interferons
interleukin inhibitors
interleukins
intravenous nutritional products
iodinated contrast media
ionic iodinated contrast media
iron products
ketolides
laxatives
leprostatics
leukotriene modifiers
lincomycin derivatives
local injectable anesthetics
local injectable anesthetics with corticosteroids
loop diuretics
lung surfactants
lymphatic staining agents
lysosomal enzymes
macrolide derivatives
macrolides
magnetic resonance imaging contrast media
mast cell stabilizers
medical gas
meglitinides
metabolic agents
methylxanthines
mineralocorticoids
minerals and electrolytes
miscellaneous agents
analgesics
antibiotics
anticonvulsants
antidepressants
antidiabetic agents
antiemetics
antifungals
antihyperlipidemic agents
antihypertensive combinations
antimalarials
antineoplastics
antiparkinson agents
ophthalmic steroids
ophthalmic steroids with anti-infectives
ophthalmic surgical agents
oral nutritional supplements
immunostimulants
immuno-suppressants
otic anesthetics
otic anti-infectives
otic preparations
otic steroids
otic steroids with anti-infectives
oxazolidinedione anticonvulsants
oxazolidinone antibiotics
parathyroid hormone and analogs
PARP inhibitors
PCSK9 inhibitors
penicillinase resistant penicillins
penicillins
peripheral opioid receptor antagonists
peripheral opioid receptor mixed agonists/antagonists
peripheral vasodilators
peripherally acting antiobesity agents
phenothiazine antiemetics
phenothiazine antipsychotics
phenylpiperazine antidepressants
phosphate binders
plasma expanders
platelet aggregation inhibitors
platelet-stimulating agents
polyenes
potassium sparing diuretics with thiazides
potassium-sparing diuretics
probiotics
progesterone receptor modulators
progestins
prolactin inhibitors
prostaglandin D2 antagonists
protease inhibitors
protease-activated receptor-1 antagonists
proteasome inhibitors
proton pump inhibitors
psoralens
psychotherapeutic agents
psychotherapeutic combinations
purine nucleosides
pyrrolidine anticonvulsants
topical debriding agents
topical depigmenting agents
topical emollients
topical keratolytics
topical non-steroidal anti-inflammatories
topical photochemo-therapeutics
topical rubefacient
topical steroids
topical steroids with anti-infectives
triazine anticonvulsants
tricyclic antidepressants
trifunctional monoclonal antibodies
ultrasound contrast media
upper respiratory combinations
urea anticonvulsants
urea cycle disorder agents
urinary anti-infectives
urinary antispasmodics
urinary pH modifiers
uterotonic agents
vaccine combinations
vaginal anti-infectives
vaginal preparations
vasodilators
vasopressin antagonists
vasopressors
VEGF/VEGFR inhibitors
viral vaccines
viscosupplementation agents
vitamin and mineral combinations
vitamins
5-alpha-reductase inhibitors
5-aminosalicylates
5HT3 receptor antagonists
chloride channel activators
cholesterol absorption inhibitors
cholinergic agonists
cholinergic muscle stimulants
cholinesterase inhibitors
CNS stimulants
coagulation modifiers
colony stimulating factors
contraceptives
corticotropin
coumarins and indandiones
cox-2 inhibitors

TABLE 2-continued

MEDICAMENTS

| | |
|---|---|
| antipsychotic agents | quinolones |
| antituberculosis agents | radiocontrast agents |
| antivirals | radiologic adjuncts |
| anxiolytics, sedatives and hypnotics | radiologic agents |
| bone resorption inhibitors | radiologic conjugating agents |
| cardiovascular agents | radiopharma-ceuticals |
| central nervous system agents | recombinant human erythropoietins |
| coagulation modifiers | anticonvulsants |
| diagnostic dyes | carbonic anhydrase inhibitors |
| diuretics | |
| genitourinary tract agents | cardiac stressing agents |
| GI agents | cardioselective beta blockers |
| hormones | |
| metabolic agents | cardiovascular agents |
| ophthalmic agents | catecholamines |
| | CD20 monoclonal antibodies |
| | CD30 monoclonal antibodies |
| | CD33 monoclonal antibodies |
| | CD38 monoclonal antibodies |
| | CD52 monoclonal antibodies |
| | central nervous system agents |
| | cephalosporins |
| | cephalosporins/beta-lactamase inhibitors |
| | cerumenolytics |
| | CFTR combinations |
| | CFTR potentiators |
| | chelating agents |
| | chemokine receptor antagonist |

What is claimed is:

1. A method for enhancing efficacy of a therapy of a cancer in a human or animal patient, wherein the method comprises
    a. contacting a microbiota of the patient with an engineered nucleic acid sequence for producing a host modifying (HM) crRNA, and
    b. producing the HM-crRNA in a host cell of a target bacterial or archaeal sub-population of a microbiota,
    wherein the HM-crRNA is operable with a Cas nuclease in the host cell to form a HM-CRISPR (Clustered Regularly Interspaced Short Palindromic Repeats)/Cas system, and wherein the HM-crRNA comprises a sequence that is capable of hybridizing to a target sequence of the host cell to guide the Cas nuclease to the target sequence in the host cell, whereby the target sequence is modified by the HM-CRISPR/Cas system and the host cell is selectively killed or growth of the target sub-population is selectively reduced, thereby increasing the relative proportion of a sub-population of non-target bacteria in the microbiota, wherein the sub-population of non-target bacteria comprise *Enterococcus*,
    wherein the therapy comprises administration of an effective amount of an immune checkpoint inhibitor to the patient, wherein the immune checkpoint inhibitor is a PD-1 (Programmed Cell Death Protein 1) inhibitor or a PD-L1 (Programmed Death-Ligand 1) inhibitor, and wherein the increasing the relative proportion of the sub-population of the second bacterial species in the microbiota modulates immune cells in the patient, whereby the efficacy of the therapy is enhanced for treatment of the cancer in the patient.

2. The method of claim 1, wherein the microbiota comprises a mixed population of human gut microbiota bacteria of different species, and wherein the selective killing comprises selectively killing cells of one or more target bacterial or archaeal species and sparing cells of non-target species.

3. The method of claim 1, wherein the sub-population of non-target bacteria comprise *Enterococcus faecalis*, *Enterococcus faecium*, or *Enterococcus durans* cells.

4. The method of claim 1, wherein the immune checkpoint inhibitor is an antibody.

5. The method of claim 4, wherein the immune checkpoint inhibitor is nivolumab, pembrolizumab, pidilizumab, durvalumab, or atezolizumab.

6. The method of claim 1, wherein the microbiota is gut microbiota.

7. The method of claim 1, wherein the cancer is melanoma, non-small-cell lung cancer (NSCLC), bladder carcinoma, or renal cell carcinoma (RCC).

8. The method of claim 1, wherein the target bacterial or archaeal sub-population comprise Bacteroidetes.

9. The method of claim 1, wherein the Cas nuclease is endogenous to the host cell.

10. The method of claim 1, wherein the immune cells comprise cells selected from CD8+ cells, tumor infiltrating lymphocytes (TILs), CD4+ cells, Treg cells and memory cells.

11. The method of claim 1, wherein the immune cells comprise CD8+ cells.

12. The method of claim 11, wherein the CD8+ immune cells comprise cells selected from tumor infiltrating lymphocytes (TILs), Treg cells, memory cells, central memory T-cells (TCM), effector memory T-cells (TEM), stem cell memory cells (TSCM), and memory effector T-cells (Teff).

13. The method of claim 11, wherein the CD8+ immune cells comprise memory cells selected from the group consisting of CD45RO+CD62L+ and CD25+CD45RA−CD45RO+CD127+cells.

14. The method of claim 1, wherein the immune cells are upregulated or expanded in the patient.

15. The method of claim 1, wherein the second cells are of a human gut commensal strain and/or a human gut probiotic strain.

16. The method of claim 1, wherein the Cas nuclease is a Type I Cas nuclease.

17. The method of claim 1, wherein the Cas nuclease is a Type II Cas nuclease.

18. The method of claim 7, wherein the cancer is melanoma.

19. The method of claim 7, wherein the cancer is non-small-cell lung cancer (NSCLC).

20. The method of claim 7, wherein the cancer is bladder carcinoma.

21. The method of claim 7, wherein the cancer is renal cell carcinoma (RCC).

22. The method of claim 3, wherein the sub-population of non-target bacteria comprise *Enterococcus faecalis* cells.

23. The method of claim 3, wherein the sub-population of non-target bacteria comprise *Enterococcus faecium* cells.

24. The method of claim 3, wherein the sub-population of non-target bacteria comprise *Enterococcus durans* cells.

* * * * *

SEQUENCE LISTING

<160> NUMBER OF SEQ ID NOS: 10

<210> SEQ ID NO 1
<211> LENGTH: 112
<212> TYPE: PRT
<213> ORGANISM: Artificial Sequence
<220> FEATURE:
<223> OTHER INFORMATION: Synthetic Construct

<400> SEQUENCE: 1

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95
```

Thr Lys Asp Thr Tyr Asp Ala Leu His Met Gln Ala Leu Pro Pro Arg
            100                 105                 110

<210> SEQ ID NO 2
<211> LENGTH: 336
<212> TYPE: DNA
<213> ORGANISM: Artificial Sequence
<220> FEATURE:
<223> OTHER INFORMATION: Synthetic Construct

<400> SEQUENCE: 2
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336

<210> SEQ ID NO 3
<211> LENGTH: 726
<212> TYPE: DNA
<213> ORGANISM: Artificial Sequence
<220> FEATURE:
<223> OTHER INFORMATION: Synthetic Construct

<400> SEQUENCE: 3
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat acactcagg agtcccatca   180 aggttcagtg gcagtgggtc tggaacagat tattctctca ccattagcaa cctggagcaa   240
gaagatattg ccacttactt ttgccaacag ggtaatacgc ttccgtacac gttcggaggg   300
gggaccaagc tggagatcac aggtggcggt ggctcgggcg gtggtgggtc gggtggcggc   360
ggatctgagt gaaactgca ggagtcagga cctggcctgg tggcgccctc acagagcctg   420
tccgtcacat gcactgtctc aggggtctca ttacccgact atggtgtaag ctggattcgc   480
cagcctccac gaaagggtct ggagtggctg ggagtaatat ggggtagtga aaccacatac   540
tataattcag ctctcaaatc cagactgacc atcatcaagg acaactccaa gagccaagtt   600
ttcttaaaaa tgaacagtct gcaaactgat gacacagcca tttactactg tgccaaacat   660
tattactacg gtggtagcta tgctatggac tactggggcc aaggaacctc agtcaccgtc   720
tcctca                                                              726

<210> SEQ ID NO 4
<211> LENGTH: 242
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile

```
                      35                  40                  45
Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 5
<211> LENGTH: 72
<212> TYPE: DNA
<213> ORGANISM: Artificial Sequence
<220> FEATURE:
<223> OTHER INFORMATION: Synthetic Construct

<400> SEQUENCE: 5
atctacatct gggcgcccct tggccgggac tgtggggtcc ttctcctgtc actggttatc    60 acccttact gc                                                         72

<210> SEQ ID NO 6
<211> LENGTH: 22
<212> TYPE: PRT
<213> ORGANISM: Artificial Sequence
<220> FEATURE:
<223> OTHER INFORMATION: Synthetic Construct

<400> SEQUENCE: 6

Ile Trp Ala Pro Leu Ala Gly Thr Cys Gly Val Leu Leu Leu Ser Leu
 1               5                  10                  15

Val Ile Thr Leu Tyr Cys
            20

<210> SEQ ID NO 7
<211> LENGTH: 135
<212> TYPE: DNA
<213> ORGANISM: Artificial Sequence
<220> FEATURE:
<223> OTHER INFORMATION: Synthetic Construct

<400> SEQUENCE: 7
```

-continued

```
accacgacgc cagcgccgcg accaccaaca ccggcgccca ccatcgcgtc gcagccctg      60 tccctgcgcc cagaggcgtg ccggccagcg gcgggggggcg cagtgcacac gaggggctg    120 gacttcgcct gtgat                                                     135

<210> SEQ ID NO 8
<211> LENGTH: 47
<212> TYPE: PRT
<213> ORGANISM: Artificial Sequence
<220> FEATURE:
<223> OTHER INFORMATION: Synthetic Construct

<400> SEQUENCE: 8

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45

<210> SEQ ID NO 9
<211> LENGTH: 126
<212> TYPE: DNA
<213> ORGANISM: Artificial Sequence
<220> FEATURE:
<223> OTHER INFORMATION: Synthetic Construct

<400> SEQUENCE: 9
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 10
<211> LENGTH: 42
<212> TYPE: PRT
<213> ORGANISM: Artificial Sequence
<220> FEATURE:
<223> OTHER INFORMATION: Synthetic Construct

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```